(12) United States Patent
Song et al.

(10) Patent No.: US 8,258,144 B2
(45) Date of Patent: Sep. 4, 2012

(54) INHIBITORS OF PROTEIN KINASES

(75) Inventors: Yonghong Song, Foster City, CA (US); Qing Xu, Foster City, CA (US); Shawn M. Bauer, Pacifica, CA (US); Zhaozhong J. Jia, San Mateo, CA (US); Mukund Mehrotra, South San Francisco, CA (US); Anjali Pandey, Fremont, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 556 days.

(21) Appl. No.: 12/386,848

(22) Filed: Apr. 22, 2009

(65) Prior Publication Data

US 2009/0298823 A1 Dec. 3, 2009

Related U.S. Application Data

(60) Provisional application No. 61/047,077, filed on Apr. 22, 2008.

(51) Int. Cl.
*C07D 487/00* (2006.01)
*A61K 31/519* (2006.01)

(52) U.S. Cl. ..................... 514/265.1; 544/280
(58) Field of Classification Search .............. 544/280; 514/265.1
See application file for complete search history.

(56) References Cited

U.S. PATENT DOCUMENTS

| | | | |
|---|---|---|---|
| 5,728,536 A | 3/1998 | Ihle et al. | |
| 6,080,747 A | 6/2000 | Uckun et al. | |
| 6,080,748 A | 6/2000 | Uckun et al. | |
| 6,133,305 A | 10/2000 | Tang et al. | |
| 6,177,433 B1 | 1/2001 | Uckun et al. | |
| 6,210,654 B1 | 4/2001 | Ihle et al. | |
| 6,313,130 B1 | 11/2001 | Uckun et al. | |
| 6,316,635 B1 | 11/2001 | Tang et al. | |
| 6,433,018 B1 | 8/2002 | Siddiqui et al. | |
| 6,486,185 B1 | 11/2002 | McMahon et al. | |
| 6,506,763 B2 | 1/2003 | Tang et al. | |
| 6,528,509 B1 | 3/2003 | Hale et al. | |
| 6,593,357 B1 | 7/2003 | Green et al. | |
| 6,608,048 B2 | 8/2003 | Tsou et al. | |

(Continued)

FOREIGN PATENT DOCUMENTS

WO   WO 95/03701 A1   2/1995

(Continued)

OTHER PUBLICATIONS

International Search Report mailed on Nov. 11, 2009, for International Application No. PCT/US2009/002512 filed on Apr. 22, 2009, 5 pages.

(Continued)

*Primary Examiner* — Shengjun Wang
(74) *Attorney, Agent, or Firm* — Kilpatrick Townsend & Stockton LLP

(57) ABSTRACT

The present invention is directed to compounds of formula I-II and pharmaceutically acceptable salts, esters, and prodrugs thereof which are inhibitors of syk and/or JAK kinase. The present invention is also directed to intermediates used in making such compounds, the preparation of such a compound, pharmaceutical compositions containing such a compound, methods of inhibition syk and/or JAK kinase activity, methods of inhibition the platelet aggregation, and methods to prevent or treat a number of conditions mediated at least in part by syk and/or JAK kinase activity, such as undesired thrombosis and Non Hodgkin's Lymphoma.

19 Claims, 65 Drawing Sheets

U.S. PATENT DOCUMENTS

| | | | |
|---|---|---|---|
| 6,610,688 B2 | 8/2003 | Liang et al. |
| 6,635,651 B2 | 10/2003 | Uckun |
| 6,677,368 B2 | 1/2004 | Cui et al. |
| 6,683,082 B2 | 1/2004 | Tang et al. |
| 6,696,448 B2 | 2/2004 | Tang et al. |
| 6,699,865 B2 | 3/2004 | Hale et al. |
| 6,777,417 B2 | 8/2004 | Liang et al. |
| 6,784,195 B2 | 8/2004 | Hale et al. |
| 6,815,439 B2 | 11/2004 | Harris et al. |
| 6,825,190 B2 | 11/2004 | Moon et al. |
| 6,949,580 B2 | 9/2005 | Hale et al. |
| 6,969,760 B2 | 11/2005 | Ihle et al. |
| 6,998,391 B2 | 2/2006 | Lyons et al. |
| 7,056,944 B2 | 6/2006 | Hale et al. |
| 7,074,793 B2 | 7/2006 | Hudkins et al. |
| 7,105,529 B2 | 9/2006 | Davis et al. |
| 7,122,542 B2 | 10/2006 | Singh et al. |
| 7,517,886 B2 | 4/2009 | Singh et al. |
| 2001/0007033 A1 | 7/2001 | Tang et al. |
| 2002/0137141 A1 | 9/2002 | Ben-Sasson |
| 2002/0155173 A1 | 10/2002 | Chopp et al. |
| 2003/0149064 A1 | 8/2003 | Pease et al. |
| 2003/0236244 A1 | 12/2003 | Ledford |
| 2004/0029902 A1 | 2/2004 | Singh et al. |
| 2004/0102455 A1 | 5/2004 | Burns et al. |
| 2004/0142404 A1 | 7/2004 | Wilks et al. |
| 2004/0147507 A1 | 7/2004 | Ledeboer et al. |
| 2004/0214817 A1 | 10/2004 | Pierce et al. |
| 2005/0234049 A1 | 10/2005 | Singh et al. |
| 2007/0142402 A1 | 6/2007 | Ding et al. |

FOREIGN PATENT DOCUMENTS

| | | |
|---|---|---|
| WO | WO 99/15500 A1 | 4/1999 |
| WO | WO 00/00202 A1 | 1/2000 |
| WO | WO 00/10981 A1 | 3/2000 |
| WO | WO 00/39101 A1 | 7/2000 |
| WO | WO 00/47583 A1 | 8/2000 |
| WO | WO 00/51587 A2 | 9/2000 |
| WO | WO 00/51587 A3 | 9/2000 |
| WO | WO 00/55159 A2 | 9/2000 |
| WO | WO 00/55159 A3 | 9/2000 |
| WO | WO 01/09134 A1 | 2/2001 |
| WO | WO 01/42246 A2 | 6/2001 |
| WO | WO 01/42246 A3 | 6/2001 |
| WO | WO 01/45641 A2 | 6/2001 |
| WO | WO 01/45641 A3 | 6/2001 |
| WO | WO 01/52892 A2 | 7/2001 |
| WO | WO 01/52892 A3 | 7/2001 |
| WO | WO 01/56993 A2 | 8/2001 |
| WO | WO 01/56993 A3 | 8/2001 |
| WO | WO 01/57022 A2 | 8/2001 |
| WO | WO 01/57022 A3 | 8/2001 |
| WO | WO 01/72758 A1 | 10/2001 |
| WO | WO 02/00661 A1 | 1/2002 |
| WO | WO 02/43735 A1 | 6/2002 |
| WO | WO 02/48336 A2 | 6/2002 |
| WO | WO 02/051843 A1 | 7/2002 |
| WO | WO 02/059110 A1 | 8/2002 |
| WO | WO 02/060492 A1 | 8/2002 |
| WO | WO 02/060927 A1 | 8/2002 |
| WO | WO 02/096909 A1 | 12/2002 |
| WO | WO 02/102800 A1 | 12/2002 |
| WO | WO 03/002542 A1 | 1/2003 |
| WO | WO 03/020698 A2 | 3/2003 |
| WO | WO 03/030909 A1 | 4/2003 |
| WO | WO 03/048162 A1 | 6/2003 |
| WO | WO 03/063794 A2 | 8/2003 |
| WO | WO 03/063794 A3 | 8/2003 |
| WO | WO 03/066601 A1 | 8/2003 |
| WO | WO 03/074515 A1 | 9/2003 |
| WO | WO 03/101989 A1 | 12/2003 |
| WO | WO 03/106416 A2 | 12/2003 |
| WO | WO 03/106416 A3 | 12/2003 |
| WO | WO 2004/014382 A1 | 2/2004 |
| WO | WO 2004/016597 A2 | 2/2004 |
| WO | WO 2004/016597 A3 | 2/2004 |
| WO | WO 2004/041789 A1 | 5/2004 |
| WO | WO 2004/041810 A1 | 5/2004 |
| WO | WO 2004/041814 A1 | 5/2004 |
| WO | WO 2004/046112 A2 | 6/2004 |
| WO | WO 2004/046112 A3 | 6/2004 |
| WO | WO 2004/046118 A2 | 6/2004 |
| WO | WO 2004/046118 A3 | 6/2004 |
| WO | WO 2004/046120 A2 | 6/2004 |
| WO | WO 2004/046120 A3 | 6/2004 |
| WO | WO 2004/047843 A1 | 6/2004 |
| WO | WO 2004/058749 A1 | 7/2004 |
| WO | WO 2004/058753 A1 | 7/2004 |
| WO | WO 2004/085388 A2 | 10/2004 |
| WO | WO 2004/085388 A3 | 10/2004 |
| WO | WO 2004/092154 A1 | 10/2004 |
| WO | WO 2005/009957 A1 | 2/2005 |
| WO | WO 2005/016344 A1 | 2/2005 |
| WO | WO 2005/016893 A2 | 2/2005 |
| WO | WO 2005/016893 A3 | 2/2005 |
| WO | WO 2005/016894 A1 | 2/2005 |
| WO | WO 2005/028475 A2 | 3/2005 |
| WO | WO 2005/028475 A3 | 3/2005 |
| WO | WO 2005/033107 A1 | 4/2005 |
| WO | WO 2005/037800 A1 | 4/2005 |
| WO | WO 2005/066156 A1 | 7/2005 |
| WO | WO 2005/097135 A2 | 10/2005 |
| WO | WO 2005/097135 A3 | 10/2005 |
| WO | WO 2005/122294 A1 | 12/2005 |
| WO | WO 2007/042298 A1 | 4/2007 |
| WO | WO 2007/071393 A2 | 6/2007 |
| WO | WO 2007/071393 A3 | 6/2007 |
| WO | WO 2008/009458 A1 | 1/2008 |
| WO | WO 2008/119792 * | 10/2008 |

OTHER PUBLICATIONS

Jørgensen, A. et al., "Phosphorus Pentoxide in Organic Synthesis, XXXVI. Synthesis of 7$H$-pyrrolo[2,3-$d$]pyrimidin-2,4-diones 7-deazaisoguanines from 7$H$-pyrrolo[2,3-$d$]pyrimidin-2,4-diones," Chemica Scripta, 1998, vol. 28, pp. 201-204.

Mócsai, A. et al., "Syk Is Required for Integrin Signaling in Neutrphils," Immunity, Apr. 2002, vol. 16, pp. 547-558.

Protest Under 37 C.F.R. § 1.291(a) of U.S. Appl. No. 12/386,848, filed Apr. 22, 2009, for Yonghong Song et al., 14 pages.

Turner, M. et al., "Tyrosine kinase SYK: essential functions for immunoreceptor signaling," Immunology Today, Mar. 2000, vol. 21, No. 3, pp. 148-154.

U.S. Appl. No. 60/630,808, filed Nov. 24, 2004, for Robin Cooper et al.

U.S. Appl. No. 60/645,424, filed Jan. 19, 2005, for Rajinder Singh et al.

U.S. Appl. No. 60/654,620, filed Feb. 18, 2005, for Rajinder Singh et al.

* cited by examiner

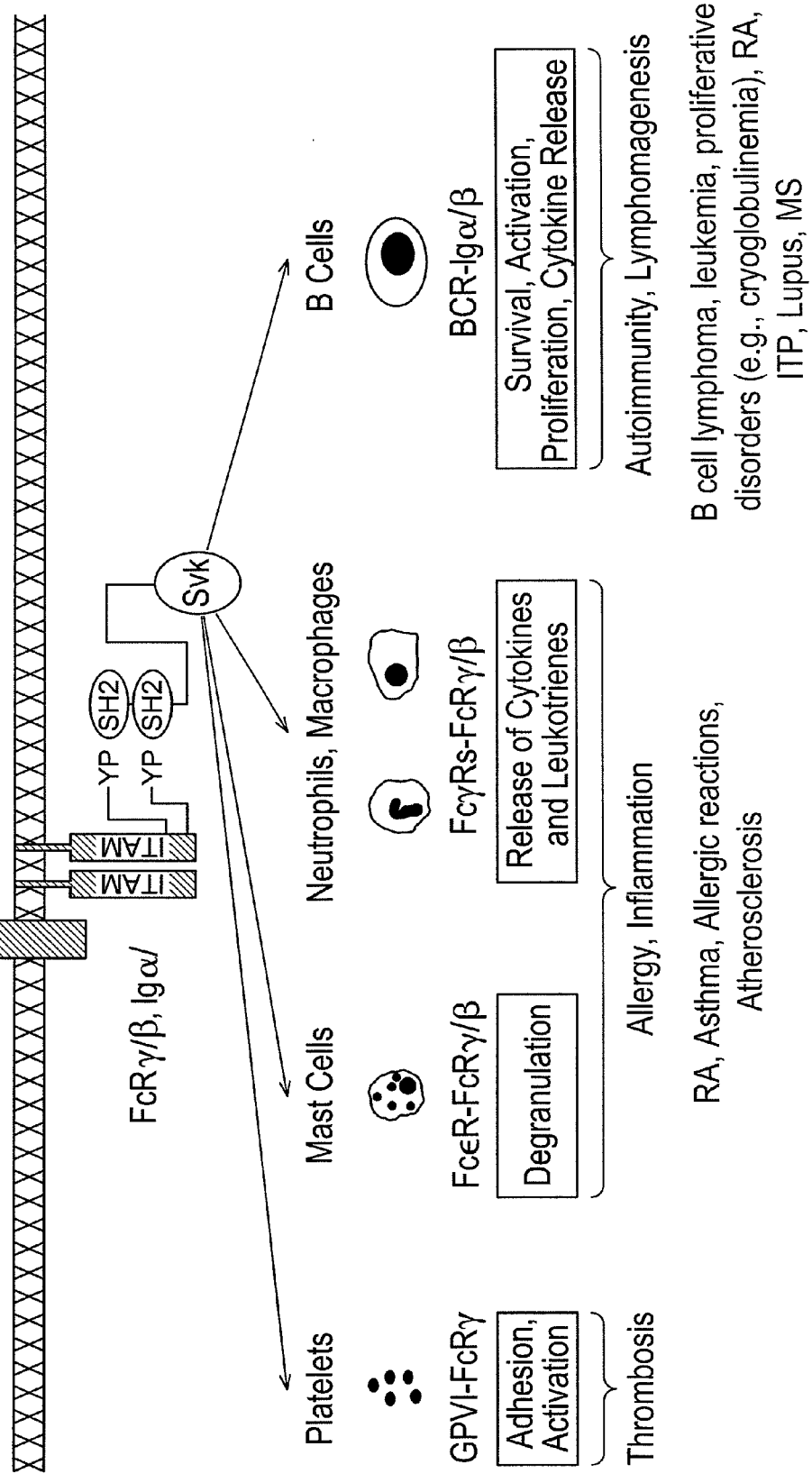

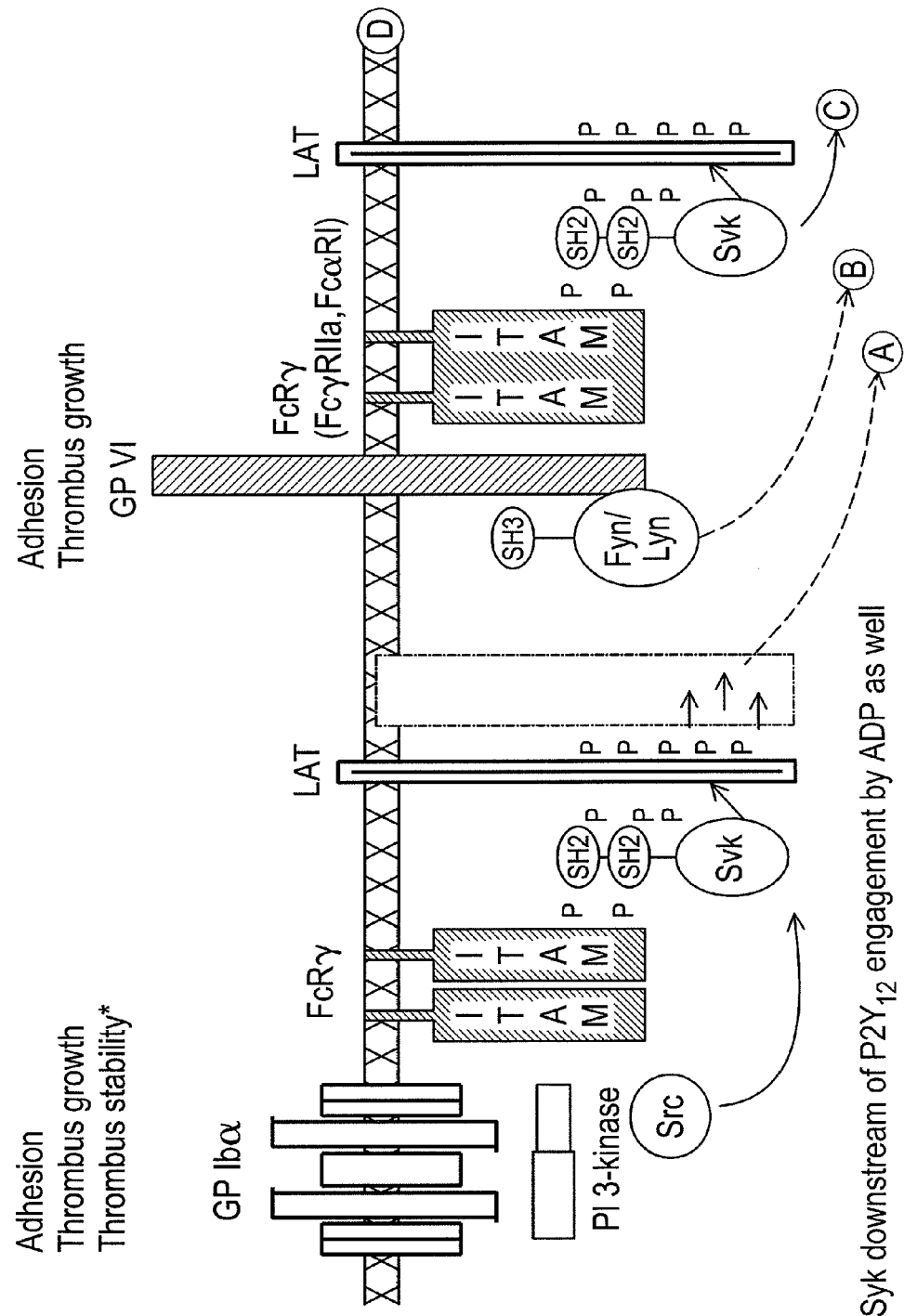
Fig. 2 (Sheet 1)

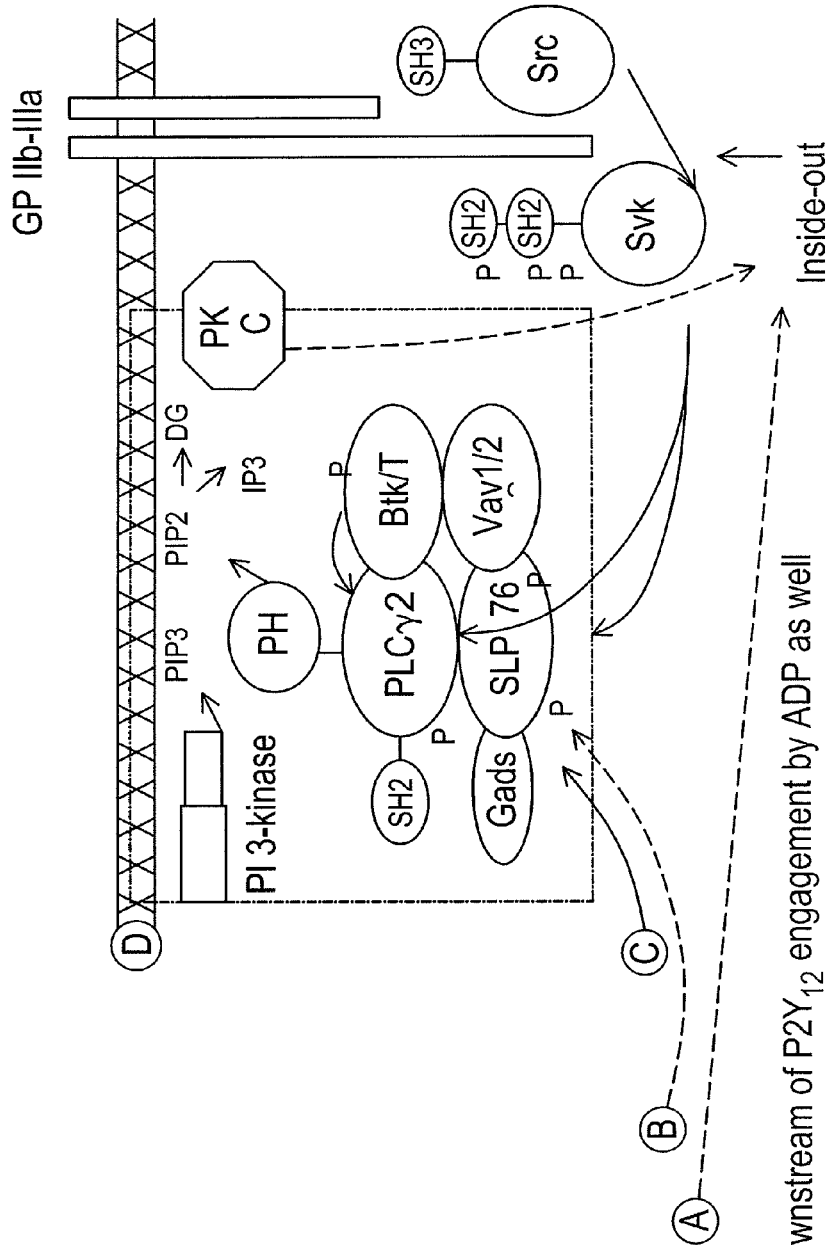
Fig. 2 (Sheet 2)

*Fig. 6*
Effect of increasing dose of
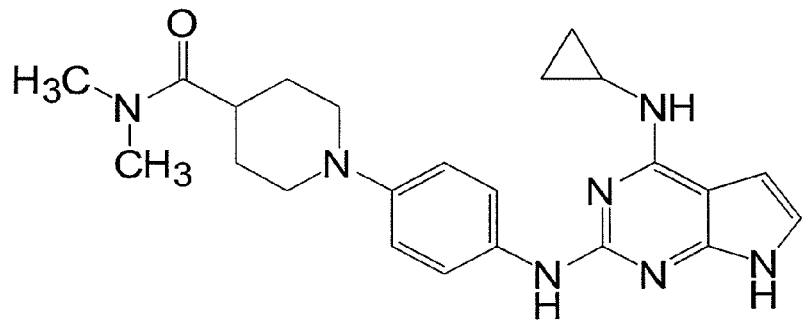
on pSTAT6 formation in response to IL4 stimulation of B Ramos cells.
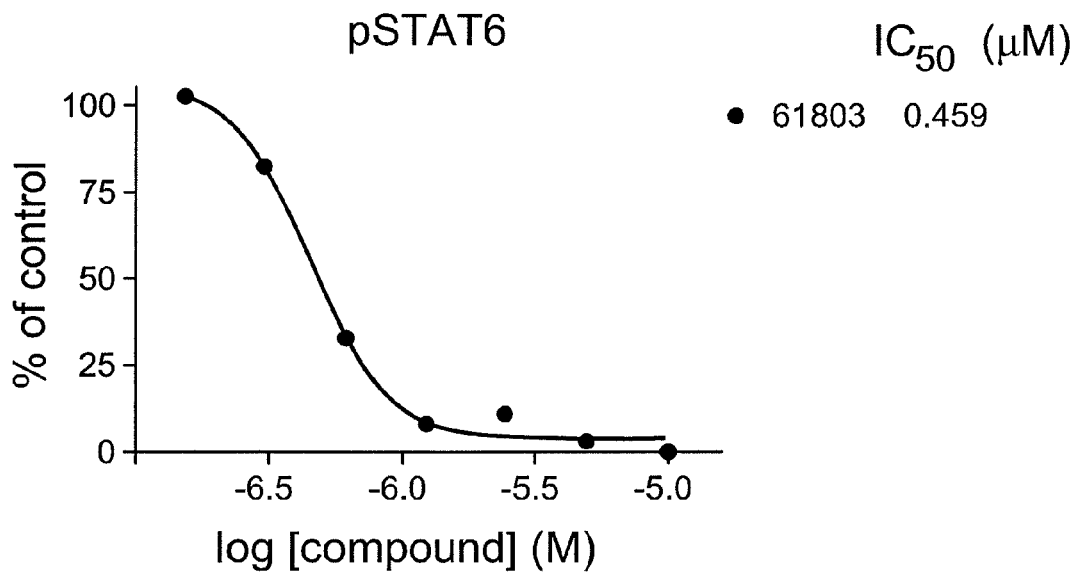

Fig. 7 (Sheet 1)
| Example No. | Compound | Syk IC 50 |
|---|---|---|
| 200 | 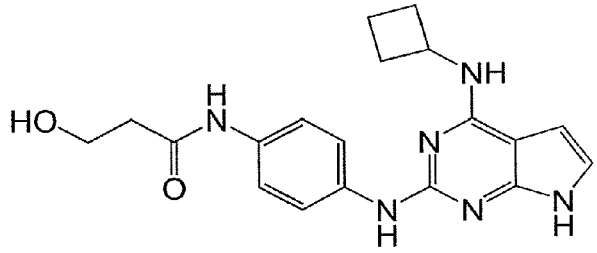 | +++ |
| 201 | 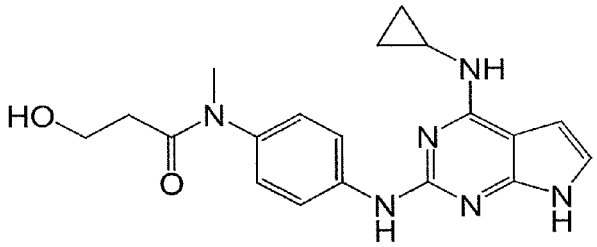 | +++ |
| 202 | 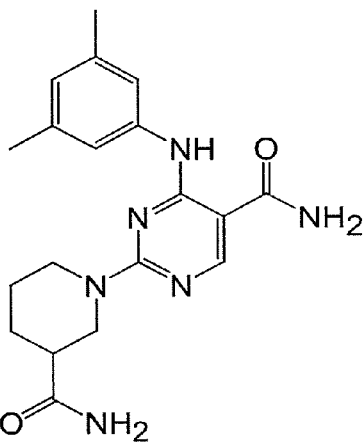 | ++ |

Fig. 7 (Sheet 2)

| Example No. | Compound | Syk IC 50 |
|---|---|---|
| 203 | | + |
| 204 | | + |
| 205 | | + |

Fig. 7 (Sheet 3)
| Example No. | Compound | Syk IC 50 |
|---|---|---|
| 206 | 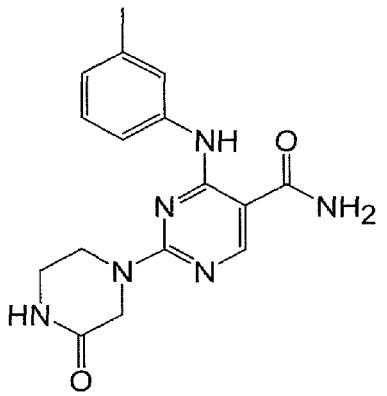 | + |
| 207 | 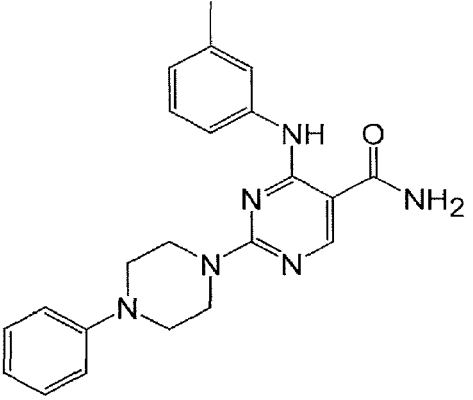 | + |
| 208 | 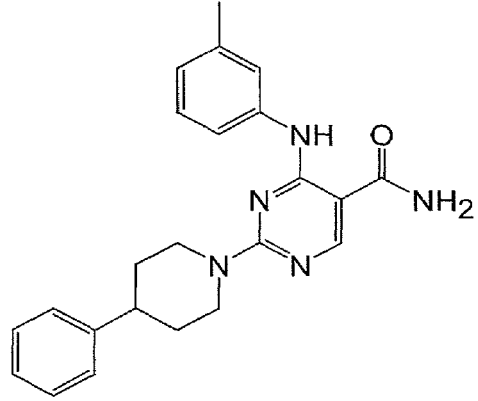 | + |

Fig. 7 (Sheet 4)
| Example No. | Compound | Syk IC 50 |
|---|---|---|
| 209 | 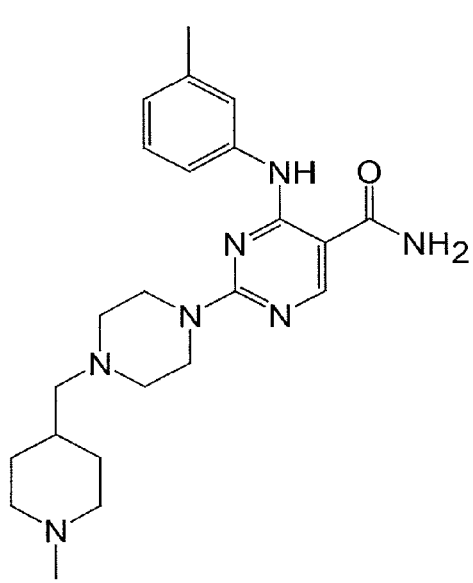 | + |
| 210 | 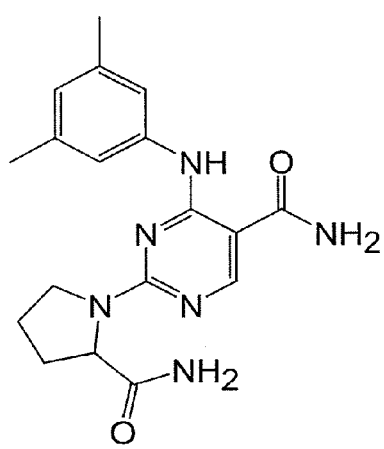 | + |

Fig. 7 (Sheet 5)
| Example No. | Compound | Syk IC 50 |
|---|---|---|
| 211 | 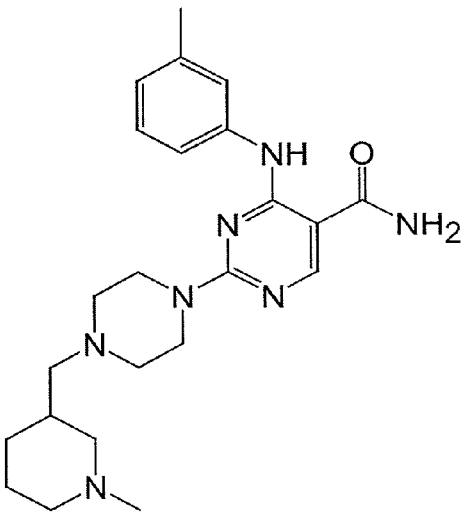 | + |
| 212 | 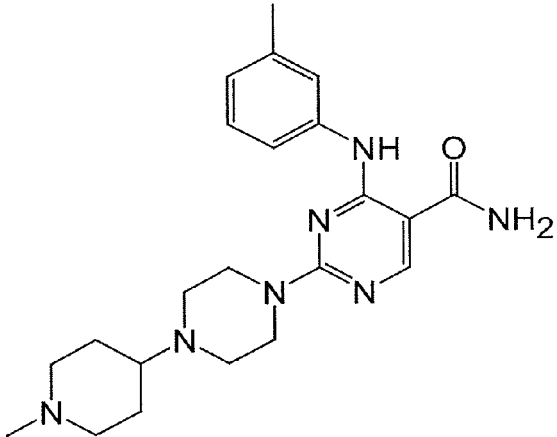 | + |

Fig. 7 (Sheet 6)

| Example No. | Compound | Syk IC 50 |
|---|---|---|
| 213 | (3-methylphenyl)NH-pyrimidine-5-carboxamide, 2-(4-(hydroxymethyl)-1H-1,2,3-triazol-1-yl) | + |
| 214 | (3-methylphenyl)NH-pyrimidine-5-carboxamide, 2-(6-amino-1H-indazol-1-yl) | + |
| 215 | (3-methylphenyl)NH-pyrimidine-5-carboxamide, 2-(5-(hydroxymethyl)-1H-imidazol-1-yl) | + |

Fig. 7 (Sheet 7)
| Example No. | Compound | Syk IC 50 |
|---|---|---|
| 216 | 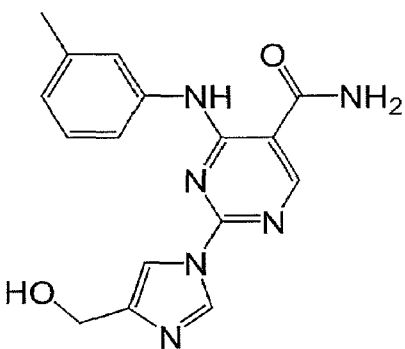 | + |
| 217 | 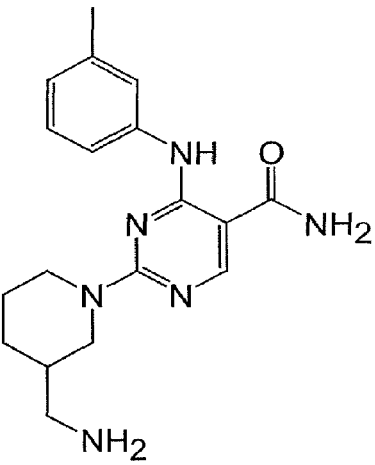 | + |
| 218 | 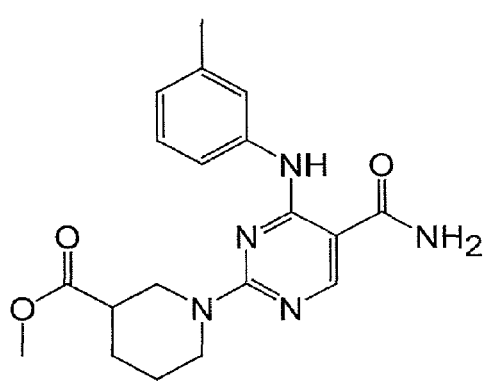 | + |

Fig. 7 (Sheet 8)
| Example No. | Compound | Syk IC 50 |
|---|---|---|
| 219 | 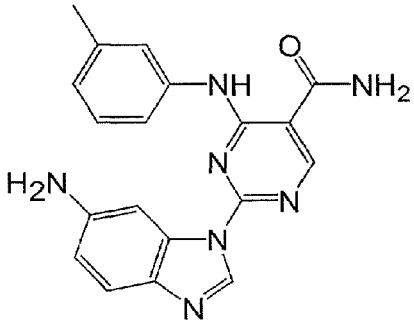 | + |
| 220 | 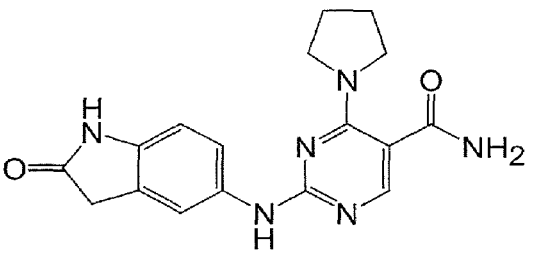 | + |
| 221 | 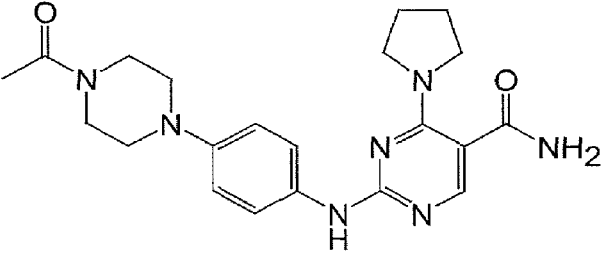 | + |
| 222 | 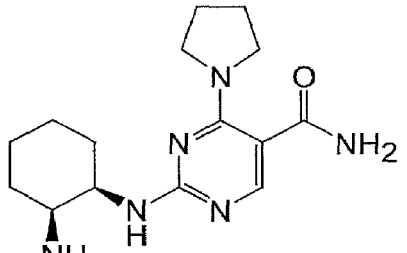 | + |

Fig. 7 (Sheet 9)
| Example No. | Compound | Syk IC 50 |
|---|---|---|
| 223 | 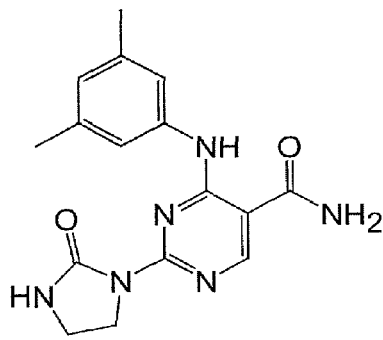 | + |
| 224 | 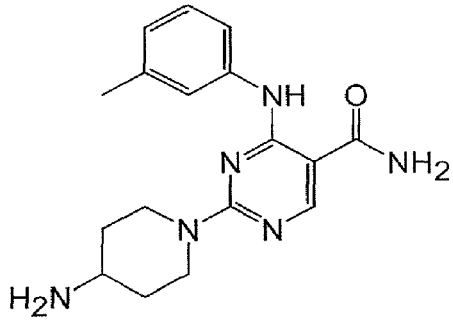 | + |
| 225 | 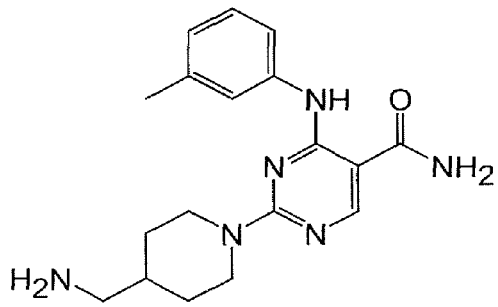 | + |

Fig. 7 (Sheet 10)

| Example No. | Compound | Syk IC 50 |
|---|---|---|
| 226 | (structure: 4-(2,4-dimethylphenylamino)-2-(2-carbamoylpyrrolidin-1-yl)pyrimidine-5-carboxamide) | + |
| 228 | (structure: tert-butyl 4-(2-((4-(4-acetylpiperazin-1-yl)phenyl)amino)-5-fluoropyrimidin-4-yl)piperazine-1-carboxylate) | + |
| 235 | (structure: 1-(4-(2-((4-(4-acetylpiperazin-1-yl)phenyl)amino)-5-fluoropyrimidin-4-yl)piperazin-1-yl)-carbamoyl-urea derivative) | + |

Fig. 7 (Sheet 11)

| Example No. | Compound | Syk IC 50 |
|---|---|---|
| 237 | | + |
| 238 | | + |
| 239 | | + |

Fig. 7 (Sheet 12)
| Example No. | Compound | Syk IC 50 |
|---|---|---|
| 241 | 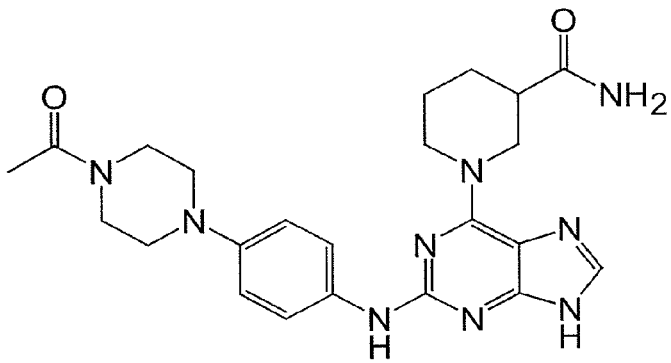 | ++ |
| 246 | 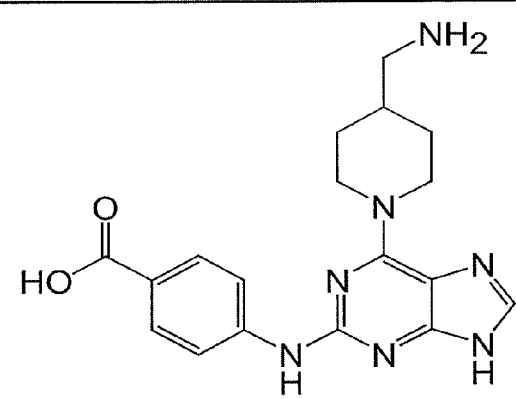 | +++ |
| 247 | 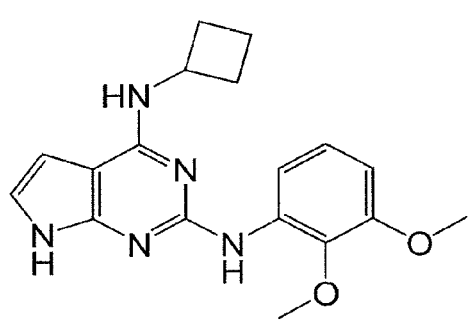 | + |
| 249 | 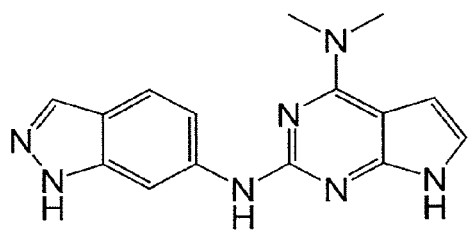 | ++ |

Fig. 7 (Sheet 13)
| Example No. | Compound | Syk IC 50 |
|---|---|---|
| 250 | 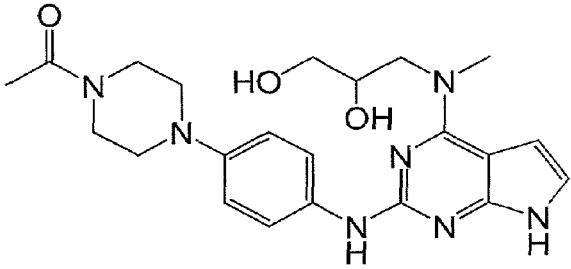 | ++ |
| 251 | 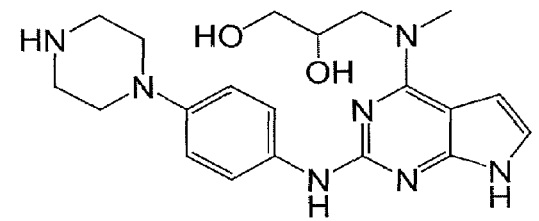 | + |
| 252 | 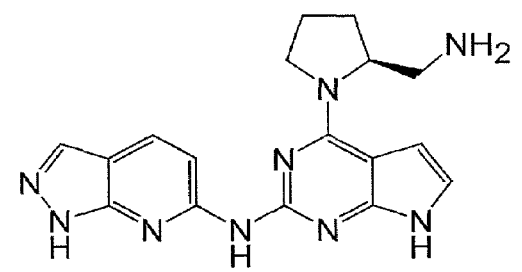 | + |
| 253 | 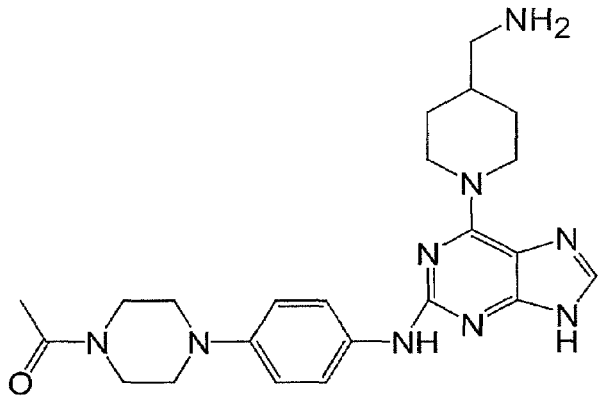 | +++ |

Fig. 7 (Sheet 14)
| Example No. | Compound | Syk IC 50 |
|---|---|---|
| 254 | 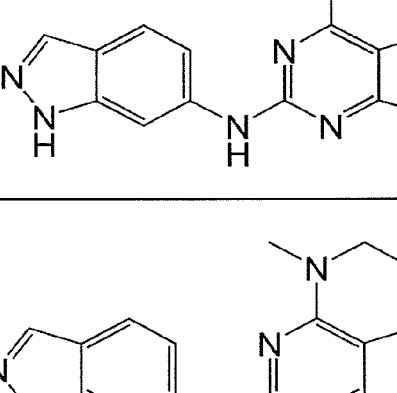 | ++ |
| 255 | 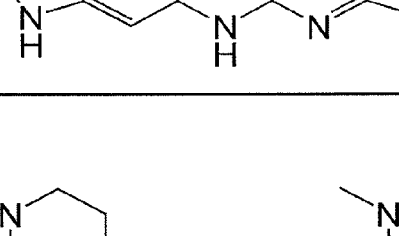 | ++ |
| 256 | 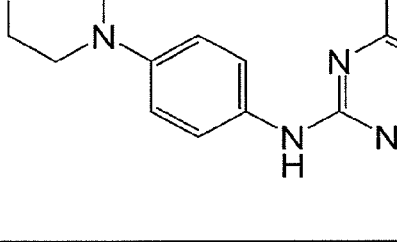 | ++ |
| 257 | 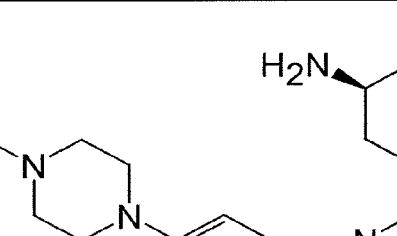 | ++ |

Fig. 7 (Sheet 15)

| Example No. | Compound | Syk IC 50 |
|---|---|---|
| 258 | (structure: 4-[[4-[4-(aminomethyl)piperidin-1-yl]-5-methylpyrimidin-2-yl]amino]benzoic acid) | ++ |

Fig. 8 (Sheet 1)
| Example No. | Compound | MW | MH+ | Syk IC 50 |
|---|---|---|---|---|
| 260 | 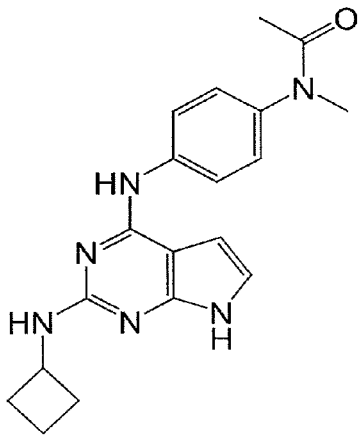 | 350.426 | 351.2 352.2 | + |
| 261 | 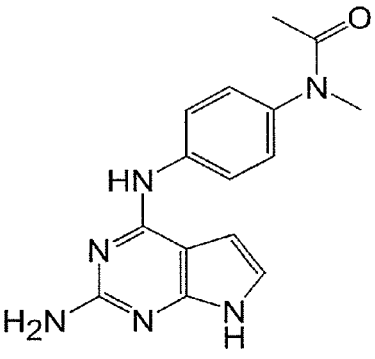 | 296.334 | | + |
| 262 | 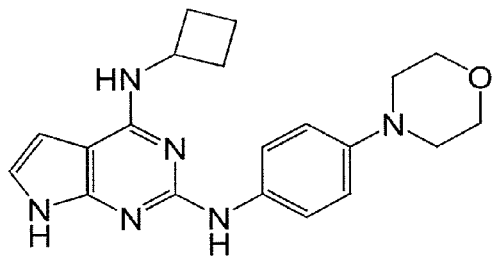 | 364.453 | | + |

Fig. 8 (Sheet 2)
| Example No. | Compound | MW | MH+ | Syk IC 50 |
|---|---|---|---|---|
| 263 | 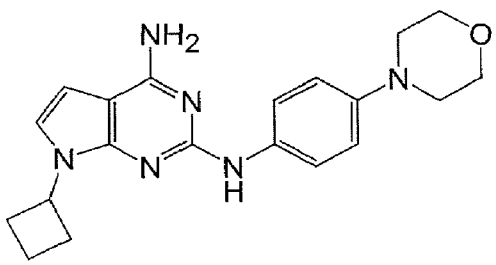 | 364.453 | | + |
| 264 | 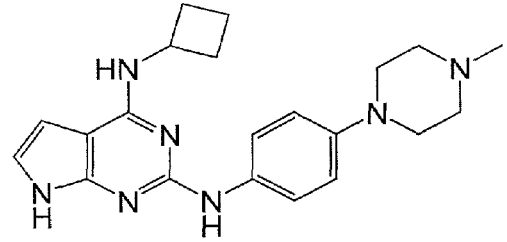 | 377.496 | | + |
| 265 | 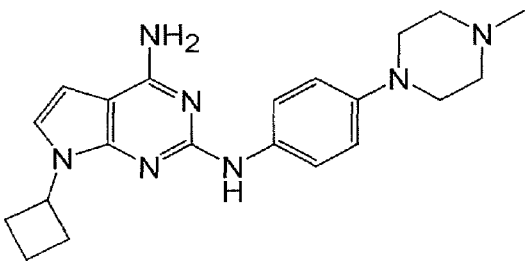 | 377.496 | | + |

Fig. 8 (Sheet 3)
| Example No. | Compound | MW | MH+ | Syk IC 50 |
|---|---|---|---|---|
| 266 | 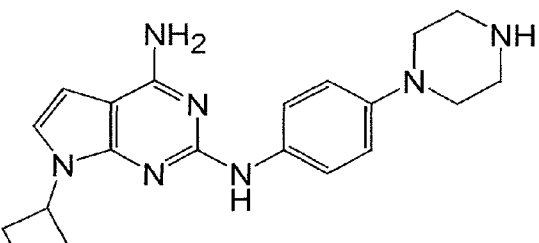 | 363.469 | | + |
| 267 | 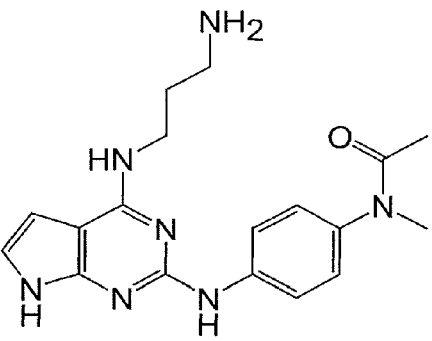 | 353.43 | | + |
| 268 | 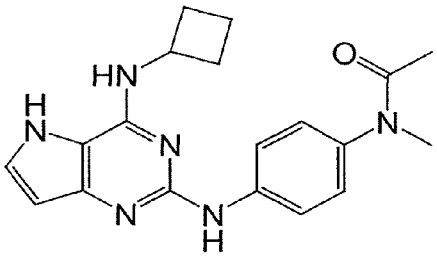 | 350.426 | | + |

*Fig. 8 (Sheet 4)*

| Example No. | Compound | MW | MH+ | Syk IC 50 |
|---|---|---|---|---|
| 269 | | 350.426 | 351.1 352.1 351.2 352.2 | +++ |
| 270 | | 405.506 | 406.2 407.2 406.2 407.3 | ++ |
| 271 | | 376.464 | 377.2 378.2 | + |

Fig. 8 (Sheet 5)
| Example No. | Compound | MW | MH+ | Syk IC 50 |
|---|---|---|---|---|
| 272 | 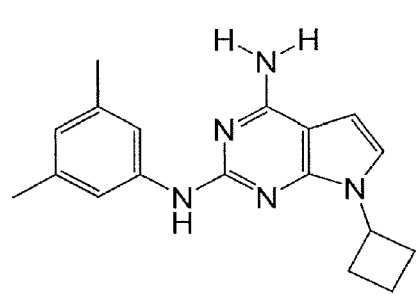 | 307.401 | 308.1 309.2 | + |
| 273 | 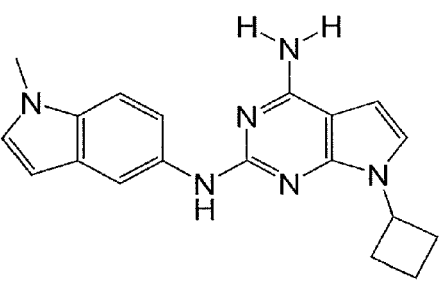 | 332.411 | 333.1 335.2 | + |
| 274 | 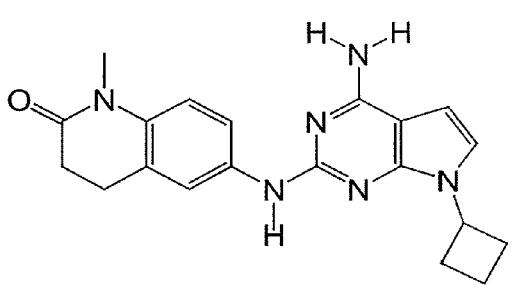 | 362.437 | 363.2 364.2 | + |

Fig. 8 (Sheet 6)
| Example No. | Compound | MW | MH+ | Syk IC 50 |
|---|---|---|---|---|
| 275 | 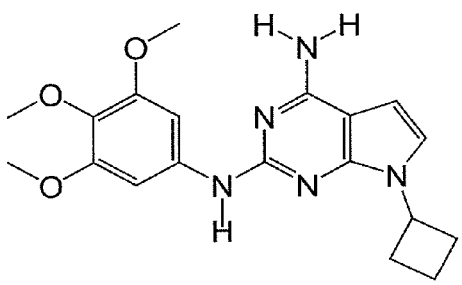 | 369.425 | 370.2 371.2 | + |
| 276 | 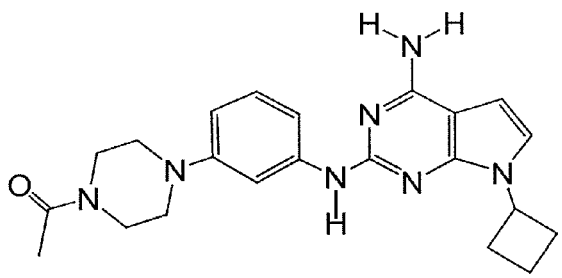 | 405.506 | 406.2 407.3 | + |
| 277 | 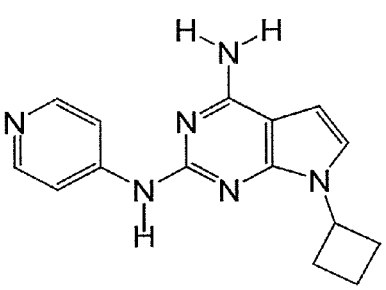 | 280.335 | 281.1 282.2 | + |

Fig. 8 (Sheet 7)

| Example No. | Compound | MW | MH+ | Syk IC 50 |
|---|---|---|---|---|
| 278 | | 405.506 | 406.2 407.2 | +++ |
| 279 | | 372.432 | 373.2 374.2 | ++ |
| 280 | | 376.464 | 377.2 378.2 | ++ |

Fig. 8 (Sheet 8)

| Example No. | Compound | MW | MH+ | Syk IC 50 |
|---|---|---|---|---|
| 281 | | 362.437 | 363.2 364.2 | +++ |
| 282 | | 350.426 | 351.1 352.1 | + |
| 283 | | 332.411 | 333.1 334.1 | ++ |

Fig. 8 (Sheet 9)
| Example No. | Compound | MW | MH+ | Syk IC 50 |
|---|---|---|---|---|
| 284 | 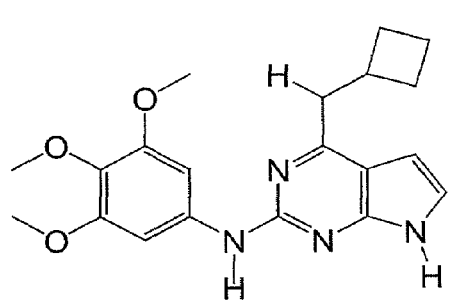 | 369.425 | 370.2 371.2 | ++ |
| 285 | 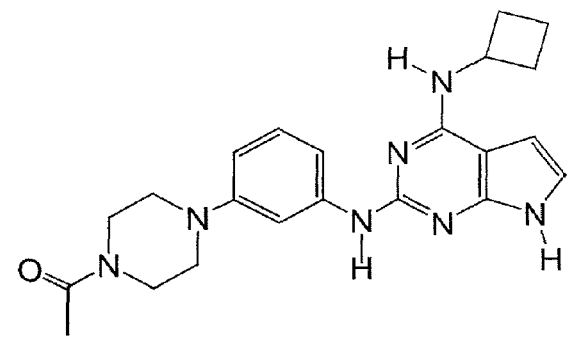 | 405.506 | 406.2 407.2 406.4 407.4 | + |
| 286 | 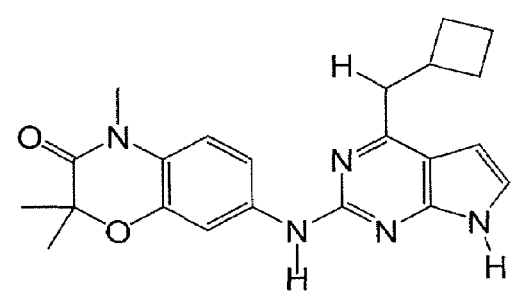 | 392.463 | 393.2 394.2 | ++ |

Fig. 8 (Sheet 10)

| Example No. | Compound | MW | MH+ | Syk IC 50 |
|---|---|---|---|---|
| 287 | | 392.463 | 393.2<br>394.2 | + |
| 288 | | 348.41 | 349.0<br>350.3<br>349.2<br>350.3 | +++ |
| 289 | | 364.409 | 365.2<br>366.3 | +++ |

Fig. 8 (Sheet 11)
| Example No. | Compound | MW | MH+ | Syk IC 50 |
|---|---|---|---|---|
| 290 | 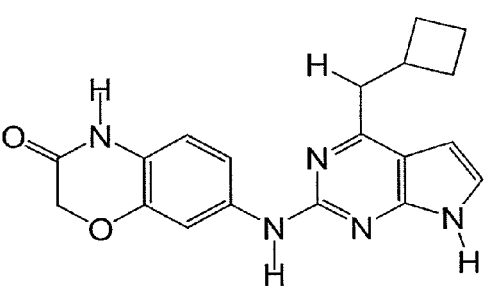 | 350.382 | 351.2 352.3 | +++ |
| 291 | 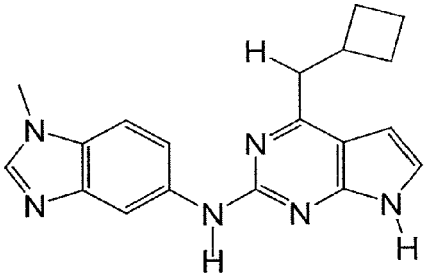 | 333.399 | 334.2 335.2 | ++ |
| 292 | 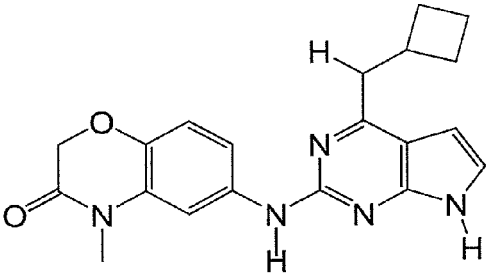 | 364.409 | 365.2 366.1 | ++ |

Fig. 8 (Sheet 12)
| Example No. | Compound | MW | MH+ | Syk IC 50 |
|---|---|---|---|---|
| 293 | 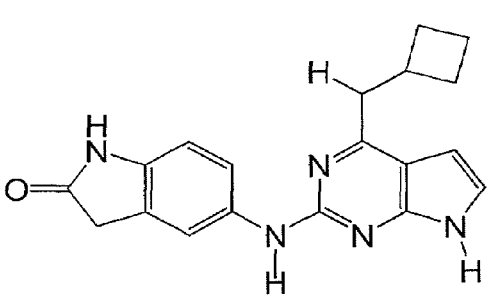 | 334.383 | 335.0 336.0 335.1 336.1 | +++ |
| 294 | 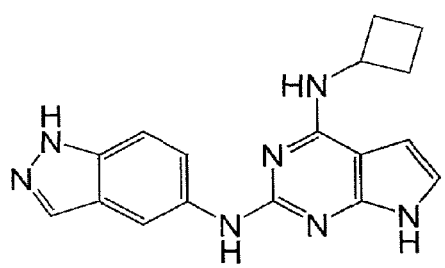 | 319.372 | 320.1 | +++ |
| 295 | 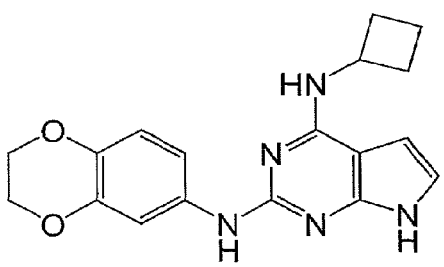 | 337.383 | 338.3 | ++ |

Fig. 8 (Sheet 13)

| Example No. | Compound | MW | MH+ | Syk IC 50 |
|---|---|---|---|---|
| 296 | | 378.436 | 379.2 380.2 | +++ |
| 297 | | 378.436 | 379.2 380.2 | ++ |
| 298 | | 335.367 | 336 | +++ |

Fig. 8 (Sheet 14)
| Example No. | Compound | MW | MH+ | Syk IC 50 |
|---|---|---|---|---|
| 299 | 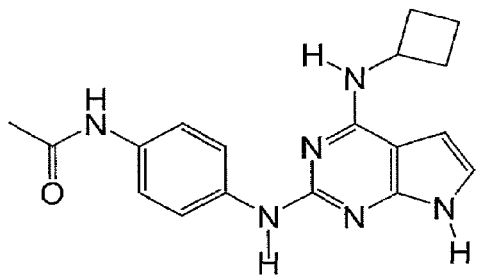 | 337.387 | 338.0 339.0 | ++ |
| 300 | 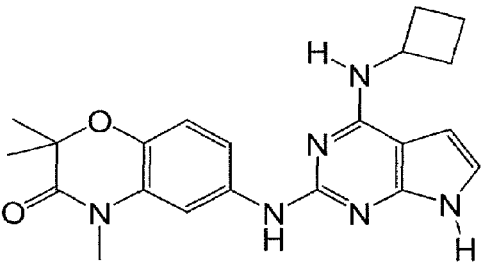 | 392.463 | 393.0 394.0 | ++ |
| 301 | 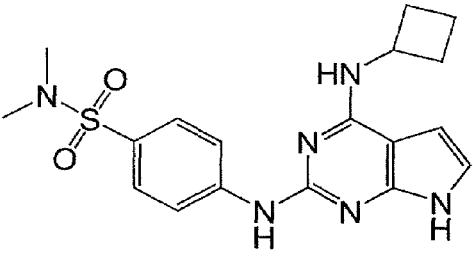 | 386.478 | 387 | +++ |

Fig. 8 (Sheet 15)
| Example No. | Compound | MW | MH+ | Syk IC 50 |
|---|---|---|---|---|
| 302 | 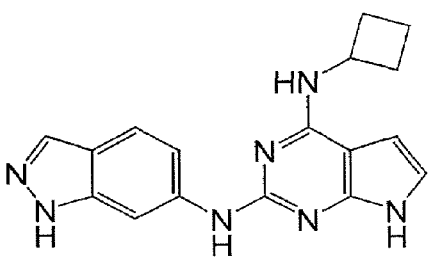 | 319.372 | 320 | +++ |
| 303 | 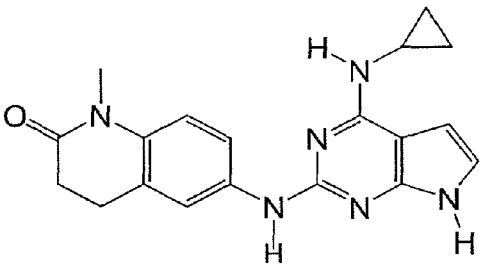 | 348.41 | 349.2 350.2 | +++ |
| 304 | 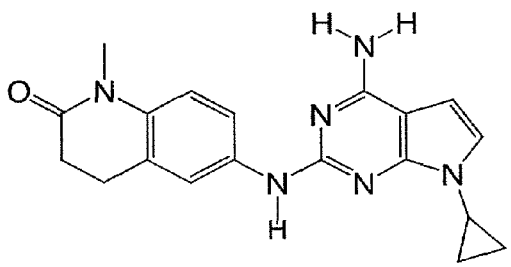 | 348.41 | 349.2 350.2 | + |

Fig. 8 (Sheet 16)
| Example No. | Compound | MW | MH+ | Syk IC 50 |
|---|---|---|---|---|
| 305 | 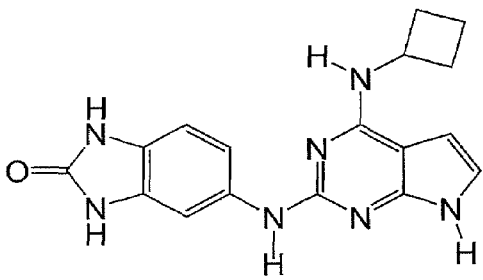 | 335.371 | 336.1 337.1 | +++ |
| 306 | 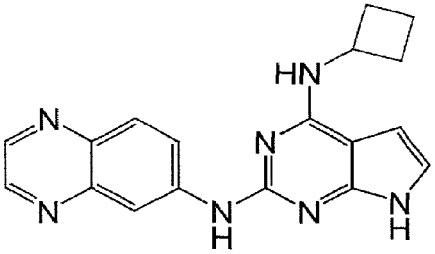 | 331.383 | 332 | ++ |
| 307 | 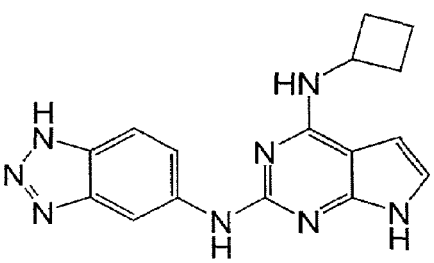 | 320.26 | 321 | +++ |

Fig. 8 (Sheet 17)

| Example No. | Compound | MW | MH+ | Syk IC 50 |
|---|---|---|---|---|
| 308 | | 428.515 | 429.1 | +++ |
| 309 | | 386.478 | 387.0 388.0 | +++ |
| 310 | | 392.463 | 393.2 394.2 | +++ |

Fig. 8 (Sheet 18)
| Example No. | Compound | MW | MH+ | Syk IC 50 |
|---|---|---|---|---|
| 311 | 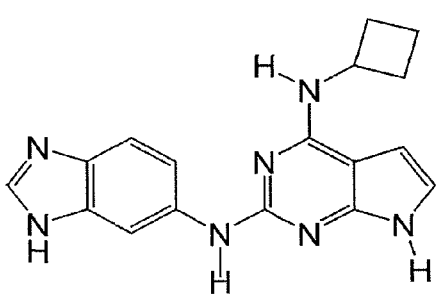 | 319.372 | 320.0 321.0 | +++ |
| 312 | 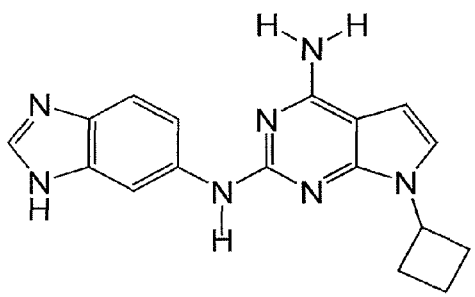 | 319.372 | 320.0 321.0 | ++ |
| 313 | 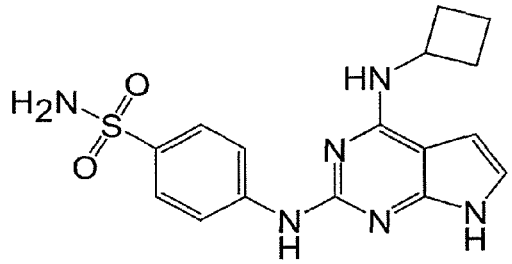 | 358.424 | 359 | +++ |

Fig. 8 (Sheet 19)
| Example No. | Compound | MW | MH+ | Syk IC 50 |
|---|---|---|---|---|
| 314 | 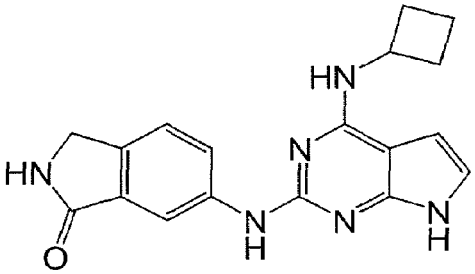 | 334.383 | 335 | ++ |
| 315 | 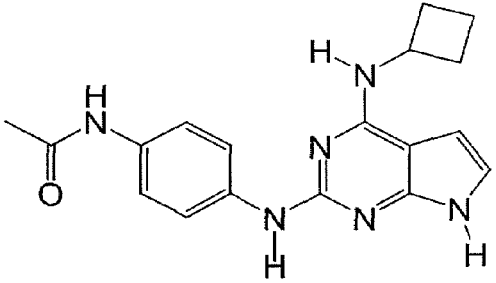 | 336.399 | 337.0 338.0 | ++ |
| 316 | 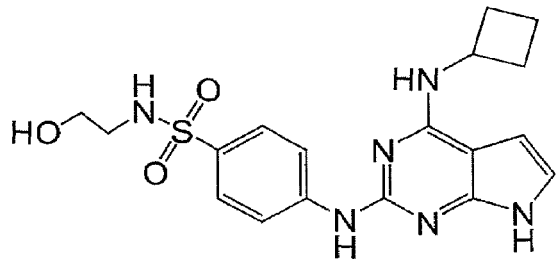 | 402.477 | 403 | +++ |

Fig. 8 (Sheet 20)
| Example No. | Compound | MW | MH+ | Syk IC 50 |
|---|---|---|---|---|
| 317 | 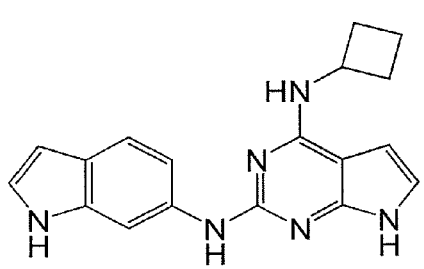 | 318.384 | 319.0 320.2 | ++ |
| 318 | 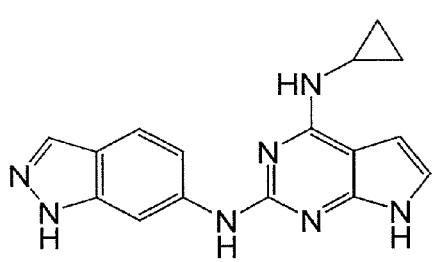 | 305.345 | 306.0 307.0 306.1 307.1 | +++ |
| 319 | 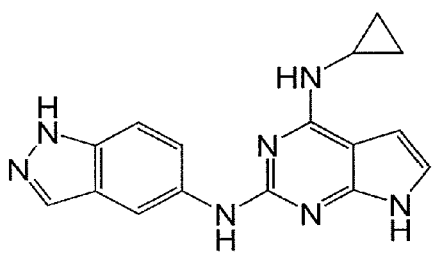 | 305.345 | 306.0 307.0 | +++ |

*Fig. 8 (Sheet 21)*

| Example No. | Compound | MW | MH+ | Syk IC 50 |
|---|---|---|---|---|
| 320 | | 320.356 | 321.2 322.2 | ++ |
| 321 | | 337.383 | 338 | ++ |
| 322 | | 322.372 | 323.2 | +++ |

Fig. 8 (Sheet 22)

| Example No. | Compound | MW | MH+ | Syk IC 50 |
|---|---|---|---|---|
| 323 | | 334.383 | 335.2 | +++ |
| 324 | | 336.355 | 337.2 338.2 | ++ |
| 325 | | 379.424 | 380.2 381.2 | + |

Fig. 8 (Sheet 23)
| Example No. | Compound | MW | MH+ | Syk IC 50 |
|---|---|---|---|---|
| 326 | 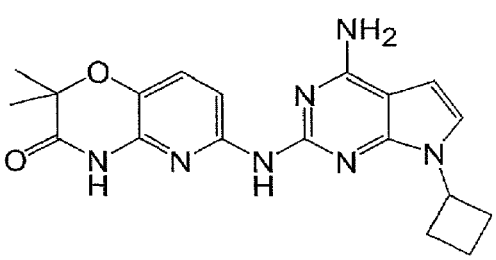 | 379.424 | 380.2 381.2 | + |
| 327 | 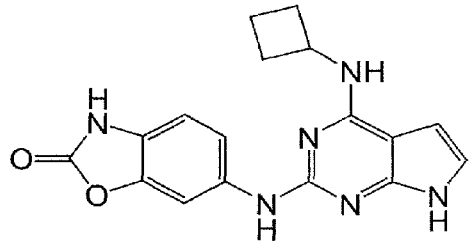 | 336.355 | 337.2 338.2 | ++ |
| 328 | 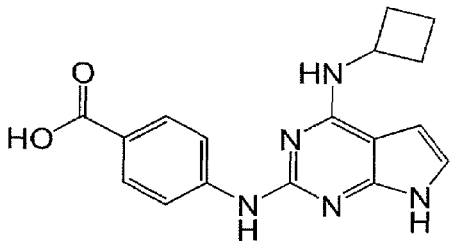 | 323.356 | 324 | +++ |

Fig. 8 (Sheet 24)
| Example No. | Compound | MW | MH+ | Syk IC 50 |
|---|---|---|---|---|
| 329 | 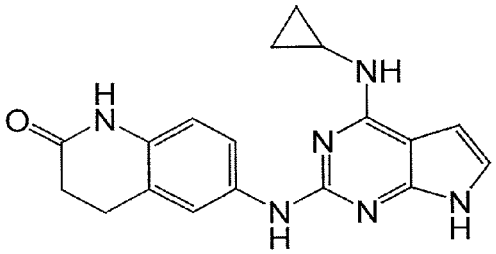 | 334.383 | 335.2 336.2 | +++ |
| 330 | 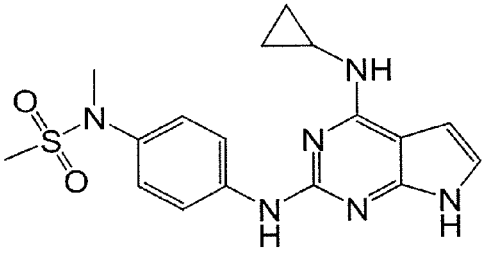 | 372.451 | 373.2 374.2 | +++ |
| 331 | 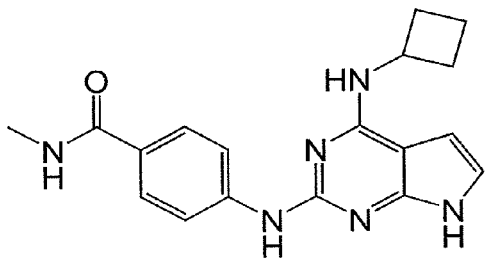 | 336.399 | 336.9 | +++ |

Fig. 8 (Sheet 25)
| Example No. | Compound | MW | MH+ | Syk IC 50 |
|---|---|---|---|---|
| 332 | 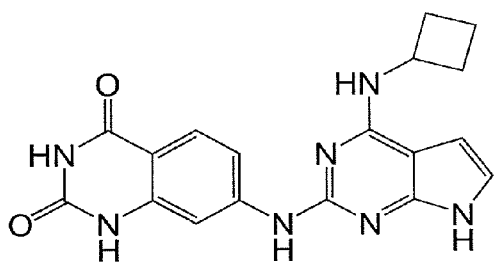 | 363.381 | 364 | +++ |
| 333 | 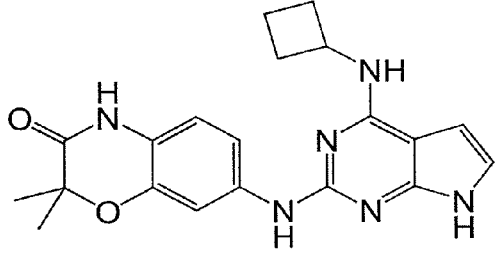 | 379.424 | 380.1 381.2 | + |
| 334 | 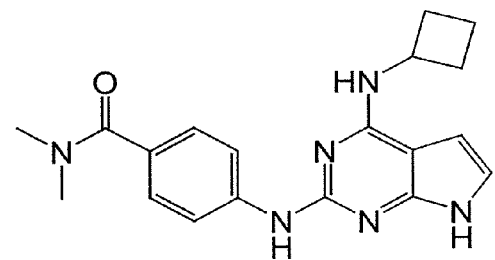 | 350.426 | 350.9 | ++ |

Fig. 8 (Sheet 26)

| Example No. | Compound | MW | MH+ | Syk IC 50 |
|---|---|---|---|---|
| 335 | | 392.463 | 393 | ++ |
| 336 | | 366.425 | 367 | ++ |
| 337 | | 416.504 | 417 | +++ |

Fig. 8 (Sheet 27)
| Example No. | Compound | MW | MH+ | Syk IC 50 |
|---|---|---|---|---|
| 338 | 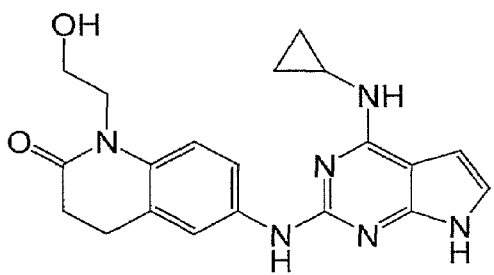 | 378.436 | 379.4 380.4 | +++ |
| 339 | 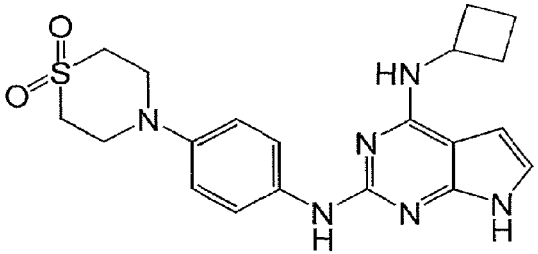 | 412.516 | 413.4 | +++ |
| 340 | 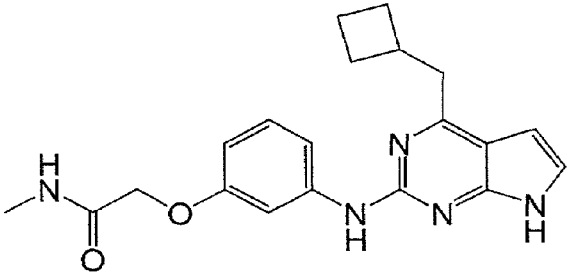 | 366.425 | 367.4 368.4 | ++ |

Fig. 8 (Sheet 28)
| Example No. | Compound | MW | MH+ | Syk IC 50 |
|---|---|---|---|---|
| 341 | 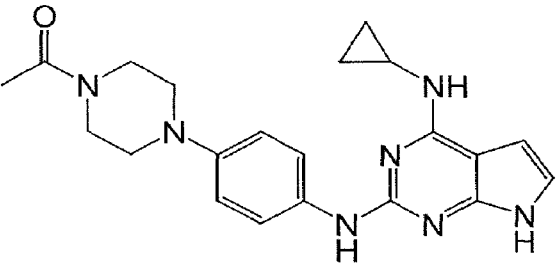 | 391.479 | 392.5 393.5 | +++ |
| 342 | 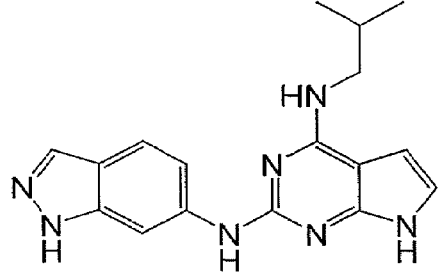 | 321.388 | 322.4 | ++ |
| 343 | 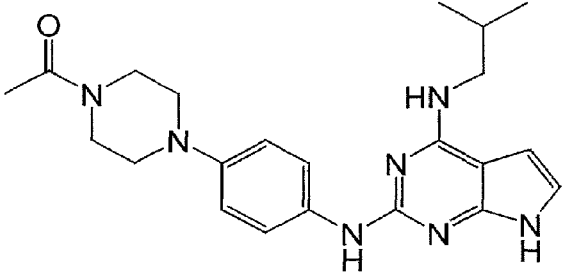 | 407.522 | 408.5 | ++ |

Fig. 8 (Sheet 29)
| Example No. | Compound | MW | MH+ | Syk IC 50 |
|---|---|---|---|---|
| 344 | 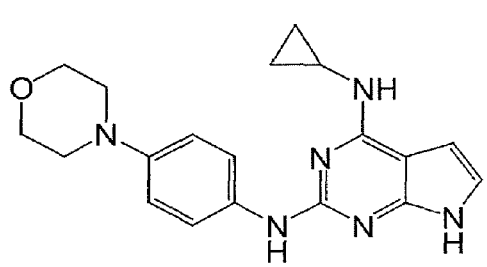 | 350.426 | 351.4 352.4 | +++ |
| 345 | 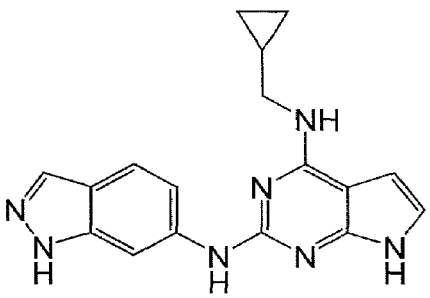 | 319.372 | 320.4 321.4 | +++ |
| 346 | 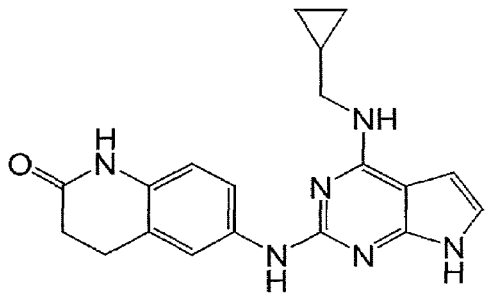 | 348.41 | 349.2 350.3 | ++ |

Fig. 8 (Sheet 30)
| Example No. | Compound | MW | MH+ | Syk IC 50 |
|---|---|---|---|---|
| 347 | 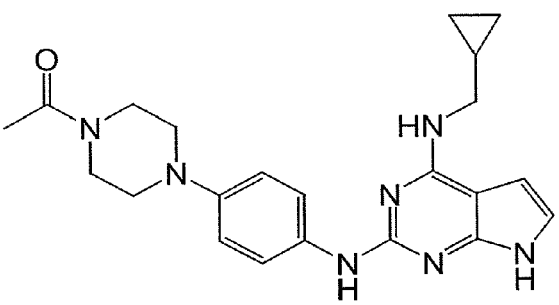 | 405.506 | 406.5 407.5 | ++ |
| 348 | 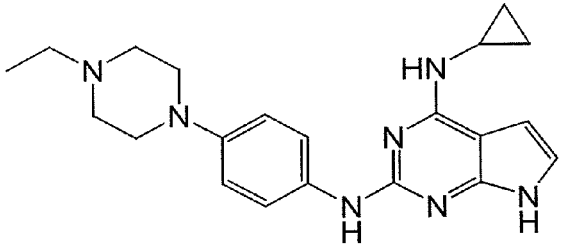 | 377.496 | 378.3 | +++ |
| 349 | 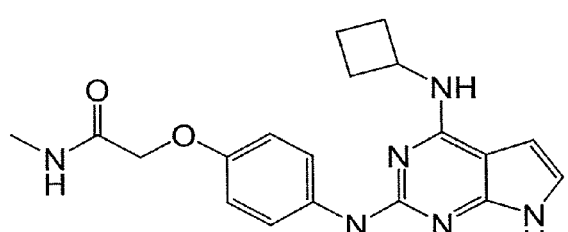 | 366.425 | 367.2 368.2 | ++ |

Fig. 8 (Sheet 31)
| Example No. | Compound | MW | MH+ | Syk IC 50 |
|---|---|---|---|---|
| 350 | 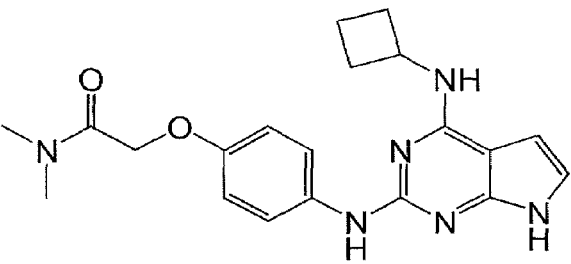 | 380.452 | 381.2 382.2 | ++ |
| 351 | 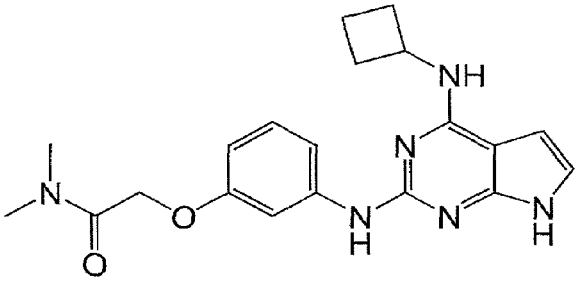 | 380.452 | 381.2 382.2 | + |
| 352 | 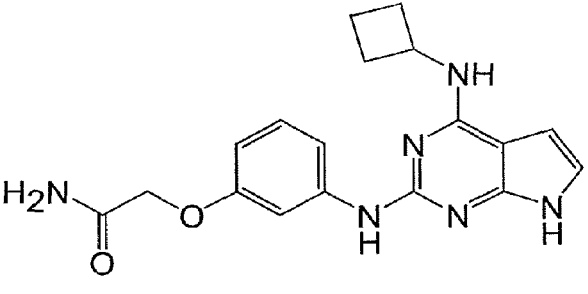 | 352.398 | 353.2 354.2 | +++ |

Fig. 8 (Sheet 32)

| Example No. | Compound | MW | MH+ | Syk IC 50 |
|---|---|---|---|---|
| 353 | | 450.51 | 451.2 | ++ |
| 354 | | 366.4 | 367.2<br>368.1 | +++ |
| 355 | | 352.373 | 353.1<br>354.1 | +++ |

Fig. 8 (Sheet 33)
| Example No. | Compound | MW | MH+ | Syk IC 50 |
|---|---|---|---|---|
| 356 | 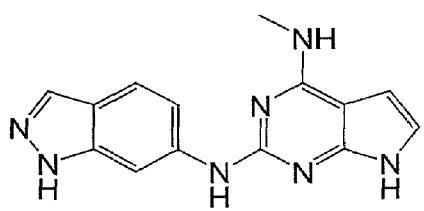 | 279.307 | 280 (M+H) 280.1, 281.1 ES(+) MS [M+H] = 280 | +++ |
| 357 | 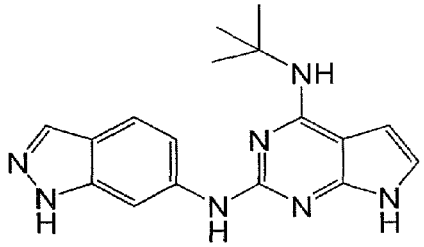 | 321.388 | 322.2 323.2 | +++ |
| 358 | 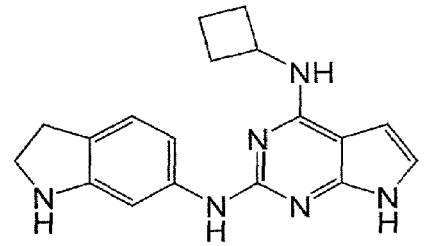 | 320.4 | 321.2 322.2 | ++ |

Fig. 8 (Sheet 34)
| Example No. | Compound | MW | MH+ | Syk IC 50 |
|---|---|---|---|---|
| 359 | 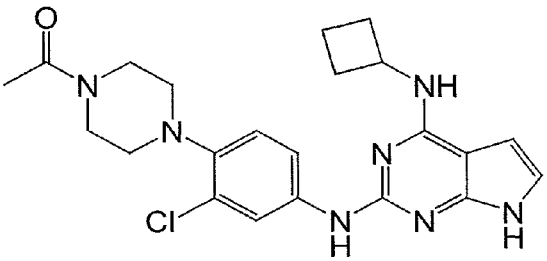 | 439.951 | 440.2 442.2 Chlorine pattern | +++ |
| 360 | 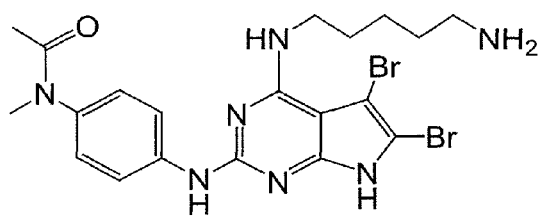 | 539.286 | 539.0 540.0 541.0 542.0 | + |
| 361 | 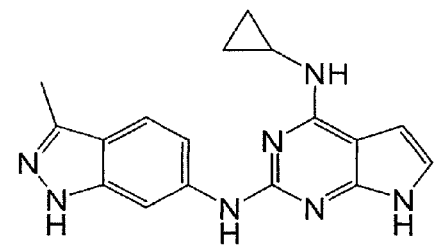 | 319.372 | 320 | +++ |

Fig. 8 (Sheet 35)
| Example No. | Compound | MW | MH+ | Syk IC 50 |
|---|---|---|---|---|
| 362 | 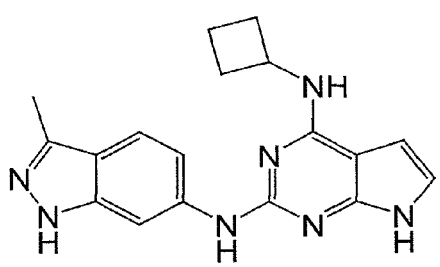 | 333.399 | 334.1 335.1 | +++ |
| 363 | 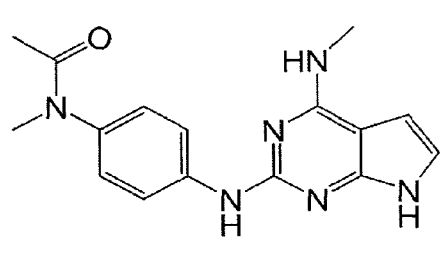 | 310.361 | 311.1 | ++ |
| 364 | 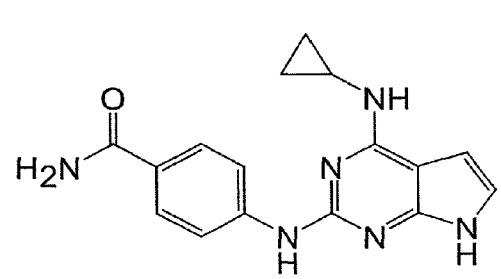 | 308.345 | 309.1 310.1 | ++ |

Fig. 8 (Sheet 36)
| Example No. | Compound | MW | MH+ | Syk IC 50 |
|---|---|---|---|---|
| 365 | 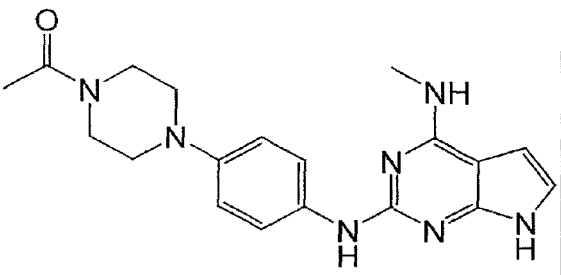 | 365.441 | 366.1<br>367.1 | ++ |
| 366 | 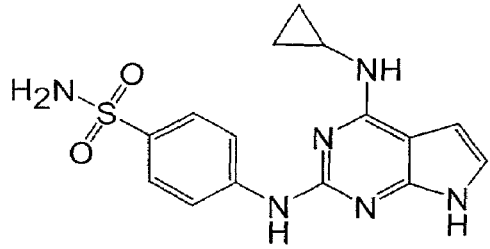 | 344.397 | 345.1<br>346.0 | +++ |
| 367 | 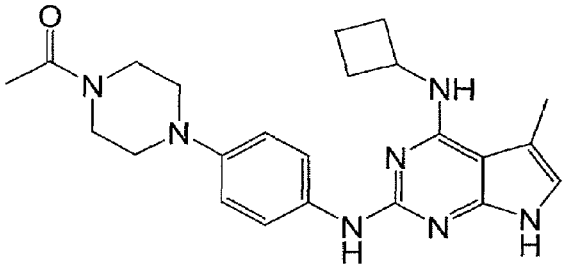 | 419.533 | 420.2<br>421.2 | ++ |

Fig. 8 (Sheet 37)
| Example No. | Compound | MW | MH+ | Syk IC 50 |
|---|---|---|---|---|
| 368 | 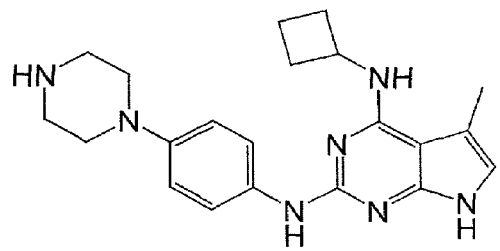 | 377.496 | 378.2 379.2 | +++ |
| 369 | 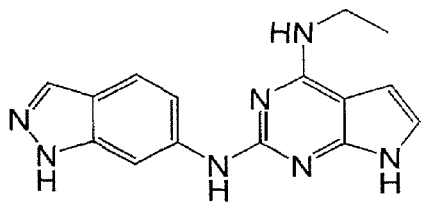 | 293.334 | 294.3 295.2 | +++ |
| 370 | 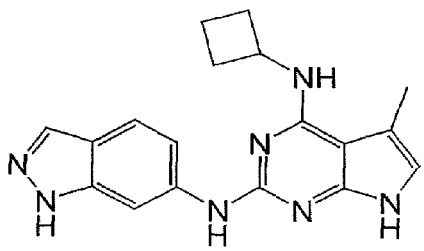 | 333.399 | 334.3 335.3 | +++ |

Fig. 8 (Sheet 38)
| Example No. | Compound | MW | MH+ | Syk IC 50 |
|---|---|---|---|---|
| 371 | 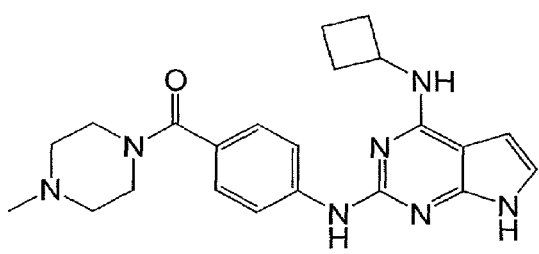 | 406.506 | 406.4 407.4 | ++ |
| 372 | 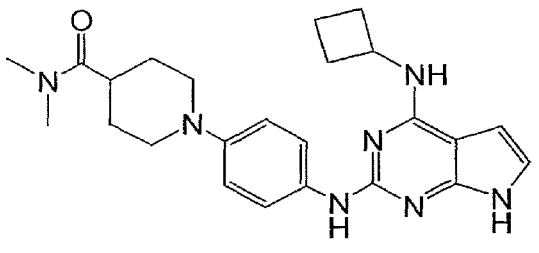 | 433.56 | 434.3 435.2 | ++ |
| 373 | 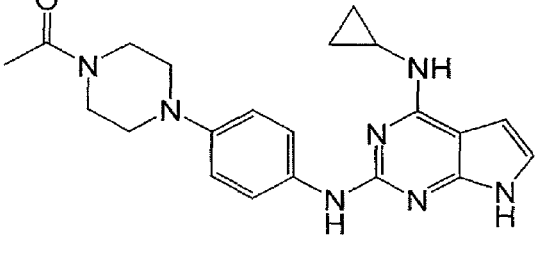 | 405.506 | 406.2 407.2 | +++ |

Fig. 8 (Sheet 39)
| Example No. | Compound | MW | MH+ | Syk IC 50 |
|---|---|---|---|---|
| 374 | 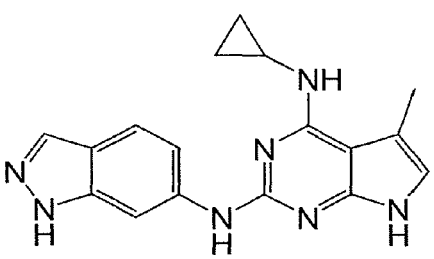 | 319.372 | 320.2 321.2 | ++++ |
| 375 | 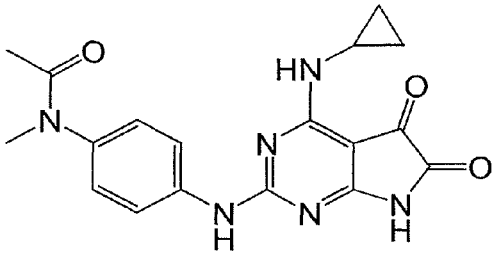 | 366.381 | 367.2 | + |
| 376 | 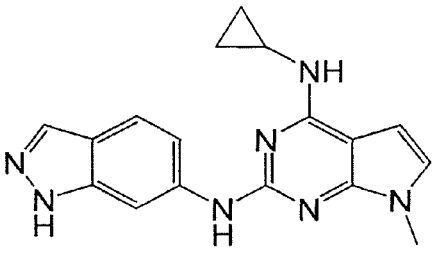 | 319.372 | 320.2 321.2 | + |

Fig. 8 (Sheet 40)

| Example No. | Compound | MW | MH+ | Syk IC 50 |
|---|---|---|---|---|
| 377 | | 405.506 | 406.2 407.2 | + |
| 378 | | 308.345 | 309.1 310.2 | ++ |
| 379 | | 326.335 | 327.1 328.1 | ++ |

Fig. 8 (Sheet 41)
| Example No. | Compound | MW | MH+ | Syk IC 50 |
|---|---|---|---|---|
| 381 | 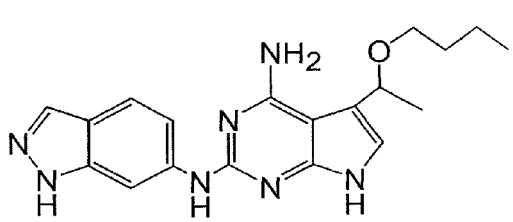 | 365.441 | 366.2 | + |
| 380 | 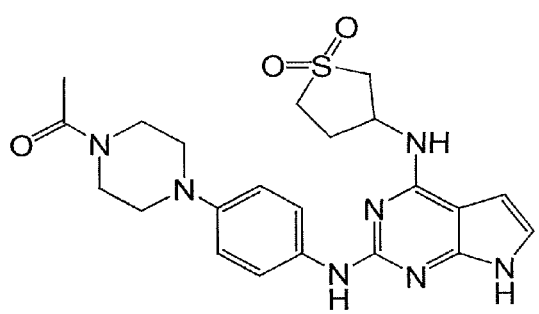 | 469.568 | 470.5 | + |
| | | | | |

| Compound | In-house IC50 (nM) | Conc. tested (uM) | Kinases inhibited (>67%) |
|---|---|---|---|
|  | 46 | 1<br>0.3<br>0.1 | 62<br>21<br>8 |

>80% inhibition @ 1uM (43)

| | |
|---|---|
| Syk | CK1γ3 |
| Reith | STK33 |
| CK1γ2 | GCK |
| JAK2 | Fes |
| RIPK2 | Aurora-A |
| TrkB | Axl |
| ARK5 | CHK2 |
| MLK1 | EGFR(T790M,L858R) |
| Flt3 | FGFR1(V561M) |
| Flt4 | Itk |
| LOK | MST2 |
| Mer | EGFR(T790M) |
| Rsk3 | PAR-1Bα |
| TrkA | Fer |
| TSSK1 | PKCγ |
| CHK2(R145W) | CaMKIIγ |
| TBK1 | PAK5 |
| CHK2(I157T) | Flt3(D835Y) |
| CK1γ1 | |
| Rsk1 | |
| Rsk1 | |
| Rsk2 | |
| RSK4 | |
| IRAK4 | |
| PDGFRα(D842V) | |

INHIBITORS OF PROTEIN KINASES

CROSS REFERENCES TO RELATED APPLICATIONS

This application is claims the benefit of U.S. Provisional Patent Application No. U.S. Provisional Patent Application No. 61/047,077, filed Apr. 22, 2008; the entire disclosure of which are incorporated herein by reference.

BACKGROUND OF THE INVENTION

1. Field of the Invention

This invention is directed to pyrimidine, pyrrolopyrimidine and purine-based analogs which act as inhibitors of Spleen tyrosine kinase (syk) and/or JAK kinases. This invention is also directed to pharmaceutical compositions containing the pyrimidine compounds and methods of using the compounds or compositions to treat a condition characterized by undesired thrombosis. The invention is also directed to methods of making the compounds described herein.

2. State of the Art

Protein kinases constitute a large family of structurally related enzymes that are responsible for the control of a variety of signal transduction processes within cells (see, e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), FASEB J. 9:576-596; Knighton et al., (1991), Science 253:407-414; Hiles et al., (1992), Cell 70:419-429; Kunz et al., (1993), Cell 73:585-596; Garcia-Bustos et al., (1994), EMBO J. 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, alzheimer's disease and hormone-related diseases. As a consequence, there has been substantial efforts in medicinal chemistry to find inhibitors of protein kinases for use as therapeutic agents.

Immunoreceptor tyrosine activation motif (ITAM)-mediated signaling has emerged as a primary event in signaling pathways responsible for human pathologies. ITAM-mediated signaling is responsible for relaying activation signals initiated at classical immune receptors such as T-cell receptors, B-cell receptors, Fc receptors in immune cells and at GPVI and FcγRIIa in platelets to downstream intracellular molecules such as syk and ZAP-70 (Underhill, D. M and Goodridge, H. S., *Trends Immunol.*, 28:66-73, 2007).

The binding of a ligand to an ITAM-containing receptor triggers signaling events which allows for the recruitment of proteins from a family of nonreceptor tyrosine kinases called the Src family. These kinases phosphorylate tyrosine residues within the ITAM sequence, a region with which the tandem SH2 domains on either syk or ZAP-70 interact.

Syk, along with Zap-70, is a member of the syk family of protein tyrosine kinases. The interaction of syk or ZAP-70 with diphosphorylated ITAM sequences induces a conformation change in the kinases that allows for tyrosine phosphorylation of the kinase itself. Phosphorylated Syk family members activate a multitude of downstream signaling pathway proteins which include Src homology 2 (SH2) domain containing leukocyte-specific phosphoprotein of 76 kDa (SLP-76), Linker of Activation of T-cells (LAT) and PLC (phospholipase C)γ2.

Human pathologies attributed to dysfunctional ITAM-mediated signaling include autoimmune diseases such as rheumatoid arthritis, systemic lupus, multiple sclerosis, hemolytic anemia, immune-thrombocytopenia purpura, and heparin-induced thrombocytopenia and arteriosclerosis. Interestingly, many of the above mentioned diseases are thought to occur through crosslinking of Fc receptors by antibodies which, via syk, activate a signaling cascade in mast, basophil and other immune cells that result in the release of cell mediators responsible for inflammatory reactions. The release of mediators and the production of cytokines in IgE stimulation-dependent allergic and inflammatory reactions from mast cells and basophiles can be controlled by inhibiting the tyrosine kinase activity of syk (Rossi, A. B. et al., *J Allergy Clin Immunol.*, 118:749-755, 2006). In immune-thrombocytopenia, antibody bound platelets are cleared by the spleen by an Fc receptor/ITAM/syk-mediated process (Crow, A. R. et al., *Blood*, 106:abstract 2165, 2005). Drug-induced thrombocytopenia, caused by heparin-platelet factor 4 immune complexes that activate platelet FcγRIIa, also involve syk signaling downstream of receptor engagement (Reilly, M. P., *Blood*, 98:2442-2447, 2001).

Platelet agonists induce inside-out integrin signaling resulting in fibrinogen binding and platelet aggregation. This initiates outside-in signaling which produces further stimulation of platelets. syk is activated during both phases of integrin signaling, and inhibition of syk is shown to inhibit platelet adhesion to immobilized proteins (Law, D. A. et al., *Blood*, 93:2645-2652, 1999). Release of arachidonic acid and serotonin and platelet aggregation induced by collagen are markedly inhibited in platelets derived from syk deficient mouse (Poole, A. et al., *EMBO J.*, 16:2333-2341, 1997). Thus syk inhibitors may also possess anticoagulation action.

Because of the role syk plays in Ig-induced platelet activations, it is likely to be important in arteriosclerosis and restenosis. Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerosis includes vascular recanalization procedures for less-serious blockages and coronary bypass surgery for major blockages. A serious shortcoming of intravascular procedures is that, in a significant number of treated individuals, some or all of the treated vessels restenose (i.e., re-narrow). For example, restenosis of an atherosclerotic coronary artery after PTCA occurs in 10-50% of patients undergoing this procedure and subsequently requires either further angioplasty or a coronary artery bypass graft. Furthermore, restenosis of an atherosclerotic coronary artery after stenting occurs in 10-20% of patients undergoing this procedure and subsequently requires repeat treatments to maintain adequate blood flow through the affected artery. Restenosis generally occurs in a relatively brief time period, e.g., roughly less than six months, after treatment.

While the exact hormonal and cellular processes promoting restenosis have not been determined, restenosis is thought to be due in part to mechanical injury to the walls of the blood vessels caused by the balloon catheter or other intravascular device. For example, the process of PTCA, in addition to opening the obstructed artery, also injures resident coronary arterial smooth muscle cells (SMCs). In response to this injury, adhering platelets, infiltrating macrophages, leukocytes, or the smooth muscle cells themselves release cell-derived growth factors such as platelet-derived growth factor (PDGF), with subsequent proliferation and migration of medial SMCs through the internal elastic lamina to the area of the vessel intima. Further proliferation and hyperplasia of intimal SMCs and, most significantly, production of large amounts of extracellular matrix over a period of three to six months results in the filling in and narrowing of the vascular space sufficient to significantly obstruct blood flow.

In addition to the role syk plays in Ig-induced platelet activations, syk plays a very important role in collagen-mediated signaling. The primary adhesive protein responsible for platelet adhesion and activation is collagen. Collagen is a filamentous protein contained within the fibrotic caps of atheromas which becomes exposed to blood during plaque rupture. Collagen functions initially by binding von Willebrand factor which tethers platelets through binding platelet membrane GPIb. Collagen functions secondarily by engaging the two collagen receptors on platelets, GPVI and integrin α2β1.

GPVI exists in platelet membranes as a complex with FcRγ, an interaction required for the expression of GPVI. Activation of FcγRIIa on platelets results in platelet shape change, secretion and thrombosis. Signaling by the GPVI/FcRγ complex is initiated by tyrosine phosphorylation of the ITAM domain of FCRγ followed by the recruitment of syk. Activation of GPVI leads to induction of multiple platelet functions including: activation of integrins α2β1 to achieve firm platelet adhesion, and GP IIb-IIIa which mediates platelet aggregation and thrombosis growth; platelet secretion, allowing for the delivery of inflammatory proteins such as CD40L, RANTES and TGFβ to the vessel wall; and the expression of P-selectin which allows for the recruitment of leukocytes. Therefore, it is believed that syk inhibitors can inhibit thrombotic events mediated by platelet adhesion, activation and aggregation.

It has been reported that the tyrosine phosphorylation of intracellular protein (activation) induced by stimulation of a receptor for IgG antibody, FcγR, and the phagocytosis mediated by FcγR are considerably inhibited in macrophages derived from syk deficient mouse (Crowley, M. T. et al., *J. Exp. Med.*, 186:1027-1039, 1997). This suggests that syk has a markedly important role in the FcγR-mediated phagocytosis of macrophages.

It has also been reported that an antisense oligonucleotide of syk suppresses the apoptosis inhibition of eosinophils induced by GM-CSF (Yousefi, S. et al., *J. E. Med.*, 183:1407-1414, 1996), showing that syk is essential for the life extending signal of eosinophils caused by GM-CSF and the like. Since life extension of eosinophils is closely related to the transition of diseases into a chronic state in allergic disorders, such as asthma, syk inhibitors can also serve as therapeutic agents for chronic eosinophilic inflammation.

Syk is important for the activation of B-cells via a B-cell antigen receptor and is involved in the phosphatidylinositol metabolism and increase in the intracellular calcium concentration caused by the antigen receptor stimulation (Hutchcroft, J E. et al., *J. Biol. Chem.*, 267:8613-8619, 1992; and Takata, M. et al., *EMBO J.*, 13:1341-1349, 1994). Thus, syk inhibitors may be used to control the function of B-cells and are, therefore, expected to serve as therapeutic agents for antibody-related diseases.

Syk binds to a T-cell antigen receptor, quickly undergoes tyrosine phosphorylation through crosslinking of the receptor and synergistically acts upon intracellular signals mediated by Src tyrosine kinases such as Lck (Couture, C. et al., *Proc. Natl. Acad. Sci. USA*, 91:5301-5305, 1994; and Couture, C. et al., *Mol. Cell. Biol.*, 14:5249-5258, 1994). syk is present in mature T-cell populations, such as intraepithelial γδ T-cells and naïve αβ T-cells, and has been reported to be capable of phosphorylation of multiple components of the TCR signaling cascade (Latour, S. et. al., *Mol Cell Biol.*, 17:4434-4441, 1997). As a consequence, syk inhibitors may serve as agents for inhibiting cellular immunity mediated by T-cell antigen receptor.

Recent comparative genomic hybridization studies have identified syk as another gene important in the pathogenesis of Mantle Cell Lymphoma (MCL) (Chen, R. et al. *Journal of Clinical Oncology*, 2007 ASCO Annual Meeting Proceedings (Post-Meeting Edition). Vol 25, No 18S (June 20 Supplement), 2007: 8056). MCL represents 5-10% of all non-Hodgkins lymphomas and it is a difficult form of lymphoma to treat. It has the worst prognosis among the B cell lymphomas with median survival of three years. It has been reported that Syk is overexpressed in MCL (Rinaldi, A, et. al, *Br. J. Haematol.*, 2006; 132:303-316) and that Syk mediates mTOR (mammalian target of Rapamycin) survival signals in follicular, mantel cell, Burkitt's, and diffuse large B-cell non-Hodgkin's lymphomas (Leseux, L., et. al, Blood, 2006; 108: 4156-4162).

Several lines of evidence suggest that many B-cell lymphomas depend upon B-cell receptor (BCR)-mediated survival signals. BCR signaling induces receptor oligomerization and phosphorylation of Igα and β immunoreceptor tyrosine-based activated motifs by SRC family kinases. ITAM phosphorylation results in the recruitment and activation of syk that initiates downstream events and amplifies the original BCR signal. Given the role of tonic BCR signaling in normal B cell and syk-dependent survival of non-Hodgkins lymphoma cell lines in vitro (Chen, L., et. al, *Blood*, 2006; 108:3428-3433), syk inhibition is a promising rational treatment target for certain B-cell lymphomas and chronic lymphocytic leukemia (CLL) (Stefania Gobessi, Luca Laurenti, Pablo Longo, Laura Carsetti, Giuseppe Leone, Dimitar G. Efremov, Constitutive activation of the protein tyrosine kinase Syk in Chronic Lymphocytic Leukemia B-cells, Blood, 2007, 110, Abstract 1123). Recent data shows that administration of a multikinase inhibitor which inhibits syk, may have significant clinical activity in CLL patients (Friedberg J W et al, Blood 2008; 112(11), Abstract 3).

The oncogenic potential of the spleen tyrosine kinase (Syk) has been described in a number of different settings. Clinically, Syk over-expression is reported in Mantle Cell Lymphoma (Rinaldi, A, et. al, *Br. J. Haematol.*, 2006; 132:303-316) and the TEL-Syk fusion protein (Translocated ETS Leukemia) generated by a chromosomal translocation (t(9; 12)(q22;p12)) leads to increased Syk activity and is associated with myelodysplastic syndrome (Kuno, Y., et. al, *Blood*, 2001; 97: 1050-1055). Leukemia is induced in mice by adoptively transferring bone marrow cells that express human TEL-Syk (Wossning, T., JEM, 2006; 203:2829-2840). Further, in mouse primary bone marrow cells, over-expression of Syk results in IL-7 independent growth in culture (Wossning, T., et. al, JEM, 2006; 203:2829-2840).

Interestingly, Syk signaling appears to be required for B-cell development and survival in humans and mouse.

Inducible loss of the B-cell receptor (Lam, K., et. al, Cell, 1997; 90:1073-1083) or Igα (Kraus, M., et. al, Cell, 2004; 117:787-800) results in loss of peripheral B-cells in mice. Over-expression of the protein tyrosine phosphatase PTP-RO, which is known to negatively regulate Syk activity, inhibits proliferation and induces apoptosis in cell lines derived from non-Hodgkin's lymphomas (Chen, L., et. al, *Blood*, 2006; 108:3428-3433). Finally, B-cell lymphomas rarely exhibit loss of BCR expression, and anti-idiotype therapy rarely leads to resistance (Kuppers, R. Nat Rev Cancer, 2005; 5:251-262).

Engagement of the antigen-specific B cell receptor (BCR) activates multiple signaling pathways that ultimately regulate the cells activation status, promoting survival and clonal expansion. Signaling through the BCR is made possible by its association with two other members of the immunoglobulin super-family; Igα and Igβ, each bearing an immuno-tyrosine based activation motif (ITAM) (Jumaa, Hendriks et al. Annu Rev Immunol 23: 415-45 (2005). The ITAM domain is directly phosphorylated by Src family kinases in response to BCR engagement. The spleen tyrosine kinase (Syk) docks with and phosphorylates the ITAM, a process that enhances its kinase activity, resulting in Syk autophosphorylation and tyrosine phosphorylation of multiple downstream substrates (Rolli, Gallwitz et al. Mol Cell 10(5): 1057-69 (2002). This signaling pathway is active in B cells beginning at the transition from pro- to pre-B cell stage of development, when the newly formed pre-BCR is expressed. In fact, B cell development arrests at the pro-B cell stage in Syk knockout mice (Cheng, Rowley et al. 1995; Turner, Mee et al. Nature 378 (6554): 303-6 (1995). Inducible loss of the B cell receptor (Lam, Kuhn et al. Cell 90(6): 1073-83 (1997) or Igα (Kraus, Alimzhanov et al. Cell 117(6): 787-800 (2004) results in loss of peripheral B cells in mice. Human B cells also appear to require Syk for proliferation and survival. Over-expression of the protein tyrosine phosphatase PTP-RO, a negative regulator of Syk activity, inhibits proliferation and induces apoptosis in cell lines derived from non-Hodgkin's lymphomas (NHL) (Chen, Juszczynski et al. Blood 108(10): 3428-33 (2006). Knock down of Syk by siRNA in the NHL line SUDHL-4 led to a block in the G1/S transition of the cell cycle (Gururajan, Dasu et al. J Immunol 178(1): 111-21 (2007). Together, these data suggest that Syk signaling is required for the development, proliferation, and even survival of human and mouse B cells.

Conversely, the oncogenic potential of Syk has been described in a number of different settings. Clinically, Syk over-expression is reported in Mantle Cell Lymphoma (Rinaldi, Kwee et al. Br J Haematol 132(3): 303-16 (2006) and the TEL-Syk fusion protein (Translocated ETS Leukemia) generated by a chromosomal translocation (t(9;12)(q22; p12)) leads to increased Syk activity and is associated with myelodysplastic syndrome (Kuno, Abe et al. Blood 97(4): 1050-5 (2001). Leukemia is induced in mice by the adoptive transfer of bone marrow cells that express human TEL-Syk (Wossning, Herzog et al. J Exp Med 203(13): 2829-40 (2006). Further, in mouse primary bone marrow cells, over-expression of Syk results in IL-7 independent growth in culture (Wossning, Herzog et al. 2006). Consistently, Syk was reported to mediate mTOR (mammalian target of Rapamycin) survival signals in follicular, mantle cell, Burkitt's, and diffuse large B-cell NHL (Leseux, Hamdi et al. Blood 108 (13): 4156-62 (2006). Additional recent studies also suggest that Syk-dependant survival signals may play a role in B-cell malignancies, including DLBCL, mantle cell lymphoma and follicular lymphoma (Gururajan, Jennings et al. 2006; Irish, Czerwinski et al. J Immunol 176(10): 5715-9 (2006). Given the role of tonic BCR signaling in normal B cells and Syk-dependent survival of NHL cell lines in vitro, the specific inhibition of Syk may prove promising for the treatment of certain B-cell lymphomas.

Recently, R406 (Rigel Pharmaceuticals) was reported to inhibit ITAM signaling in response to various stimuli, including FcεR1 and BCR induced Syk activation (Braselmann, Taylor et al. J Pharmacol Exp Ther 319(3): 998-1008 (2006). Interestingly, this ATP-competitive inhibitor of Syk was also active against Flt3, cKit, and JAK kinases, but not against Src kinsase (Braselmann, Taylor et al. 2006). Activating mutations to Flt3 are associated with AML and inhibition of this kinase is currently under clinical development (Burnett and Knapper Hematology Am Soc Hematol Educ Program 2007: 429-34 (2007). Over-activation of the tyrosine kinase cKit is also associated with hematologic malignancies, and a target for cancer therapy (Heinrich, Griffith et al. Blood 96(3): 925-32 (2000). Similarly, JAK3 signaling is implicated in leukemias and lymphomas, and is currently exploited as a potential therapeutic target (Heinrich, Griffith et al. 2000). Importantly, the multi-kinase inhibitory activity of R406 attenuates BCR signaling in lymphoma cell lines and primary human lymphoma samples, resulting in apoptosis of the former (Chen, Monti et al. Blood 111(4): 2230-7 (2008). Further, a phase II clinical trial reported favorable results by this compound in refractory NHL and chronic lymphocytic leukemia (Friedberg J W et al, Blood 2008; 112(11), Abstract 3). Although the precise mechanism of action is unclear for R406, the data suggest that inhibition of kinases that mediate survival signaling in lymphocytes is clinically beneficial.

Additional recent studies also suggest that syk-dependant survival signals may play a role in B-cell malignancies, including DLBCL, mantle cell lymphoma and follicular lymphoma (see e.g., S. Linfengshen et al. *Blood*, February 2008; 111: 2230-2237; J. M. Irish et al. *Blood*, 2006; 108: 3135-3142; A. Renaldi et al. *Brit J. Haematology*, 2006; 132: 303-316; M. Guruoajan et al. *J. Immunol*, 2006; 176: 5715-5719; L. Laseux et al. *Blood*, 2006; 108: 4156-4162.

JAK kinases (Janus Kinases) are a family of cytoplasmic protein tyrosine kinases including JAK1, JAK2, JAK3 and TYK2. The JAKs play a crucial role in cytokine signaling. Each of the JAK kinases is selective for the receptors of certain cytokines, though multiple JAK kinases can be affected by particular cytokine or signaling pathways. Studies suggest that JAK3 associates with the common cytokine receptor gamma chain (Fcγ or γc) of the various cytokine receptors. JAK3 in particular selectively binds to receptors and is part of the cytokine signaling pathway for and activated by IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

The downstream substrates of JAK family kinases include the signal transducer activator of transcription (STAT) proteins. Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), Mol. Med. 5:432:456 and Seidel et al., (2000), Oncogene 19:2645-2656.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunol. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10: 105-115).

JAK1, JAK2, and TYK2 are expressed ubiquitously, whereas JAK3 is expressed predominantly in hematopoietic cells. The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important for lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes, rheumatoid arthritis, lupus, psoriasis), and inflammation (e.g., asthma, allergic reactions). Conditions which can benefit from JAK3 inhibition are discussed in greater detail below. Recent data on JAK inhibition has been reported in kidney allograft patients treated with CP-690,550 and showed that markers of allogeneic response (interferon gamma) can be reduced (Van Gurp E A et al (2009) Transplantation 87:79-86).

In view of the numerous conditions that are contemplated to benefit by treatment involving modulation of the JAK pathway it is immediately apparent that new compounds that modulate JAK pathways and methods of using these compounds should provide substantial therapeutic benefits to a wide variety of patients. Provided herein are novel 2,4-pyrimidinediamine, pyrrolopyrimidine and purine-based compounds for use in the treatment of conditions in which targeting of the JAK pathway or inhibition of JAK kinases, particularly JAK3, are therapeutically useful.

Patents and patent applications related to modulation of the JAK pathway include: U.S. Pat. Nos. 5,728,536; 6,080,747; 6,080,748; 6,133,305; 6,177,433; 6,210,654; 6,313,130; 6,316,635; 6,433,018; 6,486,185; 6,506,763; 6,528,509; 6,593,357; 6,608,048; 6,610,688; 6,635,651; 6,677,368; 6,683,082; 6,696,448; 6,699,865; 6,777,417; 6,784,195; 6,825,190; 6,506,763; 6,784,195; 6,528,509; 6,608,048; 7,105,529; 6,699,865; 6,825,190; 6,815,439; 6,949,580; 7,056,944; 6,998,391; 7,074,793; 6,969,760; U.S. Pat. App. Pub. No. 2001/0007033 A1; 2002/0115173 A1; 2002/0137141 A1; 2003/0236244 A1; 2004/0102455 A1; 2004/0142404 A1; 2004/0147507 A1; and 2004/0214817 A1; and International patent applications WO 95/03701A1; WO 99/15500A1; WO 00/00202A1; WO 00/10981A1; WO 00/47583A1; WO 00/51587A2; WO 00/55159A2; WO 01/42246A2; WO 01/45641A2; WO 01/52892A2; WO 01/56993A2; WO 01/57022A2; WO 01/72758A1; WO 02/00661A1; WO 02/43735A1; WO 02/48336A2; WO 02/060492A1; WO 02/060927A1; WO 02/096909A1; WO 02/102800A1; WO 03/020698A2; WO 03/048162A1; WO 03/101989A1; WO 2004/016597A2; WO 2004/041789A1; WO 2004/041810A1; WO 2004/041814A1; WO 2004/046112A2; WO 2004/046120A2; WO 2004/047843A1; WO 2004/058749A1; WO 2004/058753A1; WO 2004/085388A2; WO 2004/092154A1; WO 2005/009957A1; WO 2005/016344A1; WO 2005/028475A2; and WO 2005/033107A1.

Patents and patent applications describing substituted pyrimidinediamine compounds include: U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO 04/014382), U.S. application Ser. No. 10/903,263 filed Jul. 30, 2004, and international application Serial No. PCT/US2004/24716 (WO 05/016893), the disclosures of which are incorporated herein by reference. Substituted pyrimidinediamine compounds are also described in international patent application publication numbers: WO 02/059110, WO 03/074515, WO 03/106416, WO 03/066601, WO 03/063794, WO 04/046118, WO 05/016894, WO 05/122294, WO 05/066156, WO 03/002542, WO 03/030909, WO 00/39101, WO 05/037800 and U.S. Pat. Pub. No. 2003/0149064.

While progress has been made in this field, there remains a need in the art for compounds that inhibit syk and/or JAK kinase, as well as for methods for treating conditions in a patient, such as restenosis, thrombosis, and/or inflammation that can benefit from such inhibition. Moreover, the availability of compounds that selectively inhibit one of these kinases as compared to other kinases would also be desirable. The present invention satisfies this and other needs.

BRIEF SUMMARY OF THE INVENTION

The present invention provides novel compounds having activity as inhibitors of syk activity (also referred to herein as "syk inhibitors") and/or JAK kinase activity (also referred to herein as "JAK inhibitors"), as well as to methods for their preparation and use, and to pharmaceutical compositions containing the same. Such compounds have the following structure (I-II):

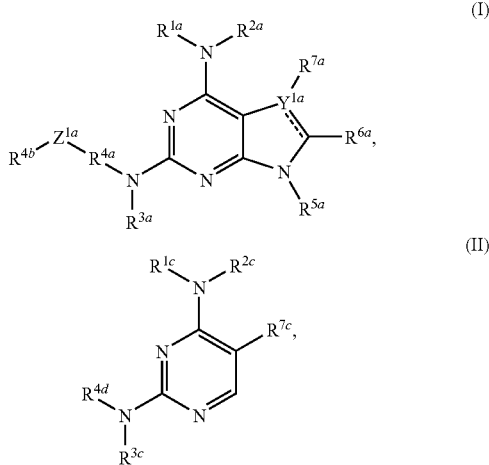

or a pharmaceutically acceptable salt thereof, wherein $Y^{1a}$, $Z^{1a}$, $R^{1a}$, $R^{1c}$, $R^{2a}$, $R^{2c}$, $R^{3a}$, $R^{3c}$, $R^{4a}$, $R^{4b}$, $R^{4d}$, $R^{5a}$, $R^{6a}$, $R^{7a}$ and $R^{7c}$ are as defined below.

The present invention also provides a pharmaceutical composition comprising a therapeutically effective amount of a compound of formula I-II, or a pharmaceutical acceptable salt thereof, and a pharmaceutically acceptable carrier and/or diluent.

The compounds of the present invention have utility over a wide range of therapeutic applications, and may be used to treat a variety of conditions, mediated at least in part by syk activity, in both men and women, as well as a mammal in general (also referred to herein as a "subject"). For example, such conditions include, but are not limited to, those associated with cardiovascular disease, inflammatory disease or autoimmune disease. More specifically, the compounds of the present invention have utility for treating conditions or disorders including, but not limited to: restenosis, thrombosis, inflammation, heparin induced thrombocytopenia, dilated cardiomyopathy, sickle cell disease, atherosclerosis, myocardial infarction, vascular inflammation, unstable angina, acute coronary syndromes, allergy, asthma, rheumatoid arthritis, B-cell mediated diseases such as Non Hodgkin's lymphoma, anti-phospholipid syndrome, lupus, psoriasis, multiple sclerosis, end stage renal disease, hemolytic anemia, immune thrombocytopenic purpura, and chronic lymphocytic leukemia. Thus, in one embodiment, methods are disclosed which include the administration of an effective amount of a compound of formula (I-II), typically in the form of a pharmaceutical composition, to a subject in need thereof.

The conditions associated with cardiovascular disease is selected from the group consisting of acute coronary syndrome, myocardial infarction, unstable angina, refractory angina, occlusive coronary thrombosis occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolism, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

The present invention also provides a method for inhibiting the syk activity of a blood sample comprising contacting said sample with a compound of the present invention.

The present invention further provides compounds in purified forms, as well as chemical intermediates.

These and other aspects, objects, features and advantages of the invention will be apparent upon reference to the following detailed description and figures. To this end, various references are set forth herein which describe in more detail certain background information, procedures, compounds and/or compositions, and are each hereby incorporated by reference in their entirety.

BRIEF DESCRIPTION OF THE DRAWINGS

FIG. 1 shows how Syk serves as a key mediator of Fc receptor mediated signaling in cellular biology and multiple diseases.

FIG. 2 shows how gene targeting of Syk indicated that Syk serves as a key mediator in arterial platelet biology and a selective target for treating arterial thrombosis.

FIG. 6 shows a graph of the effect of increasing dose of a compound of the present invention on pSTAT6 formation in response to IL4 stimulation of B Ramos cells.

FIG. 7 provides table 1 illustrating compounds of the present invention and syk $IC_{50}$s.

FIG. 8 provides table 2 illustrating compounds of the present invention and SYK $IC_{50}$s.

DETAILED DESCRIPTION OF THE INVENTION

Figure 3:
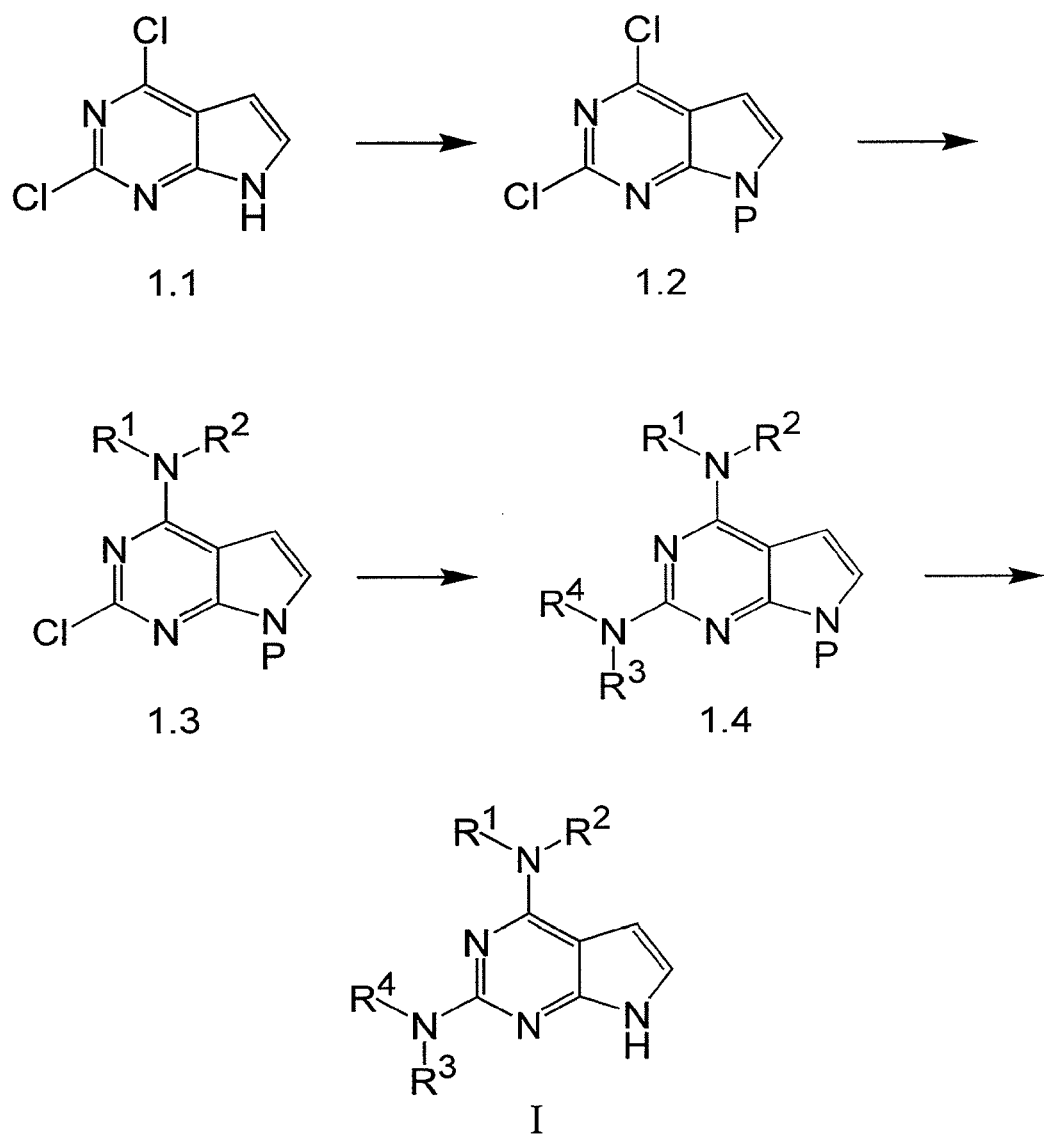
FIGS. 3-5 show a general synthesis of compounds of the present invention.

As used herein, the below terms have the following meanings unless specified otherwise:

1. Abbreviations and Definitions

The abbreviations used herein are conventional, unless otherwise defined. The following abbreviations are used: AcOH=acetic acid, AIBN=azobisisobutyronitrile (also azobisisobutylonitrile), aq.=aqueous, Boc=t-butylcarboxy, Bz—benzyl, BOP=benzotriazol-1-yloxytris(dimethylamino)-phosphonium hexafluorophosphate, BPO=benzoyl peroxide, nBuOH=n-butanol, $CBr_4$=tetrabromomethane, mCPBA=m-chloroperoxybenzoic acid, $CH_2Cl_2$ or DCM=dichloromethane, $Cs_2CO_3$=cesium carbonate, $CuCl_2$=copper chloride; DIBAL=diisobutylaluminum hydride, DIEA=Hunig's base or diisopropyl ethylamine, DME=dimethyl ether, DMF=dimethyl formamide, DMSO=dimethyl sulfoxide, DPPA=diphenyl phosphoryl azide, $Et_3N$=triethylamine, EtOAc=ethyl acetate, g=gram, HATU=2-(1H 7-Azabenzotriazol-1-yl)-1,1,3,3-tetramethyl uronium hexafluorophosphate, $H_2$=hydrogen; $H_2O$=water; HBr=hydrogen bromide; HCl=hydrogen chloride, HIV=human immunodeficiency virus, HPLC=high pressure liquid chromatography, h=hour, IgE=immunoglobulin E, $IC_{50}$=The concentration of an inhibitor that is required for 50% inhibition of an enzyme in vitro, IPA=isopropyl alcohol, kg=kilogram, KCN=potassium cyanide, KOH=potassium hydroxide, $K_2PO_4$=potassium phosphate, LDA=lithium diisopropylamine, $LiAlH_4$=lithium aluminum hydride=LiOH: lithium hydroxide; MeCN=acetonitrile; MS=Mass Spec, m/z=mass to charge ratio, MHz=Mega Hertz, MeOH=methanol, μM=micromolar, μL=microliter, mg=milligram, mm=millimeter, mM=millimolar, mmol=millimole, mL=milliliter, mOD/min=millioptical density units per minute, min=minute, M=molar, $Na_2CO_3$=sodium carbonate, ng=nanogram, $NaHCO_3$=sodium bicarbonate; $NaNO_2$=sodium nitrite; NaOH=sodium hydroxide; $Na_2S_2O_3$=sodium bisulfate; $Na_2SO_4$=sodium sulfate; NBS=N-bromosuccinamide; $NH_4Cl$=ammonium chloride; $NH_4OAc$=ammonium acetate; NaSMe=sodium methylthiolate, NBS=N-bromosuccinamide, n-BuLi=n-butyl lithium, nm=nanometer, nM=nanomolar, N=Normal, NMP=N-methylpyrrolidine, NMR=nuclear magnetic resonance, Pd/C=palladium on carbon, $Pd(PPh_3)_4$=Tetrakis-(triphenyl-phosphine)-palladium, pM=picomolar, Pin=pinacolato, PEG=polyethylene glycol, $PPh_3$ or $Ph_3P$=triphenyl phosphine, RLV=Raucher leukemia virus, Ra—Ni=Rainey Nickel, $SOCl_2$=thionyl chloride, RT=room temperature, TEA=triethylamine, THF=tetrahydrofuran, TFA=trifluoroacetic acid, TLC=thin layer chromatography, TMS=trimethylsilyl, Tf=trifluoromethylsulfonyl and TSC=trisodium citrate.

It is noted here that as used in this specification and the appended claims, the singular forms "a," "an," and "the" include plural reference unless the context clearly dictates otherwise.

"Alkyl," by itself or as part of another substituent, means, unless otherwise stated, a straight or branched chain, fully saturated aliphatic hydrocarbon radical having the number of carbon atoms designated. For example, "$C_{1-8}$alkyl" refers to a hydrocarbon radical straight or branched, containing from 1 to 8 carbon atoms that is derived by the removal of one hydrogen atom from a single carbon atom of a parent alkane. The phrase "unsubstituted alkyl" refers to alkyl groups that do not contain groups other than fully saturated aliphatic hydrocarbon radicals. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkenyl" by itself or as part of another substituent refers to a straight or branched chain, which may be mono- or polyunsaturated, having the number of carbon atoms designated. For example, "$C_2$-$C_8$ alkenyl" means an alkenyl radical having from 2, 3, 4, 5, 6, 7 or 8 atoms that is derived by the removal of one hydrogen atom from a single carbon atom of a parent alkane. Examples include, but are not limited to vinyl, 2-propenyl i.e.—CH═C(H)($CH_3$), —CH═C($CH_3$)$_2$, —C($CH_3$)═C(H)$_2$, —C($CH_3$)═C(H)($CH_3$), —C($CH_2CH_3$) ═$CH_2$, butadienyl e.g. 2-(butadienyl), pentadienyl e.g. 2,4-pentadienyl and 3-(1,4-pentadienyl), and hexadienyl, among others, and higher homologs and stereoisomers thereof. A "substituted" alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon. Each site of unsaturation may be either cis or trans configuration about the double bond(s).

The term "alkynyl", by itself or as part of another substituent, means a straight or branched chain hydrocarbon radical, which may be mono- or polyunsaturated, having the number of carbon atoms designated. For example, "$C_2$-$C_8$ alkynyl" means an alkynyl radical having from 2 to 8 carbon atoms that is derived by the removal of one hydrogen atom from a single carbon atom of a parent alkane. "Unsubstituted alkynyl" refers to straight and branched chain groups such as those described with respect to unsubstituted alkyl groups as defined above, except that at least one triple bond exists between two carbon atoms. Examples include, but are not limited to ethynyl e.g. —C≡C(H), 1-propynyl e.g. —C≡C ($CH_3$), —C≡C($CH_2CH_3$), —C($H_2$)C≡C(H), —C(H)$_2$C≡C($CH_3$), and —C($H_2$)C≡C($CH_2CH_3$) among others, and higher homologs and isomers thereof. A "substituted" alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

"Alkylene" by itself or as part of another substituent means a divalent radical derived from an alkane, as exemplified by —$CH_2CH_2CH_2CH_2$—. Typically, an alkylene group will have from 1, 2, 3, 4, 5, 6, 7 or 8 carbon atoms that is derived by the removal of one hydrogen atom from a single carbon atom of a parent alkyl.

"Cycloalkyl" or "carbocycle", by themselves or in combination with other terms, represent, unless otherwise stated, cyclic versions of "alkyl", "alkenyl" and "alkynyl" in which all ring atoms are carbon. "Cycloalkyl" or "carbocycle" refers to a mono- or polycyclic group. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more double or triple bond(s). The term "cycloalkenyl" refers to a cycloalkyl group that has at least one site of alkenyl unsaturation between the ring vertices. The term "cycloalkynyl" refers to a cycloalkyl group that has at least one site of alkynyl unsaturation between the ring vertices. When "cycloalkyl" is used in combination with "alkyl", as in $C_{3-8}$cycloalkyl$C_{3-8}$ alkylene-, the cycloalkyl portion is meant to have the stated number of carbon atoms (e.g., from three to eight carbon atoms), while the alkylene portion has from one to eight carbon atoms. Typical cycloalkyl substituents have from 3 to 8 ring atoms. Examples of cycloalkyl include cyclopentyl, cyclohexyl, 1-cyclohexenyl, 3-cyclohexenyl, cycloheptyl, and the like.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of unsubstituted aryl groups include phenyl, 1-naphthyl, 2-naphthyl and 4-biphenyl. "Substituted aryl group" includes, for example, —$CH_2OH$ (one carbon atom and one heteroatom replacing a carbon atom) and —$CH_2SH$. The term "heteroalkylene" by itself or as part of another substituent means a divalent radical derived from heteroalkyl, as exemplified by —$CH_2$-$CH_2$-S—$CH_2CH_2$-— and —$CH_2$-S—$CH_2$-$CH_2$-NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "heterocycle", "heterocyclyl" or "heterocyclic" refer to a saturated or unsaturated non-aromatic cyclic group containing at least one heteroatom. As used herein, the term "heteroatom" is meant to include oxygen (O), nitrogen (N), sulfur (S) and silicon (Si). Each heterocycle can be attached at any available ring carbon or heteroatom. Each heterocycle may have one or more rings. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, pyridine-2-one, piperidine, morpholine, piperazine, isoxazoline, pyrazoline, imidazoline, pyrazol-5-one, pyrrolidine-2,5-dione, imidazolidine-2,4-dione, pyrrolidine, tetrahydroquinolinyl, decahydroquinolinyl, tetrahydrobenzooxazepinyl dihydrodibenzooxepin and the like.

"Heteroaryl" refers to a cyclic or polycyclic aromatic radical that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein. "Substituted heteroaryl" refers to a unsubstituted heteroaryl group as defined above in which one or more of the ring members is bonded to a non-hydrogen atom such as described above with respect to substituted alkyl groups and substituted aryl groups. Representative substituents include straight and branched chain alkyl groups-$CH_3$, —$C_2H_5$, —$CH_2OH$, —OH, —$OCH_3$, —$OC_2H_5$, —$OCF_3$, —$OC(=O)CH_3$, —$OC(=O)NH_2$, —$OC(=O)N(CH_3)_2$, —CN, —$NO_2$, —$C(=O)CH_3$, —$CO_2H$, —$CO_2CH_3$, —$CONH_2$, —$NH_2$, —$N(CH_3)_2$, —$NHSO_2CH_3$, —NHCOCH_3$, —$NHC(=O)OCH_3$, —$NHSO_2CH_3$, —$SO_2CH_3$, —$SO_2NH_2$ and halo.

"Bicyclic heteroaryl" refers to bicyclic aromatic radical that contain from one to five heteroatoms selected from N, O, and S, wherein the nitrogen and sulfur atoms are optionally oxidized, and the nitrogen atom(s) are optionally quaternized. A bicyclic heteroaryl group can be attached to the remainder of the molecule through a heteroatom or through a carbon atom and can contain 5 to 10 carbon atoms. Non-limiting examples of bicyclic heteroaryl groups include 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl and 6-quinolyl. If not specifically stated, substituents for each of the above noted aryl and heteroaryl ring systems are selected from the group of acceptable substituents described herein.

In each of the above embodiments designating a number of atoms e.g. "$C_1$-" is meant to include all possible embodiments that have one fewer atom. Non-limiting examples include $C_{1-7}$, $C_{2-8}$, $C_{2-7}$, $C_{3-8}$, $C_{3-7}$ and the like.

Each of the terms herein (e.g., "alkyl," "heteroalkyl," "aryl" and "heteroaryl") is meant to include both "unsubstituted" and optionally "substituted" forms of the indicated radical, unless otherwise indicated. Typically each radical is substituted with 0, 1, 2, 3 4 or 5 substituents, unless otherwise indicated. Examples of substituents for each type of radical are provided below.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other representative "substituents" include those in which one or more bonds to a carbon(s) or hydrogen(s) atoms is replaced by a bond to an alkyl, cycloalkyl, aryl, heteroaryl, or heterocyclyl group.

The herein-defined groups may include prefixes and/or suffixes that are commonly used in the art to create additional well-recognized substituent groups. As examples, "alkylamino" refers to a group of the formula —$NR^aR^b$. Unless stated otherwise, for the following groups containing $R^a$, $R^b$, $R^c$, $R^d$ and $R^e$: $R^a$, and $R^b$ are each independently selected from H, alkyl, alkoxy, thioalkoxy, cycloalkyl, aryl, heteroaryl, or heterocyclyl or are optionally joined together with the atom(s) to which they are attached to form a cyclic group. When $R^a$ and $R^b$ are attached to the same nitrogen atom, they can be combined with the nitrogen atom to form a 5-, 6- or 7-membered ring. For example, —$NR^aR^b$ is meant to include 1-pyrrolidinyl and 4-morpholinyl.

$R^c$, $R^d$, $R^e$ and $R^f$ are each independently selected from alkyl, alkenyl, alkynyl, cycloalkyl, cycloalkenyl, aryl, heteroaryl, heterocyclyl or alkylenearyl as defined herein.

Typically, a particular radical will have 0, 1, 2 or 3 substituents, with those groups having two or fewer substituents being preferred in the present invention. More preferably, a radical will be unsubstituted or monosubstituted. Most preferably, a radical will be unsubstituted.

"Substituents" for the alkyl and heteroalkyl radicals (as well as those groups referred to as alkylene, alkenyl, heteroalkylene, heteroalkenyl, alkynyl, cycloalkyl, heterocyclyl) can be a variety of groups selected from: —OR$^a$, =O, =NR$^a$, =N—OR$^a$, —NR$^a$R$^b$, SR$^a$, halogen, —SiR$^a$R$^b$R$^c$, —OC(O)R$^a$, —C(O)R$^a$, —CO$_2$R$^a$, —CONR$^a$R$^b$, —OC(O)NR$^a$R$^b$, —NR$^b$C(O)R$^a$, —NR$^a$—C(O)NR$^a$R$^c$, —NR$^a$—SO$_2$NR$^b$R$^c$, —NR$^b$CO$_2$R$^a$, —NH—C(NH$_2$)=NH, —NR$^a$C(NH$_2$)=NH, —NH—C(NH$_2$)=NR$^a$, —S(O)R$^a$, —SO$_2$R$^a$, —SO$_2$NR$^a$R$^b$, —NR$^b$SO$_2$R, —CN and —NO$_2$, in a number ranging from zero to three, with those groups having zero, one or two substituents being particularly preferred.

In some embodiments, "substituents" for the alkyl and heteroalkyl radicals are selected from: —OR$^a$, =O, —NR$^a$R$^b$, —SR$^a$, halogen, —SiR$^a$R$^b$R$^c$, —OC(O)R$^a$, —C(O)R$^a$, —CO$_2$R$^a$, —CONR$^a$R$^b$, —OC(O)NR$^a$R$^b$, —NR$^b$C(O)R$^a$, —NR$^b$CO$_2$R$^a$, —NR$^a$—SO$_2$NR$^b$R$^c$, —S(O)R$^a$, —SO$_2$R$^a$, —SO$_2$NR$^a$R$^b$, NR$^c$SO$_2$R, —CN and —NO$_2$, where R$^a$ and R$^b$ are as defined above. In some embodiments, substituents are selected from: —OR$^a$, =O, —NR$^a$R$^b$, halogen, —OC(O)R$^a$, —CO$_2$R$^a$, —CONR$^a$R$^b$, OC(O)NR$^a$R$^b$, —NR$^b$C(O)R$^a$, —NR$^b$CO$_2$R$^a$, —NR$^a$—SO$_2$NR$^b$R$^c$, —SO$_2$R$^a$, —SO$_2$NR$^a$R$^b$, —NR"SO$_2$R, —CN and —NO$_2$.

Examples of substituted alkyl are: —(CH$_2$)$_3$NH$_2$, —(CH$_2$)$_3$NH(CH$_3$), —(CH$_2$)$_3$NH(CH$_3$)$_2$, —CH$_2$C(=CH$_2$)CH$_2$NH$_2$, —CH$_2$C(=O)CH$_2$NH$_2$, —CH$_2$S(=O)$_2$CH$_3$, —CH$_2$OCH$_2$NH$_2$, —CO$_2$H. Examples of substituents of substituted alkyl are: CH$_2$OH, —OH, —OCH$_3$, —OC$_2$H$_5$, —OCF$_3$, —OC(=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$, and halo.

Similarly, "substituents" for the aryl and heteroaryl groups are varied and are selected from: -halogen, —OR$^a$, —OC(O)R$^a$, —NR$^a$R$^b$, —SR$^a$, —R$^a$, —CN, —NO$_2$, —CO$_2$R$^a$, —CONR$^a$R$^b$, —C(O)R$^a$, OC(O)NR$^a$R$^b$, —NR$^b$C(O)R$^a$, —NR$^b$C(O)$_2$R$^a$, —NR$^a$C(O)NR$^b$R$^c$, —NH—C(NH$_2$)=NH, —NR$^a$C(NH$_2$)=NH, —NH—C(NH$_2$)=NR$^a$, —S(O)R$^a$, —S(O)$_2$R$^a$, —S(O)$_2$NR$^a$R$^b$, —N$_3$, —CH(Ph)$_2$, perfluoroC$_{1-8}$alkoxy, and perfluoroC$_{1-8}$alkyl, in a number ranging from zero to the total number of open valences on the aromatic ring system; and where R$^a$, R$^b$ and R$^c$ are independently selected from hydrogen, C$_{1-6}$alkyl and heteroalkyl, unsubstituted aryl and heteroaryl, (unsubstituted aryl)-C$_{1-8}$alkyl, and (unsubstituted aryl)oxy-C$_{1-8}$alkyl.

Two of the "substituents" on adjacent atoms of the aryl or heteroaryl ring may optionally be replaced with a substituent of the formula -T-C(O)—(CH$_2$)q-U-, wherein T and U are independently —NH—, —O—, —CH$_2$- or a single bond, and q is 0, 1 or 2. Alternatively, two of the substituents on adjacent atoms of the aryl or heteroaryl ring may optionally be replaced with a substituent of the formula -A-(CH$_2$)$_r$-B—, wherein A and B are independently —CH$_2$-, —O—, —NH—, —S—, —S(O)—, —S(O)$_2$—, —S(O)$_2$NR$^a$— or a single bond, and r is 1, 2 or 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$-X—(CH$_2$)$_t$—, where s and t are independently integers of from 0 to 3, and X is —O—, —NR$^a$—, —S—, —S(O)—, —S(O)$_2$—, or —S(O)$_2$NR$^a$—. The substituent R$^a$ in —NR$^a$— and —S(O)$_2$NR$^a$— is selected from hydrogen or unsubstituted C$_{1-6}$alkyl. Otherwise, R' is as defined above.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "acyl" refers to the group —C(=O)R$^c$ where R$^c$ is alkyl, alkenyl, alkynyl, cycloalkyl, cycloalkenyl, aryl, heteroaryl or heterocyclyl. Acyl includes the "acetyl" group —C(=O)CH$_3$.

"Acylamino-" refers to the group —NR$^a$C(=O)R$^c$ where R$^c$ is alkyl, alkenyl, alkynyl, cycloalkyl, cycloalkenyl, aryl, heteroaryl or heterocyclyl.

"Acyloxy" refers to —OC(=O)—R$^c$ where R$^c$ is alkyl, alkenyl, alkynyl, cycloalkyl, cycloalkenyl, aryl, heteroaryl or heterocyclyl.

"Alkoxy" refers to —OR$^d$ wherein R$^d$ is alkyl as defined herein. Representative examples of alkoxy groups include methoxy, ethoxy, t-butoxy, trifluoromethoxy, and the like.

"Alkoxyamino" refers to the group —NHOR$^d$ where R$^d$ is alkyl

"Alkoxyalkyleneamino" refers to the group —NR$^a$-alkylene-OR$^d$ where R$^d$ is alkyl and —NR$^a$— is defined in amino.

"Alkoxycarbonyl" refers to —C(=O)OR$^d$ wherein R$^d$ is alkyl. Representative alkoxycarbonyl groups include, for example, those shown below.

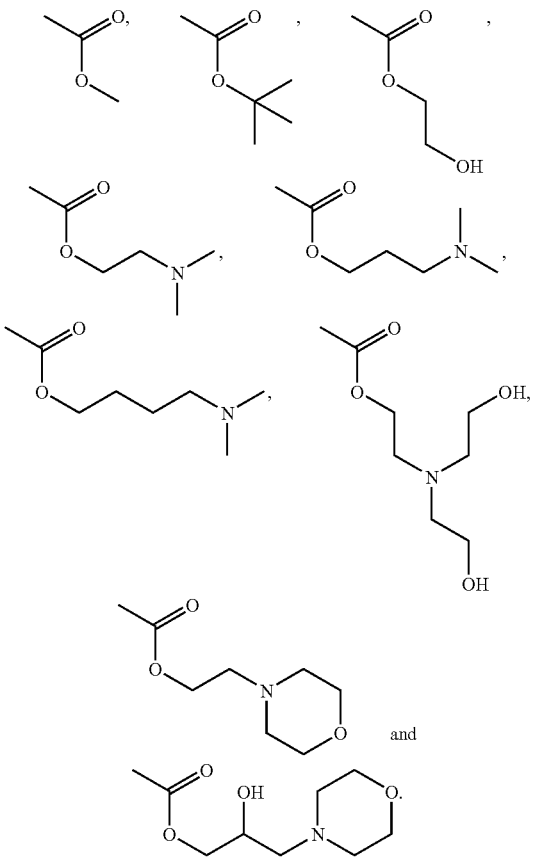

These alkoxycarbonyl groups can be further substituted as will be apparent to those having skill in the organic and medicinal chemistry arts in conjunction with the disclosure herein.

"Alkoxycarbonylalkylene" refers to the group -alkylene-C(=O)OR wherein $R^d$ is alkyl.

"Alkoxycarbonylamino" refers to —$NR^aC$(=O)$OR^d$ wherein $R^d$ is alkyl.

"Alkoxycarbonylaminoalkylene" refers to -alkylene-$NR^a$C(=O)$OR^d$ wherein $R^d$ is alkyl.

"Alkoxycarbonylalkyleneaminosulfonyl" refers to —$SO_2NR^a$-alkyleneC(=O)$OR^d$ wherein $R^d$ is alkyl.

"Alkoxysulfonylamino" refers to the group —$NR^a$S(=O)$_2$—$OR^d$ where $R^d$ is alkyl.

"Alkylcarbonyl" refers to the group —C(=O)$R^c$ where $R^c$ is alkyl.

"Alkylcarbonyloxy" refers to —OC(=O)—$R^c$ where $R^c$ is alkyl.

"Alkylcarbonylamino" refers to —$NR^a$C(=O)$R^c$ wherein $R^c$ is alkyl. Representative alkylcarbonylamino groups include, for example, —NHC(=O)$CH_3$, —NHC(=O)$CH_2CH_3$, —NHC(=O)$CH_2NH(CH_3)$, —NHC(=O)$CH_2N(CH_3)_2$, or —NHC(=O)$(CH_2)_3OH$.

"Alkylheterocyclyl" refers to the group -heterocyclyl-$R^d$. where $R^d$ is alkyl.

"Alkylheterocyclylalkylene" refers to the group -alkylene-heterocyclyl-$R^d$. where $R^d$ is alkyl.

"Alkylsulfanyl", "alkylthio", or "thioalkoxy" refers to the group S—$R^d$. where $R^d$ is alkyl.

"Alkylsulfinyl" refers to —S(=O)$R^e$ where $R^e$ is alkyl. Alkylsulfonyl groups employed in compounds of the present invention are typically $C_{1-6}$alkylsulfinyl groups.

"Alkylsulfonyl" refers to —S(=O)$_2R^e$ where $R^e$ is alkyl. Alkylsulfonyl groups employed in compounds of the present invention are typically $C_{1-6}$alkylsulfonyl groups.

"Alkylsulfonylalkylene" refers to -alkylene-S(=O)$_2R^c$ where $R^e$ is alkyl.

"Alkylsulfonyl" groups employed in compounds of the present invention are typically $C_{1-6}$alkylsulfonyl groups.

"Alkylsulfonylamino" refers to —$NR^a$S(=O)$_2$—$R^e$ wherein $R^e$ is alkyl.

"Alkynyloxy" refers to the group —O-alkynyl, wherein alkynyl is as defined herein. Alkynyloxy includes, by way of example, ethynyloxy, propynyloxy, and the like.

"Amidino" refers to the group —C(=$NR^a$)$NR^bR^c$, wherein $R^b$ and $R^c$ independently are selected from the group consisting of hydrogen, alkyl, substituted alkyl, alkenyl, alkynyl, aryl, cycloalkyl, cycloalkenyl, heteroaryl, heterocyclic, and where $R^b$ and $R^c$ are optionally joined together with the nitrogen bound thereto to form a heterocyclic or substituted heterocyclic group. $R^a$ is selected from the group consisting of hydrogen, alkyl, alkenyl, alkynyl, cycloalkynyl, aryl, cycloalkyl, cycloalkenyl, heteroaryl, heterocyclic, substituted heterocyclic, nitro, nitroso, hydroxy, alkoxy, cyano, —N=N—N-alkyl, —N(alkyl)$SO_2$-alkyl, —N=N=N-alkyl, acyl and —$SO_2$-alkyl.

"Amino" refers to a monovalent radical —$NR^aR^b$ or divalent radical —$NR^a$—. The term includes "alkylamino" which refers to the group —$NR^aR^b$ where $R^a$ is alkyl and $R^b$ is H or alkyl. The term also includes "arylamino" which refers to the group —$NR^aR^b$ where at least one $R^a$ or $R^b$ is aryl. The term also includes "(alkyl)(aryl)amino" which refers to the group —$NR^aR^b$ where $R^a$ is alkyl and $R^b$ is aryl. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

"Aminoalkoxy" refers to —O-alkylene-$NR^aR^b$.

"Aminoalkylene" refers to -alkylene-$NR^aR^b$.

"Aminoalkylenecarbonyl" refers to —C(=O)-alkylene-$NR^aR^b$.

"Aminoalkyleneaminocarbonyl" refers to —C(=O)$NR^a$-alkylene-$NR^aR^b$.

"Aminoaryl" refers to -aryl-$NR^aR^b$.

"Aminocarbonyl" or "aminoacyl" refers to the amide —C(=O)—$NR^aR^b$. The term "alkylaminocarbonyl" refers herein to the group —C(=O)—$NR^aR^b$ where $R^a$ is alkyl and $R^b$ is H or alkyl. The term "arylaminocarbonyl" refers herein to the group —C(=O)—$NR^aR^b$ where $R^a$ or $R^b$ is aryl. Representative aminocarbonyl groups include, for example, those shown below. These aminocarbonyl group can be further substituted as will be apparent to those having skill in the organic and medicinal chemistry arts in conjunction with the disclosure herein.

"Aminocarbonylalkoxy" refers to -alkylene-C(=O)—$NR^aR^b$ wherein $R^a$ is hydrogen or alkyl and $R^a$ and $R^b$ independently are selected from the group consisting of hydrogen, alkyl, alkenyl, alkynyl, aryl, cycloalkyl, cycloalkenyl, heteroaryl, heterocyclic, and where $R^a$ and $R^b$ are optionally joined together with the nitrogen bound thereto to form a heterocyclic or substituted heterocyclic group.

"Aminocarbonylalkylene" refers to -alkylene-C(=O)—$NR^aR^b$ wherein $R^a$ is hydrogen or alkyl and $R^a$ and $R^b$ independently are selected from the group consisting of hydrogen, alkyl, alkenyl, alkynyl, aryl, cycloalkyl, cycloalkenyl, heteroaryl, heterocyclic, and where $R^a$ and $R^b$ are optionally joined together with the nitrogen bound thereto to form a heterocyclic or substituted heterocyclic group.

"Aminocarbonylalkyleneaminosulfonyl" refers to —S(O)$_2NR^a$-alkylene-C(=O)—$NR^aR^b$ wherein each $R^a$ is hydrogen or alkyl and $R^a$ and $R^b$ independently are selected from the group consisting of hydrogen, alkyl, alkenyl, alkynyl, aryl, cycloalkyl, cycloalkenyl, heteroaryl, heterocyclic, and where $R^a$ and $R^b$ of the amino group are optionally joined together with the nitrogen bound thereto to form a heterocyclic or substituted heterocyclic group.

"Aminocarbonylamino" refers to the group —$NR^a$C(O)$NR^aR^b$, wherein $R^a$ is hydrogen or alkyl and $R^a$ and $R^b$ independently are selected from the group consisting of hydrogen, alkyl, alkenyl, alkynyl, aryl, cycloalkyl, cycloalkenyl, heteroaryl, heterocyclic, and where $R^a$ and $R^b$ are optionally joined together with the nitrogen bound thereto to form a heterocyclic or substituted heterocyclic group.

"Aminocarbonylaminoalkylene" refers to the group -alkylene-$NR^a$C(O)$NR^aR^b$, wherein $R^a$ is hydrogen or alkyl and $R^a$ and $R^b$ independently are selected from the group consisting of hydrogen, alkyl, alkenyl, alkynyl, aryl, cycloalkyl, cycloalkenyl, heteroaryl, heterocyclic, and where $R^a$ and $R^b$ are optionally joined together with the nitrogen bound thereto to form a heterocyclic or substituted heterocyclic group.

"Aminocarboxyalkylene" refers to the group -alkylene-OC(O)$NR^aR^b$, wherein $R^a$ is hydrogen or alkyl and $R^a$ and $R^b$ independently are selected from the group consisting of hydrogen, alkyl, alkenyl, alkynyl, aryl, cycloalkyl, cycloalkenyl, heteroaryl, heterocyclic, and where $R^a$ and $R^b$ are optionally joined together with the nitrogen bound thereto to form a heterocyclic or substituted heterocyclic group.

"Aminosulfonyl" refers to —S(O)$_2NR^aR^b$ where R is independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^a$ and $R^b$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylalkylene" refers to -alkylene-S(O)$_2$NR$^a$R$^b$ where R is independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^a$ and R$^b$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

The term "alkylaminosulfonyl" refers herein to the group —S(O)$_2$NR$^a$R$^b$ where R$^a$ is alkyl and R$^b$ is H or alkyl. The term "alkylarylsulfonyl" refers herein to the group —S(O)$_2$NR$^a$R$^b$ where R$^a$ or R$^b$ is alkylaryl.

"Aminosulfonyloxy" refers to the group —O—SO$_2$NR$^a$R$^b$, wherein R$^a$ and R$^b$ independently are selected from the group consisting of hydrogen, alkyl, alkenyl, alkynyl, aryl, cycloalkyl, cycloalkenyl, heteroaryl and heterocyclic; R$^a$ and R$^b$ are optionally joined together with the nitrogen bound thereto to form a heterocyclic or substituted heterocyclic group.

"Aminosulfonylamino" refers to the group —NR$^a$—SO$_2$NR$^b$R$^c$, wherein R$^a$ is hydrogen or alkyl and R$^b$ and R$^c$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^b$ and R$^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR$^a$R$^b$, wherein R$^a$ and R$^b$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^a$ and R$^b$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^a$C(S)NR$^a$R$^b$, wherein R$^a$ is hydrogen or alkyl and R$^b$ and R$^c$ are optionally joined together with the nitrogen bound thereto to form a heterocyclic or substituted heterocyclic group.

"Arylalkoxycarbonylamino" refers to the group —NR$^a$C(=O)O-alkylene-R$^c$ where R$^c$ is aryl.

"Arylcarbonyl" refers to the group —C(=O)R$^c$ where R$^c$ is aryl.

"Arylcarbonylamino" refers to —NR$^a$C(=O)R$^c$ wherein R$^c$ is aryl.

"Arylcarbonyloxy" refers to —OC(=O)—R$^c$ where R$^c$ is aryl.

"Aryloxy" refers to —OR$^d$ where R$^d$ is aryl. Representative examples of aryloxy groups include phenoxy, naphthoxy, and the like.

"Aryloxycarbonyl" refers to —C(=O)OR$^d$ wherein R$^d$ is aryl.

"Aryloxycarbonylamino" refers to —NR$^a$C(=O)OR$^d$ wherein R$^d$ is aryl.

"Arylsulfanyl", "arylthio", or "thioaryloxy" refers to the group S—R$^d$ where R$^d$ is aryl.

"Arylsulfonyl" refers to —S(=O)$_2$R$^e$ where R$^e$ is aryl.

"Arylsulfonylamino" refers to —NR$^a$S(=O)$_2$—R$^e$ wherein R$^e$ is aryl.

"Arylthio" refers to the group —S-aryl, wherein aryl is as defined herein. In other embodiments, sulfur may be oxidized to —S(O)— or —SO$_2$— moieties. The sulfoxide may exist as one or more stereoisomers.

"Azido" refers to —N$_3$.

"Bond" when used a element in a Markush group means that the corresponding group does not exist, and the groups of both sides are directly linked.

"Carbonyl" refers to the divalent group —C(=O)—.

"Carboxy" or "carboxyl" refers to the group —CO$_2$H.

"Carboxyalkylene" refers to the group -alkylene-CO$_2$H.

"Carboxyalkylenesulfonylamino" refers to the group —NR$^a$SO$_2$-alkylene-CO$_2$H.

"Carboxyl ester", "carbonylalkoxy" or "carboxy ester" refers to the group —C(=O)OR$^c$.

"(Carboxyl ester)amino" refers to the groups —NR$^a$—C(O)OR$^c$, where R$^a$ is alkyl or hydrogen.

"(Carboxyl ester)oxy" or "Carbonate ester" refers to the groups —O—C(=O)OR$^c$.

"Cyano" refers to —CN.

"Cyanoalkylenecarbonyl" refers to —C(=O)-alkylene-CN.

"Cycloalkoxy" refers to —OR$^d$ where R$^d$ is cycloalkyl.

"Cycloalkoxycarbonyl" refers to —C(=O)OR$^d$ wherein R$^d$ is cycloalkyl.

"Cycloalkoxycarbonylamino" refers to —NR$^a$C(=O)OR$^d$ wherein R$^d$ is cycloalkyl.

"Cycloalkylalkylene" refers to a radical —R$^x$R$^y$ wherein R$^x$ is an alkylene group and R$^y$ is a cycloalkyl group as defined herein, e.g., cyclopropylmethyl, cyclohexenylpropyl, 3-cyclohexyl-2-methylpropyl, and the like.

"Cycloalkylcarbonyl" refers to the group —C(=O)R$^c$ where R$^c$ is cycloalkyl.

"Cycloalkylcarbonylamino" refers to —NR$^a$C(=O)R$^c$ wherein R$^c$ is cycloalkyl.

"Cycloalkylcarbonyloxy" refers to —OC(=O)—R$^c$ where R$^c$ is cycloalkyl.

"Cycloalkylsulfonylamino" refers to —NR$^a$S(=O)$_2$—R$^e$ wherein R$^e$ is cycloalkyl.

"Cycloalkylthio" refers to —S-cycloalkyl. In other embodiments, sulfur may be oxidized to —S(O)— or —SO$_2$— moieties. The sulfoxide may exist as one or more stereoisomers.

"Cycloalkenylox" refers to —O-cycloalkenyl.

"Cycloalkenylthio" refers to —S-cycloalkenyl. In other embodiments, sulfur may be oxidized to sulfinyl or sulfonyl moieties. The sulfoxide may exist as one or more stereoisomers.

"Ester" refers to —C(=O)OR$^d$ wherein R$^d$ is alkyl, cycloalkyl, aryl, heteroaryl, or heterocyclyl.

"Guanidino" refers to the group —NHC(=NH)NH$_2$.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2m'+1), where m' is the total number of carbon atoms in the alkyl group. For example, the term "haloC$_{1-8}$alkyl" is meant to include trifluoromethyl, 2,2,2-trifluoroethyl, 4-chlorobutyl, 3-bromopropyl, and the like. The term "perhaloalkyl" means, unless otherwise stated, alkyl substituted with (2m'+1) halogen atoms, where m' is the total number of carbon atoms in the alkyl group. For example, the term "perhaloC$_{1-8}$alkyl", is meant to include trifluoromethyl, pentachloroethyl, 1,1,1-trifluoro-2-bromo-2-chloroethyl, and the like. Additionally, term "haloalkoxy" refers to an alkoxy radical substituted with one or more halogen atoms.

"Heteroalkyl" means an alkyl radical as defined herein with one, two or three substituents independently selected from cyano, —OR$^w$, —NR$^x$R$^y$, and —S(O)$_n$R$^z$ (where n is an integer from 0 to 2), with the understanding that the point of attachment of the heteroalkyl radical is through a carbon atom of the heteroalkyl radical. R$^w$ is hydrogen, alkyl, cycloalkyl, cycloalkyl-alkyl, aryl, araalkyl, alkoxycarbonyl, aryloxycarbonyl, carboxamido, or mono- or di-alkylcarbamoyl. R$^x$ is hydrogen, alkyl, cycloalkyl, cycloalkyl-alkyl, aryl or araalkyl. R$^y$ is hydrogen, alkyl, cycloalkyl, cycloalkyl-alkyl, aryl, araalkyl, alkoxycarbonyl, aryloxycarbonyl, carboxamido, mono- or di-alkylcarbamoyl or alkylsulfonyl. R$^z$ is hydrogen (provided that n is 0), alkyl, cycloalkyl, cycloalkyl-alkyl, aryl, araalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^w$, R$^x$, R$^y$, and R$^z$ can be further substituted by amino, fluorine, alkylamino, di-alkylamino, OH or alkoxy. Additionally, the prefix indicating the number of carbon atoms (e.g., C$_1$-C$_{10}$) refers to the total number of carbon atoms in the portion of the heteroalkyl group exclusive of the cyano, —OR$^w$, —NR$^x$R$^y$, or —S(O)$_n$R$^z$ portions.

"Heteroarylalkenyl" refers to the group -alkenyl-R$^c$ where R$^c$ is heteroaryl.

"Heteroarylcarbonyl" refers to the group —C(=O)R$^c$ where R$^c$ is heteroaryl.

"Heteroarylcarbonylamino" refers to —NR$^a$C(=O)R$^c$ wherein R$^c$ is heteroaryl.

"Heteroarylcarbonyloxy" refers to —OC(=O)—R$^c$ where R$^c$ is heteroaryl.

"Heteroaryloxy" refers to —OR$^d$ where R$^d$ is heteroaryl.

"Heteroaryloxycarbonyl" refers to —C(=O)OR$^d$ wherein R$^d$ is heteroaryl.

"Heteroaryloxycarbonylamino" refers to —NR$^a$C(=O)OR$^d$ wherein R$^d$ is heteroaryl.

"Heteroarylsulfonylamino" refers to —NR$^a$S(=O)$_2$—R$^e$ wherein R$^e$ is heteroaryl.

"Heteroarylthio" refers to the group —S-heteroaryl. In other embodiments, sulfur may be oxidized to —S(O)— or —SO$_2$— moieties. The sulfoxide may exist as one or more stereoisomers.

"Heterocyclylalkyl" or "Cycloheteroalkyl-alkyl" means a radical —R$^x$R$^y$ where R$^x$ is an alkylene group and R$^y$ is a heterocyclyl group as defined herein, e.g., tetrahydropyran-2-ylmethyl, 4-(4-substituted-phenyl)piperazin-1-ylmethyl, 3-piperidinylethyl, and the like.

"Heterocycloxycarbonylamino" refers to —NR$^a$C(=O)OR$^d$ wherein R$^d$ is heterocyclyl.

"Heterocyclylcarbonyl" refers to the —C(=O)R$^c$ where R$^c$ is heterocyclyl.

"Heterocyclylcarbonylamino" refers to —NR$^a$C(=O)R$^c$ wherein R$^c$ is heterocyclyl.

"Heterocyclylcarbonyloxy" refers to —OC(=O)—R$^c$ where R$^c$ s heterocyclyl.

"Heterocyclyloxy" refers to —OR$^d$ where R$^d$ is heterocyclyl.

"Heterocyclyloxycarbonyl" refers to —C(=O)OR$^d$ wherein R$^d$ is heterocyclyl.

"Heterocyclylsulfonyl" refers to —S(=O)$_2$R$^e$ where R$^e$ is heterocyclyl.

"Heterocyclylsulfonylanino" refers to —NR$^a$S(=O)$_2$—R$^e$ wherein R$^e$ is heterocyclyl.

"Heterocyclylthio" refers to the group —S-heterocycyl. In other embodiments, sulfur may be oxidized to —S(O)— or —SO$_2$— moieties. The sulfoxide may exist as one or more stereoisomers.

"Hydroxy" or "hydroxyl" refers to the group —OH.

"Hydroxyalkylene" refers to the group -alkylene-OH.

"Hydroxyalkyleneamino" refers to the group —NR$^a$-alkylene-OH.

"Hydroxyalkyleneaminocarbonyl" refers to the group —C(=O)NR$^a$-alkylene-OH.

"Hydroxyalkyleneaminosulfonyl" refers to the group —SO$_2$NR$^a$-alkylene-OH.

"Hydroxyamino" refers to the group —NHOH.

"Hydroxyalkylenecarbonylamino" refers to the group —NR$^a$C(=O)-alkylene-OH.

"Imino" refers to the group =NR$^a$.

"Nitro" refers to —NO$_2$.

"Nitroso" refers to the group —NO.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may but need not be present, and the description includes situations where the heterocyclo group is mono- or disubstituted with an alkyl group and situations where the heterocyclo group is not substituted with the alkyl group.

"Optionally substituted" means a ring which is optionally substituted independently with substituents. A site of a group that is unsubstituted may be substituted with hydrogen.

"Oxo" refers to the divalent group =O.

"Sulfanyl" refers to the group —SR$^f$ where R$^f$ is as defined herein.

"Sulfinyl" refers to the group —S(=O)—R$^e$ where R$^e$ is as defined herein.

"Sulfonic acid" refers to the group —S(O)$_2$—OH.

"Sulfonyl" refers to the group —S(O)$_2$—R$^e$ where R$^e$ is as defined herein.

"Sulfonylamino" refers to —NR$^a$S(=O)$_2$—R$^e$ where R$^a$ is selected from the group consisting of hydrogen, alkyl, alkenyl, alkynyl, aryl, cycloalkyl, cycloalkenyl, heteroaryl and heterocyclyl and R$^e$ is as defined herein.

"Sulfonyloxy" refers to the group —OSO$_2$—R$^c$.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

"Thioacyl" refers to the groups $R^a$—C(S)—.

"Thiol" refers to the group —SH.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to -substituted aryl-(substituted aryl)-substituted aryl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3$^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," Journal of Pharmaceutical Science, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug ester form. "Prodrug"s of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

A wide variety of progroups, as well as the resultant promoieties, suitable for masking functional groups in the active syk and/or JAK selective inhibitory compounds to yield prodrugs are well-known in the art. For example, a hydroxyl functional group may be masked as a sulfonate, ester (such as acetate or maleate) or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including methyl, ethyl, pivaloyloxymethyl, silyl esters and thioesters), amide or hydrazide promoiety, which may be hydrolyzed in vivo to provide the carboxyl group. The invention includes those esters and acyl groups known in the art for modifying the solubility or hydrolysis characteristics for use as sustained-release or prodrug formulations. Other specific examples of suitable progroups and their respective promoieties will be apparent to those of skill in the art.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

An "agonist" or "activator" refers to an agent or molecule that binds to a receptor of the invention, stimulates, increases, opens, activates, facilitates, enhances activation or enzymatic activity, sensitizes or up regulates the activity of a receptor of the invention.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

As used herein, the term "condition or disorder responsive to modulation of syk and/or JAK" and related terms and phrases refer to a condition or disorder associated with inappropriate, e.g., less than or greater than normal, activity of syk and/or JAK and at least partially responsive to or affected by modulation of syk and/or JAK (e.g., syk and/or JAK antagonist or agonist results in some improvement in patient well-being in at least some patients). Inappropriate functional activity of syk and/or JAK might arise as the result of expression of syk and/or JAK in cells which normally do not express the receptor, greater than normal production of syk and/or JAK, or slower than normal metabolic inactivation or elimination of syk and/or JAK or its active metabolites, increased expression of syk and/or JAK or degree of intracellular activation (leading to, e.g., inflammatory and immune-related disorders and conditions) or decreased expression of syk and/or JAK. A condition or disorder associated with syk and/or JAK may include a "syk and/or JAK-mediated condition or disorder".

As used herein, the phrases "a condition or disorder mediated at least in part by syk or JAK kinase activity", and related phrases and terms refer to a condition or disorder characterized by inappropriate, e.g., greater than normal, syk and/or JAK activity. Inappropriate syk and/or JAK functional activity might arise as the result of syk and/or JAK expression in cells which normally do not express syk and/or JAK or increased syk and/or JAK expression or degree of intracellular activation (leading to, e.g., inflammatory and immune-related disorders and conditions). A condition or disorder mediated at least in part by syk or JAK kinase activity may be completely or partially mediated by inappropriate syk and/or JAK functional activity. However, a condition or disorder mediated at least in part by syk or JAK kinase activity is one in which modulation of syk and/or JAK results in some effect on the underlying condition or disorder (e.g., an syk and/or JAK antagonist results in some improvement in patient well-being in at least some patients).

The term "inflammation" as used herein refers to infiltration of white blood cells (e.g., leukocytes, monocytes, etc.) into the area being treated for restenosis.

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

As used herein, the term "JAK" refers to a Janus kinase (RefSeq Accession No. P-43408) or a variant thereof that is capable of mediating gene expression in vitro or in vivo. JAK variants include proteins substantially homologous to native JAK, i.e., proteins having one or more naturally or non-naturally occurring amino acid deletions, insertions or substitutions (e.g., JAK derivatives, homologs and fragments). The amino acid sequence of JAK variant preferably is at least about 80% identical to a native JAK, more preferably at least about 90% identical, and most preferably at least about 95% identical.

The term "leukocyte" refers to any of the various blood cells that have a nucleus and cytoplasm, separate into a thin white layer when whole blood is centrifuged, and help protect the body from infection and disease. Examples of leukocytes include, without limitation, neutrophils, eosinophils, basophils, lymphocytes, and monocytes.

The term "mammal" includes, without limitation, humans, domestic animals (e.g., dogs or cats), farm animals (cows, horses, or pigs), monkeys, rabbits, mice, and laboratory animals.

The terms "modulate", "modulation" and the like refer to the ability of a compound to increase or decrease the function and/or expression of syk and/or JAK, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with syk and/or JAK, either directly or indirectly, and/or the upregulation or down-regulation of the expression of syk and/or JAK, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of syk and/or JAK can be demonstrated in a biochemical assay, e.g., binding assay, or a cell-based assay, e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Patient" refers to human and non-human animals, especially mammals. Examples of patients include, but are not limited to, humans, cows, dogs, cats, goats, sheep, pigs and rabbits.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

The term "platelet" refers to a minute, nonnucleated, disklike cell found in the blood plasma of mammals that functions to promote blood clotting.

The terms "prevent", "preventing", "prevention" and grammatical variations thereof as used herein, refers to a method of partially or completely delaying or precluding the onset or recurrence of a disorder or condition and/or one or more of its attendant symptoms or barring a subject from acquiring or reacquiring a disorder or condition or reducing a subject's risk of acquiring or reacquiring a disorder or condition or one or more of its attendant symptoms.

The term "recanalization" refers to the process of restoring flow to or reuniting an interrupted channel of the body, such as a blood vessel.

The term "restenosis" refers to a re-narrowing or blockage of an artery at the same site where treatment, such as an angioplasty or a stent procedure, has been performed.

The phrase "selectively" or "specifically" when referring to binding to a receptor, refers to a binding reaction that is determinative of the presence of the receptor, often in a heterogeneous population of receptors and other biologics.

Thus, under designated conditions, the compounds bind to a particular receptor at least two times the background and more typically more than 10 to 100 times background. Specific binding of a compound under such conditions requires a compound that is selected for its specificity for a particular receptor. For example, small organic molecules can be screened to obtain only those compounds that specifically or selectively bind to a selected receptor and not with other receptors or proteins. A variety of assay formats may be used to select compounds that are selective for a particular receptor. For example, High-throughput screening assays are routinely used to select compounds that are selective for a particular a receptor.

As used herein, the term "Sickle cell anemia" refers to an inherited disorder of the red blood cells in which both hemoglobin alleles encode the sickle hemoglobin (S) protein, i.e., the S/S genotype. The presence of abnormal hemoglobin results in the production of unusually shaped cells, which do not survive the usual length of time in the blood circulation. Thus, anemia results. "Anemia" refers to a decrease in the number of red blood cells and/or hemoglobin in the blood.

The term "Sickle cell disease" refers to an inherited disorder of the red blood cells in which one hemoglobin allele encodes the sickle hemoglobin (S) protein, and the other allele encodes another unusual hemoglobin protein, such as hemoglobin (S), (C), (D), (E), and (βThal). Examples of sickle cell disease genotypes include, without limitation, the S/S, S/C, S/D, S/E, and S/βThal genotypes. The most common types of sickle cell disease include sickle cell anemia, sickle-hemoglobin C disease, sickle beta-plus thalassemia, and sickle beta-zero thalassemia.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the term "syk" refers to a spleen tyrosine kinase (RefSeq Accession No. P-043405) or a variant thereof that is capable of mediating a cellular response to T-cell receptors in vitro or in vivo. syk variants include proteins substantially homologous to native syk, i.e., proteins having one or more naturally or non-naturally occurring amino acid deletions, insertions or substitutions (e.g., syk derivatives, homologs and fragments). The amino acid sequence of syk variant preferably is at least about 80% identical to a native syk, more preferably at least about 90% identical, and most preferably at least about 95% identical.

The term "syk inhibitor" refers to any agent that inhibits the catalytic activity of spleen tyrosine kinase.

The term "thrombosis" refers to the blockage or clotting of a blood vessel caused by a clumping of cells, resulting in the obstruction of blood flow. The term "thrombosis" refers to the clot that is formed within the blood vessel.

The terms "treat", "treating", "treatment" and grammatical variations thereof as used herein, includes partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

The term "vessel" refers to any channel for carrying a fluid, such as an artery or vein. For example, a "blood vessel" refers to any of the vessels through which blood circulates in the body. The lumen of a blood vessel refers to the inner open space or cavity of the blood vessel.

2. Embodiments of the Invention a. Compounds

The present invention provides in one embodiment, a compound having Formula (I):

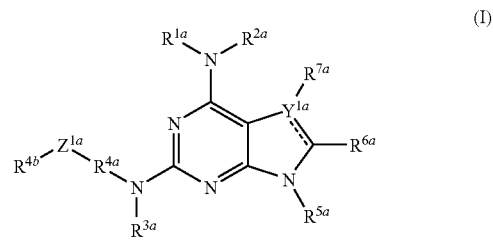

or a tautomer or pharmaceutically acceptable salt thereof, wherein:

$Y^{1a}$ is selected from the group consisting of N, CH and C;

$Z^{1a}$ is selected from the group consisting of a bond, —N($C_{1-4}$ alkyl)-, —$SO_2$—, —CO—, —$NR^{4d}SO_2$—, heterocyclyl, heterocyclylcarbonyl and heterocyclylsulfonyl;

$R^{1a}$ is selected from the group consisting of:

(a) H;

(b) $C_{1-8}$alkyl, optionally substituted with from 1 to 3 substituents selected from the group consisting of amino, hydroxy, $C_{1-8}$alkoxy, heterocyclyl, aminocarbonyl, amino$C_{1-8}$alkoxy, aryl and heteroaryl;

(c) $C_{3-8}$cycloalkyl, optionally substituted with from 1 to 3 amino substituents;

(d) aryl, optionally substituted with from 1 to 3 substituents selected from the group consisting of $C_{1-8}$alkyl, $C_{1-8}$alkoxy, $C_{1-8}$alkylamino, $C_{1-8}$alkylcarbonylamino; aminocarbonyl$C_{1-8}$ alkoxy, aminosulfonyl, aminocarbonyl, amino$C_{1-8}$ alkylene carbonyl$C_{1-8}$alkoxy and halo;

(e) heterocyclyl, halogens, cyano, optionally substituted with from 1 to 3 substituents selected from the group consisting of $C_{1-8}$alkyl, oxo and $C_{1-8}$alkoxycarbonyl, cyano $C_{1-6}$alkylcarbonyl, aminocarbonyl, aryl$C_{1-4}$alkoxycarbonyl, arylaminocarbonyl; and (f) heteroaryl, optionally substituted with from 1 to 3 substituents selected from the group consisting of $C_{1-8}$alkyl, $C_{1-8}$alkylsulfonyl and cyano$C_{1-8}$alkylenecarbonyl;

$R^{2a}$ is H, $C_{1-8}$alkyl, or is taken together with $R^{1a}$ and the nitrogen to which each is attached to form a heterocyclic or heteroaryl ring, containing 1-3 heteroatoms, including N, O or S, optionally substituted with from 1 to 2 substituents, $R^{2b}$, independently selected from the group consisting of $C_{1-8}$alkoxy, $C_{1-8}$alkoxycarbonyl, $C_{1-8}$alkoxycarbonyl$C_{1-8}$ alkylene, $C_{1-8}$alkoxycarbonylamino$C_{1-8}$alkylene, amino, amino$C_{1-8}$alkylene, aminoaryl, aminocarbonyl, aminocarbonylamino, aminocarbonyl$C_{1-8}$alkylene, aminocarbonylamino$C_{1-8}$alkylene, aminocarboxy$C_{1-8}$alkylene, aminosulfonyl, aminosulfonyl$C_{1-8}$alkylene, $C_{1-8}$alkyl, $C_{1-8}$alkylsulfonyl, $C_{1-8}$alkylsulfonyl$C_{1-8}$alkylene, $C_{1-8}$alkylheterocyclyl, $C_{1-8}$alkylheterocyclyl$C_{1-8}$alkylene, aryl, aryl$C_{1-8}$alkoxycarbonylamino, carboxy, carboxy$C_{1-8}$alkylene, cyano, $C_{3-8}$cycloalkyl, halo, heteroaryl, heteroaryl$C_{1-8}$alkylene, heterocyclyl, hydroxy, hydroxy$C_{1-8}$alkylene, hydroxycarbonyl$C_{1-8}$ alkylene, imino, oxo and =S;

$R^{3a}$ is H, $C_{1-8}$alkyl, or is taken together with the moiety $R^{4a}$—$Z^{1a}$ and the nitrogen to which each is attached to form a heterocyclic or heteroaryl ring, optionally substituted with from 1 to 2 substituents $R^{2b}$ and $R^{2c}$ each of which is independently selected from the group consisting of $C_{1-8}$alkoxy, $C_{1-8}$alkoxycarbonyl, $C_{1-8}$alkoxycarbonyl$C_{1-8}$alkylene, $C_{1-8}$alkoxycarbonylamino$C_{1-8}$alkylene, amino, amino$C_{1-8}$alkylene, aminoaryl, aminocarbonyl, aminocarbonylamino, aminocarbonylamino$C_{1-8}$alkylene, aminocarboxy$C_{1-8}$alkylene, aminosulfonyl, aminosulfonyl$C_{1-8}$alkylene, $C_{1-8}$alkyl, $C_{1-8}$alkylsulfonyl, $C_{1-8}$alkylsulfonyl$C_{1-8}$alkylene, $C_{1-8}$alkylheterocyclyl, $C_{1-8}$alkylheterocyclyl$C_{1-8}$alkylene, aryl, aryl$C_{1-8}$alkoxycarbonylamino, carboxy, carboxy$C_{1-8}$alkylene, cyano, $C_{3-8}$cycloalkyl, halo, heteroaryl, heteroaryl$C_{1-8}$alkylene, heterocyclyl, hydroxy, hydroxy$C_{1-8}$alkylene, imino, oxo and =S;

$R^{4a}$ is selected from the group consisting of:

(a) aryl, optionally substituted with from 1 to 3 substituents, $R^{4c}$, each of which is independently selected from the group consisting of $C_{1-8}$alkoxy, amino, $C_{1-8}$alkylcarbonyl and aminocarbonyl$C_{1-8}$alkoxy;

(b) heteroaryl, heterobicyclic $C_{1-8}$ alkyl, halo, hydroxyl, optionally substituted with from 1 to 3 substituents, $R^{4c}$, each of which is independently selected from the group consisting of $C_{1-8}$alkyl, halogen, hydroxyl, oxo $C_{1-8}$alkoxy and =S;

(c) heterocyclyl, each of which is optionally substituted with from 1 to 3 substituents, $R^{4c}$, each of which is independently selected from the group consisting of $C_{1-8}$alkyl and oxo;

$R^{4b}$ is selected from the group consisting of H, $C_{1-8}$alkyl, amino$C_{1-8}$alkylene, $C_{1-8}$alkylcarbonyl, $C_{1-8}$alkylcarbonylamino, $C_{1-8}$alkylsulfonyl, $C_{1-8}$alkylsulfinyl, $C_{1-8}$alkylsulfonylamino, $C_{1-8}$alkylsulfonyl $C_{1-8}$alkylene, $C_{1-8}$alkylthio, $C_{1-8}$alkoxy, $C_{1-8}$alkoxy$C_{1-8}$alkyleneamino, $C_{1-8}$alkoxycarbonylamino, $C_{1-8}$alkoxycarbonyl, $C_{1-8}$alkoxy$C_{1-8}$alkylene, $C_{1-8}$alkoxycarbonyl$C_{1-8}$alkylene, amino, aminocarbonyl, aminocarbonyl$C_{1-8}$alkylene, aminosulfonyl, $C_{1-8}$alkoxycarbonyl$C_{1-8}$alkyleneaminosulfonyl, amino$C_{1-8}$alkyleneaminocarbonyl, aminocarbonyl$C_{1-8}$alkoxy, amino$C_{1-8}$alkylene, amino$C_{1-8}$alkylenecarbonyl, aminocarbonyl$C_{1-8}$alkyleneaminoesulfonyl, carboxy, carboxy$C_{1-8}$alkyleneaminosulfonyl, carboxy$C_{1-8}$alkylene, $C_{3-8}$cycloalkylcarbonylamino, $C_{3-8}$cycloalkylcarbonyl, halo, hydroxy, hydroxy$C_{1-8}$alkylene, amino$C_{1-8}$alkyleneamino, amino$C_{1-8}$alkylenecarbonyl, amino$C_{1-8}$alkyleneaminocarbonyl$C_{1-8}$alkylene, hydroxy$C_{1-8}$ alkylenecarbonylamino, hydroxyl$C_{1-8}$alkylenecarbonyl, hydroxy$C_{1-8}$alkyleneamino, hydroxy$C_{1-8}$alkyleneaminosulfonyl, hydroxy$C_{1-8}$alkyleneaminocarbonyl, oxo and heterocyclyl;

if $R^{4b}$ is heterocyclyl, it is optionally substituted with 1-3 substituents, $R^{4d}$, independently selected from the group consisting of $C_{1-8}$alkyl, $C_{1-8}$alkoxy, hydroxy, amino, halo, cyano, oxo, =S, $C_{1-8}$alkoxycarbonyl, carboxy, aminocarbonyl, aminosulfonyl, $C_{1-8}$alkylcarbonyl and $C_{1-8}$alkylaminocarbonyl;

$R^{5a}$ is selected from the group consisting of H, $C_{1-8}$alkyl, $C_{3-8}$cycloalkyl and $C_{1-8}$alkylarylsulfonyl;

$R^{6a}$ is selected from the group consisting of H, $C_{1-8}$alkyl, halo, hydroxyl and oxo;

$R^{7a}$ is selected from the group consisting of H, $C_{1-8}$alkyl, cyano, $C_{1-8}$alkoxy$C_{1-8}$alkylene, $C_{2-8}$alkynyl, $C_{3-8}$cycloalkyl, $C_{1-8}$alkylcarbonyl, hydroxy, oxo, halo and aryl, wherein each aryl and heteroaryl can be optionally substituted with halo, $C_{1-8}$alkyl, $C_{1-8}$alkoxy, cyano, amino, hydroxyl, heteroaryl; and the dashed line indicates a double or single bond.

In another group of embodiments, $R^{1a}$ is H. In another group of embodiments, $R^{1a}$ is $C_{1-8}$alkyl. In another group of embodiments, $R^{1a}$ is $C_{3-8}$cycloalkyl. In another group of embodiments, $R^{1a}$ is cyclohexyl, cyclopropyl or cyclobutyl. In another group of embodiments, $R^{1a}$ is aryl. In another group of embodiments, $R^{1a}$ is phenyl. In another group of embodiments, $R^{1a}$ is heterocyclyl. In another group of embodiments, $R^{1a}$ is heteroaryl.

In another group of embodiments, $R^{2a}$ is H. In another group of embodiments, $R^{2a}$ is $C_{1-8}$alkyl. In another group of embodiments, $R^{2a}$ is taken together with $R^{1a}$ and the nitrogen to which each is attached to form a heterocyclic ring selected from the group consisting of piperidine, piperazine, homopiperazine and pyrrolidine.

In another group of embodiments, each $R^{2b}$ is independently selected from the group consisting of —$CH_2NH_2$, —$CH_2NHCH_3$, —$CH_2N(CH_3)_2$, —$CH_2CH_2NH_2$, —$C(CH_3)_2NH_2$, —$NH_2$, —OH, —$CH_2OH$, —$CH_2CH_2OH$, —$CH_2NHC(O)NH_2$, —$C(O)NH_2$ and —$CH_2C(O)NH_2$— $CH(NH_2)CO_2CH_3$, —$CHNH_2)CH_2CO_2Et$.

In another group of embodiments, $Y^1$ is N. In another group of embodiments, $Y^{1a}$ is CH. In another group of embodiments, $Y^{1a}$ is C.

In another group of embodiments, $R^{3a}$ is H. In another group of embodiments, $R^{3a}$ is $C_{1-8}$alkyl. In another group of embodiments, $R^{3a}$ is taken together with the moiety $R^{4a}$—$Z^{1a}$ and the nitrogen to which each is attached to form a heterocyclic ring. In another group of embodiments, $R^{3a}$ is taken together with the moiety $R^{4a}$—$Z^{1a}$ and the nitrogen to which each is attached to form a heteroaryl ring.

In another group of embodiments, $R^{4a}$ is aryl. In another group of embodiments, $R^{4a}$ is phenyl. In another group of embodiments, $R^{4a}$ is heteroaryl. In another group of embodiments, $R^{4a}$ is heterocyclyl.

In another group of embodiments, $Z^1$ is a bond. In another group of embodiments, $Z^1$ is —N($C_{1-8}$alkyl)-. In another group of embodiments, $Z^1$ is —$SO_2$—. In another group of embodiments, $Z^1$ is —CO—. In another group of embodiments, $Z^1$ is —$NR^{4d}SO_2$—. In another group of embodiments, $Z^1$ is heterocyclyl. In another group of embodiments, $Z^1$ is heterocyclylcarbonyl. In another group of embodiments, $Z^1$ is heterocyclylsulfonyl.

In another group of embodiments, $R^{5a}$ is H.

In another group of embodiments, $R^{6a}$ is H.

In another group of embodiments, $R^{7a}$ is selected from the group consisting of H, cyano, phenyl and pyridyl.

In another group of embodiments, $R^{4b}$ is selected from the group consisting of H, $C_{1-8}$alkyl, $C_{1-8}$alkylcarbonyl, $C_{1-8}$alkylcarbonylamino, $C_{1-8}$alkylsulfonyl, $C_{1-8}$alkylsulfinyl, $C_{1-8}$alkylsulfonylamino, $C_{1-8}$alkylsulfonyl $C_{1-8}$alkylene, $C_{1-8}$alkylthio, $C_{1-8}$alkoxy, $C_{1-8}$alkoxycarbonylamino, $C_{1-8}$alkoxycarbonyl, $C_{1-8}$alkoxycarbonyl $C_{1-8}$alkylene, aminocarbonyl, aminosulfonyl, $C_{1-8}$alkoxycarbonyl $C_{1-8}$alkyleneaminosulfonyl, amino$C_{1-8}$alkyleneaminocarbonyl, amino$C_{1-8}$alkyleneaminocarbonyl, aminocarbonyl$C_{1-8}$alkoxy, aminocarbonyl, aminocarbonyl$C_{1-8}$alkyleneaminosulfonyl, carboxy, carboxy$C_{1-8}$alkyleneaminosulfonyl, $C_{3-8}$cycloalkylcarbonylamino, halo, hydroxy, hydroxy$C_{1-8}$alkylene, hydroxy$C_{1-8}$alkylenecarbonylamino, hydroxy$C_{1-8}$alkyleneamino-, hydroxy$C_{1-8}$alkyleneaminosulfonyl, hydroxy$C_{1-8}$alkyleneaminocarbonyl, oxo and heterocyclyl.

The present invention provides in another embodiment, a compound, having the formula Ia:

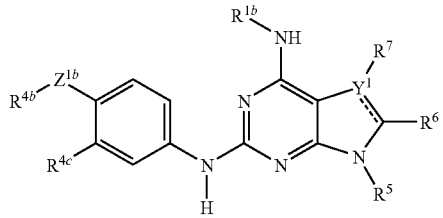

or tautomer or a pharmaceutically acceptable salt thereof, wherein:
$Y^{1b}$ is N, CH or C;
$Z^{1b}$ is heterocyclyl, —$NR^{4d}SO_2$—, heterocyclylsulfonyl or a bond,
$R^{1b}$ is selected from the group consisting of
(a) H,
(b) $C_{1-8}$alkyl, optionally substituted with amino, amino$C_{1-8}$alkyl, aminocarbonyl, alkoxy, $C_{1-8}$alkylaminocarbonyl, amino$C_{1-8}$alkylene, amino$C_{1-8}$alkoxy, aryl, hydroxy or heterocyclyl,
(c) $C_{3-8}$cycloalkyl, optionally substituted with alkyl, amino, hydroxyl, $C_{1-8}$alkoxy, $C_{1-8}$alkylaminocarbonyl, amino$C_{1-8}$alkylene, amino$C_{1-8}$alkoxy;
(d) aryl, optionally substituted with alkyl, amino, aminosulfonyl, amino$C_{1-8}$alkylene, $C_{1-8}$alkylaminocarbonyl$C_{1-8}$alkoxy, hydroxyl, $C_{1-8}$alkoxy, $C_{1-8}$alkylaminocarbonyl, amino$C_{1-8}$alkylene, amino$C_{1-8}$alkoxy or halo;
(e) heterocyclyl, optionally substituted with $C_{1-8}$ alkyl, $C_{1-8}$alkoxycarbonyl, amino, hydroxyl, $C_{1-8}$alkoxy, $C_{1-8}$alkylaminocarbonyl, amino$C_{1-8}$alkylene, amino$C_{1-8}$alkoxy, oxo, or cyano$C_{1-8}$alkylenecarbonyl;
(f) heteroaryl, optionally substituted with alkyl, amino, hydroxyl, $C_{1-8}$alkoxy, $C_{1-8}$alkylaminocarbonyl, amino$C_{1-8}$alkylene or amino$C_{1-8}$alkoxy;
$R^{4b}$ is selected from the group consisting of H, hydroxy, $C_{1-8}$alkylcarbonyl-, $C_{1-8}$alkoxycarbonyl$C_{1-8}$alkylene, $C_{1-8}$alkoxycarbonylamino, aminocarbonyl$C_{1-8}$alkylene, hydroxycarbonyl, hydroxycarbonyl$C_{1-8}$alkylene, aminocarbonyl, amino$C_{1-8}$alkylene, hydroxy, hydroxy$C_{1-8}$alkylenecarbonylamino, $C_{1-8}$alkylamino$C_{1-8}$alkylene, $C_{1-8}$alkylamino$C_{1-8}$alkyleneaminocarbonyl, aminocarbonylamino, $C_{1-8}$alkylsulfonyl$C_{1-8}$alkylene, $C_{3-8}$cycloalkylcarbonylamino and $C_{1-8}$alkylcarbonylamino; and
$R^{4c}$ is H, amino, $C_{1-8}$alkylcarbonyl, aminocarbonyl$C_{1-8}$alkoxy;
$R^{4d}$ is H or $C_{1-8}$alkyl;
$R^5$ is H or $C_{1-8}$alkyl;
$R^6$ is selected from the group consisting of H, $C_{1-8}$alkyl, halo, hydroxy and oxo;
$R^7$ is selected from the group consisting of H, $C_{1-8}$alkyl, cyano, $C_{1-8}$alkoxy$C_{1-8}$alkylene, $C_{1-8}$alkylcarbonyl, hydroxy, oxo, halo, aryl and heteroaryl; and the dashed line indicates a double or single bond; or the moiety $R^{4b}$—$Z^{1b}$ combines with $R^{4c}$ to form 5-7 membrane heterocyclic ring, containing 1-3 heteroatoms, including N, O, S, optionally substituted with $C_{1-8}$alkyl, halo, cyano, oxo, =S, amino, hydroxyl, $C_{1-8}$alkylcarbonyl, $C_{1-8}$alkoxy or aryloxycarbonyl$C_{1-8}$alkylene.

The present invention provides in another embodiment, a compound, having the formula selected from the group consisting of:

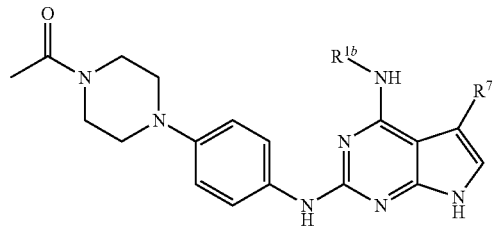

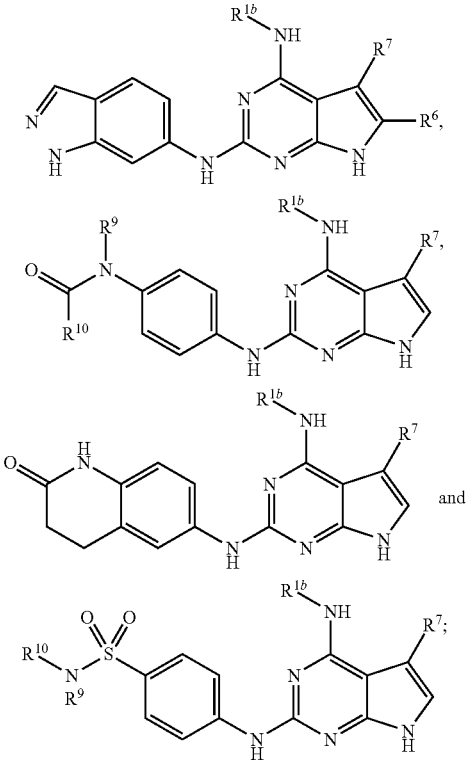

wherein $R^{1b}$ is $C_{1-8}$alkyl, optionally substituted with amino, heterocyclyl or aminoheterocyclyl, and $C_{3-8}$cycloalkyl, optionally substituted with amino; $R^7$ is halo, hydroxy, $C_{1-8}$alkoxy$C_{1-8}$alkylene, $C_{1-8}$alkylcarbonyl, cyano or phenyl, pyridinyl; and $R^6$ is H, $C_{1-8}$alkyl or halo; $R^9$ is H or $C_{1-8}$alkyl; and $R^{10}$ is H, $C_{1-8}$alkyl, $C_{1-8}$alkoxy, $C_{1-8}$alkoxycarbonyl$C_{1-8}$alkylene, amino$C_{1-8}$alkylene, aminocarbonyl$C_{1-8}$alkylene, carboxy$C_{1-8}$-alkylene, $C_{3-8}$cycloalkyl and hydroxy$C_{1-8}$alkylene; or a tautomer or a pharmaceutically acceptable salt thereof.

In another group of embodiments, $R^{1b}$ is $C_{1-8}$alkyl, optionally substituted. In another group of embodiments, $R^{1b}$ is $C_{3-8}$cycloalkyl, optionally substituted. In another group of embodiments, $R^{1b}$ is cyclohexyl, cyclopropyl or cyclobutyl, each of which is optionally substituted. In another group of embodiments, $R^{1b}$ is heterocyclyl, optionally substituted. In another group of embodiments, $R^{1b}$ is heterocyclyl, which is selected from the group consisting of piperidinyl, morpholino and tetrahydrothiophenyl. In another group of embodiments, $R^{1b}$ is aryl. In another group of embodiments, $R^{1b}$ is monocyclic heteroaryl. In another group of embodiments, $R^{1b}$ is pyrazole.

In another group of embodiments, $Z^{1b}$ is heterocyclyl, which is selected from the group consisting of:

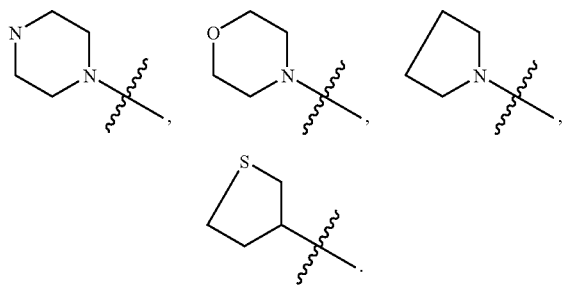

In another group of embodiments, the moiety

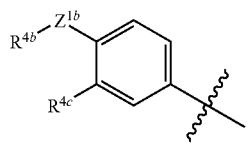

is selected from the group consisting of:

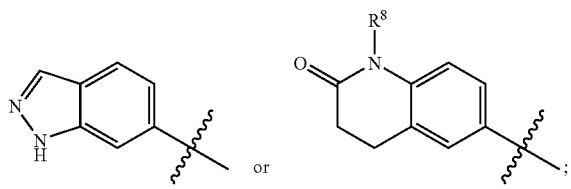

wherein $R^8$ is selected from the group consisting of H, $C_{1-8}$alkyl, hydroxycarbonyl$C_{1-8}$alkylene, alkoxycarbonyl$C_{1-8}$ alkylene and $C_{1-8}$alkylamino$C_{1-8}$alkyleneaminocarbonyl$C_{1-8}$alkylene.

The present invention provides in another group of embodiments, a compound having the formula:

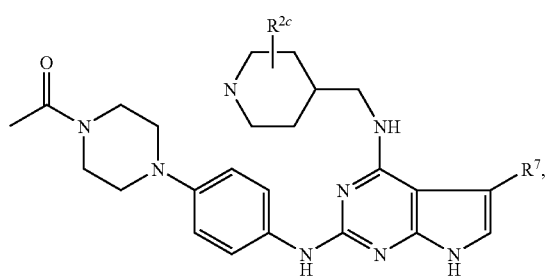

wherein $R^{2c}$ is aminocarbonyl, amino$C_{1-8}$alkylene or hydroxy; and $R^7$ is selected from the group consisting of halo, hydroxy, $C_{1-8}$alkoxy$C_{1-8}$alkylene, $C_{1-8}$alkylcarbonyl, cyano, phenyl and pyridinyl.

The present invention provides in another group of embodiments, a compound having the formula:

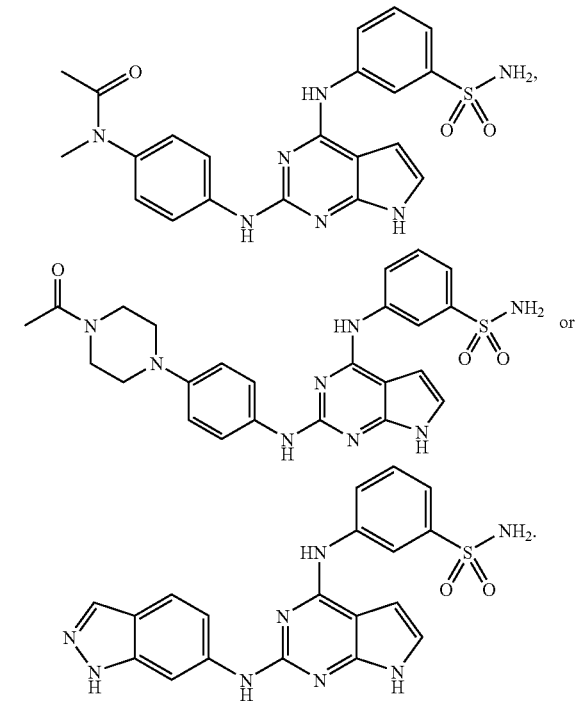

The present invention provides in another group of embodiments, a compound having the formula:

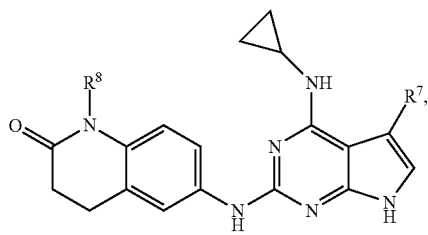

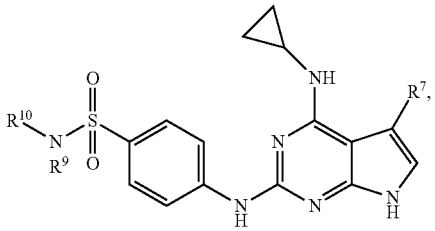

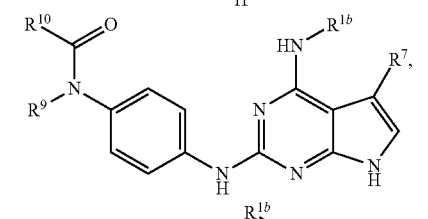

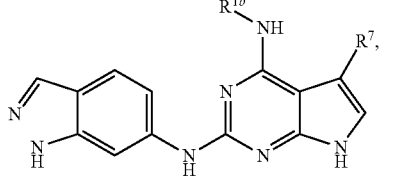

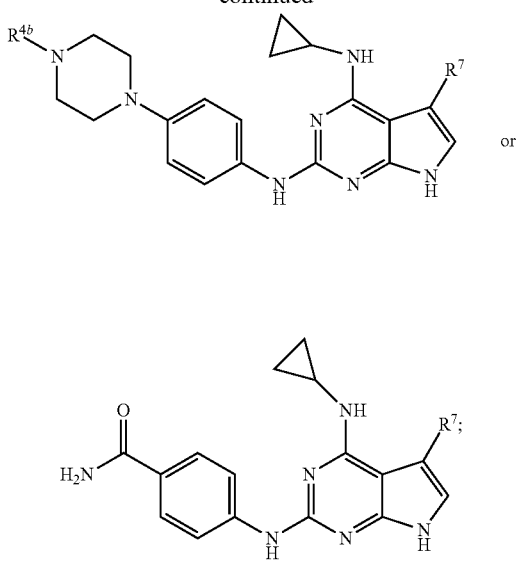

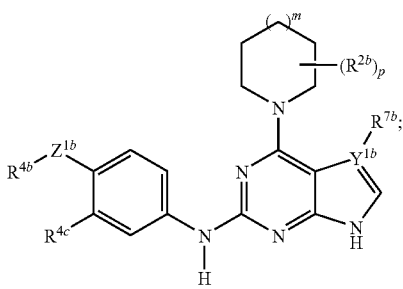

wherein $R^{1b}$ is $C_{1-8}$alkyl, $C_{3-8}$cycloalkyl, aryl or heteroaryl; each of which is optionally substituted with hydroxy, $C_{1-8}$alkoxy or amino$C_{1-8}$alkoxy; $R^{4b}$ is H or $CH_3CO$—; $R^7$ is H, $C_{1-8}$alkyl, $C_{1-8}$alkylcarbonyl, aminocarbonyl, cyano, phenyl or pyridinyl; $R^9$ is H or $C_{1-8}$alkyl; and $R^{10}$ is H, $C_{1-8}$alkyl, $C_{1-8}$alkoxy, $C_{1-8}$alkoxycarbonyl$C_{1-8}$alkylene, amino$C_{1-8}$alkylene, aminocarbonyl$C_{1-8}$alkylene, carboxy$C_{1-8}$alkylene, $C_{3-8}$cycloalkyl and hydroxy$C_{1-8}$alkylene.

The present invention provides in another group of embodiments, a compound having the formula Ib:

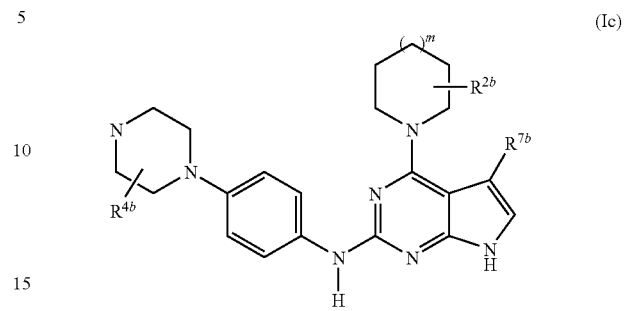

or a tautomer or pharmaceutically acceptable salt thereof wherein:

$Y^{1b}$ is C or N;

each $R^{2b}$ is independently selected from the group consisting of amino, amino$C_{1-8}$alkylene, aminocarbonyl, aminocarbonyl$C_{1-8}$alkylene, carboxy, carboxy$C_{1-8}$alkylene, $C_{1-8}$alkoxycarbonyl, $C_{1-8}$alkoxycarbonyl$C_{1-8}$alkylene and hydroxy;

$R^{4b}$ is $C_{1-8}$alkylcarbonyl;

$Z^{1b}$ is -heterocyclyl;

$R^{4c}$ is H;

$R^{7b}$ is H, cyano, pyridinyl or null;

m is 0 or 1; and p is 0 or 1.

The present invention provides in another group of embodiments, a compound having the formula Ic:

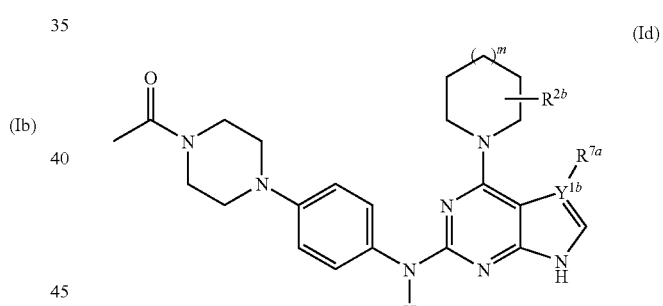

or a tautomer or a pharmaceutically acceptable salt thereof; wherein:

$R^{2b}$ is selected from the group consisting of H, amino$C_{1-8}$alkylene, aminocarbonyl, aminocarbonyl$C_{1-8}$alkylene, hydroxy, hydroxycarbonyl$C_{1-8}$alkylene, $C_{1-8}$alkoxycarbonyl and $C_{1-8}$alkoxycarbonyl$C_{1-8}$alkylene;

$R^{4b}$ is H or $CH_3CO$—;

$R^{7b}$ is H, cyano or pyridinyl; and m is 0 or 1.

The present invention provides in another group of embodiments, a compound having the formula Id:

(Id)

[structure]

or a tautomer or a pharmaceutically acceptable salt thereof; wherein:

$Y^{1b}$ is C or N;

$R^{2b}$ is selected from the group consisting of H, amino, amino$C_{1-8}$alkylene, aminocarbonyl, aminocarbonyl$C_{1-8}$alkylene, hydroxy, hydroxycarbonyl$C_{1-8}$alkylene, carboxy, $C_{1-8}$carboxyalkylene, $C_{1-8}$alkoxycarbonyl and $C_{1-8}$alkoxycarbonyl$C_{1-8}$alkylene;

$R^{7a}$ is H, $C_{1-8}$alkyl, halo, hydroxy, $C_{1-8}$alkoxy$C_{1-8}$alkylene, $C_{1-8}$alkylcarbonyl, cyano or pyridinyl; and m is 0 or 1.

In another group of embodiments, m is 0; and $R^{7a}$ is selected from the group consisting of H, cyano or pyridinyl. In another group of embodiments, m is 1; and $R^{7a}$ is selected from the group consisting of H, cyano or pyridinyl.

The present invention provides in another group of embodiments, a compound having the formula:

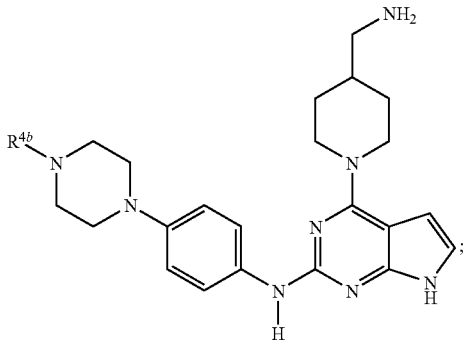

and $R^{4b}$ is H or $CH_3CO-$.

The present invention provides in another group of embodiments, a compound having the formula Ie:

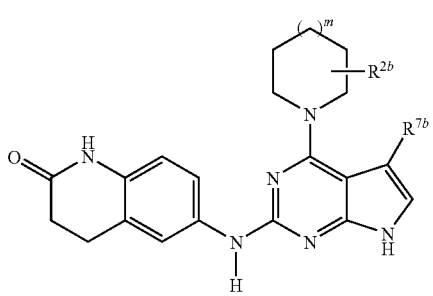

(Ie)

or a tautomer or pharmaceutically acceptable salt thereof, wherein:

$R^{2b}$ is selected from the group consisting of H, amino$C_{1-8}$alkylene, aminocarbonyl, aminocarbonyl$C_{1-8}$alkylene, hydroxy, hydroxycarbonyl$C_{1-8}$alkylene, $C_{1-8}$alkoxycarbonyl and $C_{1-8}$alkoxycarbonyl$C_{1-8}$alkylene;

$R^{7b}$ is H, cyano, or pyridinyl; and m is 0 or 1.

The present invention provides in another embodiment, a compound having the formula:

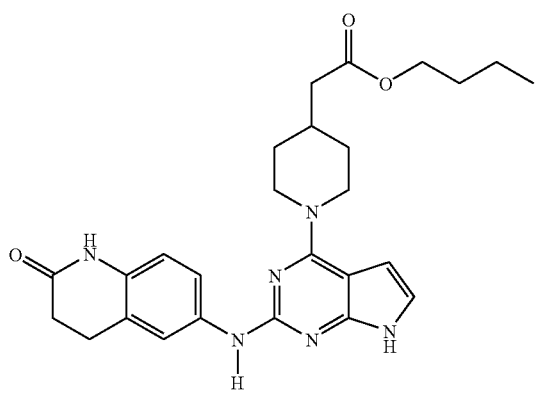

or a tautomer or a pharmaceutically acceptable salt thereof.

The present invention provides in another group of embodiments, a compound having the formula II:

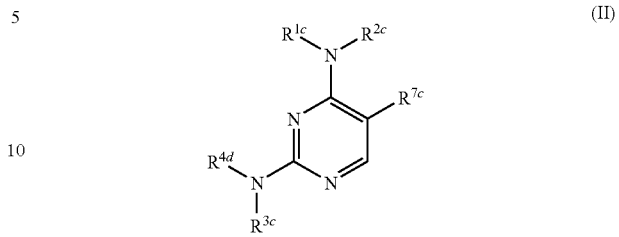

(II)

or a tautomer or a pharmaceutically acceptable salt thereof, wherein:

$R^{1c}$ is selected from the group consisting of (a) $C_{3-8}$cycloalkyl, and (b) aryl, each of which is optionally substituted with from 1 to 2 substituents selected from the group consisting of $C_{1-8}$alkyl, amino and hydroxyl; or is taken together with $R^{2c}$ to form a heterocyclic ring, containing 1-3 heteroatoms, including N, O, S, optionally substituted with from 1 to 2 substituents, each of which is independently selected from the group consisting of aminocarbonyl$C_{1-8}$alkylene, $C_{1-8}$alkoxycarbonyl, amino $C_{1-8}$ alkylene, hydroxy$C_{1-8}$alkylene, $C_{1-8}$alkoxycarbonylamino$C_{1-8}$alkylene, amino, aminocarbonylaminocarbonylamino, aryl$C_{1-8}$alkoxycarbonylamino, aminocarbonylamino and oxo;

$R^{2c}$ is H or is taken together with $R^{1c}$ to form a heterocyclic ring, optionally cyano$C_{1-8}$alkylcarbonyl, cyano$C_{1-6}$alkylcarbonylamino substituted with from 1 to 2 substituents independently selected from the group consisting of aminocarbonyl$C_{1-8}$alkylene, $C_{1-8}$alkoxycarbonyl, amino$C_{1-8}$alkylene, hydroxy$C_{1-8}$alkylene, $C_{1-8}$alkoxycarbonylamino$C_{1-8}$alkylene, amino, aminocarbonylaminocarbonylamino, aryl$C_{1-8}$alkoxycarbonylamino, aminocarbonylamino and oxo;

$R^{3c}$ is H or taken together with $R^{4d}$ to form a heterocyclic or heteroaryl ring, each of which is optionally substituted with from 1 to 2 substituents independently selected from the group consisting of $C_{1-8}$alkyl, $C_{1-8}$alkylheterocyclyl, amino$C_{1-8}$alkylene, aminoaryl, hydroxy$C_{1-8}$alkylene, aminocarbonyl, $C_{1-8}$alkoxycarbonyl, amino, imino, $C_{1-8}$alkylcarbonylamino, oxo, halo, aryl, heterocyclyl, heterocyclyl$C_{1-8}$alkylene and $C_{1-8}$alkylheterocyclyl$C_{1-8}$alkylene;

$R^{4d}$ is independently selected from the group consisting of (a) $C_{3-8}$cycloalkyl, (b) aryl, (c) heteroaryl, and (d) heterocyclyl; each of which is optionally substituted with from 1 to 3 substituents $R^{4e}$, $R^{4f}$ and $-Z^{1c}R^{4g}$, each of which is independently selected from the group consisting of $C_{1-8}$alkyl, amino$C_{1-8}$alkylene, hydroxy$C_{1-8}$alkylene, aminocarbonyl, $C_{1-8}$alkoxycarbonyl, carboxy, amino, imino, $C_{1-8}$alkylcarbonylamino, oxo, halo, aryl, heterocyclyl and heterocyclyl$C_{1-8}$alkylene, provided that at least one of $R^{1c}$ and $R^{2c}$ or $R^{3c}$ and $R^{4d}$ are combined with the nitrogen to which each is attached to form a heterocyclyl or heteroaryl ring; and $R^{7c}$ is selected from the group consisting of H, $C_{1-8}$alkyl, $C_{2-8}$alkynyl, cyano, aminocarbonyl, nitro, $C_{1-8}$alkoxy, halogen, aryl, heteroaryl and $C_{3-8}$cycloalkyl.

The present invention provides in another group of embodiments, a compound having the formula IIa:

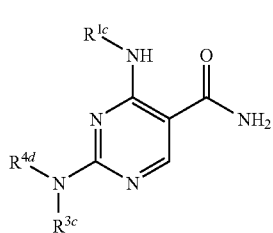

(IIa)

or a tautomer or a pharmaceutically acceptable salt thereof.

In another group of embodiments, $R^{3c}$ is H.

In another group of embodiments, $R^{4d}$ is phenyl. In another group of embodiments, $R^{4d}$ is indazyl. In another group of embodiments, $R^{4d}$ is cyclohexyl. In another group of embodiments, $R^{4d}$ is dihydroindoyl.

In another group of embodiments, $R^{3c}$ is taken together with $R^{4d}$ and the nitrogen to which is each is attached to form heterocyclic ring selected from the group consisting of pyridinyl, imidazolyl, tetrahydroimidazoyl, indazolyl, piperidinyl, piperazinyl, pyrrolidinyl, triazoyl and benzamidazoyl.

In another group of embodiments, $R^{4d}R^{3c}N-$ is selected from the group consisting of:

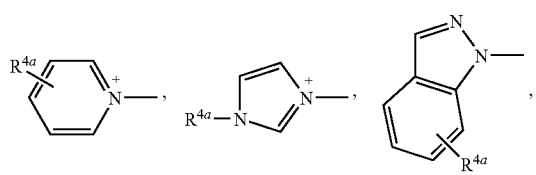

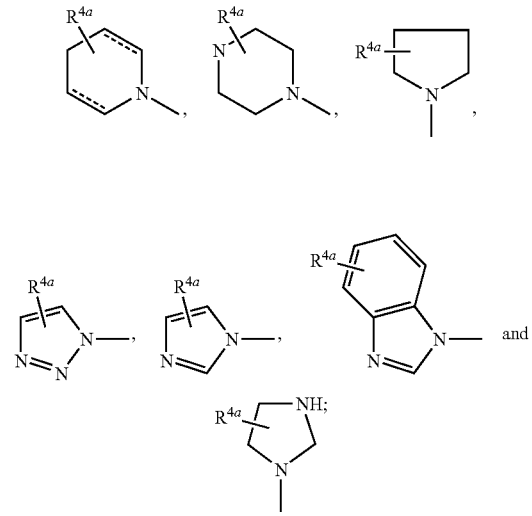

the dashed lined indicates a single or double bond; and the wavy line indicates the point of attachment to the remainder of the molecule.

The present invention provides in another group of embodiments, a compound having the formula IIb:

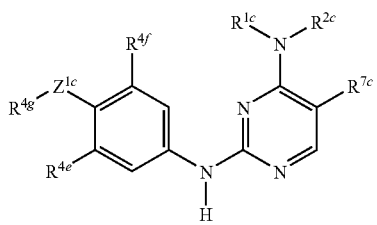

(IIb)

or a tautomer or a pharmaceutically acceptable salt thereof, wherein:

$R^{7c}$ is halo;

$R^{1c}$ and $R^{2c}$ are taken together to form a heterocyclic ring, optionally substituted with from 1 to 2 substituents independently selected from the group consisting of:

aminocarbonyl$C_{1-8}$alkylene, $C_{1-8}$alkoxycarbonyl, amino$C_{1-8}$alkylene, hydroxy$C_{1-8}$alkylene, $C_{1-8}$alkoxycarbonylamino$C_{1-8}$alkylene, amino, aminocarbonylaminocarbonylamino, aryl$C_{1-8}$alkoxycarbonylamino, aminocarbonylamino and oxo;

$Z^{1c}$ is heterocyclyl, $-N(C_{1-4}\text{alkyl})-$, $-SO_2-$ or $-CO-$;

$R^{4g}$ is selected from the group consisting of H, $C_{1-8}$alkoxy, $C_{1-8}$alkylcarbonyl, $C_{1-8}$alkylcarbonylamino, amino, aminocarbonylamino$C_{1-8}$alkylene, aminocarbonyl and aminosulfonyl;

each $R^{4e}$ and $R^{4f}$ is independently selected from the group consisting of H—, $C_{1-8}$alkoxy and $C_{1-8}$alkylcarbonyl; or can be taken together with $-Z^{1c}-R^{4g}$ and the benzene ring to which each is attached to form a fused heterocyclic ring system, optionally substituted with from 1 to 2 oxo substituents, halogens, $C_{1-8}$alkyl, $C_{1-8}$alkyl.

The present invention provides in another group of embodiments, a compound, wherein the moiety

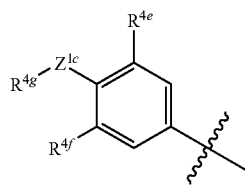

is selected from the group consisting of:

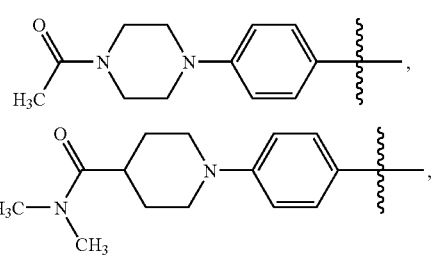

-continued

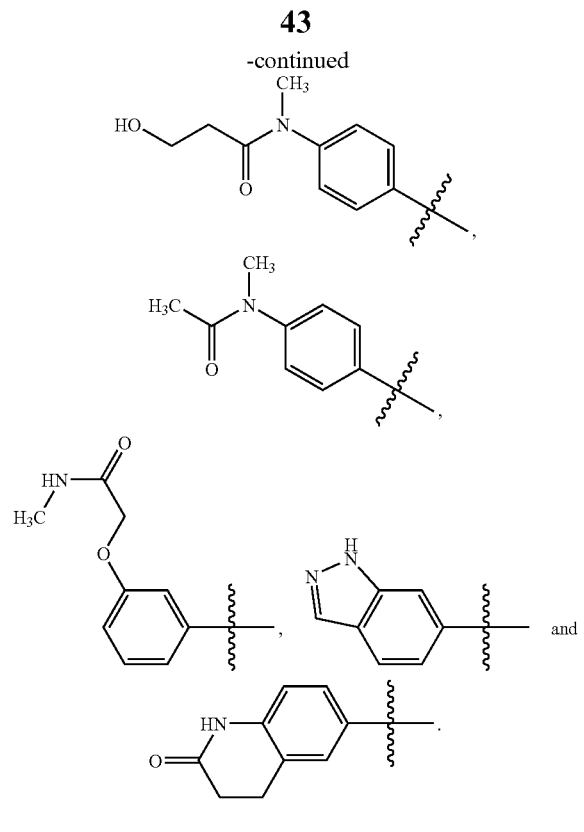

In another group of embodiments, $R^{7c}$ is selected from the group consisting of F, Cl, Br, cyano and aminocarbonyl. In another group of embodiments, $R^{7c}$ is $CONH_2$ or F. In another group of embodiments, $R^{1c}$ is $C_{3-8}$cycloalkyl. In another group of embodiments, $R^{1c}$ is cyclohexyl. In another group of embodiments, $R^{1c}$ is cyclopropyl. In another group of embodiments, $R^{1c}$ is cyclobutyl. In another group of embodiments, $R^{1c}$ is aryl. In another group of embodiments, $R^{1c}$ is phenyl.

In another group of embodiments, $R^{2c}$ is taken together with $R^{1c}$ and the nitrogen to which each is attached to form a pyrrolidinyl, piperidinyl or piperazinyl, diazapenyl ring.

The present invention provides in another group of embodiments, a compound having the formula:

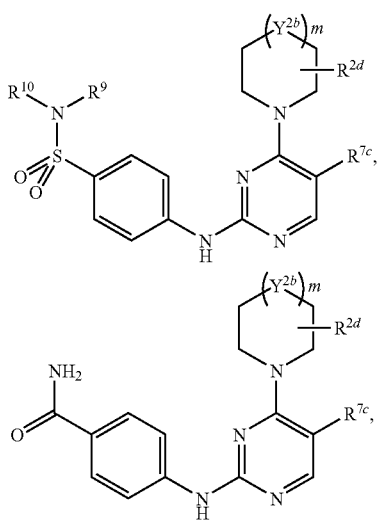

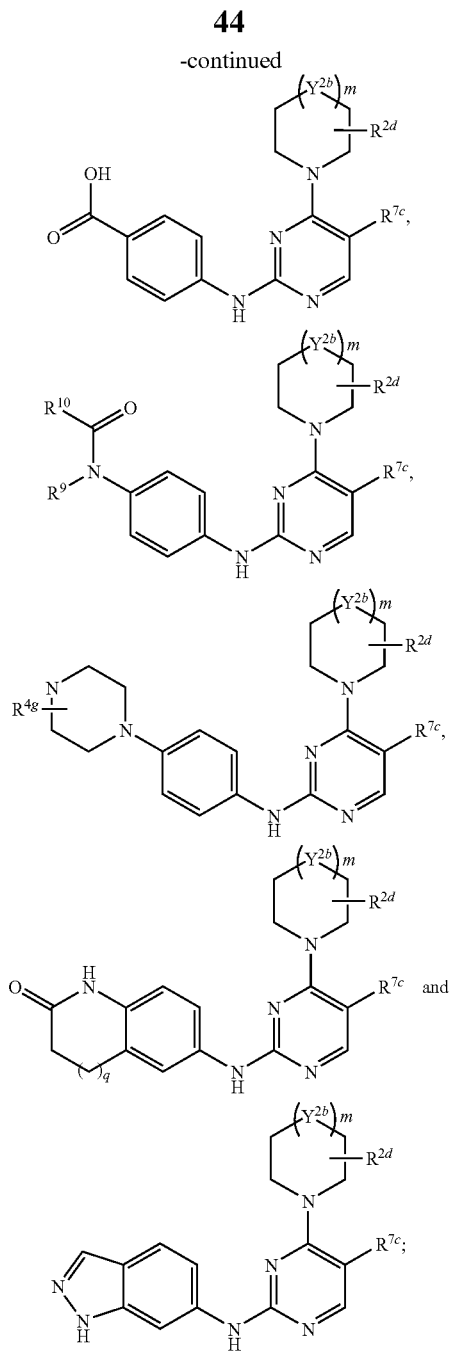

wherein $Y^{2b}$ is N, NH, C or CH; $R^{2d}$ is H, $C_{1-8}$alkylamino$C_{1-8}$alkylene, aminocarbonyl, aminocarbonylamino, aminocarbonylaminocarbonylamino, amino, oxo, amino$C_{1-8}$alkylene, aminocarbonylamino$C_{1-8}$alkylene, hydroxy$C_{1-8}$alkylene, arylalkoxycarbonylamino; cyano$C_{1-8}$alkylenecarbonyl, cyano$C_{1-8}$alkylenecarbonylamino, hydroxyl, $C_{1-8}$alkoxycarbonyl, alkoxycarbonyl$C_{1-8}$alkylene, optionally substituted by amino; and $R^{7c}$ is H, halo, aminocarbonyl, cycloalkyl, cyano or pyridinyl; $R^9$ is H or $C_{1-8}$alkyl; $R^{10}$ is H, $C_{1-8}$alkyl, $C_{1-8}$alkoxy, $C_{1-8}$alkoxycarbonyl$C_{1-8}$alkylene, amino$C_{1-8}$alkylene, aminocarbonyl$C_{1-8}$alkylene, carboxy$C_{1-8}$alkylene, $C_{3-8}$cycloalkyl and hydroxy$C_{1-8}$alkylene; m is 0 or 1; and q is 0 or 1.

In another group of embodiments, $R^{7c}$ is selected from the group consisting of F, Cl, Br, cyano and aminocarbonyl. In another group of embodiments, $R^{7c}$ is $CONH_2$ or F.

The present invention provides in another group of embodiments, a compound having the formula:

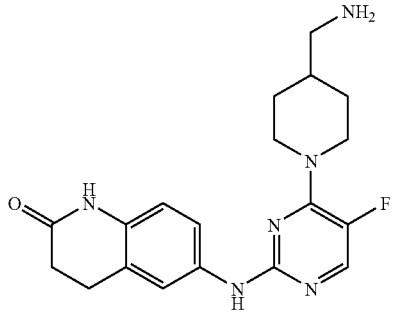

or a tautomer or a pharmaceutically acceptable salt thereof.

The present invention provides in another embodiment, a compound selected from the group consisting of N2-(1H-indazol-6-yl)-N4-methyl-5-(pyridin-4-yl)-7H-pyrrolo[2,3-d]pyrimidine-2,4-diamine; 1-(4-(4-(4-(methylamino)-5-(pyridin-4-yl)-7H-pyrrolo[2,3-d]pyrimidin-2-ylamino)phenyl)piperazin-1-yl)ethanone; N2-(1H-indazol-6-yl)-N4-methyl-5-(pyridin-3-yl)-7H-pyrrolo[2,3-d]pyrimidine-2,4-diamine; 1-(4-(4-(4-(cyclopropylamino)-5-(pyridin-4-yl)-7H-pyrrolo[2,3-d]pyrimidin-2-ylamino)phenyl)piperazin-1-yl)ethanone; 4-(4-aminophenyl)-1-(5-carbamoyl-4-(cyclopropylamino)pyrimidin-2-yl)pyridinium; 1-(4-aminophenyl)-3-(5-carbamoyl-4-(cyclopropylamino)pyrimidin-2-yl)-1H-imidazol-3-ium; 2-(6-amino-7-chloro-1H-indazol-1-yl)-4-(cyclopropylamino)pyrimidine-5-carboxamide; 1-(2-(4-(piperazin-1-yl)phenylamino)-7H-pyrrolo[2,3-d]pyrimidin-4-yl)piperidine-3-carboxamide; 1-(2-(4-(4-acetylpiperazin-1-yl)phenylamino)-7H-pyrrolo[2,3-d]pyrimidin-4-yl)piperidine-3-carboxamide; 4-(4-(aminomethyl)piperidin-1-yl)-N-(4-(piperazin-1-yl)phenyl)-7H-pyrrolo[2,3-d]pyrimidin-2-amine; 1-(4-(4-(4-(aminomethyl)piperidin-1-yl)-7H-pyrrolo[2,3-d]pyrimidin-2-ylamino)phenyl)piperazin-1-yl)ethanone; (S)-1-(2-(4-(piperazin-1-yl)phenylamino)-7H-pyrrolo[2,3-d]pyrimidin-4-yl)pyrrolidin-3-ol; (S)-1-(4-(4-(4-(3-hydroxypyrrolidin-1-yl)-7H-pyrrolo[2,3-d]pyrimidin-2-ylamino)phenyl)piperazin-1-yl)ethanone; 2-(4-(4-acetylpiperazin-1-yl)phenylamino)-4-(4-(aminomethyl)piperidin-1-yl)-7H-pyrrolo[2,3-d]pyrimidine-5-carbonitrile; 1-(4-(4-(6-(4-(aminomethyl)piperidin-1-yl)-9H-purin-2-ylamino)phenyl)piperazin-1-yl)ethanone; N-(4-(4-(aminomethyl)piperidin-1-yl)-5-fluoropyrimidin-2-yl)-1H-indazol-6-amine; 4-(4-(aminomethyl)piperidin-1-yl)-5-fluoro-N-(3,4,5-trimethoxyphenyl)pyrimidin-2-amine; 1-(4-(4-(4-(aminomethyl)piperidin-1-yl)-5-fluoropyrimidin-2-ylamino)phenyl)piperazin-1-yl)ethanone; N-(4-(piperazin-1-yl)phenyl)-4-(piperidin-1-yl)-7H-pyrrolo[2,3-d]pyrimidin-2-amine and 1-(4-(4-(4-(piperidin-1-yl)-7H-pyrrolo[2,3-d]pyrimidin-2-ylamino)phenyl)piperazin-1-yl)ethanone; N-(4-(piperazin-1-yl)phenyl)-4-(pyrrolidin-1-yl)-7H-pyrrolo[2,3-d]pyrimidin-2-amine and 1-(4-(4-(4-(pyrrolidin-1-yl)-7H-pyrrolo[2,3-d]pyrimidin-2-ylamino)phenyl)piperazin-1-yl)ethanone; 1-(2-(4-(piperazin-1-yl)phenylamino)-7H-pyrrolo[2,3-d]pyrimidin-4-yl)piperidine-4-carboxamide and 1-(2-(4-(4-acetylpiperazin-1-yl)phenylamino)-7H-pyrrolo[2,3-d]pyrimidin-4-yl)piperidine-4-carboxamide; 2-(4-(4-acetylpiperazin-1-yl)phenylamino)-4-(4-(aminomethyl)piperidin-1-yl)pyrimidine-5-carboxamide; 1-(2-(1H-indazol-6-ylamino)-5-fluoropyrimidin-4-yl)piperidine-3-carboxamide; 1-(2-(4-(4-acetylpiperazin-1-yl)phenylamino)-5-fluoropyrimidin-4-yl)piperidine-3-carboxamide; tert-butyl (1-(5-fluoro-2-(4-(N-methylacetamido)phenylamino)pyrimidin-4-yl)piperidin-4-yl)methylcarbamate; N-(4-(4-(4-(aminomethyl)piperidin-1-yl)-5-fluoropyrimidin-2-ylamino)phenyl)-N-methylacetamide; tert-butyl (1-(2-(4-carbamoylphenylamino)-5-fluoropyrimidin-4-yl)piperidin-4-yl)methylcarbamate; 4-(4-(4-(aminomethyl)piperidin-1-yl)-5-fluoropyrimidin-2-ylamino)benzamide; 4-(4-(4-(aminomethyl)piperidin-1-yl)-5-fluoropyrimidin-2-ylamino)benzenesulfonamide; 6-(4-(4-(aminomethyl)piperidin-1-yl)-5-fluoropyrimidin-2-ylamino)-3,4-dihydroquinolin-2(1H)-one; 1-(4-(4-(4-(2-(aminomethyl)piperidin-1-yl)-5-fluoropyrimidin-2-ylamino)phenyl)piperazin-1-yl)ethanone; tert-butyl (1-(2-(1H-indazol-6-ylamino)-5-fluoropyrimidin-4-yl)piperidin-2-yl)methylcarbamate and N-(4-(2-(aminomethyl)piperidin-1-yl)-5-fluoropyrimidin-2-yl)-1H-indazol-6-amine; 1-((1-(5-fluoro-2-(2-oxo-1,2,3,4-tetrahydroquinolin-6-ylamino)pyrimidin-4-yl)piperidin-4-yl)methyl)urea; 1-(4-(4-(5-fluoro-4-(hydroxymethyl)piperidin-1-yl)pyrimidin-2-ylamino)phenyl)piperazin-1-yl)ethanone; 6-(5-fluoro-4-(hydroxymethyl)piperidin-1-yl)pyrimidin-2-ylamino)-3,4-dihydroquinolin-2(1H)-one; 2-(1H-indazol-6-ylamino)-4-(cyclopropylamino)-7H-pyrrolo[2,3-d]pyrimidine-5-carbonitrile; 5-(1-butoxyethyl)-N4-cyclopropyl-N2-(1H-indazol-6-yl)-7H-pyrrolo[2,3-d]pyrimidine-2,4-diamine; 1-(2-(1H-indazol-6-ylamino)-4-(cyclopropylamino)-7H-pyrrolo[2,3-d]pyrimidin-5-yl)ethanone; N4-cyclopropyl-N2-(1H-indazol-6-yl)-5-(pyridin-4-yl)-7H-pyrrolo[2,3-d]pyrimidine-2,4-diamine; 1-(4-(4-(4-(piperidin-4-ylmethylamino)-5-(pyridin-4-yl)-7H-pyrrolo[2,3-d]pyrimidin-2-ylamino)phenyl)piperazin-1-yl)ethanone; 2-(4-(4-acetylpiperazin-1-yl)phenylamino)-4-(piperidin-4-ylmethylamino)-7H-pyrrolo[2,3-d]pyrimidine-5-carbonitrile; 2-(4-(4-acetylpiperazin-1-yl)phenylamino)-4-(4-(aminomethyl)piperidin-1-yl)-7H-pyrrolo[2,3-d]pyrimidine-5-carbonitrile; N-(4-(4-(cyclopropylamino)-5-(pyridin-4-yl)-7H-pyrrolo[2,3-d]pyrimidin-2-ylamino)phenyl)-N-methylacetamide; 6-(4-(cyclopropylamino)-5-(pyridin-4-yl)-7H-pyrrolo[2,3-d]pyrimidin-2-ylamino)-3,4-dihydroquinolin-2(1H)-one; 5-bromo-N4-cyclobutyl-N2-(1H-indazol-6-yl)-7H-pyrrolo[2,3-d]pyrimidine-2,4-diamine; 5-chloro-N4-cyclobutyl-N2-(1H-indazol-6-yl)-7H-pyrrolo[2,3-d]pyrimidine-2,4-diamine; 2-(1H-indazol-6-ylamino)-4-(cyclobutylamino)-6,7-dihydropyrrolo[2,3-d]pyrimidin-5-one; 1-(2-(4-(piperazin-1-yl)phenylamino)-7H-pyrrolo[2,3-d]pyrimidin-4-yl)piperidine-3-carboxamide; 1-(2-(4-(4-acetylpiperazin-1-yl)phenylamino)-7H-pyrrolo[2,3-d]pyrimidin-4-yl)piperidine-3-carboxamide; 4-(4-(aminomethyl)piperidin-1-yl)-N-(4-(piperazin-1-yl)phenyl)-7H-pyrrolo[2,3-d]pyrimidin-2-amine; 1-(4-(4-(4-(aminomethyl)piperidin-1-yl)-7H-pyrrolo[2,3-d]pyrimidin-2-ylamino)phenyl)piperazin-1-yl)ethanone; (S)-4-(2-(aminomethyl)pyrrolidin-1-yl)-N-(1H-indazol-6-yl)-7H-pyrrolo[2,3-d]pyrimidin-2-amine; (S)-1-(2-(4-(piperazin-1-yl)phenylamino)-7H-pyrrolo[2,3-d]pyrimidin-4-yl)pyrrolidin-3-ol; (S)-1-(4-(4-(4-(3-hydroxypyrrolidin-1-yl)-7H-pyrrolo[2,3-d]pyrimidin-2-ylamino)phenyl)piperazin-1-yl)ethanone; 2-(4-(4-acetylpiperazin-1-yl)phenylamino)-4-(4-(aminomethyl)piperidin-1-yl)-7H-pyrrolo[2,3-d]pyrimidine-5-carbonitrile; 2-(4-(4-acetylpiperazin-1-yl)phenylamino)-4-(3-(hydroxymethyl)piperidin-1-yl)pyrimidine-5-carboxamide; 2-(4-(4-acetylpiperazin-1-yl)phenylamino)-4-(2-(2-hydroxyethyl)piperidin-1-yl)pyrimidine-5-carboxamide; 1-(4-(4-(6-(4-(aminomethyl)

piperidin-1-yl)-9H-purin-2-ylamino)phenyl)piperazin-1-yl)ethanone; (S)-4-(3-aminopiperidin-1-yl)-N-(1H-indazol-6-yl)-7H-pyrrolo[2,3-d]pyrimidin-2-amine; (S)-1-(4-(4-(4-(3-aminopiperidin-1-yl)-7H-pyrrolo[2,3-d]pyrimidin-2-ylamino)phenyl)piperazin-1-yl)ethanone; N-(4-(4-(aminomethyl)piperidin-1-yl)-5-fluoropyrimidin-2-yl)-1H-indazol-6-amine; 4-(4-(aminomethyl)piperidin-1-yl)-5-fluoro-N-(3,4,5-trimethoxyphenyl)pyrimidin-2-amine; 1-(4-(4-(4-(aminomethyl)piperidin-1-yl)-5-fluoropyrimidin-2-ylamino)phenyl)piperazin-1-yl)ethanone; N-(4-(piperazin-1-yl)phenyl)-4-(piperidin-1-yl)-7H-pyrrolo[2,3-d]pyrimidin-2-amine; 1-(4-(4-(4-(piperidin-1-yl)-7H-pyrrolo[2,3-d]pyrimidin-2-ylamino)phenyl)piperazin-1-yl)ethanone; N-(4-(piperazin-1-yl)phenyl)-4-(pyrrolidin-1-yl)-7H-pyrrolo[2,3-d]pyrimidin-2-amine; 1-(4-(4-(4-(pyrrolidin-1-yl)-7H-pyrrolo[2,3-d]pyrimidin-2-ylamino)phenyl)piperazin-1-yl)ethanone; 1-(2-(4-(piperazin-1-yl)phenylamino)-7H-pyrrolo[2,3-d]pyrimidin-4-yl)piperidine-4-carboxamide; 1-(2-(4-(4-acetylpiperazin-1-yl)phenylamino)-7H-pyrrolo[2,3-d]pyrimidin-4-yl)piperidine-4-carboxamide; 2-(4-(4-acetylpiperazin-1-yl)phenylamino)-4-(4-(aminomethyl)piperidin-1-yl)pyrimidine-5-carboxamide; 1-(2-(1H-indazol-6-ylamino)-5-fluoropyrimidin-4-yl)piperidine-3-carboxamide; 1-(2-(4-(4-acetylpiperazin-1-yl)phenylamino)-5-fluoropyrimidin-4-yl)piperidine-3-carboxamide; 2-(4-(4-acetylpiperazin-1-yl)phenylamino)-4-(4-(2-hydroxyethyl)-1,4-diazepan-1-yl)pyrimidine-5-carboxamide; tert-butyl (1-(5-fluoro-2-(4-(N-methylacetamido)phenylamino)pyrimidin-4-yl)piperidin-4-yl)methylcarbamate; tert-butyl (1-(2-(4-carbamoylphenylamino)-5-fluoropyrimidin-4-yl)piperidin-4-yl)methylcarbamate; 4-(4-(4-(aminomethyl)piperidin-1-yl)-5-fluoropyrimidin-2-ylamino)benzamide; 4-(4-(4-(aminomethyl)piperidin-1-yl)-5-fluoropyrimidin-2-ylamino)benzenesulfonamide; N-(4-(4-(4-(aminomethyl)piperidin-1-yl)-5-fluoropyrimidin-2-ylamino)phenyl)-N-methylacetamide; 6-(4-(4-(aminomethyl)piperidin-1-yl)-5-fluoropyrimidin-2-ylamino)-3,4-dihydroquinolin-2(1H)-one; 1-(4-(4-(4-(2-(aminomethyl)piperidin-1-yl)-5-fluoropyrimidin-2-ylamino)phenyl)piperazin-1-yl)ethanone; tert-butyl (1-(2-(1H-indazol-6-ylamino)-5-fluoropyrimidin-4-yl)piperidin-2-yl)methylcarbamate; and N-(4-(2-(aminomethyl)piperidin-1-yl)-5-fluoropyrimidin-2-yl)-1H-indazol-6-amine.

The present invention provides in another embodiment, a compound selected from the group consisting of 1-(4-(4-(cyclobutylamino)-7H-pyrrolo[2,3-d]pyrimidin-2-ylamino)phenylsulfonyl)piperidin-4-ol; butyl 2-(4-(4-(cyclobutylamino)-7H-pyrrolo[2,3-d]pyrimidin-2-ylamino)-N-methylphenylsulfonamido)acetate; 2-(4-(4-(cyclobutylamino)-7H-pyrrolo[2,3-d]pyrimidin-2-ylamino)phenylsulfonamido)acetamide; 2-(4-(4-(cyclobutylamino)-7H-pyrrolo[2,3-d]pyrimidin-2-ylamino)-N-methylphenylsulfonamido)acetic acid; 1-(4-(4-(cyclobutylamino)-7H-pyrrolo[2,3-d]pyrimidin-2-ylamino)phenyl)piperidin-4-ol; tert-butyl 4-(2-(1H-indazol-6-ylamino)-7H-pyrrolo[2,3-d]pyrimidin-4-ylamino)piperidine-1-carboxylate; N2-(1H-indazol-6-yl)-N4-(piperidin-4-yl)-7H-pyrrolo[2,3-d]pyrimidine-2,4-diamine; N4-cyclobutyl-N2-(1H-indazol-6-yl)-6-methyl-7H-pyrrolo[2,3-d]pyrimidine-2,4-diamine; N4-(3-amino-2,2-dimethylpropyl)-N2-(1H-indazol-6-yl)-7H-pyrrolo[2,3-d]pyrimidine-2,4-diamine; N2-(1H-indazol-6-yl)-N4-(3-morpholinopropyl)-7H-pyrrolo[2,3-d]pyrimidine-2,4-diamine; N-(4-(4-aminobutylamino)-7H-pyrrolo[2,3-d]pyrimidin-2-ylamino)phenyl)-N-methylacetamide; N-(4-(4-(2-aminocyclohexylamino)-7H-pyrrolo[2,3-d]pyrimidin-2-ylamino)phenyl)-N-methylacetamide; N-(4-(4-(2-aminoethylamino)-7H-pyrrolo[2,3-d]pyrimidin-2-ylamino)phenyl)-N-methylacetamide; N-(4-(4-(5-aminopentylamino)-7H-pyrrolo[2,3-d]pyrimidin-2-ylamino)phenyl)-N-methylacetamide; 1-(4-(4-(4-aminocyclohexylamino)-7H-pyrrolo[2,3-d]pyrimidin-2-ylamino)phenyl)piperazin-1-yl)ethanone; N-(4-(4-(5-aminopentylamino)-5-bromo-7H-pyrrolo[2,3-d]pyrimidin-2-ylamino)phenyl)-N-methylacetamide; N-(4-(4-(5-aminopentylamino)-5,6-dibromo-7H-pyrrolo[2,3-d]pyrimidin-2-ylamino)phenyl)-N-methylacetamide; N-(4-(4-(3-aminosulfonylphenylamino)-7H-pyrrolo[2,3-d]pyrimidin-2-ylamino)phenyl)-N-methylacetamide; Ethyl 2-(6-(4-(cyclobutyamino)-7H-pyrrolo[2,3-d]pyrimidine-2-ylamino)-2-oxo-3,4-dihydroquinolin-1(2H)-yl)acetate; 2-(6-(4-(cyclobutyamino)-7H-pyrrolo[2,3-d]pyrimidine-2-ylamino)-2-oxo-3,4-dihydroquinolin-1(2H)-yl)acetic acid; 2-(6-(4-(cyclobutyamino)-7H-pyrrolo[2,3-d]pyrimidine-2-ylamino)-2-oxo-3,4-dihydroquinolin-1(2H)-yl)-N-(2-(dimethylamino)ethyl)acetamide; methyl 4-(4-(cyclobutylamino)-7H-pyrrolo[2,3-d]pyrimidin-2-ylamino)phenyl(methyl)carbamate; methyl 4-(4-(cyclobutylamino)-7H-pyrrolo[2,3-d]pyrimidin-2-ylamino)phenyl(methyl)carbamate; N-(4-(4-(cyclobutylamino)-7H-pyrrolo[2,3-d]pyrimidin-2-ylamino)phenyl)-2-hydroxy-N-methylacetamide; N-(4-(4-(cyclopropylamino)-7H-pyrrolo[2,3-d]pyrimidin-2-ylamino)phenyl)-2-hydroxy-N-methylacetamide; $N^4$-cyclobutyl-$N^2$-(4-methylsulfonylmethyl)phenyl)-7H-pyrrolo[2,3-d]pyrimidin-2,4-diamine; $N^4$-cyclobutyl-$N^2$-(3-methylsulfonylmethyl)phenyl)-7H-pyrrolo[2,3-d]pyrimidin-2,4-diamine; 2-(3-(2-(1H-indazol-6-ylamino)-7H-pyrrolo[2,3-d]pyrimidin-4-ylamino)phenoxy-N-methylacetamide; $N^2$-(1H-indazol-6-yl)-7H-pyrrolo[2,3-d]pyrimidin-2,4-diamine; N-(4-(4-(cyclobutylamino)-7H-pyrrolo[2,3-d]pyrimidin-2-ylamino)phenyl)-N-methylcyclopropanecarboxamide; N-(4-(4-(cyclopropylamino)-7H-pyrrolo[2,3-d]pyrimidin-2-ylamino)phenyl)-N-methylcyclopropanecarboxamide; N-(4-(4-(methylamino)-7H-pyrrolo[2,3-d]pyrimidin-2-ylamino)phenyl)-N-methylcyclopropanecarboxamide; 2-(2-(1H-indazol-6-ylamino)-7H-pyrrolo[2,3-d]pyrimidin-4-ylamino)acetamide; N-(4-(4-(cyclobutylamino)-7H-pyrrolo[2,3-d]pyrimidin-2-ylamino)phenyl)-2-(dimethylamino)-N-methylacetamide; N-(4-(4-(cyclobutylamino)-7H-pyrrolo[2,3-d]pyrimidin-2-ylamino)-N-(3-dimethylaminopropyl)benzamide; N-(4-(4-(cyclobutylamino)-7H-pyrrolo[2,3-d]pyrimidin-2-ylamino)phenyl)-3-hydroxy-N-methylpropanamide; N-(4-(4-(cyclopropylamino)-7H-pyrrolo[2,3-d]pyrimidin-2-ylamino)phenyl)-3-hydroxy-N-methypropanamide; $N^2$-(1H-indazol-6-ylamino)-$N^4$-(1H-pyrazol-5-yl)-7H-pyrrolo[2,3-d]pyrimidine-2,4-diamine; $N^2$-(1H-indazol-6-ylamino)-$N^4$-(2-methoxyethyl)-7H-pyrrolo[2,3-d]pyrimidine-2,4-diamine; 1-(4-(4-(4-(2-methoxyethylamino)-7H-pyrrolo[2,3-d]pyrimidin-2-ylamino)phenyl)piperazin-1-yl)ethanone; $N^2$-(1H-indazol-6-ylamino)-$N^4$-(2-hydroxyethyl)-7H-pyrrolo[2,3-d]pyrimidine-2,4-diamine; $N^4$-(2-2-(aminoethoxy)ethyl)-$N^2$-(1H-indazol-6-ylamino)-7H-pyrrolo[2,3-d]pyrimidine-2,4-diamine; 1-(4-(4-(2-(2-aminoethoxy)amino)-7H-pyrrolo[2,3-d]pyrimidin-2-ylamino)phenyl)piperazin-1-yl)ethanone; (S)-1-(4-(4-(2-(2-aminoethoxy)ethylamino)-7H-pyrrolo[2,3-d]pyrimidin-2-ylamino)phenyl)pyrrolidine-2-carboxamide; 3-(2-(4-(4-acetylpiperazin-1-yl)phenylamino)-7H-pyrrolo[2,3-d]pyrimidin-4-ylamino)benzamide; 3-(2-(4-(piperazin-1-yl)phenylamino)-7H-pyrrolo[2,3-d]pyrimidin-4-ylamino)benzamide; 3-(2-(4-(4-acetylpiperazin-1-yl)phenylamino)-

7H-pyrrolo[2,3-d]pyrimidin-4-ylamino)benzenesulfonamide; 3-(2-(4-(piperazin-1-yl)phenylamino)-7H-pyrrolo[2,3-d]pyrimidin-4-ylamino)benzenesulfonamide; N-(4-(4-(3-(aminomethyl)phenylamino)-7H-pyrrolo[2,3-d]pyrimidin-2-ylamino)phenyl)-N-methylacetamide; (R)-1-(4-(4-(4-(1-hydroxypropan-2-ylamino)-7H-pyrrolo[2,3-d]pyrimidin-2-ylamino)phenyl)piperazin-1-yl)ethanone; (R)-2-(2-(4-(piperazin-1-yl)phenylamino)-7H-pyrrolo[2,3-d]pyrimidin-4-ylamino)propan-1-ol; (S)-1-(4-(4-(4-(1-hydroxypropan-2-ylamino)-7H-pyrrolo[2,3-d]pyrimidin-2-ylamino)phenyl)piperazin-1-yl)ethanone; (S)-2-(2-(4-(piperazin-1-yl)phenylamino)-7H-pyrrolo[2,3-d]pyrimidin-4-ylamino)propan-1-ol; 1-(4-(4-(4-(1,1-dioxy-tetrahydrothiophen-3-ylamino)-7H-pyrrolo[2,3-d]pyrimidin-2-ylamino)phenyl)piperazin-1-yl)ethanone; N2-(4-(piperazin-1-yl)phenyl)-N4-(1,1-dioxy-tetrahydrothiophen-3-yl)-7H-pyrrolo[2,3-d]pyrimidine-2,4-diamine; 4-(4-(cyclopropylamino)-5-(pyridin-4-yl)-7H-pyrrolo[2,3-d]pyrimidin-2-ylamino)benzamide; 4-(4-amino-5-(pyridin-4-yl)-7H-pyrrolo[2,3-d]pyrimidin-2-ylamino)benzoic acid; 4-(cyclopropylamino)-2-(2-oxo-1,2,3,4-tetrahydroquinolin-6-ylamino)-7H-pyrrolo[2,3-d]pyrimidine-5-carbonitrile; 4-(5-cyano-4-(cyclopropylamino)-7H-pyrrolo[2,3-d]pyrimidin-2-ylamino)benzamide; N-(4-(5-cyano-4-(cyclopropylamino)-7H-pyrrolo[2,3-d]pyrimidin-2-ylamino)phenyl)-N-methylacetamide; 4-(5-cyano-4-(cyclopropylamino)-7H-pyrrolo[2,3-d]pyrimidin-2-ylamino)benzenesulfonamide; 2-(4-(4-acetylpiperazin-1-yl)phenylamino)-4-(cyclopropylamino)-7H-pyrrolo[2,3-d]pyrimidine-5-carbonitrile; 4-(cyclopropylamino)-2-(2-oxo-1,2,3,4-tetrahydroquinolin-6-ylamino)-7H-pyrrolo[2,3-d]pyrimidine-5-carboxamide; 4-(4-(1-(2-cyanoacetyl)piperidin-4-ylamino)-7H-pyrrolo[2,3-d]pyrimidin-2-ylamino)benzamide; 4-(4-(1-(2-cyanoacetyl)piperidin-3-ylamino)-7H-pyrrolo[2,3-d]pyrimidin-2-ylamino)benzamide; 4-(4-methoxyphenylamino)-2-(2-oxo-1,2,3,4-tetrahydroquinolin-6-ylamino)-7H-pyrrolo[2,3-d]pyrimidine-5-carbonitrile; 6-(4-(4-fluorophenylamino)-5-(pyridin-4-yl)-7H-pyrrolo[2,3-d]pyrimidin-2-ylamino)-1-methyl-3,4-dihydroquinolin-2(1H)-one; 6-(4-Amino-5-(4-fluorophenyl)-7H-pyrrolo[2,3-d]pyrimidin-2-ylamino)-1-methyl-3,4-dihydroquinolin-2(1H)-one; 6-(4-(benzylamino)-5-(pyridin-4-yl)-7H-pyrrolo[2,3-d]pyrimidin-2-ylamino)-1-methyl-3,4-dihydroquinolin-2(1H)-one; 4-(Benzylamino)-2-(1-methyl-2-oxo-1,2,3,4-tetrahydroquinolin-6-ylamino)-7H-pyrrolo[2,3-d]pyrimidine-5-carbonitrile; Butyl 1-(2-(4-(4-acetylpiperazin-1-yl)phenylamino)-9H-purin-6-yl)piperidine-3-carboxylate; 1-(2-(4-(4-acetylpiperazin-1-yl)phenylamino)-9H-purin-6-yl)piperidine-3-carboxylic acid; 1-(2-(4-(piperazin-1-yl)phenylamino)-9H-purin-6-yl)piperidine-3-carboxylic acid; 1-(2-(4-(4-acetylpiperazin-1-yl)phenylamino)-9H-purin-6-yl)piperidine-3-carboxamide; butyl 2-(1-(2-(2-oxo-1,2,3,4-tetrahydroquinolin-6-ylamino)-7H-pyrrolo[2,3-d]pyrimidin-4-yl)piperidin-4-yl)acetate; 2-(1-(2-(2-oxo-1,2,3,4-tetrahydroquinolin-6-ylamino)-7H-pyrrolo[2,3-d]pyrimidin-4-yl)piperidin-4-yl)acetic acid; 2-(1-(2-(2-oxo-1,2,3,4-tetrahydroquinolin-6-ylamino)-7H-pyrrolo[2,3-d]pyrimidin-4-yl)piperidin-4-yl)acetamide; 1-(4-(4-(4-(aminomethyl)piperidin-1-yl)-5-chloropyrimidin-2-ylamino)phenyl)piperazin-1-yl)ethanone; 6-(5-fluoro-4-(3-oxopiperazin-1-yl)pyrimidin-2-ylamino)-3,4-dihydroquinolin-2(1H)-one; 1-(4-(4-(5-fluoro-4-(piperazin-1-yl)pyrimidin-2-ylamino)phenyl)piperazin-1-yl)ethanone; 4-(2-(4-(4-acetylpiperazin-1-yl)phenylamino)-5-fluoropyrimidin-4-yl)piperazine-1-carboxamide; 2-(1-(2-(4-(4-acetylpiperazin-1-yl)phenylamino)-5-fluoropyrimidin-4-yl)piperidin-4-yl)acetamide; Benzyl 1-(2-(4-(4-acetylpiperazin-1-yl)phenylamino)-5-fluoropyrimidin-4-yl)piperidin-4-ylcarbamate; 1-(4-(4-(4-(4-aminopiperidin-1-yl)-5-fluoropyrimidin-2-ylamino)phenyl)piperazin-1-yl)ethanone; 1-(1-(2-(4-(4-acetylpiperazin-1-yl)phenylamino)-5-fluoropyrimidin-4-yl)piperidin-4-yl)urea; 2-(4-(4-acetylpiperazin-1-yl)phenylamino)-4-(4-(ureidomethyl)piperidin-1-yl)pyrimidine-5-carboxamide; 4-(4-(4-(aminomethyl)piperidin-1-yl)-5-fluoropyrimidin-2-ylamino)benzoic acid; 6-(4-(4-(aminomethyl)piperidin-1-yl)-5-bromopyrimidin-2-ylamino)-3,4-dihydroquinolin-2(1H)-one; 4-(4-(4-((dimethylamino)methyl)piperidin-1-yl)-5-fluoropyrimidin-2-ylamino)benzamide; ethyl 3-amino-3-(1-(5-fluoro-2-(2-oxo-1,2,3,4-tetrahydroquinolin-6-ylamino)pyrimidin-4-yl)piperidin-4-yl)propanoate; methyl 2-amino-2-(1-(5-fluoro-2-(2-oxo-1,2,3,4-tetrahydroquinolin-6-ylamino)pyrimidin-4-yl)piperidin-4-yl)acetate; N-(1-(2-(4-(4-acetylpiperazin-1-yl)phenylamino)-5-fluoropyrimidin-4-yl)piperidin-4-yl)-2-cyanoacetamide; 3-(4-(2-(4-(4-acetylpiperazin-1-yl)phenylamino)-5-fluoropyrimidin-4-yl)piperazin-1-yl)-3-oxopropanenitrile; 6-(4-(4-(aminomethyl)piperidin-1-yl)-5-(pyridin-4-yl)pyrimidin-2-ylamino)-3,4-dihydroquinolin-2(1H)-one; 6-(4-(4-(aminomethyl)piperidin-1-yl)-5-cyclopropylpyrimidin-2-ylamino)-3,4-dihydroquinolin-2(1H)-one; 6-(4-((1s,4s)-4-aminocyclohexylamino)-5-fluoropyrimidin-2-ylamino)-3,4-dihydroquinolin-2(1H)-one; 4-(4-((1s,4s)-4-aminocyclohexylamino)-5-fluoropyrimidin-2-ylamino)benzamide; 1-(4-(4-(4-((1s,4s)-4-aminocyclohexylamino)-5-fluoropyrimidin-2-ylamino)phenyl)piperazin-1-yl)ethanone; 6-(4-((1s,4s)-4-aminocyclohexylamino)-5-(pyridin-4-yl)pyrimidin-2-ylamino)-3,4-dihydroquinolin-2(1H)-one and 6-(4-((1s,4s)-4-aminocyclohexylamino)-5-cyclopropylpyrimidin-2-ylamino)-3,4-dihydroquinolin-2(1H)-one.

The present invention provides in another embodiment, a compound of the examples.

The present invention provides in another embodiment, a compound of any one of the tables.

The present invention provides in another embodiment, a compound of any one of the figures.

It is understood that in another group of embodiments, any of the above embodiments may also be combined with other embodiments listed herein, to form other embodiments of the invention.

b. Methods of Synthesis

The compounds of the present invention may be prepared by known organic synthesis techniques, including the methods described in more detail in the Examples. In general, the compounds of structure (I) above may be made by the following FIG. 1, wherein all substituents are as defined above unless indicated otherwise.

Compounds having formula I may be prepared according to FIG. 1. 2,4-dichloropyrrolopyrimidine 1.1 is protected with a protecting group, such as a tosyl group. Selective displacement of the 4-chloro group of the 2,4-dichloropyrrolopyrimidine by an appropriate amine, such as $R^2$—NH—$R^1$ (available commercially or synthesized using methods known to those skilled in the art), under basic conditions, such as with diisopropylamine (DIA), provides compounds of formula 1.3. Subsequent displacement of the chloro group with an appropriate amine, such as $R^4$—NH.$R^3$ (available commercially or synthesized using methods known to those skilled in the art), gives compound 1.4. Subsequent hydrolysis of the protecting group with hydroxide in an alcohol solvent gives the desired product I, wherein $R^1$, $R^2$, $R^3$ and $R^4$ are as previously defined, wherein $R^1$, $R^2$, $R^3$ and $R^4$ are as previously defined.

Compounds having formula II may be prepared according to FIG. 2. Carboxylic acid 2.1 is converted to acid chloride 2.2 via a one-step procedure by treatment with a chlorination agent, such as thionyl chloride, and esterification with an alcohol, such as ethanol, to form compound 2.3 using conditions similar to that described below. Ester 2.3 is dichlorinated with a chlorinating agent, such as phosphorous oxychloride. Selective displacement of the 4-chloro group of the 2,4-dichloropyrimidine by an appropriate amine, such as $R^2$—NH—$R^1$ (available commercially or synthesized using methods known to those skilled in the art), under basic conditions, such as with diisopropylamine (DIA), provides compounds of formula 2.5. Subsequent hydrolysis of the ester, displacement of the second chloro group with EDC and treatment with ammonia gives compound 2.7. Benzotriazolyl ether compound 2.7 may also be prepared through a linear route. Displacement of the benzotriazolyl ether group with an appropriate amine, such as $R^4$—NH.$R^3$ (available commercially or synthesized using methods known to those skilled in the art), gives the desired product IIa, wherein $R^1$, $R^2$, $R^3$ and $R^4$ are as previously defined.

Compounds having formula II may be prepared according to FIG. 3. Selective displacement of the 4-chloro group of the 2,4-dichloropyrimidine by an appropriate amine, such as $R^2$—NH—$R^1$ (available commercially or synthesized using methods known to those skilled in the art), under basic conditions, such as with diisopropylamine (DIA), provides compounds of formula 3.2. Displacement of the chloro group with an appropriate amine, such as $R^4$—NH—$R^3$ (available commercially or synthesized using methods known to those skilled in the art), gives the desired product IIb, wherein $R^1$, $R^2$, $R^3$ and $R^4$ are as previously defined.

One skilled in the art will recognize that in certain embodiments of structures (I-II) when $R^1$ or $R^2$ comprises a terminal heteroatom, it may be advantageous to use a protecting group strategy. The protecting group can be removed using methods known to those skilled in the art to yield compounds of structure (I-II).

The compounds of the present invention may generally be utilized as the free base. Alternatively, the compounds of this invention may be used in the form of acid addition salts as described below.

c. Inhibition of syk and JAK Kinases

The activity of a specified compound as an inhibitor of a JAK kinase may be assessed in vitro or in vivo. In some embodiments, the activity of a specified compound can be tested in a cellular assay. Selectivity could also be ascertained in biochemical assays with isolated kinases.

Similar types of assays can be used to assess JAK kinase inhibitory activity and to determine the degree of selectivity of the particular compound as compared to syk kinase. One means of assaying for such inhibition is detection of the effect of the compounds of the present invention on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (e.g., the 2,4-substituted pyrimindinediamine compounds described herein) on the JAK1 and JAK3 kinases, human Ramos B-cells are stimulated with human IL-4. 10' post-stimulation, cells are subjected to intracellular flow cytometry to measure the extent of STAT-6 phosphorylation. 20 to 24 hours post-stimulation, cells are stained for upregulation of CD23 and analyzed using flow cytometry. A reduction of the amount of phosphohorylated STAT-6 and/or cell surface CD23 present compared to control conditions indicates that the test compound actively inhibits the JAK kinase pathway.

Additionally, IL-6 stimulation of Ramos B-cells induces JAKs 1, 2, and Tyk2, leading to Stat-3 and Erk phosphorylation. 10' post-stimulation, cells are subjected to intracellular flow cytometry to measure the ability of compound to inhibit these phosphorylation events. To specifically measure the activity of JAK2, the CellSensor irf1-bla HEL cell line expressing the beta-lactamase reporter gene controlled by Stat5 will be used (Invitrogen, Carlsbad, Calif.). These cells express a constitutively active JAK2 mutant (JAK2V617F), found naturally in myeloproliferative neoplasms (Constantinescu, S., et. al, *Trends Biochem Sci.*, 2008; 33:122-31). A reduction in the amount of beta-lactamase reporter gene expression is used a measure of the JAK2 inhibitory activity of compounds.

The activity of the compounds of the invention may additionally be characterized by assaying the effect of the compounds of the present invention described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFN.gamma. induces ICAM-1 up-regulation through activation of the JAK1/JAK2 pathway. The up-regulation of ICAM-1 can be quantified by flow cytometry across a compound dose curve and $EC_{50}$ values are calculated.

The activity of the compounds of the invention may additionally be characterized by assaying the effect of the compounds of the present invention described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFN.gamma. induces ICAM-1 up-regulation through activation of the JAK1/JAK2 pathway. The up-regulation of ICAM-1 can be quantified by flow cytometry across a compound dose curve and $EC_{50}$ values are calculated. Exemplary assays of this type are described in greater detail in the Examples.

Active compounds as described herein generally inhibit the JAK kinase pathway with an $IC_{50}$ in the range of about 1 mM or less, as measured in the assays described herein. Of course, skilled artisans will appreciate that compounds which exhibit lower $IC_{50}$s, (on the order, for example, of 100 μM, 75 μM, 50 μM, 40 μM, 30 μM, 20 μM, 15 μM, 10 μM, 5 μM, 1 μM, 500 nM, 100 nM, 10 nM, 1 nM, or even lower) can be particularly useful in therapeutic applications. In instances where activity specific to a particular cell type is desired, the compound can be assayed for activity with the desired cell type and counter-screened for a lack of activity against other cell types. The desired degree of "inactivity" in such counter screens, or the desired ratio of activity vs. inactivity, may vary for different situations and can be selected by the user.

The active compounds also typically inhibit IL-4 stimulated expression of CD23 in B-cells with an $IC_{50}$ in the range of about 20 µM or less, typically in the range of about 10 µM, 1 µM, 500 nM, 100 nM, 10 nM, 1 nM, or even lower. A suitable assay that can be used is the assay described in the Examples, "Assay for Ramos B-cell Line Stimulated with IL-4." In certain embodiments, the active compounds of the present invention have an $IC_{50}$ of less than or equal to 5 µM, greater than 5 µM but less than 20 µM, greater than 20 µM, or greater than 20 µM but less than 50 µM in the assay described in the Examples.

The active compounds also typically inhibit expression of ICAM1 (CD54) induced by IFN.gamma. exposure in U937 or A549 cells with an $IC_{50}$ in the range of about 20 µM or less, typically in the range of about 10 µM, 1 µM, 500 nM, 100 nM, 10 nM, 1 nM, or even lower. The $IC_{50}$ against expression of ICAM (CD54) in IFN.gamma. stimulated cells can be determined in a functional cellular assay with an isolated A549 or U937 cell line. Suitable assays that can be used are the assays described in the Examples, "A549 Epithelial Line Stimulated with IFNγ" and "U937 IFN.gamma. ICAM1 FACS Assay," respectively. In certain embodiments, the active compounds of the present invention have an $IC_{50}$ of less than or equal to 20 µM, greater than 20 µM, or greater than 20 µM but less than 50 µM in the assays described in the Examples.

d. Compositions and Methods of Administration

The present invention further provides compositions comprising one or more compounds of formula (I) or a pharmaceutically acceptable salt, ester or prodrug thereof, and a pharmaceutically acceptable carrier or diluent. It will be appreciated that the compounds of formula (I)) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula (I), similar to metabolically labile esters or carbamates, which are capable of producing the parent compounds of formula (I) in vivo, are within the scope of this invention.

As used herein, the term "pharmaceutically acceptable salts" refers to any acid or base addition salt whose counterions are non-toxic to the patient in pharmaceutical doses of the salts. A host of pharmaceutically acceptable salts are well known in the pharmaceutical field. If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

The term "unit dosage form" refers to physically discrete units suitable as unitary dosages for human subjects and other mammals, each unit containing a predetermined quantity of drug calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of one or more syk and/or JAK inhibitors.

Methods for preparing such dosage forms are known to those skilled in the art (see, for example, REMINGTON'S PHARMACEUTICAL SCIENCES, 18TH ED., Mack Publishing Co., Easton, Pa. (1990)). In addition, pharmaceutically acceptable salts of the syk and/or JAK inhibitors of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of one or more syk and/or JAK inhibitors, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The compositions can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents.

Administration of a composition comprising one or more syk and/or JAK inhibitors with one or more suitable pharmaceutical excipients as advantageous can be carried out via any of the accepted modes of administration. Thus, administration can be, for example, oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation. According to a representative embodiment, the compositions of this invention are formulated for pharmaceutical administration to a mammal, preferably a human being.

The compositions of the present invention containing one or more syk and/or JAK inhibitors can be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical compositions of this invention may be in any orally acceptable dosage form, including tablets, capsules, cachets, emulsions, suspensions, solutions, syrups, elixirs, sprays, boluses, lozenges, powders, granules, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, the compositions take the form of a pill, tablet, or capsule, and thus, the composition can contain, along with one or more syk and/or JAK inhibitors, a diluent such as lactose, sucrose, dicalcium phosphate, and the like; a disintegrant such as starch or derivatives thereof; a lubricant such as magnesium stearate and the like; and/or a binder such a starch, gum acacia, polyvinylpyrrolidone, gelatin, cellulose and derivatives thereof. A tablet can be made by any compression or molding process known to those of skill in the art. Compressed tablets may be prepared by compressing in a suitable machine the syk and/or JAK inhibitors in a free-flowing form, e.g., a powder or granules, optionally mixed with accessory ingredients, e.g., binders, lubricants, diluents, disintegrants, or dispersing agents. Molded tablets can be made by molding in a suitable machine a mixture of the powdered syk and/or JAK inhibitors with any suitable carrier.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax, polyethylene glycol (PEG), hard fat, and/or hydrogenated cocoglyceride. Compositions suitable for rectal administration may also comprise a rectal enema unit containing one or more syk and/or JAK inhibitors and pharmaceutically-acceptable vehicles (e.g., 50% aqueous ethanol or an aqueous salt solution) that are physiologically compatible with the rectum and/or colon. The rectal enema unit contains an applicator tip protected by an inert cover, preferably comprised of polyethylene, lubricated with a lubricant such as white petrolatum, and preferably protected by a one-way valve to prevent back-flow of the dispensed formula. The rectal enema unit is also of sufficient length, preferably two inches, to be inserted into the colon via the anus.

Liquid compositions can be prepared by dissolving or dispersing one or more syk and/or JAK inhibitors and optionally one or more pharmaceutically acceptable adjuvants in a carrier such as, for example, aqueous saline, aqueous dextrose, glycerol, ethanol, and the like, to form a solution or suspension, e.g., for oral, topical, or intravenous administration. Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs. For topical administration, the composition containing one or more syk and/or JAK inhibitors can be in the form of emulsions, lotions, gels, foams, creams, jellies, solutions, suspensions, ointments, and transdermal patches.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

The pharmaceutical compositions of this invention may also be administered by nasal aerosol or inhalation. For delivery by inhalation, the compositions can be delivered as a dry powder or in liquid form via a nebulizer. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

For parenteral administration, the compositions can be in the form of sterile injectable solutions and sterile packaged powders. Preferably, injectable solutions are formulated at a pH of about 4.5 to about 7.5.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Any of the above dosage forms containing effective amounts are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

e. Methods of Use

The invention provides methods of inhibiting or decreasing syk and/or JAK activity as well as treating or ameliorating a syk and/or JAK associated state, symptom, condition, disorder or disease in a patient in need thereof (e.g., human or non-human). In one embodiment, the syk and/or JAK associated state, symptom, condition, disorder or disease is mediated, at least in part by syk and/or JAK kinase activity. In more specific embodiments, the present invention provides a method for treating a condition or disorder mediated at least in part by syk and/or JAK kinase activity is cardiovascular disease, inflammatory disease or autoimmune disease.

In one embodiment, the invention provides methods for preventing or treating a condition in a mammal characterized by undesired thrombosis comprising the step of administering to the mammal a therapeutically effective amount of a compound of the present invention. Such conditions include, but are not limited, to restenosis, acute coronary syndrome, myocardial infarction, unstable angina, refractory angina, occlusive coronary thrombosis occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolism, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

In a further embodiment, the present invention provides a method for treating thrombosis, immune thrombocytic purura, heparin induced thrombocytopenia, dilated cardiomypathy, sickle cell disease, atherosclerosis, myocardial infarction, vascular inflammation, unstable angina or acute coronary syndromes.

In another embodiment, the present invention also provides a method for treating allergy, asthma, rheumatoid arthritis, B Cell mediated disease such as Non-Hodgkin's Lymphoma, anti phospholipids syndrome, lupus, psoriasis, multiple sclerosis, end stage renal disease or chronic lymphocytic leukemia.

In another embodiment, the present invention provides a method for treating hemolytic anemia or immune thrombocytopenic purpura.

The compounds described herein are also potent and/or selective inhibitors of JAK kinases. As a consequence of this activity, the compounds can be used in a variety of in vitro, in vivo, and ex vivo contexts to regulate or inhibit JAK kinase activity, signaling cascades in which JAK kinases play a role, and the biological responses effected by such signaling cascades. For example, in one embodiment, the compounds can be used to inhibit JAK kinase, either in vitro or in vivo, in virtually any cell type expressing the JAK kinase, such as in hematopoietic cells in which, for example, JAK3 is predominantly expressed. They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15, and IL-21 receptor signaling cascades. The compounds may also be used in vitro or in vivo to regulate, and in particular to inhibit, cellular or biological responses affected by such JAK-dependent signal transduction cascades. Such cellular or biological responses include, but are not limited to, IL-4/ramos CD23 upregulation and IL-2 mediated T-cell proliferation. Importantly, the compounds can be used to inhibit JAK kinases in vivo as a therapeutic approach towards the treatment or prevention of diseases mediated, either wholly or in part, by a JAK kinase activity (referred to herein as "JAK kinase mediated diseases"). Non-limiting examples of JAK kinase mediated diseases that can be treated or prevented with the compounds include, but are not limited to, the following: allergies; asthma; autoimmune diseases such as transplant rejection (e.g., kidney, heart, lung, liver, pancreas, skin, small intestine, large intestine, host versus graft reaction (HVGR), and graft versus host reaction (GVHR)), rheumatoid arthritis, and amyotrophic lateral sclerosis; T-cell mediated autoimmune diseases such as multiple sclerosis, psoraiasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliteraus and primary pulmonary hypertension; solid, delayed Type IV hypersensitivity reactions; and hematologic malignancies such as leukemia and lymphomas.

Examples of diseases that are mediated, at least in part, by JAK kinases that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoraiasis and Sjogren's syndrome, Type II inflammatory disease such as vascular inflammation (including vasculitis, ateritis, atherosclerosis and coronary artery disease) or other inflammatory diseases such as osteoarthritis, inflammatory bowel disease, ulcerative colitis, Crohn's disease, idiopathic inflammatory bowel disease, irritable bowel syndrome, spastic colon, low grade scarring (e.g., scleroderma, increased fibrosis, keloids, post-surgical scars, pulmonary fibrosis, vascular spasms, migraine, reperfusion injury and post myocardial infarction), and sicca complex or syndrome, diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lyphomas.

In another embodiment, this invention provides a method of inhibiting an activity of a JAK kinase, comprising contacting the JAK kinase with an amount of a compound effective to inhibit an activity of the JAK kinase, wherein the compound is selected from the compounds of this invention. In certain embodiments of the methods described herein, the method is carried out in vivo.

In another embodiment, this invention provides a method of inhibiting an activity of a JAK kinase, comprising contacting in vitro a JAK3 kinase with an amount of a compound effective to inhibit an activity of the JAK kinase, wherein the compound is selected from the compounds of this invention.

In a specific embodiment, the compounds can be used to treat and/or prevent rejection in organ and/or tissue transplant recipients (i.e., treat and/or prevent allograft rejection). Allografts can be rejected through either a cell-mediated or humoral immune reaction of the recipient against transplant (histocompability) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophages and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the compounds described herein can be used to treat and/or prevent many aspects of transplant rejection, and are particularly useful in the treatment and/or prevention of rejection reactions that are mediated, at least in part, by T-cells, such as HVGR or GVHR. The compounds can also be used to treat and/or prevent chronic rejection in transplant recipients and, in particular, in renal transplant recipients. The compound can also be administered to a tissue or an organ prior to transplanting the tissue or organ in the transplant recipient.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention. In certain embodiments of the methods the autoimmune disease is multiple sclerosis (MS), psoraisis, or Sjogran's syndrome. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be .beta.-cell (humoral) based or T-cell based, include Cogan's syndrome, ankylosing spondylitis, Wegener's granulomatosis, autoimmune alopecia, Type I or juvenile onset diabetes, and thyroiditis.

The types of autoimmune diseases that may be treated or prevented with such prodrugs generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the prodrugs according to structural formulae (I) and (Ia). In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated.

Therapy using the compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the compounds could be administered either in combination or adjunctively with an inhibitor of a syk kinase. syk kinase is a tyrosine kinase known to play a critical role in Fcγ receptor signaling, as well as in other signaling cascades, such as those involving B-cell receptor signaling (Turner et al., (2000), Immunology Today 21:148-154) and integrins beta (1), beta (2), and beta (3) in neutrophils (Mocsai et al., (2002), Immunity 16:547-558). For example, syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed or cell-mediated Type IV hypersensitivity reactions, syk kinase helps regulate the pathways involved in immediate IgE-mediated, Type I hypersensitivity reactions. Certain compounds that affect the syk pathway may or may not also affect the JAK pathways.

Suitable syk inhibitory compounds are described, for example, in Ser. No. 10/355,543 filed Jan. 31, 2003 (publication no. 2004/0029902); WO 03/063794; Ser. No. 10/631,029 filed Jul. 29, 2003; WO 2004/014382; Ser. No. 10/903,263 filed Jul. 30, 2004; PCT/US2004/24716 filed Jul. 30, 2004 (WO005/016893); Ser. No. 10/903,870 filed Jul. 30, 2004; PCT/US2004/24920 filed Jul. 30, 2004; Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The described herein and syk inhibitory compounds could be used alone or in combination with one or more conventional transplant rejection treatments, as described above.

In a specific embodiment, the compounds can be used to treat or prevent these diseases in patients that are either initially non-responsive (resistant) to or that become non-responsive to treatment with a syk inhibitory compound or one of the other current treatments for the particular disease. The compounds could also be used in combination with syk inhibitory compounds in patients that are syk-compound resistant or non-responsive. Suitable syk-inhibitory compounds with which the compounds can be administered are provided infra.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compound is administered in combination with or adjunctively to a compound that inhibits syk kinase with an $IC_{50}$ in the range of at least 10 µM.

In another embodiment, this invention provides a method of treating or preventing allograft transplant rejection in a transplant recipient, comprising administering to the transplant recipient an amount of a compound effective to treat or prevent the rejection wherein the compound is selected from the compounds of the invention, as described herein. In a further embodiment, the compound is administered to a tissue or an organ prior to transplanting the tissue or organ in the transplant recipient.

In another embodiment, this invention provides a method of treating or preventing allograft transplant rejection in a transplant recipient, in which the rejection is acute rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is chronic rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is mediated by HVGR or GVHR, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection wherein the compound is selected from the compounds of the invention, as described herein, in which the compound is administered in combination with or adjunctively to another immunosuppressant.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of the invention, as described herein, in which the compound is administered in combination with or adjunctively to another immunosuppressant, in which the immunosuppressant is selected from cyclosporine, tacrolimus, sirolimus, an inhibitor of IMPDH, mycophenolate, mycophanolate mofetil, an anti-T-Cell antibody, and OKT3.

The compounds described herein are cytokine moderators of IL-4 signaling. As a consequence, the compounds could slow the response of Type I hypersensitivity reactions. Thus, in a specific embodiment, the compounds could be used to treat such reactions and, therefore, the diseases associated with, mediated by, or caused by such hypersensitivity reactions (for example, allergies), prophylactically. For example, an allergy sufferer could take one or more of the JAK selective compounds described herein prior to expected exposure to allergens to delay the onset or progress of, or eliminate altogether, an allergic response.

When used to treat or prevent such diseases, the compounds can be administered singly, as mixtures of one or more compounds, or in mixture or combination with other agents useful for treating such diseases and/or the symptoms associated with such diseases. The compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, beta.-agonists, tryptase inhibitors, aspirin, cyclooxygenase (COX) inhibitors, methotrexate, anti-TNF drugs, anti CD20 antibody, PD4 inhibitors, p38 inhibitors, PDE4 inhibitors, and antihistamines, to name a few. The compounds can be administered per se in the form of prodrugs or as pharmaceutical compositions, comprising an active compound or prodrug.

In another embodiment, this invention provides a method of treating or preventing a Type IV hypersensitivity reaction, comprising administering to a subject an amount of a compound effective to treat or prevent the hypersensitivity reaction, wherein the compound is selected from the compounds of this invention, as described herein.

In another embodiment, this invention provides a method of treating or preventing a Type IV hypersensitivity reaction, which is practical prophylactically, comprising administering to a subject an amount of a compound effective to treat or prevent the hypersensitivity reaction, wherein the compound is selected from the compounds of this invention, as described herein, and is administered prior to exposure to an allergen.

In another embodiment, this invention provides a method of inhibiting a signal transduction cascade in which JAK3 kinase plays a role, comprising contacting a cell expressing a receptor involved in such a signaling cascade with a compound wherein the compound is selected from the compounds of this invention, as described herein.

In another embodiment, this invention provides a method of treating or preventing a JAK kinase-mediated disease, comprising administering to a subject an amount of compound effective to treat or prevent the JAK kinase-mediated disease, wherein the compound is selected from the compounds of this invention, as described herein.

In another embodiment, this invention provides a method of treating or preventing a JAK kinase-mediated disease, in which the JAK-mediated disease is HVGR or GVHR, comprising administering to a subject an amount of compound effective to treat or prevent the JAK kinase-mediated disease, wherein the compound is selected from the compounds of the invention, as described herein.

In another embodiment, this invention provides a method of treating or preventing a JAK kinase-mediated disease, in which the JAK-mediated disease is acute allograft rejection, comprising administering to a subject an amount of compound effective to treat or prevent the JAK kinase-mediated disease, wherein the compound is selected from the compounds of the invention, as described herein.

In another embodiment, this invention provides a method of treating or preventing a syk and/or JAK kinase-mediated disease, in which the JAK-mediated disease is chronic allograft rejection, comprising administering to a subject an amount of compound effective to treat or prevent the JAK kinase-mediated disease, wherein the compound is selected from the compounds of the invention, as described herein.

Active compounds of the invention typically inhibit thesyk and/or JAK/Stat pathway. The activity of a specified compound as an inhibitor of a syk and/or JAK kinase can be assessed in vitro or in vivo. In some embodiments, the activity of a specified compound can be tested in a cellular assay.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds disclosed herein relate to any disorder characterized by aberrant cell proliferation. These include various tumors and cancers, benign or malignant, metastatic or nonmetastatic. Specific properties of cancers, such as tissue invasiveness or metastasis, can be targeted using the methods described herein. Cell proliferative disorders include a variety of cancers, including, among others, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) (Cynthia K. Hahn, Kenneth N. Ross, Rose M. Kakoza, Steven Karr, Jinyan Du, Shao-E Ong, Todd R. Golub, Kimberly Stegmaier, Syk is a new target for AML differentiation, Blood, 2007, 110, Abstract 209) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the syk and/or JAK inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9; 22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant syk and/or JAK activity can be treated with the syk and/or JAK inhibitory compounds.

In some embodiments, the compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16) (p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

"Treating" within the context of the invention means an alleviation of symptoms associated with a disorder or disease, or halt of further progression or worsening of those symptoms, or prevention or prophylaxis of the disease or disorder.

The term "mammal" includes organisms which express syk and/or JAK. Examples of mammals include mice, rats, cows, sheep, pigs, goats, horses, bears, monkeys, dogs, cats and, preferably, humans. Transgenic organisms which express syk and/or JAK are also included in this definition.

The inventive methods comprise administering an effective amount of a compound or composition described herein to a mammal or non-human animal. As used herein, "effective amount" of a compound or composition of the invention includes those amounts that antagonize or inhibit syk and/or JAK. An amount which antagonizes or inhibits syk and/or JAK is detectable, for example, by any assay capable of determining syk and/or JAK activity, including the one described below as an illustrative testing method. Effective amounts may also include those amounts which alleviate symptoms of a syk and/or JAK associated disorder treatable by inhibiting syk and/or JAK. Accordingly, "antagonists of syk" or "antagonists of JAK" include compounds which interact with the syk or JAK, respectively, and modulate, e.g., inhibit or decrease, the ability of a second compound, e.g., another syk or JAK ligand, to interact with the syk or JAK, respectively. The syk or JAK binding compounds are preferably antagonists of syk or JAK, respectively. The language "syk binding compound" and "JAK-binding compound" (e.g., exhibits binding affinity to the receptor) includes those compounds which interact with syk or JAK resulting in modulation of the activity of syk or JAK, respectively. syk and/or JAK binding compounds may be identified using an in vitro (e.g., cell and non-cell based) or in vivo method. A description of in vitro methods are provided below.

The amount of compound present in the methods and compositions described herein should be sufficient to cause a detectable decrease in the severity of the disorder, as measured by any of the assays described in the examples. The amount of syk and/or JAK modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the formula I, another therapeutic agent (e.g., methotrexate) or a pharmaceutically acceptable salt, ester or prodrug thereof, and a pharmaceutically acceptable excipient or carrier.

The invention comprises a compound having the formula I, a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease IBD, asthma, chronic obstructive pulmonary disease COPD and MS. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

All of the compounds of the present invention are either potent inhibitors of syk and/or JAK kinases, exhibiting $IC_{50}$s in the respective assay in the range of less than 5 μM, with most being in the nanomolar, and several in the sub-nanomolar, range. In some embodiments, the compounds of the present invention may be "dual" syk/JAK inhibitors in that they inhibit both syk and JAK kinase to some degree. In other embodiments, the compounds of the present invention may selectively inhibit syk kinase, but not appreciably inhibit one or more JAK kinases. In other embodiments, the compounds of the present invention may selectively inhibit JAK kinase, but not appreciably inhibit one or more syk kinases.

f. Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where syk and/or JAK plays a role.

EXAMPLES

The following examples are offered to illustrate, but not to limit, the claimed invention.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates may be characterized by high performance liquid chromatography (HPLC) using a Waters Alliance chromatography system with a 2695 Separation Module (Milford, Mass.). The analytical columns may be C-18 SpeedROD RP-18E Columns from Merck KGaA (Darmstadt, Germany). Alternately, characterization may be performed using a Waters Unity (HPLC) system with Waters Acquity HPLC BEH C-18 2.1 mm×15 mm columns. A gradient elution may be used, typically starting with 5% acetonitrile/95% water and progressing to 95% acetonitrile over a period of 5 minutes for the Alliance system and 1 minute for the Acquity system. All solvents may contain 0.1% trifluoroacetic acid (TFA). Compounds may be detected by ultraviolet light (UV) absorption at either 220 nm or 254 nm. HPLC solvents may be from EMD Chemicals, Inc. (Gibbstown, N.J.). In some instances, purity may be assessed by thin layer chromatography (TLC) using glass backed silica gel plates, such as, for example, EMD Silica Gel 60 2.5 cm×7.5 cm plates. TLC results may be readily detected visually under ultraviolet light, or by employing well known iodine vapor and other various staining techniques.

Mass spectrometric analysis may be performed on one of two Agilent 1100 series LCMS instruments with acetonitrile/water as the mobile phase. One system may use TFA as the modifier and measure in positive ion mode [reported as MH+, (M+1) or (M+H)+] and the other may use either formic acid or ammonium acetate and measure in both positive [reported as MH+, (M+1) or (M+H)+] and negative [reported as M−, (M−1) or (M−H)−] ion modes.

Nuclear magnetic resonance (NMR) analysis may be performed on some of the compounds with a Varian 400 MHz NMR (Palo Alto, Calif.). The spectral reference may be either TMS or the known chemical shift of the solvent.

The purity of some of the invention compounds may be assessed by elemental analysis (Robertson Microlit, Madison, N.J.).

Melting points may be determined on a Laboratory Devices MeI-Temp apparatus (Holliston, Mass.).

Preparative separations may be carried out as needed, using either an Sq16x or an Sg100c chromatography system and prepackaged silica gel columns all purchased from Teledyne Isco, (Lincoln, Nebr.). Alternately, compounds and intermediates may be purified by flash column chromatography using silica gel (230-400 mesh) packing material, or by HPLC using a C-18 reversed phase column. Typical solvents employed for the Isco systems and flash column chromatography may be dichloromethane, methanol, ethyl acetate, hexane, acetone, aqueous hydroxyamine and triethyl amine. Typical solvents employed for the reverse phase HPLC may be varying concentrations of acetonitrile and water with 0.1% trifluoroacetic acid.

General Methods

The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

Example 1

N2-(1H-indazol-6-yl)-N4-methyl-5-(pyridin-4-yl)-7H-pyrrolo[2,3-d]pyrimidine-2,4-diamine

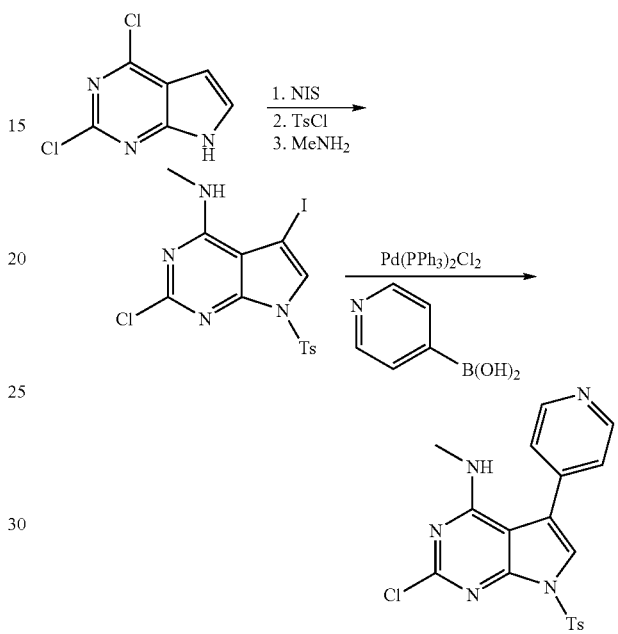

To a suspension of 2,4-dichloro-7H-pyrrolo[2,3-d]pyrimidine (2.0 g, 10.6 mmol) in DCM (32 mL) was added NIS (2.4 g, 10.6 mmol) at room temperature. After stirring for 1 h, the resulting precipitate was collected by filtration to give 2,4-dichloro-5-iodo-7H-pyrrolo[2,3-d]pyrimidine (1.8 g).

To a mixture of 2,4-dichloro-5-iodo-7H-pyrrolo[2,3-d]pyrimidine (1.80 g, 5.73 mmol) in DCM (20 ml) was added TsCl (1.09 g, 5.73 mmol) and TEA (1.60 mL, 11.46 mmol), followed by DMAP (70 mg, 0.573 mmol). After stirring for 1 h at room temperature, the solution was concentrated, and the residue was partitioned between EtOAc and H₂O, the organic layer was separated, washed with 1N HCl, 5% NaHCO₃, dried and concentrated to give 2,4-dichloro-5-iodo-7-tosyl-7H-pyrrolo[2,3-d]pyrimidine (2.0 g).

To a mixture of 2,4-dichloro-5-iodo-7-tosyl-7H-pyrrolo[2,3-d]pyrimidine (0.6 g, 1.28 mmol) in nBuOH (2 mL) was added methylamine (2M THF, 0.77 mL, 1.54 mmol) and DIPEA (0.274 mL, 1.54 mmol). After stirring at ambient temperature for 1 h, the resulting precipitate was collected by filtration to give 2-chloro-N-methyl-5-iodo-7-tosyl-7H-pyrrolo[2,3-d]pyrimidin-4-amine (0.275 g).

To a mixture of 2-chloro-N-methyl-5-iodo-7H-pyrrolo[2,3-d]pyrimidin-4-amine (0.05 g, 0.11 mmol), Pd(PPh₃)₂Cl₂ (0.015 g, 0.022 mmol) and pyridine-4-ylboronic acid (0.03 g, 0.24 mmol) in p-dioxane (0.7 mL) was added a solution of Na₂CO₃ (0.035 g, 0.33 mmol) in water (0.3 mL). After degassing, the mixture was heated at 100° C. for 1.5 h. The mixture was purified by flash column chromatography (Hexane/EtOAc=1:1) to give 2-chloro-N-methyl-5-(pyridin-4-yl)-7-tosyl-7H-pyrrolo[2,3-d]pyrimidin-4-amine (0.02 g).

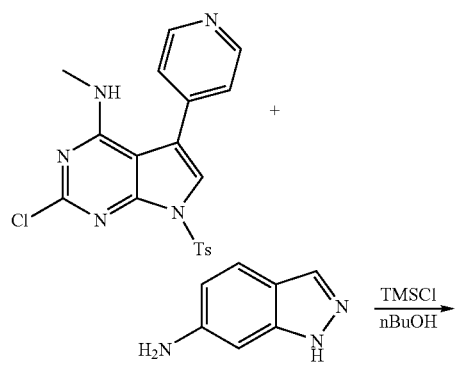

To a mixture of 2-chloro-N-methyl-5-(pyridin-4-yl)-7-tosyl-7H-pyrrolo[2,3-d]pyrimidin-4-amine (0.041 g, 0.091 mmol) in nBuOH (0.8 mL) was added 6-aminoindazole (0.024 g, 0.18 mmol) and TMSCl (0.03 mL, 0.23 mmol). After heating at 115° C. for 48 h, the mixture was purified by preparative HPLC to give $N^2$-(1H-indazol-6-yl)-$N^4$-methyl-5-(pyridin-4-yl)-7H-pyrrolo[2,3-d]pyrimidine-2,4-diamine (0.011 g), MS (MH 357.1), λ=214.5, 247.5, 306.8.

Example 2

1-(4-(4-(4-(methylamino)-5-(pyridin-4-yl)-7H-pyrrolo[2,3-d]pyrimidin-2-ylamino)phenyl)piperazin-1-yl)ethanone

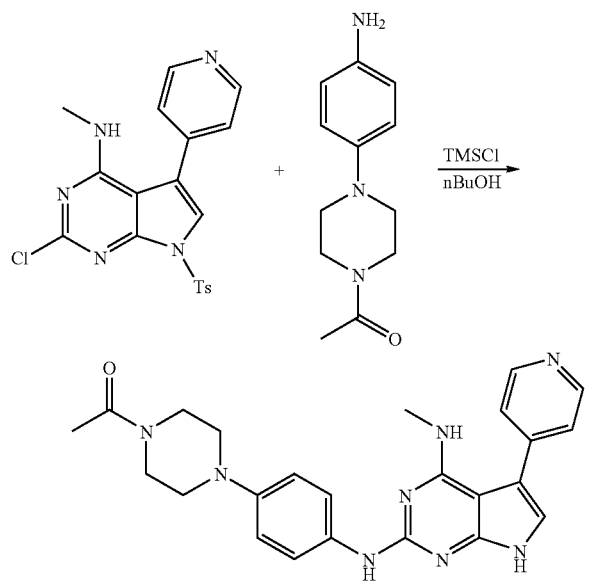

To a mixture of 2-chloro-N-methyl-5-(pyridin-4-yl)-7-tosyl-7H-pyrrolo[2,3-d]pyrimidin-4-amine (0.044 g, 0.11 mmol) in nBuOH (0.6 mL) was added 1-(4-4-aminophenyl)piperazin-1-yl)ethanone (0.047 g, 0.22 mmol) and TMSCl (0.043 mL, 0.33 mmol). After heating at 115° C. for 48 h, the mixture was purified by preparative HPLC to give 1-(4-(4-(4-(methylamino-5-(pyridin-4-yl)-7H-pyrrolo[2,3-d]pyrimidine-2-ylamino)phenyl)piperizine-1-yl)ethanone (0.015 g), MS (MH 443.3), λ=259.4, 302.1.

Example 3

N2-(1H-indazol-6-yl)-N4-methyl-5-(pyridin-3-yl)-7H-pyrrolo[2,3-d]pyrimidine-2,4-diamine

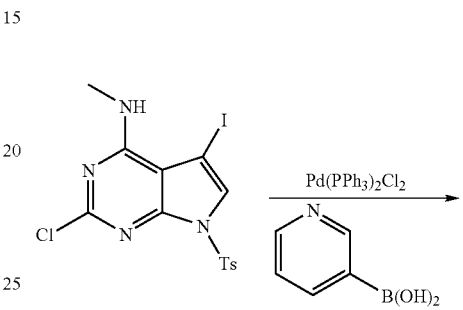

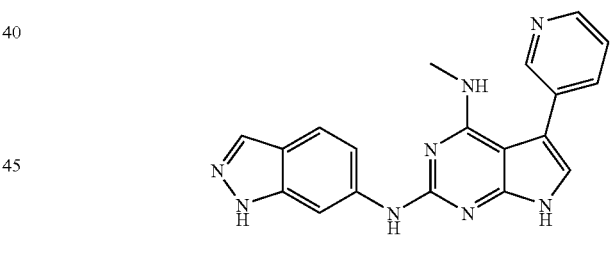

To a mixture of 2-chloro-N-methyl-5-iodo-7-tosyl-7H-pyrrolo[2,3-d]pyrimidin-4-amine (0.175 g, 0.38 mmol), Pd(PPh$_3$)$_2$Cl$_2$ (0.053 g, 0.076 mmol) and pyridine-3-ylboronic acid (0.102 g, 0.83 mmol) in dioxane (2 mL) was added a solution of Na$_2$CO$_3$ (0.12 g, 1.14 mmol) in water (1 mL). After degassing, the mixture was heated at 100° C. for 1.5 h. The mixture was purified by flash column chromatography (Hexane/EtOAc=1:1) to give 2-chloro-N-methyl-5-(pyridin-3-yl)-7-tosyl-7H-pyrrolo[2,3-d]pyrimidin-4-amine (0.084 g).

To a mixture of 2-chloro-N-methyl-5-(pyridin-3-yl)-7-tosyl-7H-pyrrolo[2,3-d]pyrimidin-4-amine (0.075 g, 0.182 mmol) in nBuOH (1 mL) was added 6-aminoindazole (0.048 g, 0.36 mmol) and TMSCl (0.06 mL, 0.46 mmol). After heating at 115° C. for 72 h, the mixture was purified by preparative HPLC to give $N^2$-(1H-indazol-6-yl)-$N^4$-methyl- 5-(pyridin-3-yl)-7H-pyrrolo[2,3-d]pyrimidine-2,4-diamine (0.03 g), MS (MH 357.2), λ=203.9, 246.3, 305.6.

Example 4

1-(4-(4-(4-(cyclopropylamino)-5-(pyridin-4-yl)-7H-pyrrolo[2,3-d]pyrimidin-2-ylamino)phenyl)piperazin-1-yl)ethanone

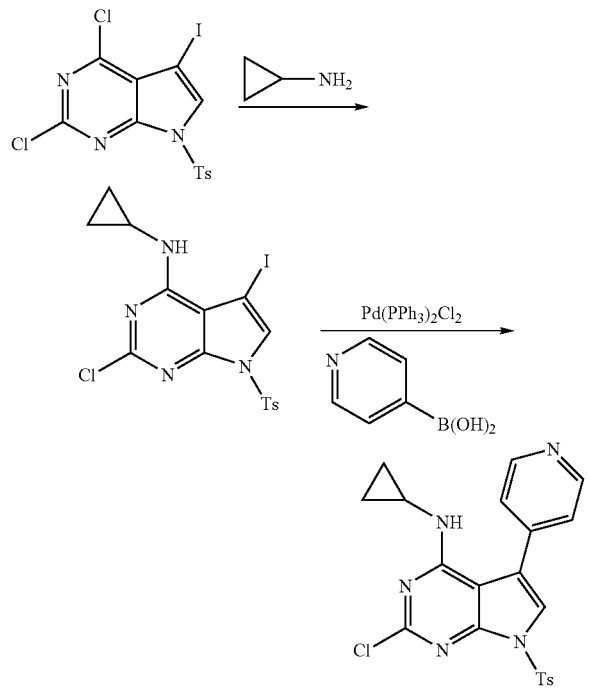

To a mixture of 2,4-dichloro-5-iodo-7-tosyl-7H-pyrrolo[2,3-d]pyrimidine (0.414 g, 0.88 mmol) in nBuOH (1.5 mL) was added cyclopropylamine (0.0674 mL, 1.06 mmol) and DIPEA (0.188 mL, 1.06 mmol). After stirring at ambient temperature for 15 h, the resulting precipitate was collected by filtration to give 2-chloro-N-cyclopropyl-5-iodo-7-tosyl-7H-pyrrolo[2,3-d]pyrimidin-4-amine (0.3 g).

To a mixture of 2-chloro-N-cyclopropyl-5-iodo-7-tosyl-7H-pyrrolo[2,3-d]pyrimidin-4-amine (0.3 g, 0.61 mmol), Pd(PPh$_3$)$_2$Cl$_2$ (0.086 g, 0.122 mmol) and pyridine-4-ylboronic acid (0.165 g, 1.342 mmol) in dioxane (3 mL) was added a solution of Na$_2$CO$_3$ (0.2 g, 1.83 mmol) in water (1.5 mL). After degassing, the mixture was heated at 100° C. for 1.5 h. The mixture was purified by flash column chromatography (Hexane/EtOAc=1:1) to give 2-chloro-N-cyclopropyl-5-(pyridin-4-yl)-7-tosyl-7H-pyrrolo[2,3-d]pyrimidin-4-amine (0.241 g).

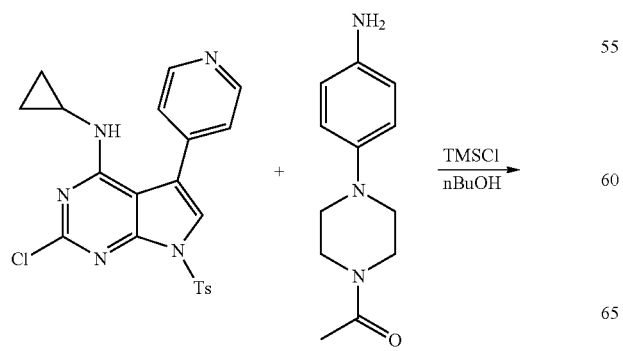

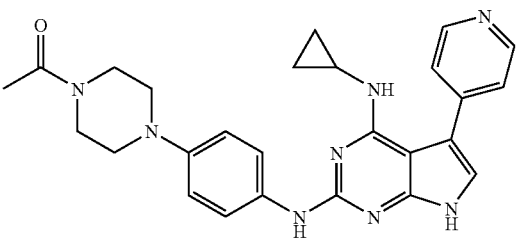

To a mixture of 2-chloro-N-cyclopropyl-5-(pyridin-4-yl)-7-tosyl-7H-pyrrolo[2,3-d]pyrimidin-4-amine (0.12 g, 0.27 mmol) in nBuOH (1 mL) was added 1-(4-4-aminophenyl)piperazin-1-yl)ethanone (0.12 g, 0.54 mmol) and TMSCl (0.087 mL, 0.68 mmol). After heating at 115° C. for 48 h, the mixture was purified by preparative HPLC to give 1-(4-(4-(4-(cyclopropylamino-5-(pyridin-4-yl)-7H-pyrrolo[2,3-d]pyrimidine-2-ylamino)phenyl)piperizine-1-yl)ethanone (0.015 g), MS (MH 469.4), λ=203.9, 280.7 nm.

Example 5

4-(4-aminophenyl)-1-(5-carbamoyl-4-(cyclopropylamino)pyrimidin-2-yl)pyridinium

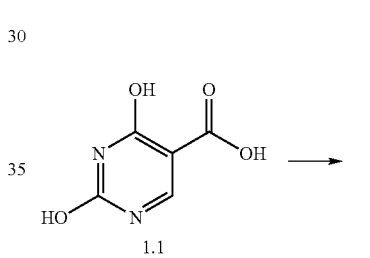
1.1

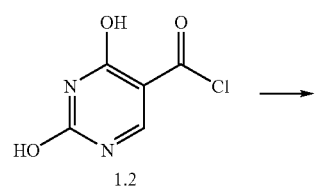
1.2

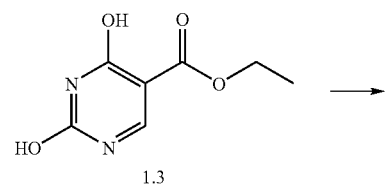
1.3

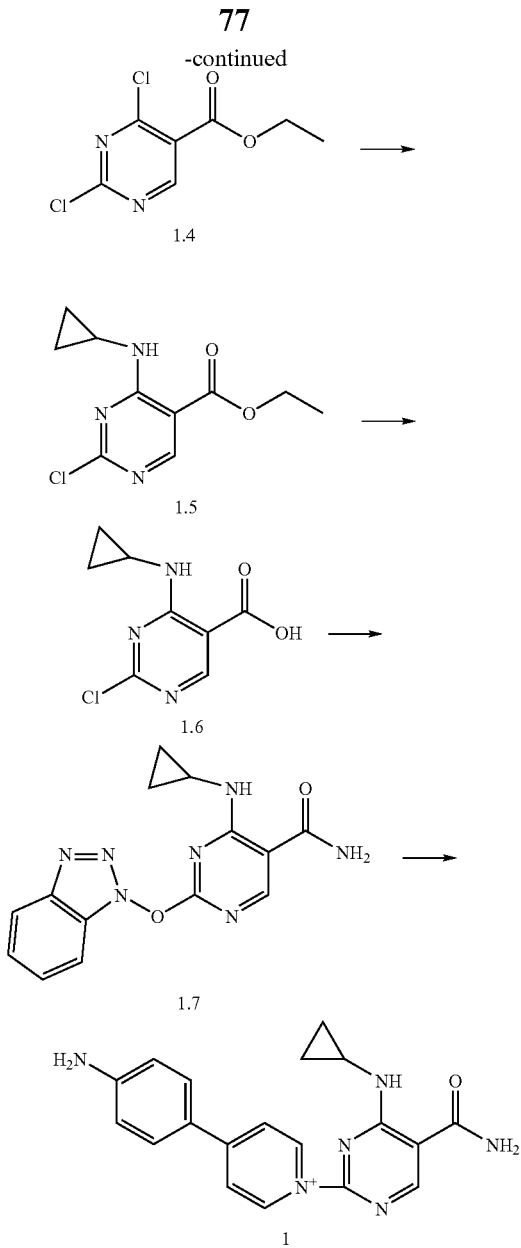

beige precipitate which was collected by filtration and dried under vacuum affording the desired dichloride (1.4) as a light yellow powder (22.5 g, 85%). $^1$H NMR (DMSO-d$_6$, 400 MHz): δ 9.13 (s, 1H), 4.37 (q, 2H), 1.32 (t, 3H).

Step 4: Dichloropyrimidine 1.4 (5.9 g, 27 mmol) was dissolved in acetonitrile (50 mL) and treated sequentially with diisopropylamine (5.2 mL, 30 mmol) followed by cyclopropyl amine (1.9 g, 27 mmol) and stirred at rt until all starting material had been consumed. The reaction mixture was then diluted with water to a total volume of 150 mL and the precipitate collected by filtration affording the desired product as a light yellow solid (6.02 g, 87%). $^1$H NMR (DMSO-d$_6$, 400 MHz): δ 8.60 (S, 1H), 8.48 (d, 1H), 4.52 (m, 1H), 4.29 (q, 2H), 2.30 (m, 2H), 2.04 (m, 2H), 1.73 (m, 2H), 1.30 (t, 3H).

Step 5: Ethyl ester 1.5 (6.02 g, 24 mmol) was diluted with 1,4-dioxane (26 mL) followed by aqueous lithium hydroxide (1.0 M, 26 mL, 26 mmol) and stirred at rt until all starting material had been converted to the carboxylic acid. The reaction was then diluted with water to a total volume of 100 mL and acidified to pH=2 with 6 M HCl. The resulting suspension was then filtered and dried by aspiration giving 3.51 g of the carboxylic acid (64%). $^1$H NMR (DMSO-d$_6$, 400 MHz): δ 8.64 (d, 1H), 8.74 (s, 1H), 4.50 (m, 1H), 2.31 (m, 2H), 2.03 (m, 2H), 1.72 (m, 2H).

Step 6: Carboxylic acid 1.6 (3.15 g, 15 mmol) was dissolved in N,N-dimethylformamide (70 mL) and treated with HOBt (3.13 g, 23 mmol) and EDC (4.4 g, 23 mmol). After stirring ca. 25 min ammonia (0.5 M in 1,4-dioxane, 72 mL, 36 mmol) was added and the reaction stirred overnight. The following morning the reaction was diluted with water to a total volume of 500 mL and the desired product collected by filtration affording 3.62 g (74%) of a light-beige solid. $^1$H NMR (DMSO-d$_6$, 400 MHz): δ 9.30 (d, 1H), 8.54 (s, 1H), 8.15 (d, 1H), 8.09 (s, 1H), 7.74 (d, 1H), 7.64 (m, 2H), 7.51 (t, 1H), 3.77 (m, 1H), 1.79 (m, 2H), 1.74 (m, 2H), 1.53 (m, 1H), 1.41 (m, 1H).

Step 7: Benzotriazolyl ether 1.7 (50 mg, 0.17 mmol), 4-(pyridyl)-aniline (0.26 mmol) and p-toluenesulfonic acid (30 mg, 0.17 mmol) were diluted with 1,4-dioxane (5 mL) and stirred at 120° C. until all starting material had been consumed. The reaction was cooled to rt, diluted with water and directly purified by preparative HPLC affording the desired product, 1, after lyophilization. MS found for $C_{19}H_{19}N_6O$ as (M)$^+$ 347.3.

Example 6

1-(4-aminophenyl)-3-(5-carbamoyl-4-(cyclopropylamino)pyrimidin-2-yl)-1H-imidazol-3-ium

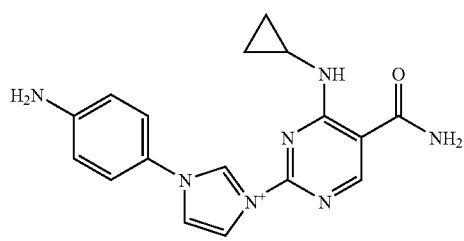

Step 1: To a stirring solution of carboxylic acid 1.1 (85 g, 540 mmol) in thionyl chloride (425 mL) was added pyridine (8.5 mL, 0.11 mmol), slowly. The reaction was stirred at 75° C. overnight at which time it was concentrated and dried under vacuum to a light yellow powder which was used immediately for the next step.

Step 2: The yellow solid from the Step 1 was slowly diluted with 750 mL of ethanol and refluxed overnight. The next day the reaction was determined to be complete by HPLC and then cooled in an ice bath and the solid filtered and washed with diethyl ether affording the desired ethyl ester 1.3 as an off-white powder (91 g, 87% for two steps). MS found for $C_7H_8N_2O_4$ as (M+H)$^+$ 185.0.

Step 3: Ester 1.3 (22 g, 120 mmol) was dissolved in phosphorous oxychloride (60 mL, 600 mmol) and the mixture treated with N,N-diethylaniline (27 mL, 167 mmol) and the mixture heated to 105° C. until the reaction was determined to be complete by HPLC. It was then cooled to rt and slowly added to 1 L of crushed ice resulting in the formation of a The above compound was prepared using a procedure similar to that described in Example 5, Step 7 using 4-(1H-imidazol-1-yl)aniline. MS found for $C_{17}H_{18}N_7O$ as $(M)^+$ 336.0.

Example 7

2-(6-amino-7-chloro-1H-indazol-1-yl)-4-(cyclopropylamino)pyrimidine-5-carboxamide

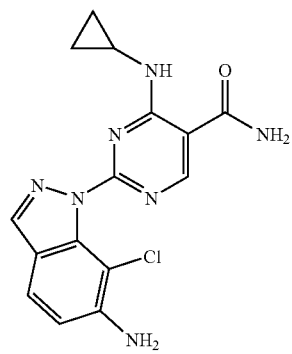

The above compound was prepared using a procedure similar to that described in Example 5, Step 7 using 7-chloro-1H-indazol-6-amine (synthesized from 6-aminoindazole using N-chlorosuccinimide in one step). MS found for $C_{15}H_{17}N_7OCl$ as $(M+H)^+$ 344.2, 346.2.

Examples 8 and 9

1-(2-(4-(piperazin-1-yl)phenylamino)-7H-pyrrolo[2,3-d]pyrimidin-4-yl)piperidine-3-carboxamide and 1-(2-(4-(4-acetylpiperazin-1-yl)phenylamino)-7H-pyrrolo[2,3-d]pyrimidin-4-yl)piperidine-3-carboxamide

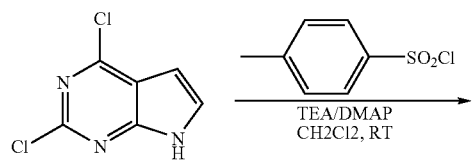

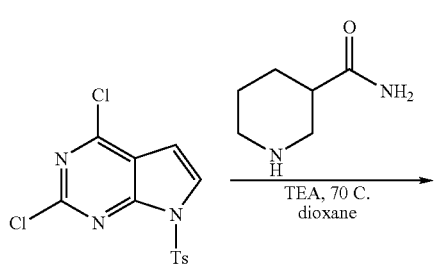

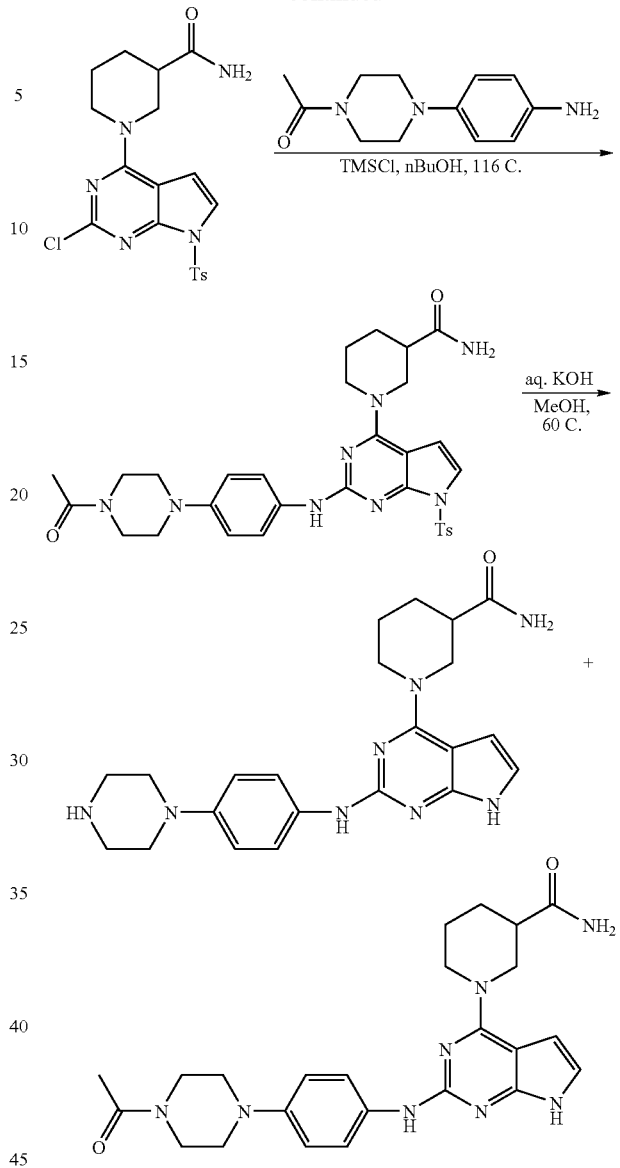

To a mixture of 2,4-dichloro-7H-pyrrolo[2,3-d]pyrimidine (1.67 g, 8.88 mmol), p-toluenesulfonyl chloride (1.72 g, 9.02 mmol) and triethylamine (2.50 mL, 18.0 mmol) in $CH_2C_2$ (15 mL), dimethylaminopyridine (30 mg, 0.24 mmol) was added. It was stirred at room temperature for 20 h. Water and $CH_2Cl_2$ were added. The organic phase was separated, washed with 1N HCl, then with 5% $NaHCO_3$, dried over $Na_2SO_4$, concentrated in vacuo to give 2,4-dichloro-7-tosyl-7H-pyrrolo[2,3-d]pyrimidine as a solid (3.03 g).

A solution of 2,4-dichloro-7-tosyl-7H-pyrrolo[2,3-d]pyrimidine (200 mg, 0.584 mmol), nipecotamide (75 mg, 0.586 mmol) and triethylamine (0.130 mL, 0.934 mmol) in dioxane (5 mL) was stirred at 70° C. for 20 h. Water and EtOAc were added. The organic phase was separated, dried over $Na_2SO_4$, concentrated in vacuo to give 1-(2-chloro-7-tosyl-7H-pyrrolo[2,3-d]pyrimidin-4-yl)piperidine-3-carboxamide (250 mg).

A mixture of 1-(2-chloro-7-tosyl-7H-pyrrolo[2,3-d]pyrimidin-4-yl)piperidine-3-carboxamide (125 mg, 0.288 mmol), 1-(4-(4-aminophenyl)piperazin-1-yl)ethanone (100 mg, 0.456 mmol) and trimethylsilyl chloride (0.100 mL, 0.79 mmol) in n-BuOH (3 mL) was stirred at 116° C. for 20 h.

n-BuOH was removed in vacuo. The residue was purified by HPLC to give 1-(2-(4-(4-acetylpiperazin-1-yl)phenylamino)-7-tosyl-7H-pyrrolo[2,3-d]pyrimidin-4-yl)piperidine-3-carboxamide (12 mg).

To a solution of 1-(2-(4-(4-acetylpiperazin-1-yl)phenylamino)-7-tosyl-7H-pyrrolo[2,3-d]pyrimidin-4-yl)piperidine-3-carboxamide (12 mg, 0.019 mmol) in MeOH (2 mL), aq. 1N KOH (1 mL) was added. It was stirred at 60° C. for 2 h. After being concentrated in vacuo, the residue was acidified with HOAc (1 mL). The mixture was then purified by HPLC to give 1-(2-(4-(piperazin-1-yl)phenylamino)-7H-pyrrolo[2,3-d]pyrimidin-4-yl)piperidine-3-carboxamide (2 mg) (MS 421.5 (M+H)) and 1-(2-(4-(4-acetylpiperazin-1-yl)phenylamino)-7H-pyrrolo[2,3-d]pyrimidin-4-yl)piperidine-3-carboxamide (8 mg) (MS 463.6 (M+H)); UV 202.6, 274.6 nm).

Examples 10 and 11

4-(4-(aminomethyl)piperidin-1-yl)-N-(4-(piperazin-1-yl)phenyl)-7H-pyrrolo[2,3-d]pyrimidin-2-amine and 1-(4-(4-(4-(4-(aminomethyl)piperidin-1-yl)-7H-pyrrolo[2,3-d]pyrimidin-2-ylamino)phenyl)piperazin-1-yl)ethanone

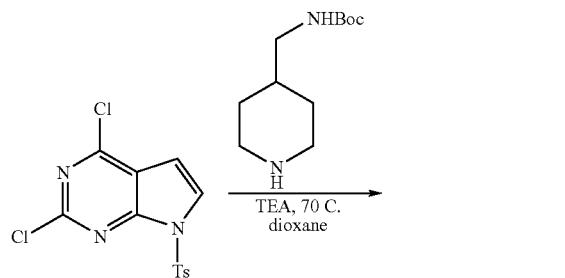

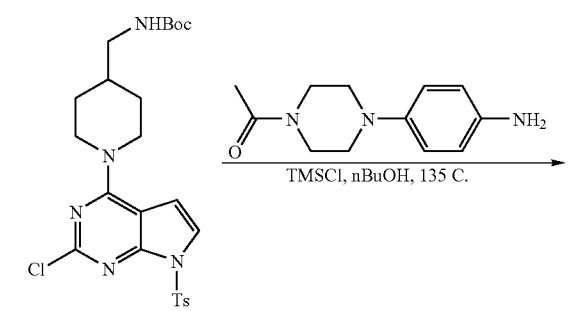

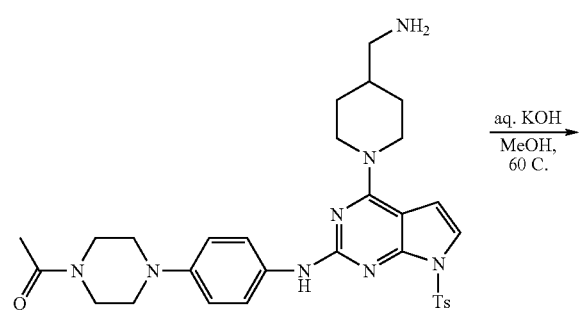

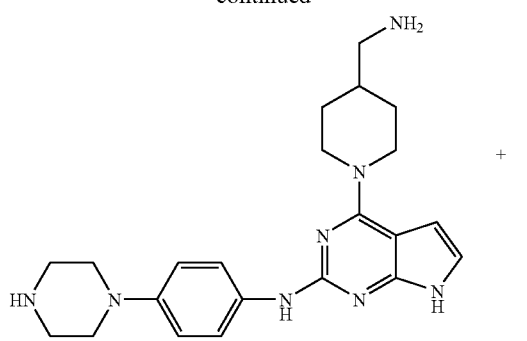

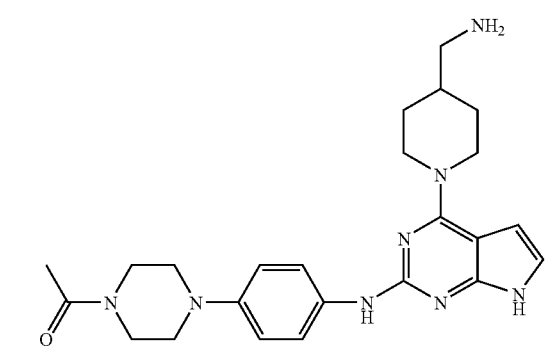

A solution of 2,4-dichloro-7-tosyl-7H-pyrrolo[2,3-d]pyrimidine (200 mg, 0.584 mmol), 4-N-Boc-aminomethylpiperidine (125 mg, 0.584 mmol) and triethylamine (0.160 mL, 1.15 mmol) in dioxane (5 mL) was stirred at 70° C. for 20 h. Water and EtOAc were added. The organic phase was separated, dried over Na₂SO₄, concentrated in vacuo to give tert-butyl (1-(2-chloro-7-tosyl-7H-pyrrolo[2,3-d]pyrimidin-4-yl)piperidin-4-yl)methylcarbamate (303 mg).

A mixture of tert-butyl (1-(2-chloro-7-tosyl-7H-pyrrolo[2,3-d]pyrimidin-4-yl)piperidin-4-yl)methylcarbamate (303 mg, 0.583 mmol), 1-(4-(4-aminophenyl)piperazin-1-yl)ethanone (191 mg, 0.872 mmol) and trimethylsilyl chloride (0.400 mL, 3.16 mmol) in n-BuOH (6 mL) was stirred at 135° C. for 40 h. n-BuOH was removed in vacuo. The residue was purified by HPLC to give 1-(4-(4-(4-(4-(aminomethyl)piperidin-1-yl)-7-tosyl-7H-pyrrolo[2,3-d]pyrimidin-2-ylamino)phenyl)piperazin-1-yl)ethanone (60 mg).

To a solution of 1-(4-(4-(4-(4-(aminomethyl)piperidin-1-yl)-7-tosyl-7H-pyrrolo[2,3-d]pyrimidin-2-ylamino)phenyl)piperazin-1-yl)ethanone (60 mg, 0.10 mmol) in MeOH (3 mL), aq. 1N KOH (1 mL) was added. It was stirred at 60° C. for 3 h. After being concentrated in vacuo, the residue was acidified with HOAc (1 mL). The mixture was then purified by HPLC to give 4-(4-(aminomethyl)piperidin-1-yl)-N-(4-(piperazin-1-yl)phenyl)-7H-pyrrolo[2,3-d]pyrimidin-2-amine (3 mg) (MS 407.5 (M+H); UV 202.6, 269.9 nm) and 1-(4-(4-(4-(4-(aminomethyl)piperidin-1-yl)-7H-pyrrolo[2, 3-d]pyrimidin-2-ylamino)phenyl)piperazin-1-yl)ethanone (15 mg) (MS 449.5 (M+H); UV 202.6, 273.4 nm).

Examples 12 and 13

(S)-1-(2-(4-(piperazin-1-yl)phenylamino)-7H-pyrrolo[2,3-d]pyrimidin-4-yl)pyrrolidin-3-ol and (S)-1-(4-(4-(4-(3-hydroxypyrrolidin-1-yl)-7H-pyrrolo[2,3-d]pyrimidin-2-ylamino)phenyl)piperazin-1-yl)ethanone

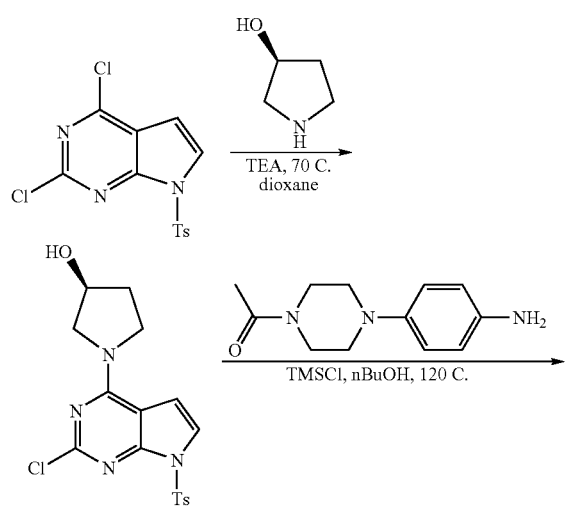

A solution of 2,4-dichloro-7-tosyl-7H-pyrrolo[2,3-d]pyrimidine (200 mg, 0.584 mmol), (S)-3-hydroxypyrrolidine (58 mg, 0.667 mmol) and triethylamine (0.160 mL, 1.15 mmol) in dioxane (5 mL) was stirred at 70° C. for 20 h. Water and EtOAc were added. The organic phase was separated, dried over Na$_2$SO$_4$, concentrated in vacuo to give (S)-1-(2-chloro-7-tosyl-7H-pyrrolo[2,3-d]pyrimidin-4-yl)pyrrolidin-3-ol (201 mg). MS 393.3 and 395.3 (M+H, Cl pattern).

A mixture of (S)-1-(2-chloro-7-tosyl-7H-pyrrolo[2,3-d]pyrimidin-4-yl)pyrrolidin-3-ol (201 mg, 0.512 mmol), 1-(4-(4-aminophenyl)piperazin-1-yl)ethanone (160 mg, 0.730 mmol) and trimethylsilyl chloride (0.200 mL, 1.58 mmol) in n-BuOH (5 mL) was stirred at 120° C. for 40 h. n-BuOH was removed in vacuo. The residue was purified by HPLC to give (S)-1-(4-(4-(4-(3-hydroxypyrrolidin-1-yl)-7-tosyl-7H-pyrrolo[2,3-d]pyrimidin-2-ylamino)phenyl)piperazin-1-yl)ethanone (80 mg). MS 576.5 (M+H)

To a solution of (S)-1-(4-(4-(4-(3-hydroxypyrrolidin-1-yl)-7-tosyl-7H-pyrrolo[2,3-d]pyrimidin-2-ylamino)phenyl)piperazin-1-yl)ethanone (80 mg, 0.14 mmol) in MeOH (3 mL), aq. 1N KOH (1 mL) was added. It was stirred at 60° C. for 4 h. After being concentrated in vacuo, the residue was acidified with HOAc (1 mL). The mixture was then purified by HPLC to give (S)-1-(2-(4-(piperazin-1-yl)phenylamino)-7H-pyrrolo[2,3-d]pyrimidin-4-yl)pyrrolidin-3-ol (5 mg) (MS 380.5 (M+H)) and (S)-1-(4-(4-(4-(3-hydroxypyrrolidin-1-yl)-7H-pyrrolo[2,3-d]pyrimidin-2-ylamino)phenyl)piperazin-1-yl)ethanone (20 mg) (MS 422.5 (M+H)).

Example 14

2-(4-(4-acetylpiperazin-1-yl)phenylamino)-4-(4-(aminomethyl)piperidin-1-yl)-7H-pyrrolo[2,3-d]pyrimidine-5-carbonitrile

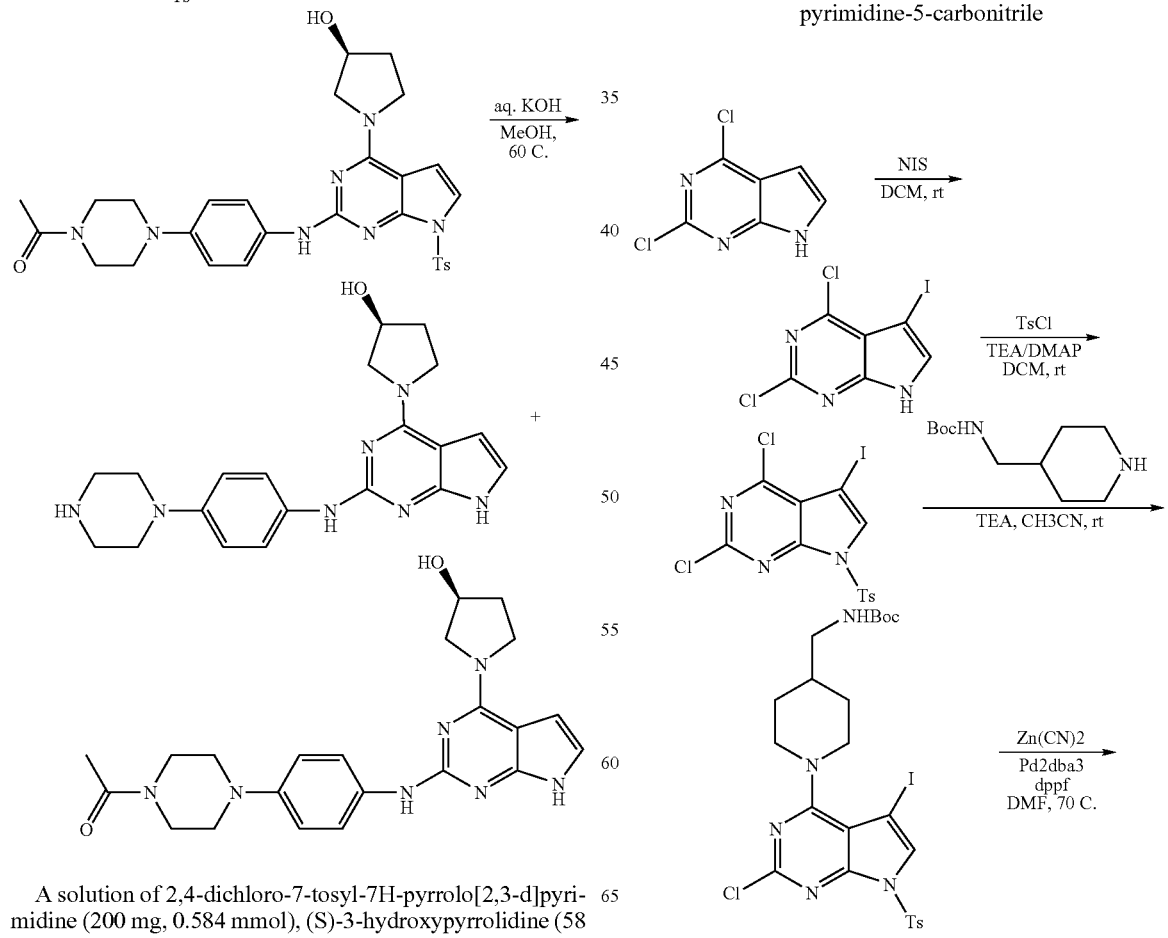

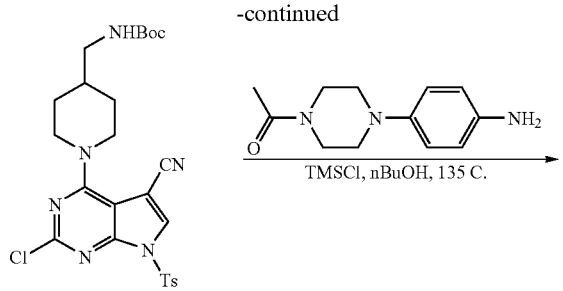

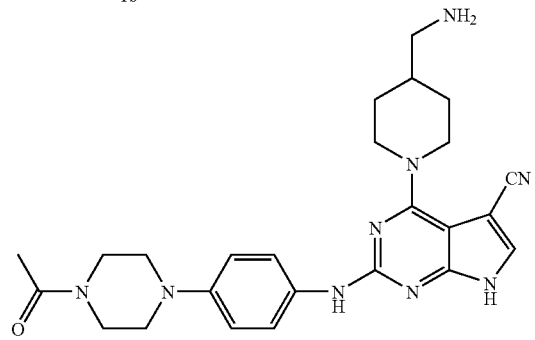

To a suspension of 2,4-dichloro-7H-pyrrolo[2,3-d]pyrimidine (3.00 g, 16.0 mmol) in CH$_2$Cl$_2$ (30 mL), N-iodosuccinimide (3.60 g, 16.0 mmol) was added. It was stirred at room temperature for 20 h. The fine precipitate was collected, dried on vacuum to give 2,4-dichloro-5-iodo-7H-pyrrolo[2,3-d]pyrimidine (2.80 g). MS 314.1 and 316.1 (M+H)

To a suspension of 2,4-dichloro-5-iodo-7H-pyrrolo[2,3-d]pyrimidine (2.80 g, 8.92 mmol) and p-toluenesulfonyl chloride (1.65 g, 8.66 mmol) in CH$_2$Cl$_2$ (30 mL), triethylamine (3.0 mL, 21.6 mmol) and dimethylaminopyridine (0.047 g, 0.38 mmol) were added. The mixture was stirred at room temperature for 2 h. Water and CH$_2$Cl$_2$ were added. The organic phase was separated, washed with 1N HCl, then with 5% NaHCO$_3$, dried over Na$_2$SO$_4$, concentrated in vacuo to give 2,4-dichloro-5-iodo-7-tosyl-7H-pyrrolo[2,3-d]pyrimidine as a solid (4.00 g). MS 468.2 and 470.2 (M+H)

A mixture of 2,4-dichloro-5-iodo-7-tosyl-7H-pyrrolo[2,3-d]pyrimidine (310 mg, 0.662 mmol), 4-N-Boc-aminomethyl piperidine (142 mg, 0.663 mmol) and triethylamine (0.200 mL, 1.44 mmol) in CH$_3$CN (10 mL) was stirred at room temperature for 20 h. Water and EtOAc were added. The organic phase was separated, washed with 1N HCl, then with 5% NaHCO$_3$, dried over Na$_2$SO$_4$, concentrated in vacuo to give tert-butyl (1-(2-chloro-5-iodo-7-tosyl-7H-pyrrolo[2,3-d]pyrimidin-4-yl)piperidin-4-yl)methylcarbamate (418 mg). MS 646.5 and 648.4 (M+H)

A mixture of tert-butyl (1-(2-chloro-5-iodo-7-tosyl-7H-pyrrolo[2,3-d]pyrimidin-4-yl)piperidin-4-yl)methylcarbamate (418 mg, 0.647 mmol), Pd2(dba)$_3$ (60 mg, 0.065 mmol), dppf (72 mg, 0.130 mmol) and Zn(CN)$_2$ (91 mg, 0.778 mmol) in DMF (5 mL) was stirred at 70° C. for 20 h. DMF was removed in vacuo. The residue was loaded to a flash column, eluted with a gradient of 10-30% EtOAc in hexane to give tert-butyl (1-(2-chloro-5-cyano-7-tosyl-7H-pyrrolo[2,3-d]pyrimidin-4-yl)piperidin-4-yl)methylcarbamate (180 mg).

A mixture of tert-butyl (1-(2-chloro-5-cyano-7-tosyl-7H-pyrrolo[2,3-d]pyrimidin-4-yl)piperidin-4-yl)methylcarbamate (180 mg, 0.330 mmol), 1-(4-(4-aminophenyl)piperazin-1-yl)ethanone (137 mg, 0.625 mmol) and trimethylsilyl chloride (0.300 mL, 2.37 mmol) in n-BuOH (5 mL) was stirred at 135° C. for 40 h. n-BuOH was removed in vacuo.

The residue was purified by HPLC to give the titled compound (25 mg). MS 474.5 (M+H); UV 200.8, 277.8 nm.

Example 15

1-(4-(4-(6-(4-(aminomethyl)piperidin-1-yl)-9H-purin-2-ylamino)phenyl)piperazin-1-yl)ethanone

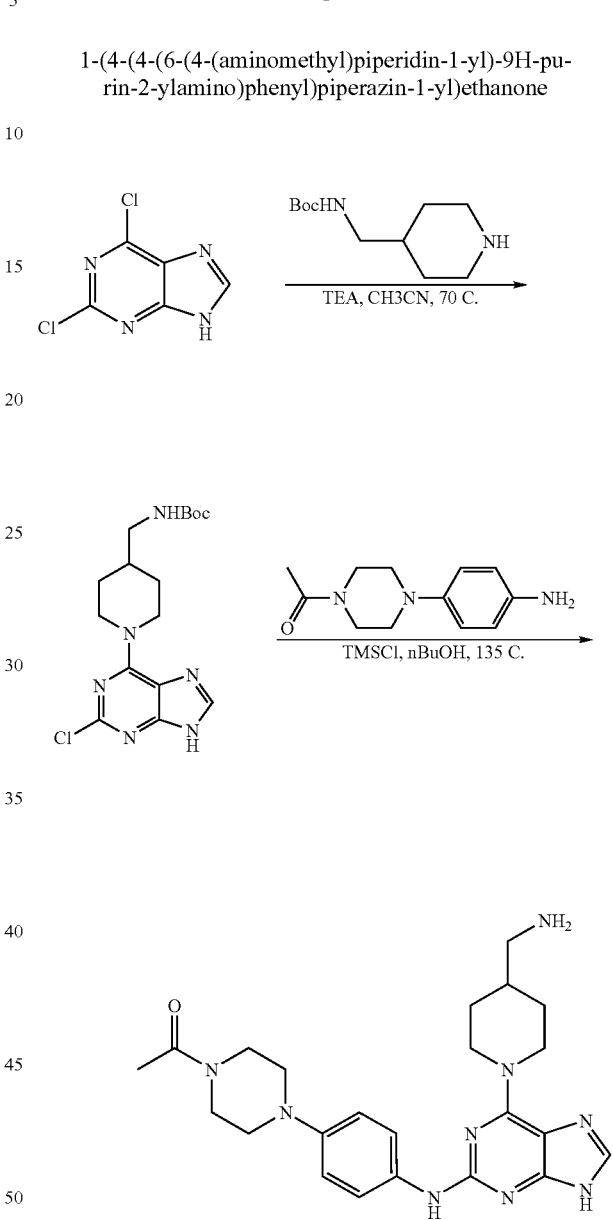

A mixture of 2,6-dichloropurine (189 mg, 1.00 mmol), 4-N-Boc-aminomethyl piperidine (214 mg, 1.00 mmol) and triethylamine (0.300 mL, 2.15 mmol) in CH$_3$CN (4 mL) was stirred at 70° C. It turned clear solution initially, then white precipitates crashed out, which were collected and dried on vacuum to give tert-butyl (1-(2-chloro-9H-purin-6-yl)piperidin-4-yl)methylcarbamate (310 mg). MS 367.4 and 369.4 (M+H, Cl pattern)

A mixture of tert-butyl (1-(2-chloro-9H-purin-6-yl)piperidin-4-yl)methylcarbamate (100 mg, 0.272 mmol), 1-(4-(4-aminophenyl)piperazin-1-yl)ethanone (120 mg, 0.548 mmol) and trimethylsilyl chloride (0.300 mL, 2.37 mmol) in n-BuOH (4 mL) was stirred at 135° C. for 70 h. n-BuOH was removed in vacuo. The residue was purified by HPLC to give the titled compound (12 mg). MS 450.6 (M+H); UV 200.0, 270.8 nm.

Example 16

N-(4-(4-(aminomethyl)piperidin-1-yl)-5-fluoropyrimidin-2-yl)-1H-indazol-6-amine

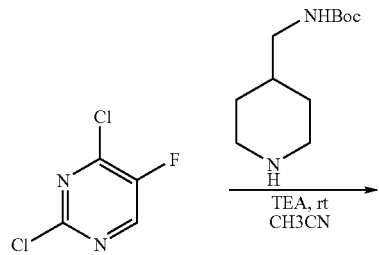

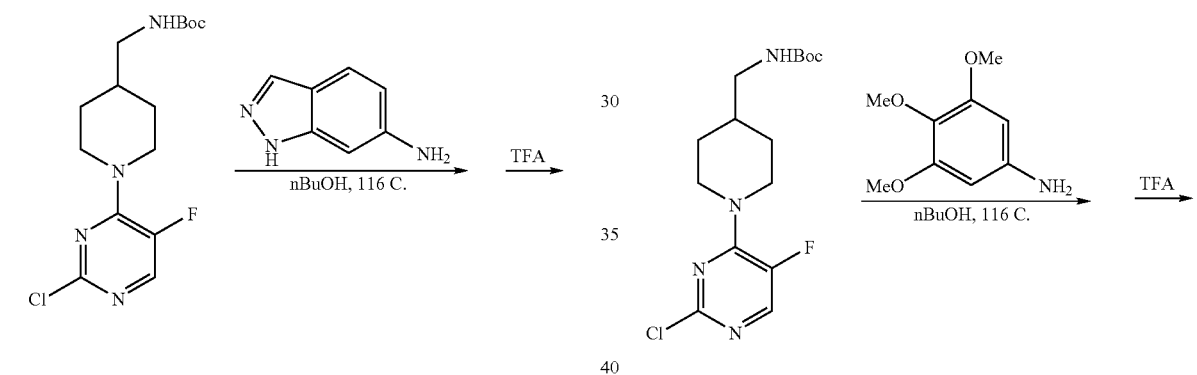

A mixture of 2,4-dichloro-5-fluoropyrimidine (167 mg, 1.00 mmol), 4-N-Boc-aminomethyl piperidine (214 mg, 1.00 mmol) and triethylamine (0.300 mL, 2.15 mmol) in CH$_3$CN (4 mL) was stirred at room temperature for 20 h. It was concentrated in vacuo. The residue was dissolved in nBuOH (6 mL). 2 mL of the nBuOH solution was taken, to which 6-aminoindazole (66 mg, 0.49 mmol) was added. The solution was stirred at 116° C. for 20 h. nBuOH was removed in vacuo. The residue was dissolved in TFA (2 mL). After being stirred at room temperature for 2 h, TFA was removed in vacuo. The residue was purified by HPLC to give the titled compound (40 mg). MS 342.5 (M+H); UV 205.8, 246.8, 276.8 nm.

Example 17

4-(4-(aminomethyl)piperidin-1-yl)-5-fluoro-N-(3,4,5-trimethoxyphenyl)pyrimidin-2-amine

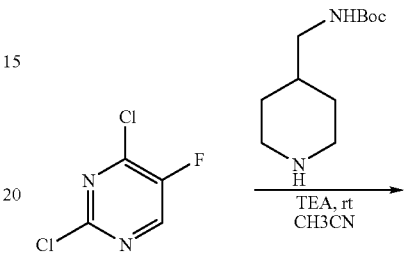

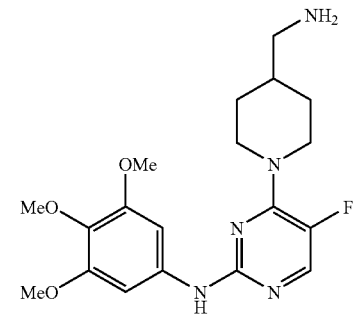

A mixture of 2,4-dichloro-5-fluoropyrimidine (167 mg, 1.00 mmol), 4-N-Boc-aminomethyl piperidine (214 mg, 1.00 mmol) and triethylamine (0.300 mL, 2.15 mmol) in CH$_3$CN (4 mL) was stirred at room temperature for 20 h. It was concentrated in vacuo. The residue was dissolved in nBuOH (6 mL). 2 mL of the nBuOH solution was taken, to which 3,4,5-trimethoxyaniline (91 mg, 0.50 mmol) was added. The solution was stirred at 116° C. for 20 h. nBuOH was removed in vacuo. The residue was dissolved in TFA (2 mL). After being stirred at room temperature for 2 h, TFA was removed in vacuo. The residue was purified by HPLC to give the titled compound (42 mg). MS 392.5 (M+H); UV 223.8, 257.8 nm.

Example 18

1-(4-(4-(4-(4-(aminomethyl)piperidin-1-yl)-5-fluoro-pyrimidin-2-ylamino)phenyl)piperazin-1-yl)ethanone

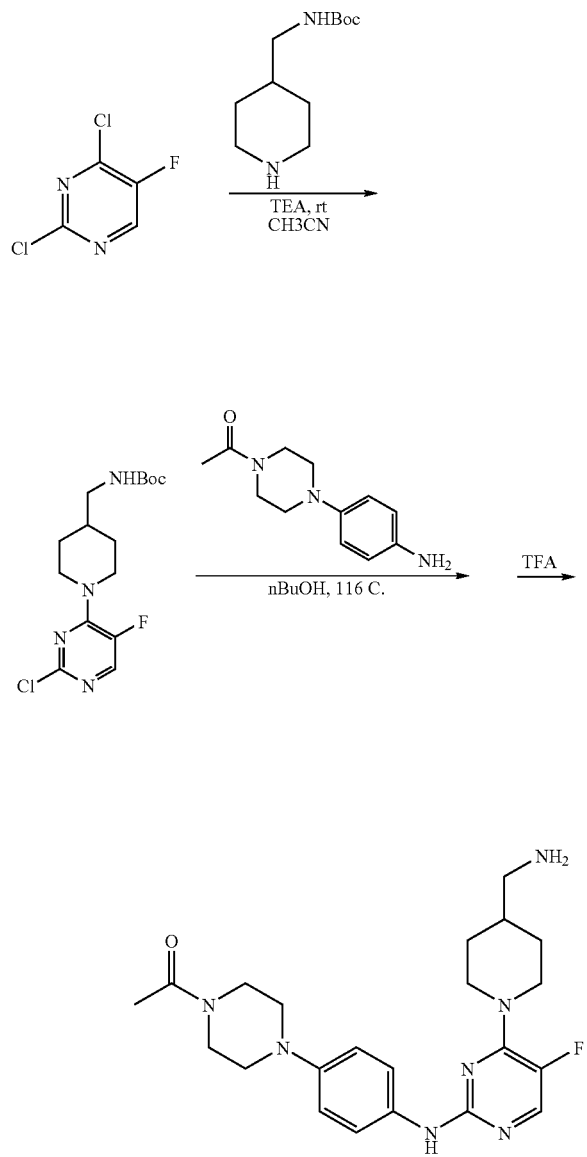

A mixture of 2,4-dichloro-5-fluoropyrimidine (167 mg, 1.00 mmol), 4-N-Boc-aminomethyl piperidine (214 mg, 1.00 mmol) and triethylamine (0.300 mL, 2.15 mmol) in $CH_3CN$ (4 mL) was stirred at room temperature for 20 h. It was concentrated in vacuo. The residue was dissolved in nBuOH (6 mL). 2 mL of the nBuOH solution was taken, to which 1-(4-(4-aminophenyl)piperazin-1-yl)ethanone (108 mg, 0.49 mmol) was added. The solution was stirred at 116° C. for 20 h. nBuOH was removed in vacuo. The residue was dissolved in TFA (2 mL). After being stirred at room temperature for 2 h, TFA was removed in vacuo. The residue was purified by HPLC to give the titled compound (43 mg). MS 428.6 (M+H); UV 206.8, 265.8 nm.

Examples 19 and 20

N-(4-(piperazin-1-yl)phenyl)-4-(piperidin-1-yl)-7H-pyrrolo[2,3-d]pyrimidin-2-amine and 1-(4-(4-(4-(piperidin-1-yl)-7H-pyrrolo[2,3-d]pyrimidin-2-ylamino)phenyl)piperazin-1-yl)ethanone

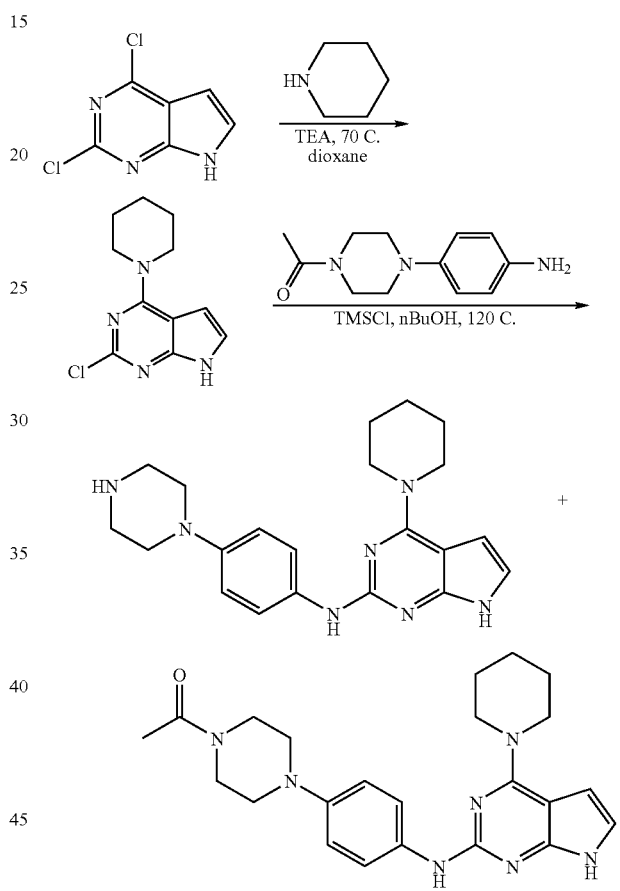

A mixture of 2,4-dichloro-7H-pyrrolo[2,3-d]pyrimidine (100 mg, 0.531 mmol), piperidine (0.060 mL, 0.607 mmol) and triethylamine (0.200 mL, 1.43 mmol) in dioxane (4 mL) was stirred at 70° C. for 20 h. Water and EtOAc were added. The organic phase was separated, dried over $Na_2SO_4$, concentrated in vacuo to give 2-chloro-4-(piperidin-1-yl)-7H-pyrrolo[2,3-d]pyrimidine (123 mg). MS 237.3 and 239.3 (M+H, Cl pattern)

A mixture of 2-chloro-4-(piperidin-1-yl)-7H-pyrrolo[2,3-d]pyrimidine (123 mg, 0.520 mmol), 1-(4-(4-aminophenyl)piperazin-1-yl)ethanone (200 mg, 0.913 mmol) and trimethylsilyl chloride (0.200 mL, 1.58 mmol) in n-BuOH (5 mL) was stirred at 120° C. for 20 h. n-BuOH was removed in vacuo. The residue was purified by HPLC to give N-(4-(piperazin-1-yl)phenyl)-4-(piperidin-1-yl)-7H-pyrrolo[2,3-d]pyrimidin-2-amine (5 mg) (MS 378.5 (M+H)) and 1-(4-(4-

(4-(piperidin-1-yl)-7H-pyrrolo[2,3-d]pyrimidin-2-ylamino)phenyl)piperazin-1-yl)ethanone (31 mg) (MS 420.5 (M+H); UV 205.8, 275.8 nm).

Examples 21 and 22

N-(4-(piperazin-1-yl)phenyl)-4-(pyrrolidin-1-yl)-7H-pyrrolo[2,3-d]pyrimidin-2-amine and 1-(4-(4-(4-(pyrrolidin-1-yl)-7H-pyrrolo[2,3-d]pyrimidin-2-ylamino)phenyl)piperazin-1-yl)ethanone

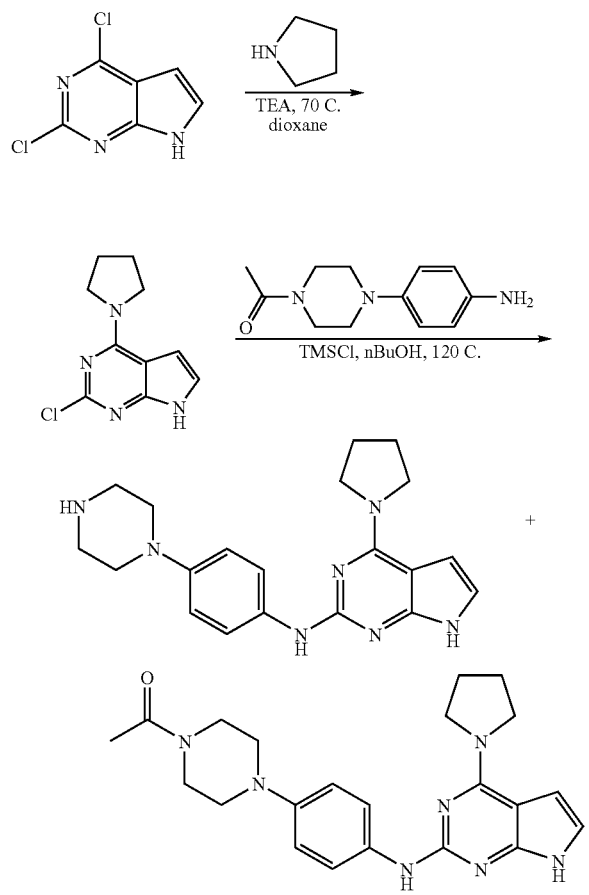

A mixture of 2,4-dichloro-7H-pyrrolo[2,3-d]pyrimidine (100 mg, 0.531 mmol), pyrrolidine (0.050 mL, 0.600 mmol) and triethylamine (0.200 mL, 1.43 mmol) in dioxane (4 mL) was stirred at 70° C. for 20 h. Water and EtOAc were added. The organic phase was separated, dried over $Na_2SO_4$, concentrated in vacuo to give 2-chloro-4-(pyrrolidin-1-yl)-7H-pyrrolo[2,3-d]pyrimidine (116 mg). MS 223.3 and 225.3 (M+H, Cl pattern)

A mixture of 2-chloro-4-(pyrrolidin-1-yl)-7H-pyrrolo[2,3-d]pyrimidine (116 mg, 0.521 mmol), 1-(4-(4-aminophenyl)piperazin-1-yl)ethanone (200 mg, 0.913 mmol) and trimethylsilyl chloride (0.200 mL, 1.58 mmol) in n-BuOH (5 mL) was stirred at 120° C. for 20 h. n-BuOH was removed in vacuo. The residue was purified by HPLC to give N-(4-(piperazin-1-yl)phenyl)-4-(pyrrolidin-1-yl)-7H-pyrrolo[2,3-d]pyrimidin-2-amine (3 mg) (MS 364.5 (M+H)) and 1-(4-(4-

(4-(pyrrolidin-1-yl)-7H-pyrrolo[2,3-d]pyrimidin-2-ylamino)phenyl)piperazin-1-yl)ethanone (30 mg) (MS 406.5 (M+H)).

Examples 23 and 24

1-(2-(4-(piperazin-1-yl)phenylamino)-7H-pyrrolo[2,3-d]pyrimidin-4-yl)piperidine-4-carboxamide and 1-(2-(4-(4-acetylpiperazin-1-yl)phenylamino)-7H-pyrrolo[2,3-d]pyrimidin-4-yl)piperidine-4-carboxamide

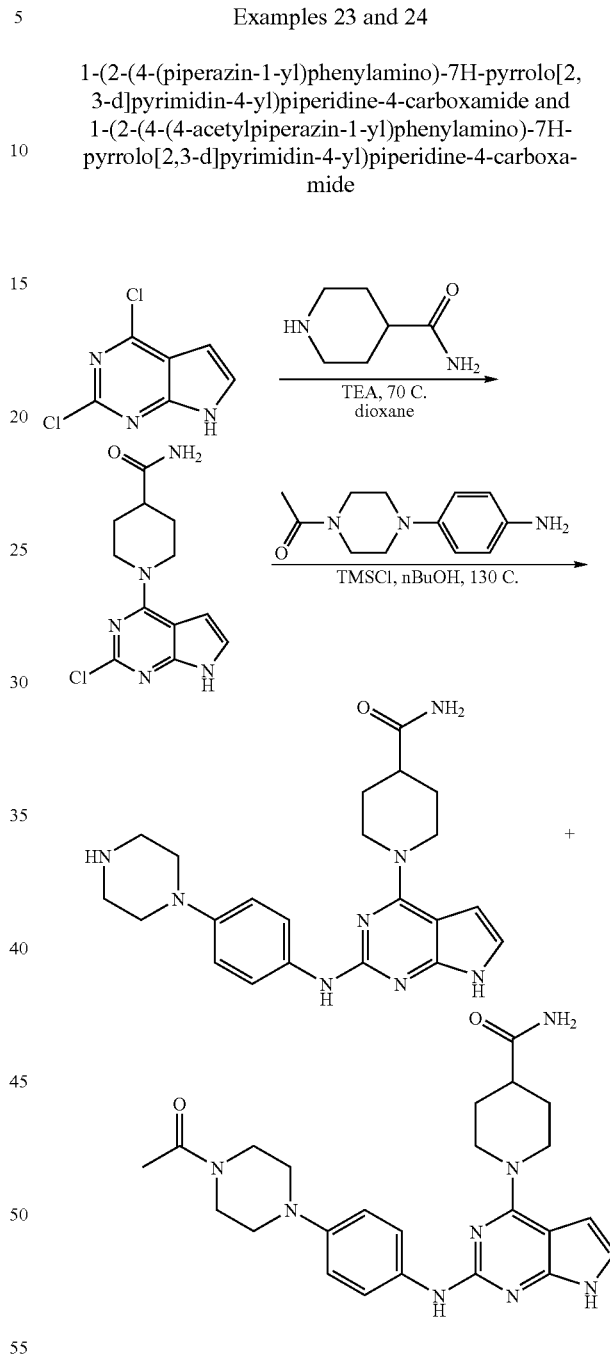

A mixture of 2,4-dichloro-7H-pyrrolo[2,3-d]pyrimidine (140 mg, 0.744 mmol), isonipecotamide (95 mg, 0.742 mmol) and triethylamine (0.300 mL, 2.15 mmol) in dioxane (4 mL) was stirred at 70° C. for 20 h. The precipitates were collected and dried on vacuum to give 1-(2-chloro-7H-pyrrolo[2,3-d]pyrimidin-4-yl)piperidine-4-carboxamide (205 mg). MS 280.3 and 282.3 (M+H, Cl pattern).

A mixture of 1-(2-chloro-7H-pyrrolo[2,3-d]pyrimidin-4-yl)piperidine-4-carboxamide (80 mg, 0.28 mmol), 1-(4-(4-aminophenyl)piperazin-1-yl)ethanone (125 mg, 0.57 mmol) and trimethylsilyl chloride (0.200 mL, 1.58 mmol) in n-BuOH (3 mL) was stirred at 130° C. for 20 h. n-BuOH was removed in vacuo. The residue was purified by HPLC to give 1-(2-(4-(piperazin-1-yl)phenylamino)-7H-pyrrolo[2,3-d]pyrimidin-4-yl)piperidine-4-carboxamide (4 mg) (MS 421.5 (M+H)) and 1-(2-(4-(4-acetylpiperazin-1-yl)phenylamino)-7H-pyrrolo[2,3-d]pyrimidin-4-yl)piperidine-4-carboxamide (6 mg) (MS 463.5 (M+H); UV 200.0, 272.8 nm).
Example 25
2-(4-(4-acetylpiperazin-1-yl)phenylamino)-4-(4-(aminomethyl)piperidin-1-yl)pyrimidine-5-carboxamide
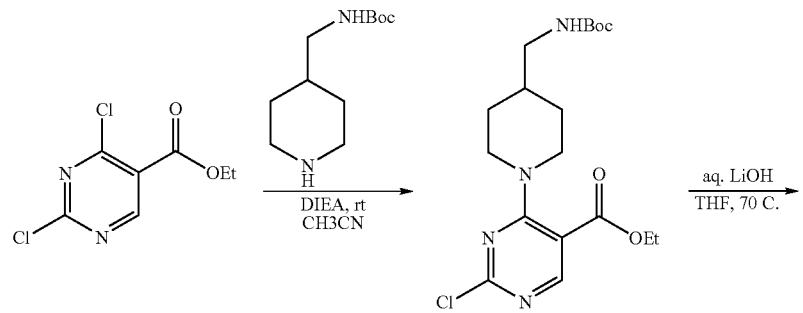
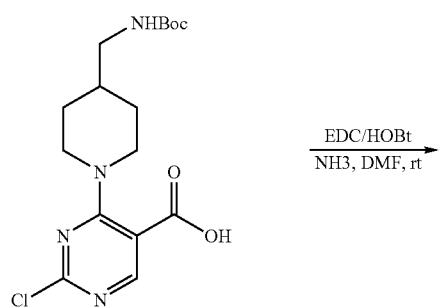
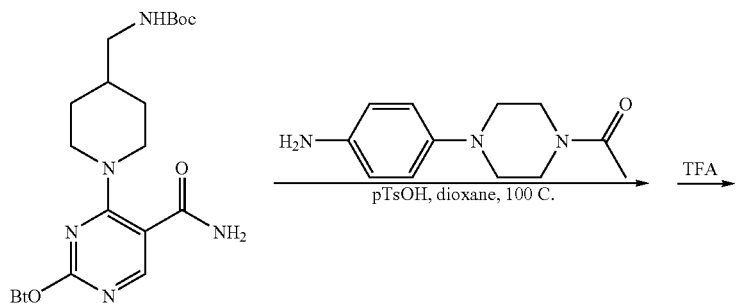
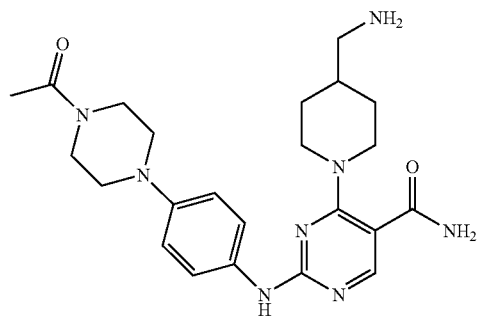

To a solution of ethyl 2,4-dichloropyrimidine-5-carboxylate (221 mg, 1.00 mmol) and DIEA (0.347 mL, 2.00 mmol) in CH₃CN (4 mL), a suspension of 4-N-Boc-aminomethyl piperidine (214 mg, 1.00 mmol) in CH₃CN (4 mL) was added. The mixture was stirred at room temperature for 20 h. Water and EtOAc were added. The organic phase was separated, washed with 1N HCl, then with 5% NaHCO₃, dried over Na₂SO₄, concentrated in vacuo to give ethyl 4-(4-((tert-butoxycarbonyl)methyl)piperidin-1-yl)-2-chloropyrimidine-5-carboxylate (368 mg). MS 399.5 and 401.5 (M+H, Cl pattern).

To a solution of ethyl 4-(4-((tert-butoxycarbonyl)methyl)piperidin-1-yl)-2-chloropyrimidine-5-carboxylate (368 mg, 0.923 mmol) in THF (5 mL), aq. 1M LiOH (2.20 mL, 2.20 mmol) was added. It was heated to reflux for 5 h. THF was removed in vacuo. After being acidified with HOAc (2 mL), the residue was purified by HPLC to give 4-(4-((tert-butoxycarbonyl)methyl)piperidin-1-yl)-2-chloropyrimidine-5-carboxylic acid (150 mg). MS 371.4 and 373.4 (M+H, Cl pattern).

To a solution of 4-(4-((tert-butoxycarbonyl)methyl)piperidin-1-yl)-2-chloropyrimidine-5-carboxylic acid (150 mg, 0.40 mmol) and HOBt (93 mg, 0.61 mmol) in DMF (2 mL), EDC (116 mg, 0.61 mmol) was added. After being stirred for 90 min, NH3 (0.5 M in dioxane, 4.00 mL, 2.00 mmol) was added. The mixture was stirred at room temperature for 20 h. Water and EtOAc were added. The organic phase was separated, washed with 5% NaHCO₃, dried over Na₂SO₄, concentrated in vacuo to give tert-butyl (1-(2-(1H-benzo[d][1,2,3]triazol-1-yloxy)-5-carbamoylpyrimidin-4-yl)piperidin-4-yl)methylcarbamate (138 mg). MS 469.6 (M+H).

A mixture of tert-butyl (1-(2-(1H-benzo[d][1,2,3]triazol-1-yloxy)-5-carbamoylpyrimidin-4-yl)piperidin-4-yl)methylcarbamate (138 mg, 0.294 mmol), 1-(4-(4-aminophenyl)piperazin-1-yl)ethanone (84 mg, 0.38 mmol) and p-toluenesulfonic acid (56 mg, 0.294 mmol) in dioxane (4 mL) was stirred at 100° C. for 3 h. dioxane was removed in vacuo. The residue was dissolved in CH₂Cl₂ (5 mL) and TFA (5 mL). The solution was stirred at room temperature for 30 min. It was then concentrated in vacuo. The residue was purified by HPLC to give the titled compound (15 mg). MS 453.6 (M+H); UV 222.8, 263.8 nm.

Example 26

1-(2-(1H-indazol-6-ylamino)-5-fluoropyrimidin-4-yl)piperidine-3-carboxamide

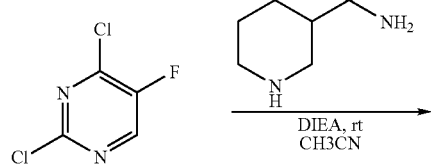

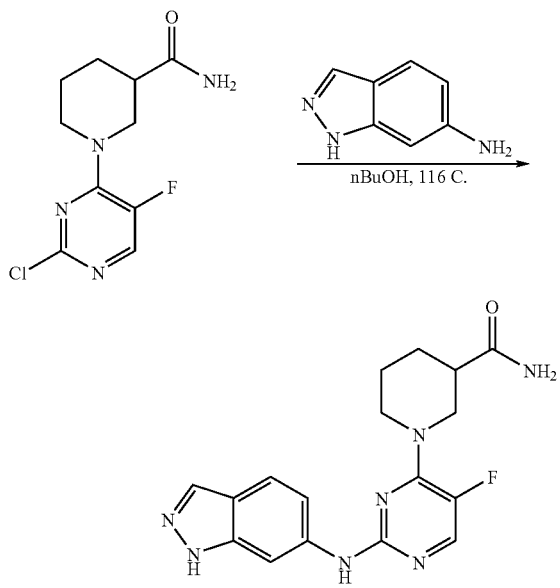

A mixture of 2,4-dichloro-5-fluoropyrimidine (167 mg, 1.00 mmol), nipecotamide (128 mg, 1.00 mmol) and DEA (0.350 mL, 2.01 mmol) in CH₃CN (4 mL) was stirred at room temperature for 20 h. It was concentrated in vacuo. The residue was dissolved in nBuOH (4 mL). 2 mL of the nBuOH solution was taken, to which 6-aminoindazole (100 mg, 0.75 mmol) was added. The solution was stirred at 116° C. for 6 h. nBuOH was removed in vacuo. The residue was purified by HPLC to give the titled compound (63 mg). MS 356.3 (M+H); UV 206.8, 249.8, 276.8, 291.8 nm.

Example 27

1-(2-(4-(4-acetylpiperazin-1-yl)phenylamino)-5-fluoropyrimidin-4-yl)piperidine-3-carboxamide

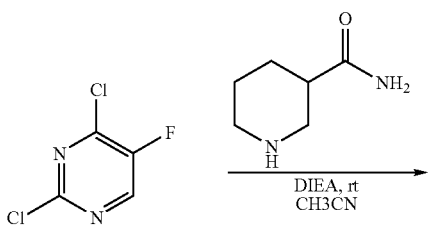

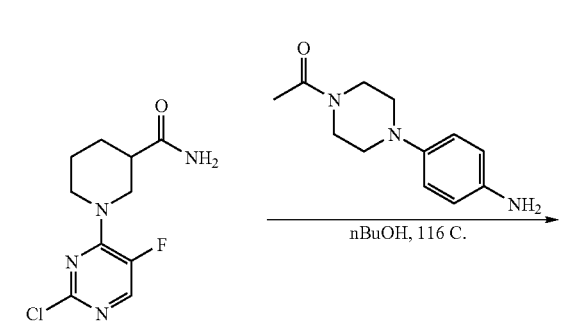

97

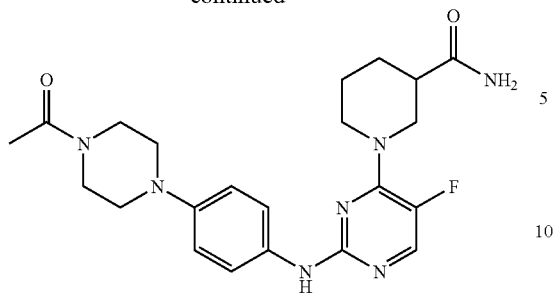

A mixture of 2,4-dichloro-5-fluoropyrimidine (167 mg, 1.00 mmol), nipecotamide (128 mg, 1.00 mmol) and DEA (0.350 mL, 2.01 mmol) in CH₃CN (4 mL) was stirred at room temperature for 20 h. It was concentrated in vacuo. The residue was dissolved in nBuOH (4 mL). 2 mL of the nBuOH solution was taken, to which 1-(4-(4-aminophenyl)piperazin-1-yl)ethanone (150 mg, 0.68 mmol) was added. The solution was stirred at 116° C. for 6 h. nBuOH was removed in vacuo. The residue was purified by HPLC to give the titled compound (75 mg). MS 442.4 (M+H); UV 208.8, 261.8 nm.

Examples 28 and 29 tert-butyl (1-(5-fluoro-2-(4-(N-methylacetamido)phenylamino)pyrimidin-4-yl)piperidin-4-yl)methylcarbamate and N-(4-(4-(4-(aminomethyl)piperidin-1-yl)-5-fluoropyrimidin-2-ylamino)phenyl)-N-methylacetamide

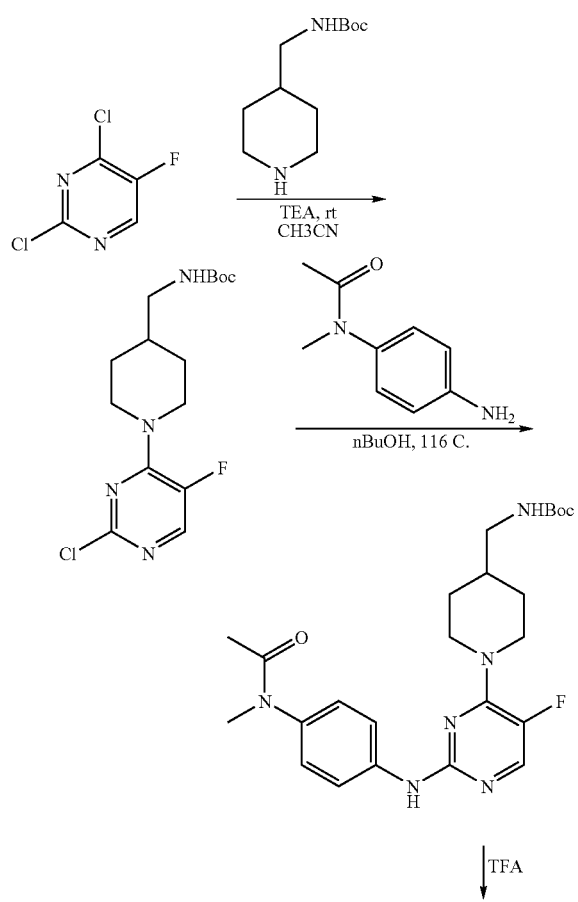

98

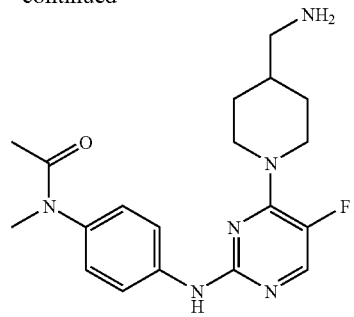

A mixture of 2,4-dichloro-5-fluoropyrimidine (334 mg, 2.00 mmol), 4-N-Boc-aminomethyl piperidine (428 mg, 2.00 mmol) and DIEA (0.700 mL, 4.02 mmol) in CH₃CN (8 mL) was stirred at room temperature for 20 h. It was concentrated in vacuo. The residue was dissolved in nBuOH (12 mL). 3 mL of the nBuOH solution was taken, to which N-(4-aminophenyl)-N-methylacetamide (98 mg, 0.60 mmol) was added. The solution was stirred at 116° C. for 20 h. nBuOH was removed in vacuo. The residue was purified by HPLC to give tert-butyl (1-(5-fluoro-2-(4-(N-methylacetamido)phenylamino)pyrimidin-4-yl)piperidin-4-yl)methylcarbamate (65 mg). MS 473.4 (M+H); UV 205.8, 262.8 nm.

A solution of tert-butyl (1-(5-fluoro-2-(4-(N-methylacetamido)phenylamino)pyrimidin-4-yl)piperidin-4-yl)methylcarbamate (60 mg, 0.13 mmol) in TFA (2 mL) was stirred at room temperature for 60 min. TFA was removed in vacuo. The residue was purified by HPLC to give N-(4-(4-(4-(aminomethyl)piperidin-1-yl)-5-fluoropyrimidin-2-ylamino)phenyl)-N-methylacetamide (25 mg). MS 373.3 (M+H); UV 201.8, 266.8 nm.

Examples 30 and 31 tert-butyl (1-(2-(4-carbamoylphenylamino)-5-fluoropyrimidin-4-yl)piperidin-4-yl)methylcarbamate and 4-(4-(4-(aminomethyl)piperidin-1-yl)-5-fluoropyrimidin-2-ylamino)benzamide

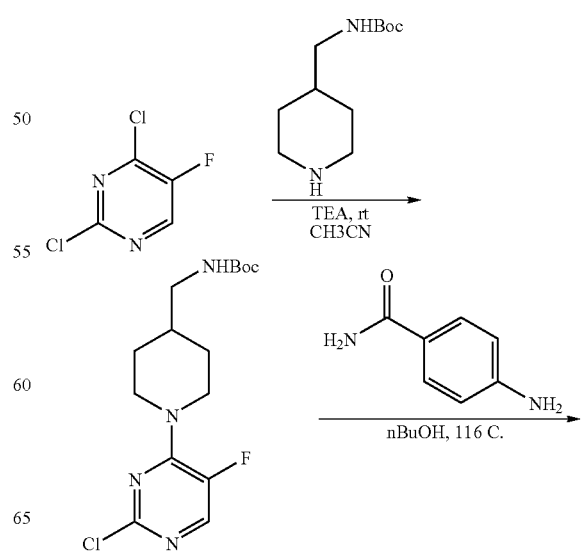

99
-continued

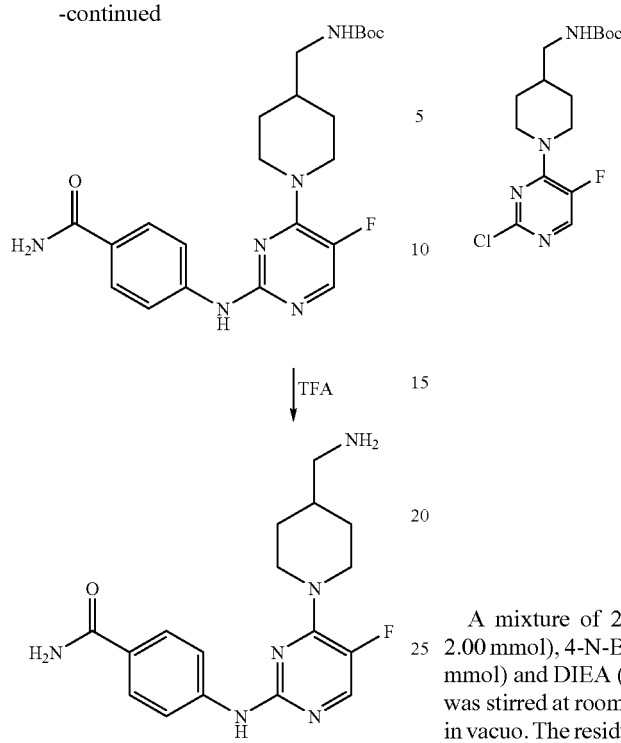

A mixture of 2,4-dichloro-5-fluoropyrimidine (334 mg, 2.00 mmol), 4-N-Boc-aminomethyl piperidine (428 mg, 2.00 mmol) and DIEA (0.700 mL, 4.02 mmol) in CH$_3$CN (8 mL) was stirred at room temperature for 20 h. It was concentrated in vacuo. The residue was dissolved in nBuOH (12 mL). 3 mL of the nBuOH solution was taken, to which 4-aminobenzamide (82 mg, 0.60 mmol) was added. The solution was stirred at 116° C. for 20 h. nBuOH was removed in vacuo. The residue was purified by HPLC to give tert-butyl (1-(2-(4-carbamoylphenylamino)-5-fluoropyrimidin-4-yl)piperidin-4-yl)methylcarbamate (15 mg). MS 445.4 (M+H); UV 212.0, 282.8 nm.

A solution of tert-butyl (1-(2-(4-carbamoylphenylamino)-5-fluoropyrimidin-4-yl)piperidin-4-yl)methylcarbamate (10 mg, 0.023 mmol) in TFA (2 mL) was stirred at room temperature for 60 min. TFA was removed in vacuo. The residue was purified by HPLC to give 4-(4-(4-(aminomethyl)piperidin-1-yl)-5-fluoropyrimidin-2-ylamino)benzamide (5 mg) MS 345.3 (M+H); UV 210.0, 281.8 nm.

Example 32

4-(4-(4-(aminomethyl)piperidin-1-yl)-5-fluoropyrimidin-2-ylamino)benzenesulfonamide

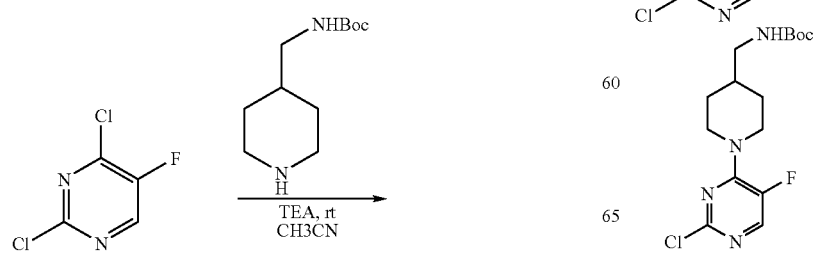

100
-continued

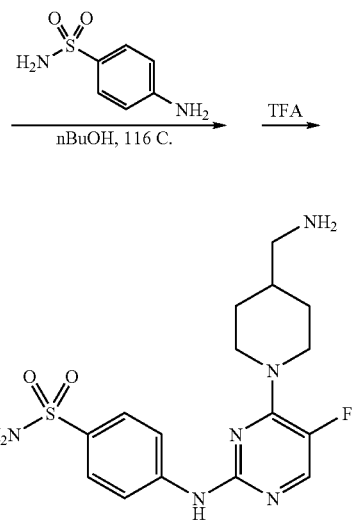

A mixture of 2,4-dichloro-5-fluoropyrimidine (334 mg, 2.00 mmol), 4-N-Boc-aminomethyl piperidine (428 mg, 2.00 mmol) and DIEA (0.700 mL, 4.02 mmol) in CH$_3$CN (8 mL) was stirred at room temperature for 20 h. It was concentrated in vacuo. The residue was dissolved in nBuOH (12 mL). 3 mL of the nBuOH solution was taken, to which sulfanilamide (103 mg, 0.60 mmol) was added. The solution was stirred at 116° C. for 20 h. nBuOH was removed in vacuo. The residue was purified by HPLC to give 4-(4-(4-(N-tBoc-aminomethyl)piperidin-1-yl)-5-fluoropyrimidin-2-ylamino)benzenesulfonamide (10 mg). MS 481.3 (M+H).

A solution of 4-(4-(4-(N-tBoc-aminomethyl)piperidin-1-yl)-5-fluoropyrimidin-2-ylamino)benzenesulfonamide (10 mg, 0.021 mmol) in TFA (2 mL) was stirred at room temperature for 60 min. TFA was removed in vacuo. The residue was purified by HPLC to give the titled compound (5 mg) MS 381.3 (M+H)

Example 33

6-(4-(4-(aminomethyl)piperidin-1-yl)-5-fluoropyrimidin-2-ylamino)-3,4-dihydroquinolin-2(1H)-one

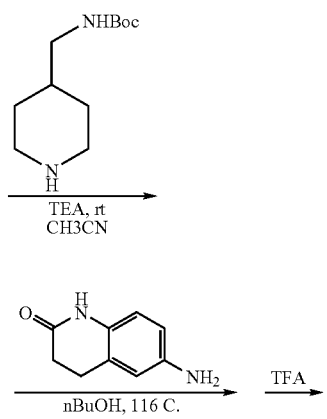

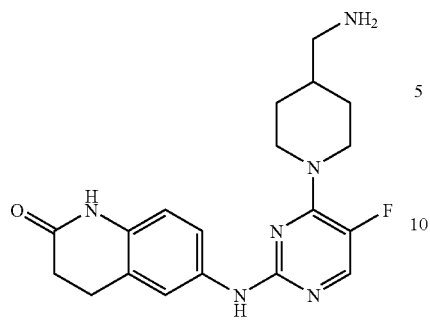

A mixture of 2,4-dichloro-5-fluoropyrimidine (334 mg, 2.00 mmol), 4-N-Boc-aminomethyl piperidine (428 mg, 2.00 mmol) and DIEA (0.700 mL, 4.02 mmol) in CH$_3$CN (8 mL) was stirred at room temperature for 20 h. It was concentrated in vacuo. The residue was dissolved in nBuOH (12 mL). 3 mL of the nBuOH solution was taken, to which 6-amino-3,4-dihydroquinolin-2(1H)-one (98 mg, 0.60 mmol) was added. The solution was stirred at 116° C. for 20 h. nBuOH was removed in vacuo. The residue was purified by HPLC to give tert-butyl (1-(5-fluoro-2-(2-oxo-1,2,3,4-tetrahydroquinolin-6-ylamino)pyrimidin-4-yl)piperidin-4-yl)methylcarbamate (55 mg). MS 471.4 (M+H).

A solution of tert-butyl (1-(5-fluoro-2-(2-oxo-1,2,3,4-tetrahydroquinolin-6-ylamino)pyrimidin-4-yl)piperidin-4-yl)methylcarbamate (55 mg, 0.12 mmol) in TFA (3 mL) was stirred at room temperature for 60 min. TFA was removed in vacuo. The residue was purified by HPLC to give the titled compound (30 mg) MS 371.3 (M+H); UV 206.8, 274.8 nm.

Example 34

1-(4-(4-(4-(2-(aminomethyl)piperidin-1-yl)-5-fluoropyrimidin-2-ylamino)phenyl)piperazin-1-yl)ethanone

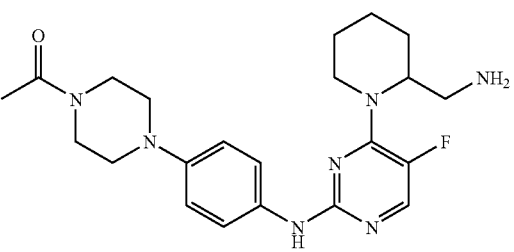

A mixture of 2,4-dichloro-5-fluoropyrimidine (167 mg, 1.00 mmol), 2-N-Boc-aminomethyl piperidine (214 mg, 1.00 mmol) and DIEA (0.400 mL, 2.30 mmol) in CH$_3$CN (4 mL) was stirred at room temperature for 20 h. It was concentrated in vacuo. The residue was dissolved in nBuOH (6 mL). 3 mL of the nBuOH solution was taken, to which 1-(4-(4-aminophenyl)piperazin-1-yl)ethanone (142 mg, 0.65 mmol) was added. The solution was stirred at 116° C. for 20 h. nBuOH was removed in vacuo. The residue was purified by HPLC to give tert-butyl (1-(2-(4-(4-acetylpiperazin-1-yl)phenylamino)-5-fluoropyrimidin-4-yl)piperidin-2-yl)methylcarbamate (56 mg). MS 528.4 (M+H).

A solution of tert-butyl (1-(2-(4-(4-acetylpiperazin-1-yl)phenylamino)-5-fluoropyrimidin-4-yl)piperidin-2-yl)methylcarbamate (56 mg, 0.11 mmol) in TFA (3 mL) was stirred at room temperature for 60 min. TFA was removed in vacuo. The residue was purified by HPLC to give the titled compound (35 mg) MS 428.4 (M+H); UV 213.8, 258.8 nm.

Examples 35 and 36 tert-butyl (1-(2-(1H-indazol-6-ylamino)-5-fluoropyrimidin-4-yl)piperidin-2-yl)methylcarbamate and N-(4-(2-(aminomethyl)piperidin-1-yl)-5-fluoropyrimidin-2-yl)-1H-indazol-6-amine

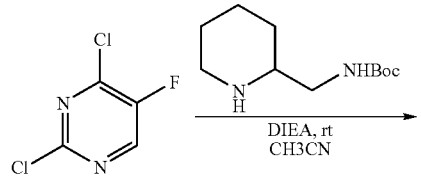

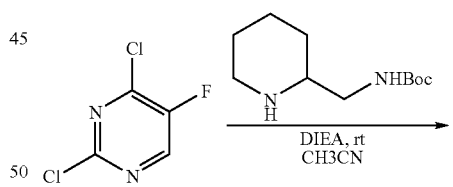

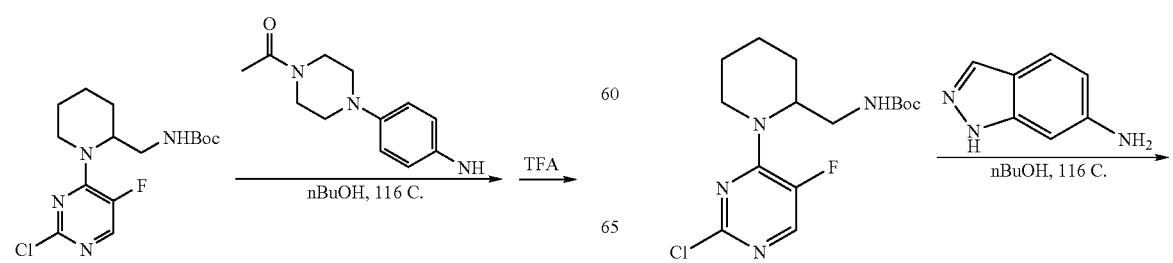

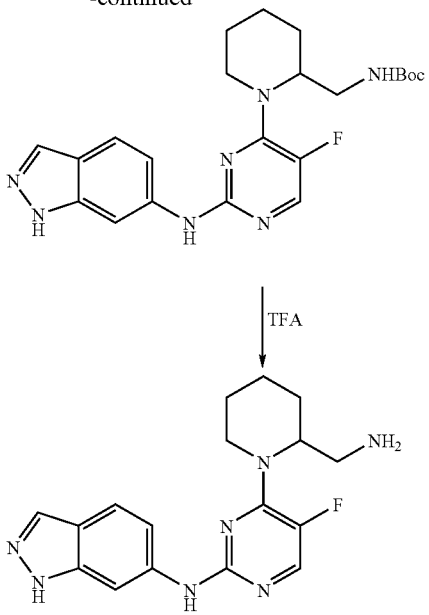

A mixture of 2,4-dichloro-5-fluoropyrimidine (167 mg, 1.00 mmol), 2-N-Boc-aminomethyl piperidine (214 mg, 1.00 mmol) and DIEA (0.400 mL, 2.30 mmol) in $CH_3CN$ (4 mL) was stirred at room temperature for 20 h. It was concentrated in vacuo. The residue was dissolved in nBuOH (6 mL). 3 mL of the nBuOH solution was taken, to which 6-aminoindazole (86 mg, 0.65 mmol) was added. The solution was stirred at 116° C. for 20 h. nBuOH was removed in vacuo. The residue was purified by HPLC to give tert-butyl (1-(2-(H-indazol-6-ylamino)-5-fluoropyrimidin-4-yl)piperidin-2-yl)methylcarbamate (41 mg). MS 442.3 (M+H); UV 201.8, 246.8, 281.8 nm.

A solution of tert-butyl (1-(2-(1H-indazol-6-ylamino)-5-fluoropyrimidin-4-yl)piperidin-2-yl)methylcarbamate (41 mg, 0.093 mmol) in TFA (4 mL) was stirred at room temperature for 60 min. TFA was removed in vacuo. The residue was purified by HPLC to give N-(4-(2-(aminomethyl)piperidin-1-yl)-5-fluoropyrimidin-2-yl)-1H-indazol-6-amine (25 mg) MS 342.3 (M+H); UV 201.8, 246.8, 278.8 nm.

Example 37

1-((1-(5-fluoro-2-(2-oxo-1,2,3,4-tetrahydroquinolin-6-ylamino)pyrimidin-4-yl)piperidin-4-yl)methyl)urea

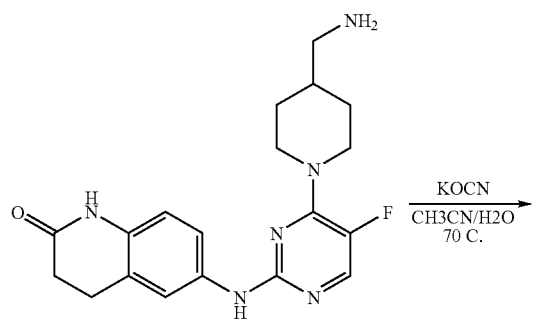

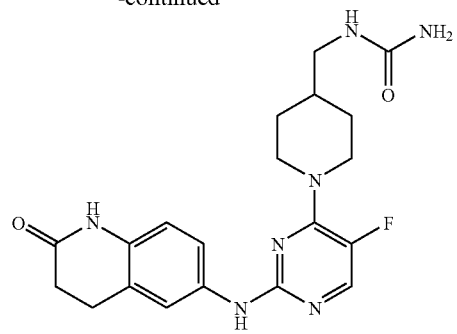

To a suspension of 6-(4-(4-(aminomethyl)piperidin-1-yl)-5-fluoropyrimidin-2-ylamino)-3,4-dihydroquinolin-2(1H)-one (26 mg, 0.070 mmol) in $CH_3CN$ (1 mL), an aqueous solution of potassium cyanate (34 mg, 0.42 mmol) in $H_2O$ (1 mL) was added. The mixture was stirred at 70° C. for 1 h. Solvents were removed in vacuo. The residue was purified by HPLC to give the titled compound (8 mg). MS 414.3 (M+H); UV 205.8, 276.8 nm Example 38

1-(4-(4-(5-fluoro-4-(4-(hydroxymethyl)piperidin-1-yl)pyrimidin-2-ylamino)phenyl)piperazin-1-yl)ethanone

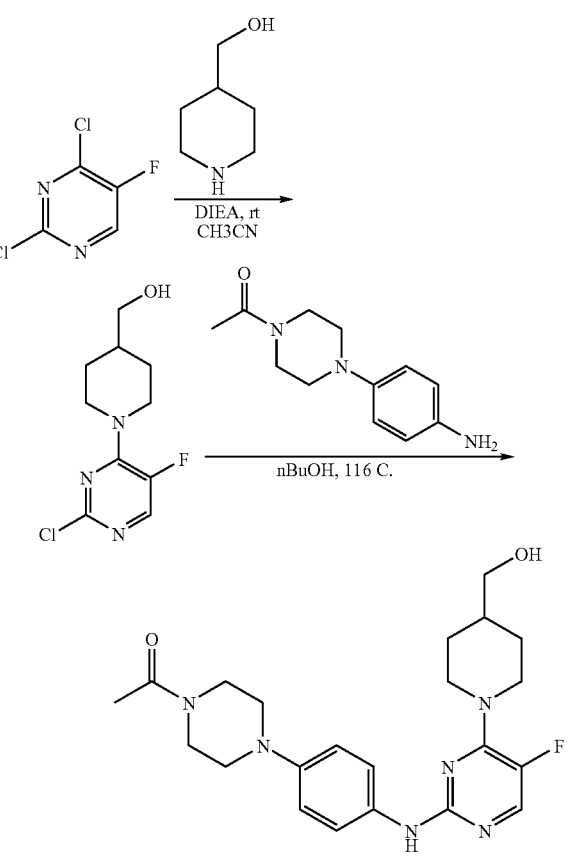

A mixture of 2,4-dichloro-5-fluoropyrimidine (167 mg, 1.00 mmol), 4-piperidinemethanol (115 mg, 1.00 mmol) and DIEA (0.400 mL, 2.30 mmol) in CH₃CN (4 mL) was stirred at room temperature for 2 h. It was concentrated in vacuo. The residue was dissolved in nBuOH (6 mL). 3 mL of the nBuOH solution was taken, to which 1-(4-(4-aminophenyl)piperazin-1-yl)ethanone (120 mg, 0.55 mmol) was added. The solution was stirred at 116° C. for 20 h. nBuOH was removed in vacuo. The residue was purified by HPLC to give the titled compound (53 mg). MS 429.3 (M+H); UV 207.8, 266.8 nm.

Example 39

6-(5-fluoro-4-(4-(hydroxymethyl)piperidin-1-yl)pyrimidin-2-ylamino)-3,4-dihydroquinolin-2(1H)-one

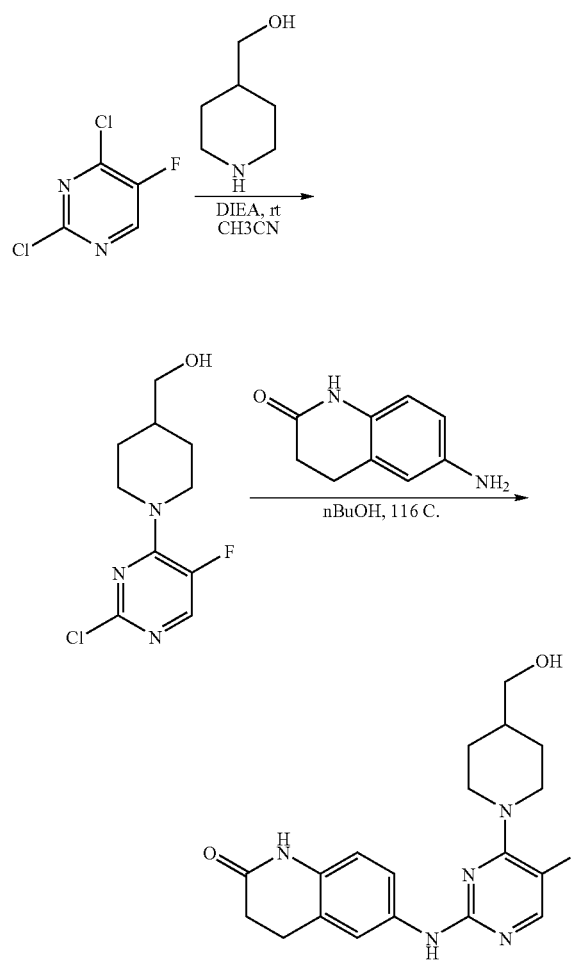

A mixture of 2,4-dichloro-5-fluoropyrimidine (167 mg, 1.00 mmol), 4-piperidinemethanol (115 mg, 1.00 mmol) and DIEA (0.400 mL, 2.30 mmol) in CH₃CN (4 mL) was stirred at room temperature for 2 h. It was concentrated in vacuo. The residue was dissolved in nBuOH (6 mL). 3 mL of the nBuOH solution was taken, to which 6-amino-3,4-dihydroquinolin-2(1H)-one (88 mg, 0.54 mmol) was added. The solution was stirred at 116° C. for 20 h. nBuOH was removed in vacuo. The residue was purified by HPLC to give the titled compound (52 mg). MS 372.3 (M+H); UV 208.8, 275.8 nm.

The following compound was prepared using a procedure similar to that described in Example 5 with reagent A in place of cyclobutylamine in Step 4.

Example 40

2-(1H-indazol-6-ylamino)-4-(cyclopropylamino)-7H-pyrrolo[2,3-d]pyrimidine-5-carbonitrile

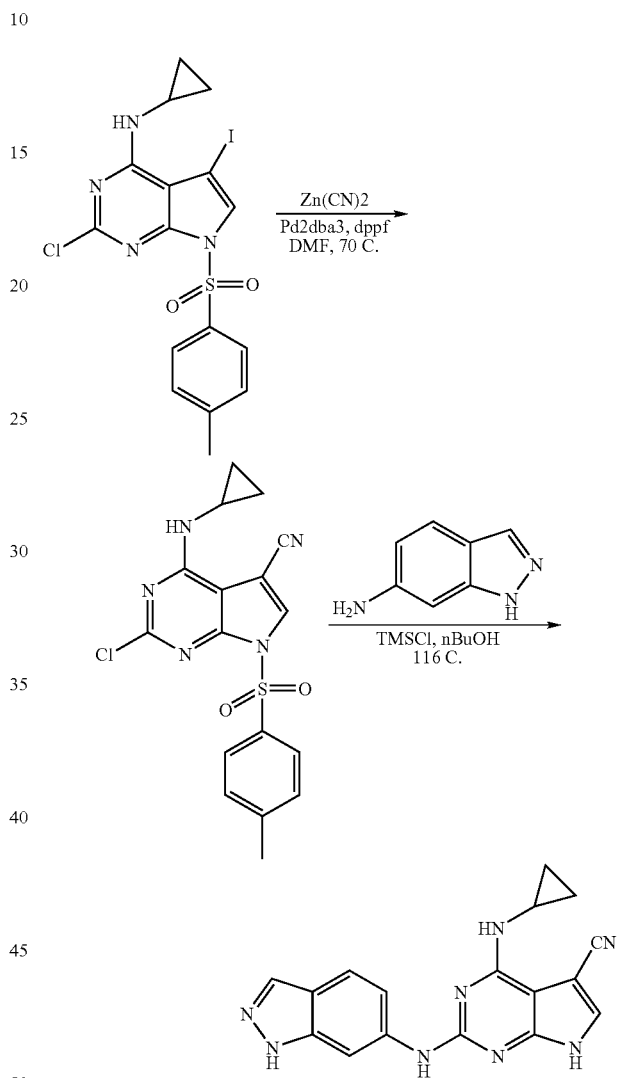

A solution of 2-chloro-N-cyclopropyl-5-iodo-7-tosyl-7H-pyrrolo[2,3-d]pyrimidin-4-amine (200 mg, 0.409 mmol), Pd2dba3 (23 mg, 0.025 mmol) and dppf (45 mg, 0.081 mmol) in DMF (2 mL) was degassed with Ar before being charged with Zn(CN)₂ (28 mg, 0.24 mmol). The mixture was stirred at 70° C. for 2 h. Water and EtOAc were added. The organic phase was separated, dried over Na₂SO₄, concentrated in vacuo. The residue was purified by a flash silica gel column, eluted with EtOAc/hexane (0-15%) to give 2-chloro-4-(cyclopropylamino)-7-tosyl-7H-pyrrolo[2,3-d]pyrimidine-5-carbonitrile (110 mg).

A mixture of 2-chloro-4-(cyclopropylamino)-7-tosyl-7H-pyrrolo[2,3-d]pyrimidine-5-carbonitrile (109 mg, 0.28 mmol), 6-aminoindazole (75 mg, 0.56 mmol) and TMSCl (0.089 mL, 0.70 mmol) in nBuOH (4 mL) was stirred at 116° C. for 18 h. It was then concentrated in vacuo. The residue was purified by HPLC to give the titled compound (6 mg). MS 331.1 (M+H); UV 246.2, 307.9 nm.

Example 41

5-(1-butoxyethyl)-N4-cyclopropyl-N2-(1H-indazol-6-yl)-7H-pyrrolo[2,3-d]pyrimidine-2,4-diamine

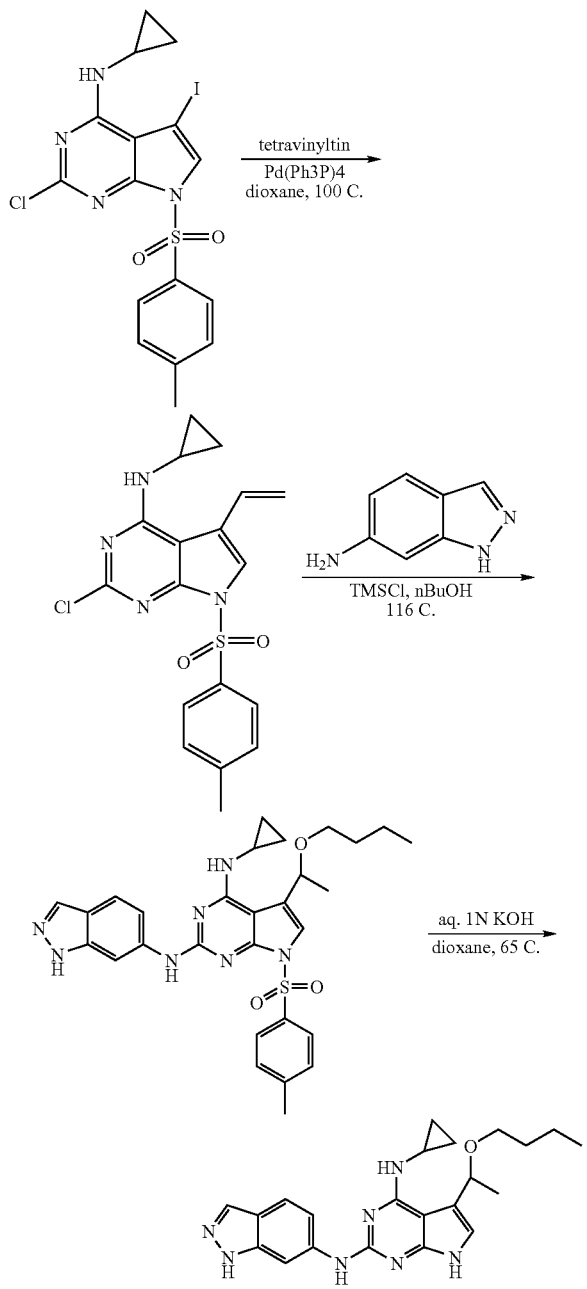

A solution of 2-chloro-N-cyclopropyl-5-iodo-7-tosyl-7H-pyrrolo[2,3-d]pyrimidin-4-amine (190 mg, 0.389 mmol) in dioxane (3 mL) was degassed with Ar before being charged with tetravinyltin (0.105 mL, 0.576 mmol) and Pd(Ph3P)4 (41 mg, 0.035 mmol). The mixture was stirred at 100° C. for 3 h. Water and EtOAc were added. The organic phase was separated, dried over Na₂SO₄, concentrated in vacuo. The residue was purified by HPLC to give 2-chloro-N-cyclopropyl-7-tosyl-5-vinyl-7H-pyrrolo[2,3-d]pyrimidin-4-amine (39 mg).

A mixture of 2-chloro-N-cyclopropyl-7-tosyl-5-vinyl-7H-pyrrolo[2,3-d]pyrimidin-4-amine (39 mg, 0.10 mmol), 6-aminoindazole (40 mg, 0.30 mmol) and TMSCl (0.050 mL, 0.40 mmol) in nBuOH (1 mL) was stirred at 116° C. for 18 h. It was then concentrated in vacuo. The residue was purified by HPLC to give 5-(1-butoxyethyl)-N4-cyclopropyl-N-2-(1H-indazol-6-yl)-7-tosyl-7H-pyrrolo[2,3-d]pyrimidine-2,4-diamine (20 mg).

To a solution of 5-(1-butoxyethyl)-N4-cyclopropyl-N2-(1H-indazol-6-yl)-7-tosyl-7H-pyrrolo[2,3-d]pyrimidine-2,4-diamine (20 mg, 0.036 mmol) in dioxane (2 mL), aq. 1N KOH (1.0 mL, 1.0 mmol) was added. The mixture was stirred at 65° C. for 18 h. After being concentrated in vacuo, the residue was acidified with HOAc (1 mL); it was then purified by HPLC to give the titled compound (3 mg). MS 406.2 (M+H); UV 203.8, 223.8, 243.8, 315.0 nm.

Example 42

1-(2-(1H-indazol-6-ylamino)-4-(cyclopropylamino)-7H-pyrrolo[2,3-d]pyrimidin-5-yl)ethanone

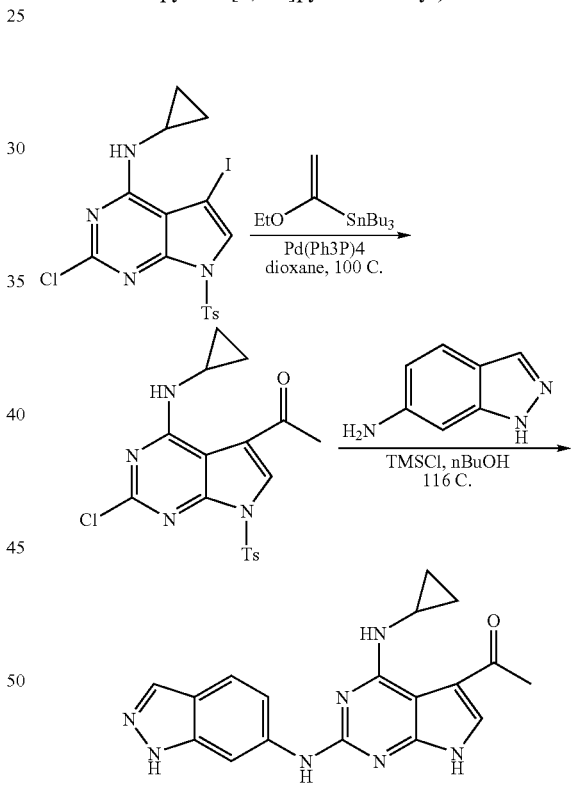

A solution of 2-chloro-N-cyclopropyl-5-iodo-7-tosyl-7H-pyrrolo[2,3-d]pyrimidin-4-amine (489 mg, 1.00 mmol) in dioxane (6 mL) was degassed with Ar before being charged with tributyl(ethoxyvinyl)tin (0.371 mL, 1.10 mmol) and Pd(Ph3P)4 (90 mg, 0.078 mmol). The mixture was stirred at 100° C. for 18 h. Water and EtOAc were added. The organic phase was separated, dried over Na₂SO₄, concentrated in vacuo. The residue was purified by HPLC to give 1-(2-chloro-4-(cyclopropylamino)-7-tosyl-7H-pyrrolo[2,3-d]pyrimidin-5-yl)ethanone (185 mg).

A mixture of 1-(2-chloro-4-(cyclopropylamino)-7-tosyl-7H-pyrrolo[2,3-d]pyrimidin-5-yl)ethanone (85 mg, 0.21 mmol), 6-aminoindazole (56 mg, 0.42 mmol) and TMSCl (0.070 mL, 0.55 mmol) in nBuOH (3 mL) was stirred at 116° C. for 18 h. It was then concentrated in vacuo. The residue was purified by HPLC to give the titled compound (30 mg). MS 348.1 (M+H); UV 248.7, 305.7 nm.

Example 43

N4-cyclopropyl-N2-(1H-indazol-6-yl)-5-(pyridin-4-yl)-7H-pyrrolo[2,3-d]pyrimidine-2,4-diamine

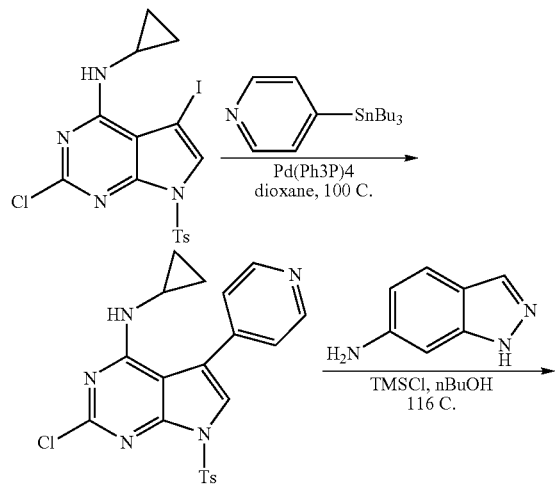

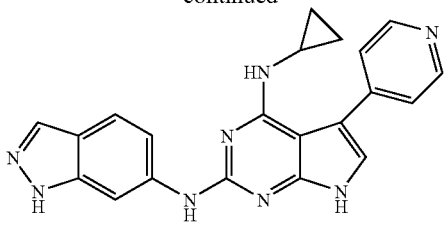

A solution of 2-chloro-N-cyclopropyl-5-iodo-7-tosyl-7H-pyrrolo[2,3-d]pyrimidin-4-amine (225 mg, 0.460 mmol) in dioxane (3 mL) was degassed with Ar before being charged with 4-tributylstannylpyridine (371 mg, 1.01 mmol) and Pd(Ph3P)4 (98 mg, 0.085 mmol). The mixture was stirred at 100° C. for 18 h. Water and EtOAc were added. The organic phase was separated, dried over $Na_2SO_4$, concentrated in vacuo. The residue was purified by HPLC to give 2-chloro-N-cyclopropyl-5-(pyridin-4-yl)-7-tosyl-7H-pyrrolo[2,3-d]pyrimidin-4-amine (51 mg).

A mixture of 2-chloro-N-cyclopropyl-5-(pyridin-4-yl)-7-tosyl-7H-pyrrolo[2,3-d]pyrimidin-4-amine (51 mg, 0.12 mmol), 6-aminoindazole (31 mg, 0.23 mmol) and TMSCl (0.040 mL, 0.32 mmol) in nBuOH (2 mL) was stirred at 116° C. for 18 h. It was then concentrated in vacuo. The residue was purified by HPLC to give the titled compound (12 mg). MS 383.2 (M+H); UV 204.9, 250.9, 307.9 nm.

Example 44

1-(4-(4-(4-(piperidin-4-ylmethylamino)-5-(pyridin-4-yl)-7H-pyrrolo[2,3-d]pyrimidin-2-ylamino)phenyl)piperazin-1-yl)ethanone

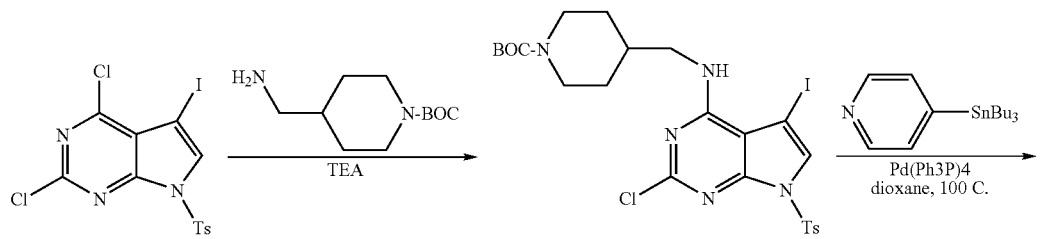

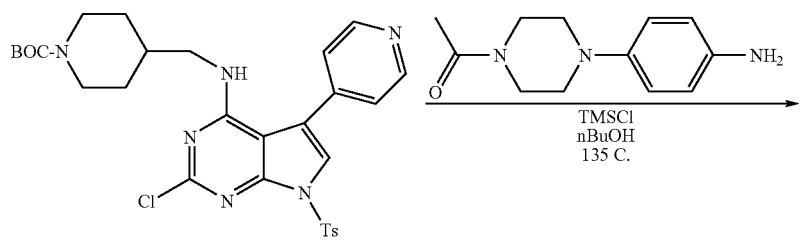

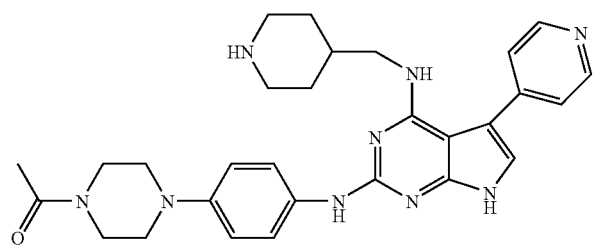

A mixture of 2,4-dichloro-5-iodo-7-tosyl-7H-pyrrolo[2,3-d]pyrimidine (244 mg, 0.520 mmol), 1-N—BOC-4-aminomethyl piperidine hydrochloride (130 mg, 0.520 mmol) and TEA (0.200 mL, 1.44 mmol) in CH$_3$CN (6 mL) was stirred at room temperature for 16 h. Water and EtOAc were added. The organic phase was separated, washed with 1N HCl, then with 5% NaHCO$_3$, dried over Na$_2$SO$_4$, concentrated in vacuo to give tert-butyl 4-((2-chloro-5-iodo-7-tosyl-7H-pyrrolo[2,3-d]pyrimidin-4-ylamino)methyl)piperidine-1-carboxylate (336 mg).

A solution of tert-butyl 4-((2-chloro-5-iodo-7-tosyl-7H-pyrrolo[2,3-d]pyrimidin-4-ylamino)methyl)piperidine-1-carboxylate (336 mg, 0.520 mmol) in dioxane (4 mL) was degassed with Ar before being charged with 4-tributylstannylpyridine (452 mg, 1.23 mmol) and Pd(Ph$_3$P)$_4$ (110 mg, 0.095 mmol). The mixture was stirred at 100° C. for 4 h. Water and EtOAc were added. The organic phase was separated, dried over Na$_2$SO$_4$, concentrated in vacuo. The residue was purified by a flash column, eluted with EtOAc/hexane (0-100%) to give tert-butyl 4-((2-chloro-5-(pyridine-4-yl)-7-tosyl-7H-pyrrolo[2,3-d]pyrimidin-4-ylamino)methyl)piperidine-1-carboxylate (90 mg).

A mixture of tert-butyl 4-((2-chloro-5-(pyridine-4-yl)-7-tosyl-7H-pyrrolo[2,3-d]pyrimidin-4-ylamino)methyl)piperidine-1-carboxylate (90 mg, 0.15 mmol), 1-(4-(4-aminophenyl)piperazin-1-yl)ethanone (66 mg, 0.30 mmol) and TMSCl (0.100 mL, 0.79 mmol) in nBuOH (4 mL) was stirred at 135° C. for 68 h. It was then concentrated in vacuo. The residue was purified by HPLC to give the titled compound (26 mg). MS 526.47 (M+H); UV 202.6, 259.2, 304.3 nm.

Example 45

2-(4-(4-acetylpiperazin-1-yl)phenylamino)-4-(piperidin-4-ylmethylamino)-7H-pyrrolo[2,3-d]pyrimidine-5-carbonitrile

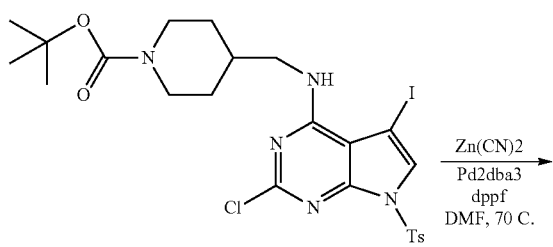

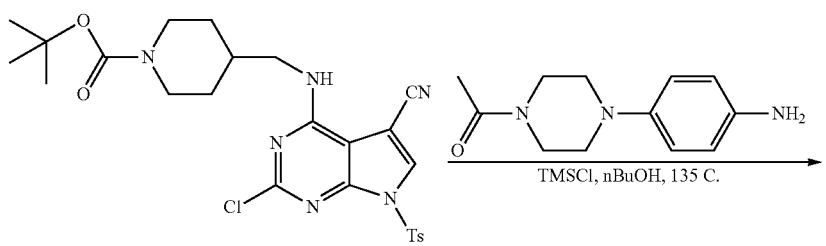

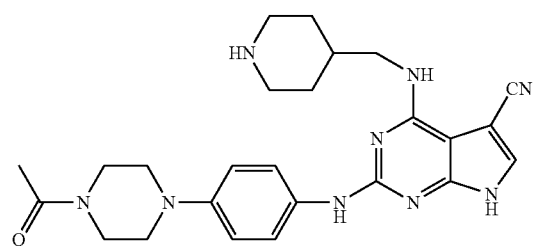

A solution of tert-butyl 4-((2-chloro-5-iodo-7-tosyl-7H-pyrrolo[2,3-d]pyrimidin-4-ylamino)methyl)piperidine-1-carboxylate (360 mg, 0.557 mmol), Pd2 dba3 (50 mg, 0.055 mmol) and dppf (62 mg, 0.11 mmol) in DMF (5 mL) was degassed with Ar before being charged with Zn(CN)$_2$ (80 mg, 0.68 mmol). The mixture was stirred at 70° C. for 18 h. Water and EtOAc were added. The organic phase was separated, dried over Na$_2$SO$_4$, concentrated in vacuo. The residue was purified by a flash silica gel column, eluted with EtOAc/hexane (0-35%) to give tert-butyl 4-((2-chloro-5-cyano-7-tosyl-7H-pyrrolo[2,3-d]pyrimidin-4-ylamino)methyl)piperidine-1-carboxylate (127 mg).

A mixture of tert-butyl 4-((2-chloro-5-cyano-7-tosyl-7H-pyrrolo[2,3-d]pyrimidin-4-ylamino)methyl)piperidine-1-carboxylate (127 mg, 0.233 mmol), 1-(4-(4-aminophenyl)piperazin-1-yl)ethanone (100 mg, 0.456 mmol) and TMSCl (0.200 mL, 1.58 mmol) in nBuOH (5 mL) was stirred at 135° C. for 68 h. It was then concentrated in vacuo. The residue was purified by HPLC to give the titled compound (25 mg). MS 475 (M+H); UV 204.9, 265.1, 297.2 nm.

Example 46

2-(4-(4-acetylpiperazin-1-yl)phenylamino)-4-(4-(aminomethyl)piperidin-1-yl)-7H-pyrrolo[2,3-d]pyrimidine-5-carbonitrile

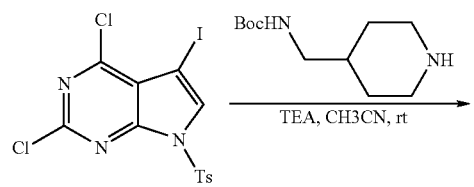

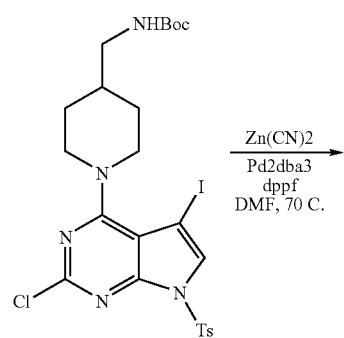

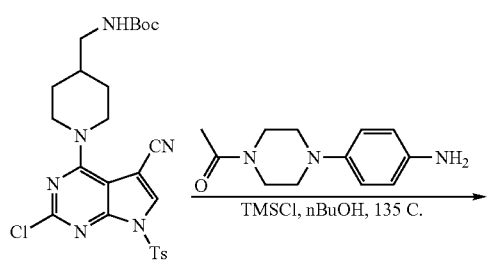

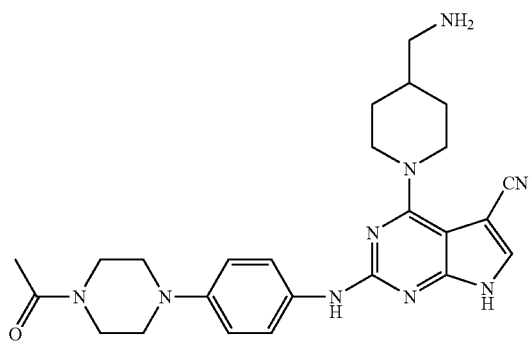

A mixture of 2,4-dichloro-5-iodo-7-tosyl-7H-pyrrolo[2,3-d]pyrimidine (310 mg, 0.662 mmol), 4-N-BOC-aminomethyl piperidine (142 mg, 0.663 mmol) and TEA (0.200 mL, 1.44 mmol) in CH$_3$CN (10 mL) was stirred at room temperature for 16 h. Water and EtOAc were added. The organic phase was separated, washed with 1N HCl, then with 5% NaHCO$_3$, dried over Na$_2$SO$_4$, concentrated in vacuo to give tert-butyl (1-(2-chloro-5-iodo-7-tosyl-7H-pyrrolo[2,3-d]pyrimidin-4-yl)piperidin-4-yl)methylcarbamate (418 mg).

A solution of tert-butyl (1-(2-chloro-5-iodo-7-tosyl-7H-pyrrolo[2,3-d]pyrimidin-4-yl)piperidin-4-yl)methylcarbamate (418 mg, 0.647 mmol), Pd$_2$ dba$_3$ (60 mg, 0.065 mmol) and dppf (72 mg, 0.13 mmol) in DMF (5 mL) was degassed with Ar before being charged with Zn(CN)$_2$ (91 mg, 0.78 mmol). The mixture was stirred at 70° C. for 18 h. Water and EtOAc were added. The organic phase was separated, dried over Na$_2$SO$_4$, concentrated in vacuo. The residue was purified by a flash silica gel column, eluted with EtOAc/hexane (10-30%) to give tert-butyl (1-(2-chloro-5-cyano-7-tosyl-7H-pyrrolo[2,3-d]pyrimidin-4-yl)piperidin-4-yl)methylcarbamate (180 mg).

A mixture of tert-butyl (1-(2-chloro-5-cyano-7-tosyl-7H-pyrrolo[2,3-d]pyrimidin-4-yl)piperidin-4-yl)methylcarbamate (180 mg, 0.330 mmol), 1-(4-(4-aminophenyl)piperazin-1-yl)ethanone (137 mg, 0.625 mmol) and TMSCl (0.300 mL, 2.37 mmol) in nBuOH (5 mL) was stirred at 135° C. for 48 h. It was then concentrated in vacuo. The residue was purified by HPLC to give the titled compound (25 mg). MS 474.5 (M+H).

Example 47

N-(4-(4-(cyclopropylamino)-5-(pyridin-4-yl)-7H-pyrrolo[2,3-d]pyrimidin-2-ylamino)phenyl)-N-methylacetamide

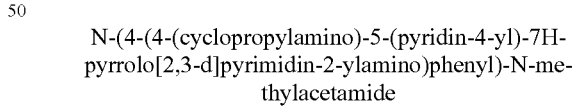

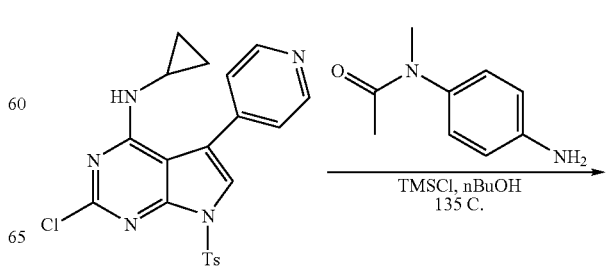

-continued

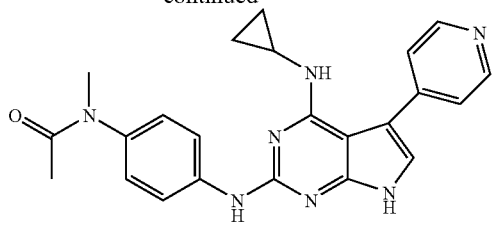

A mixture of 2-chloro-N-cyclopropyl-5-(pyridin-4-yl)-7-tosyl-7H-pyrrolo[2,3-d]pyrimidin-4-amine (85 mg, 0.19 mmol), N-(4-aminophenyl)-N-methylacetamide (72 mg, 0.44 mmol) and TMSCl (0.100 mL, 0.79 mmol) in nBuOH (3 mL) was stirred at 135° C. for 18 h. It was then concentrated in vacuo. The residue was purified by HPLC to give the titled compound (25 mg). MS 414.3 (M+H); UV 202.8, 280.8 nm.

Example 48

6-(4-(cyclopropylamino)-5-(pyridin-4-yl)-7H-pyrrolo[2,3-d]pyrimidin-2-ylamino)-3,4-dihydroquinolin-2(1H)-one

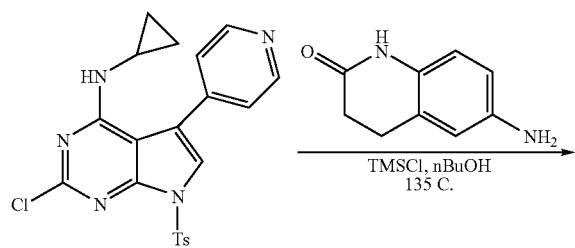

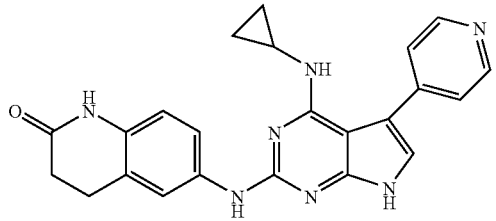

A mixture of 2-chloro-N-cyclopropyl-5-(pyridin-4-yl)-7-tosyl-7H-pyrrolo[2,3-d]pyrimidin-4-amine (85 mg, 0.19 mmol), 6-amino-3,4-dihydroquinolin-2(1H)-one (70 mg, 0.43 mmol) and TMSCl (0.100 mL, 0.79 mmol) in nBuOH (3 mL) was stirred at 135° C. for 18 h. More TMSCl (0.200 mL) was added. Stirring was continued at 135° C. for another 68 h. It was then concentrated in vacuo. The residue was purified by HPLC to give the titled compound (5 mg). MS 412.3 (M+H); UV 201.8, 295.8 nm.

Example 49

5-bromo-N4-cyclobutyl-N2-(1H-indazol-6-yl)-7H-pyrrolo[2,3-d]pyrimidine-2,4-diamine

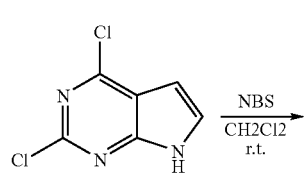

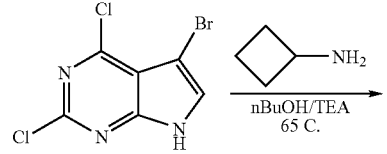

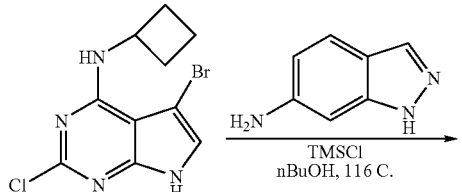

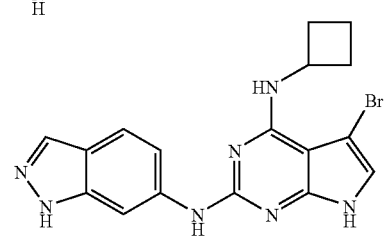

To a suspension of 2,4-dichloro-7H-pyrrolo[2,3-d]pyrimidine (105 mg, 0.560 mmol) in CH$_2$Cl$_2$ (7 mL) at room temperature, NBS (109 mg, 0.610 mmol) was added. The mixture was stirred at room temperature for 18 h. CH$_2$Cl$_2$ was removed in vacuo. The residue was partitioned between water and EtOAc. The organic phase was separated, washed with 5% NaHCO$_3$, dried over Na$_2$SO$_4$, concentrated in vacuo to give 5-bromo-2,4-dichloro-7H-pyrrolo[2,3-d]pyrimidine (142 mg).

A solution of 5-bromo-2,4-dichloro-7H-pyrrolo[2,3-d]pyrimidine (142 mg, 0.530 mmol), cyclobutylamine (0.090 mL, 1.06 mmol) and TEA (0.150 mL, 1.08 mmol) in nBuOH (6 mL) was stirred at 70° C. for 18 h. CH$_2$Cl$_2$ and H$_2$O were added. The organic phase was separated, washed with 5% NaHCO$_3$, then with 1N HCl, dried over Na$_2$SO$_4$, concentrated in vacuo to give 5-bromo-2-chloro-N-cyclobutyl-7H-pyrrolo[2,3-d]pyrimidin-4-amine (154 mg).

A mixture of 5-bromo-2-chloro-N-cyclobutyl-7H-pyrrolo[2,3-d]pyrimidin-4-amine (64 mg, 0.21 mmol), 6-aminoindazole (56 mg, 0.42 mmol) and TMSCl (0.050 mL, 0.40 mmol) in nBuOH (2 mL) was stirred at 116° C. for 4 h. It was then concentrated in vacuo. The residue was purified by HPLC to give a sample, which was further purified by preparative TLC using CH$_2$Cl$_2$/MeOH (95/5) as developing solvents to give the titled compound (1 mg). MS 398.3, 400.3 (M+H, Br pattern); UV 203.8, 247.4, 309.1 nm.

Example 50

5-chloro-N4-cyclobutyl-N2-(1H-indazol-6-yl)-7H-pyrrolo[2,3-d]pyrimidine-2,4-diamine

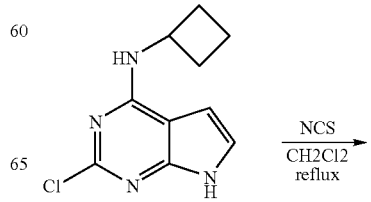

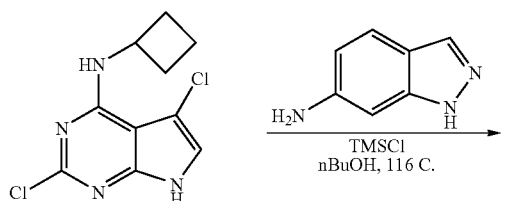

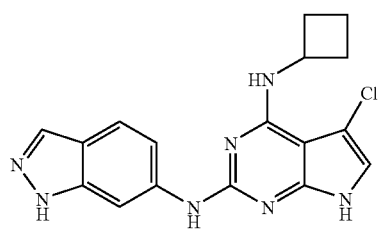

To a suspension of 2-chloro-N-cyclobutyl-7H-pyrrolo[2,3-d]pyrimidin-4-amine (102 mg, 0.460 mmol) in CH$_2$Cl$_2$ (5 mL) at room temperature, NCS (68 mg, 0.51 mmol) was added. The mixture was stirred at reflux for 18 h. After being concentrated in vacuo, the residue was purified by HPLC to give 2,5-dichloro-N-cyclobutyl-7H-pyrrolo[2,3-d]pyrimidin-4-amine (23 mg).

A mixture of 2,5-dichloro-N-cyclobutyl-7H-pyrrolo[2,3-d]pyrimidin-4-amine (23 mg, 0.089 mmol), 6-aminoindazole (40 mg, 0.30 mmol) and TMSCl (0.040 mL, 0.32 mmol) in nBuOH (2 mL) was stirred at 116° C. for 18 h. It was then concentrated in vacuo. The residue was purified by HPLC to give the titled compound (8 mg). MS 354.0, 356.0 (M+H, Cl pattern); UV 201.4, 246.2, 307.9 nm.

Example 51

2-(1H-indazol-6-ylamino)-4-(cyclobutylamino)-6,7-dihydropyrrolo[2,3-d]pyrimidin-5-one

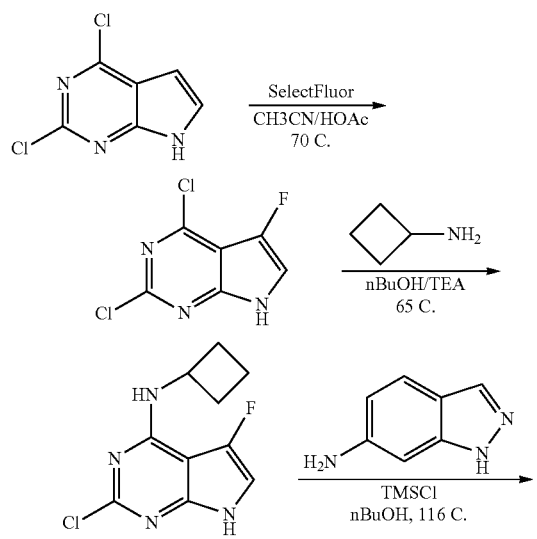

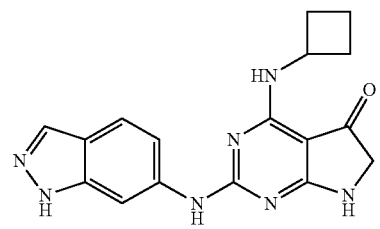

A mixture of 2,4-dichloro-7H-pyrrolo[2,3-d]pyrimidine (200 mg, 1.06 mmol) and SelectFluor (560 mg, 1.58 mmol) in CH$_3$CN (5 mL) and HOAc (1 mL) was stirred at 70° C. for 18 h. The mixture was then concentrated in vacuo. The residue was purified by HPLC to give 2,4-dichloro-5-fluoro-7H-pyrrolo[2,3-d]pyrimidine (50 mg).

A solution of 2,4-dichloro-5-fluoro-7H-pyrrolo[2,3-d]pyrimidine (50 mg, 0.24 mmol), cyclobutylamine (0.041 mL, 0.48 mmol) and TEA (0.070 mL, 0.50 mmol) in nBuOH (2 mL) was stirred at 70 C for 5 h. CH$_2$Cl$_2$ and H$_2$O were added. The organic phase was separated, washed with 5% NaHCO$_3$, then with 1N HCl, dried over Na$_2$SO$_4$, concentrated in vacuo to give 2-chloro-N-cyclobutyl-5-fluoro-7H-pyrrolo[2,3-d]pyrimidin-4-amine (54 mg).

A mixture of 2-chloro-N-cyclobutyl-5-fluoro-7H-pyrrolo[2,3-d]pyrimidin-4-amine (54 mg, 0.22 mmol), 6-aminoindazole (90 mg, 0.68 mmol) and TMSCl (0.090 mL, 0.71 mmol) in nBuOH (3 mL) was stirred at 116° C. for 18 h. It was then concentrated in vacuo. The residue was purified by HPLC to give a sample, which was further purified by preparative TLC using CH$_2$Cl$_2$/MeOH (95/5) as developing solvents to give the titled compound (2 mg). MS 336.1 (M+H)

Example 52

1-(4-(4-(cyclobutylamino)-7H-pyrrolo[2,3-d]pyrimidin-2-ylamino)phenylsulfonyl)piperidin-4-ol

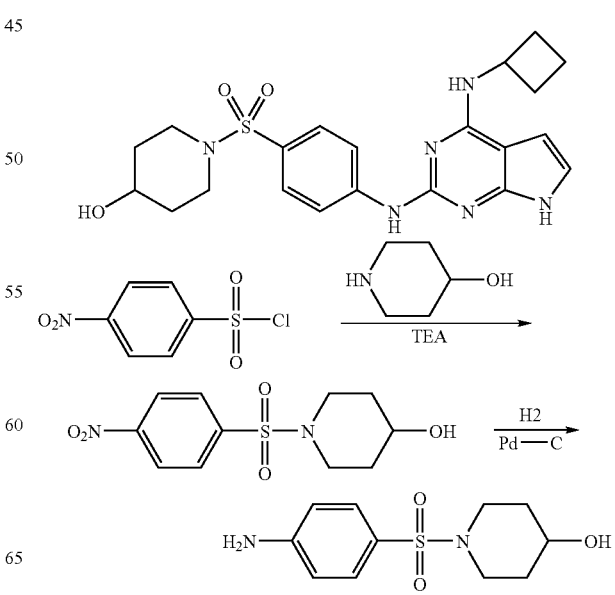

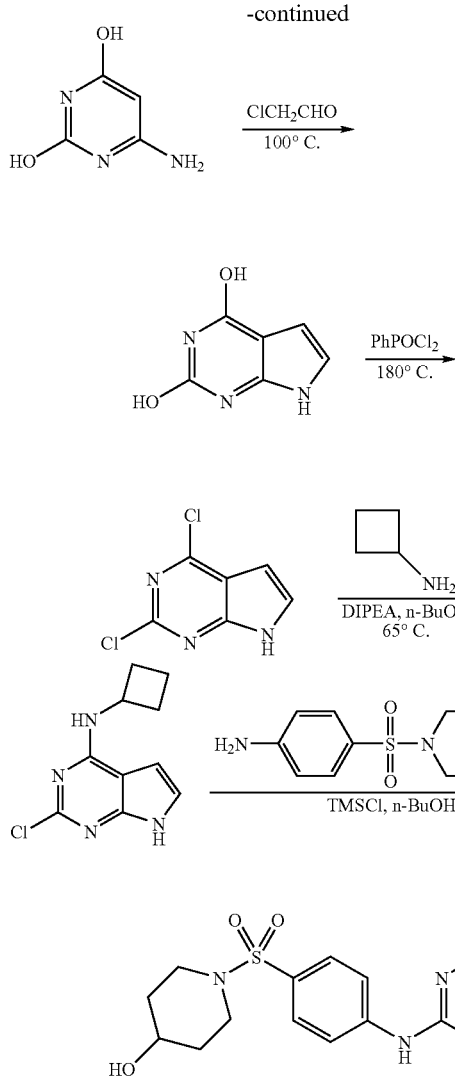

To a solution of 4-nitrobenzenesulfonyl chloride (512 mg, 2.31 mmol) in CH$_2$Cl$_2$ (8 mL) at room temperature, 4-hydroxypiperidine (404 mg, 4.00 mmol) was added. Triethylamine (0.400 mL, 2.88 mmol) was also added. The mixture was stirred at room temperature overnight. Water and EtOAc were added. The organic phase was separated, washed with 1N HCl, dried over Na$_2$SO$_4$, concentrated in vacuo to give 1-(4-nitrophenylsulfonyl)piperidin-4-ol as a solid (559 mg).

A mixture of the solid (559 mg, 1.95 mmol) and Pd—C (10%, 90 mg) in MeOH (15 mL) containing HOAc (0.15 mL) was hydrogenated under balloon H$_2$ overnight. It was filtered through celite. The filtrate was concentrated in vacuo to give a solid (491 mg) as 1-(4-aminophenylsulfonyl)piperidin-4-ol.

To a suspension of 6-aminouracil (15.0 g, 0.118 mol) in H$_2$O (600 mL) was added NaOAc (15.0 g, 0.183 mol) and ClCH$_2$CHO (50% in H$_2$O, 30 mL). The mixture was heated at reflux for 4 h and was cooled to room temperature. The resulting dark brown precipitates were collected by filtration to afford crude 7H-pyrrolo[2,3-d]pyrimidine-2,4-diol (14.4 g, 81% yield).

A suspension of 7H-pyrrolo[2,3-d]pyrimidine-2,4-diol (2.25 g, 0.015 mol) in PhPOCl$_2$ was heated at 165° C. for 3 h and 180° C. for additional 3 h, the resulting dark syrup was poured slowly to ice water, the black precipitates were filtered off, and the filtrate was extracted with ether. Ether layers were combined, washed with Sat NaHCO$_3$, brine, dried over Na$_2$SO$_4$ and concentrated to give 2,4-dichloro-7H-pyrrolo[2,3-d]pyrimidine (0.800 g, 28% yield).

To a suspension of 2,4-dichloro-7H-pyrrolo[2,3-d]pyrimidine-(0.765 g, 4.05 mmol) in n-BuOH (7.5 mL) was added cyclobutyl amine (0.415 mL, 4.86 mmol) and DIPEA (0.865 mL, 4.86 mmol). The mixture was heated at 65° C. for 4 h, and was then cooled to room temperature. The mixture was diluted with CHCl$_3$, washed with water, sat. NaHCO$_3$, brine, dried and concentrated to give crude 2-chloro-N-cylclobutyl-7H-pyrrolo[2,3-d]pyrimidin-4-amine (0.800 g, 88%), which was used directly for next step without purification.

General procedure for final coupling: a mixture of 2-chloro-N-cylclobutyl-7H-pyrrolo[2,3-d]pyrimidin-4-amine (80 mg, 0.36 mmol), 1-(4-aminophenylsulfonyl)piperidin-4-ol (138 mg, 0.54 mmol) and trimethylsilyl chloride (0.030 mL, 0.24 mmol) in nBuOH (2 mL) was stirred at 116° C. for 4 h. The mixture was purified by reverse phase HPLC using a gradient of 10-55% CH$_3$CN in water over 10 min. as eluents to give a powder (8 mg). MS 443.1 (M+H); UV 228.5, 306.7 nm.

Example 53 butyl 2-(4-(4-(cyclobutylamino)-7H-pyrrolo[2,3-d]pyrimidin-2-ylamino)-N-methylphenylsulfonamido)acetate

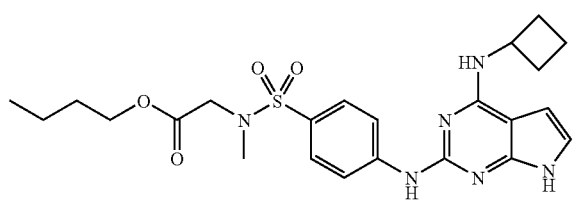

The titled compound was prepared analogously to the procedures described in the Example for 1-(4-(4-(cyclobutylamino)-7H-pyrrolo[2,3-d]pyrimidin-2-ylamino)phenylsulfonyl)piperidin-4-ol. MS 487.0 (M+H); UV 206.1, 311.5 nm.

Example 54

2-(4-(4-(cyclobutylamino)-7H-pyrrolo[2,3-d]pyrimidin-2-ylamino)phenylsulfonamido)acetamide

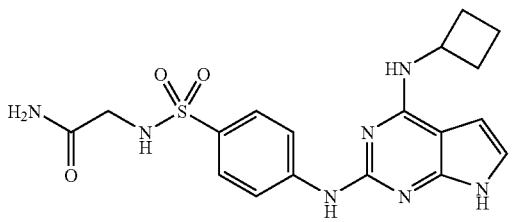

The titled compound was prepared analogously to the procedures described in the Example for 1-(4-(4-(cyclobutylamino)-7H-pyrrolo[2,3-d]pyrimidin-2-ylamino)phenylsulfonyl)piperidin-4-ol. MS 416.1 (M+H); UV 202.6, 227.3, 311.5 nm.

Example 55

2-(4-(4-(cyclobutylamino)-7H-pyrrolo[2,3-d]pyrimidin-2-ylamino)-N-methylphenylsulfonamido)acetic acid

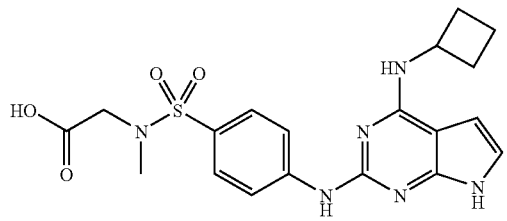

To a solution of butyl 2-(4-(4-(cyclobutylamino)-7H-pyrrolo[2,3-d]pyrimidin-2-ylamino)-N-methylphenylsulfonamido)acetate (15 mg, 0.031 mmol) in MeOH (2 mL), aqueous 1N NaOH (1.00 mL, 1.00 mmol) was added. The mixture was stirred at room temperature for 3 h. Glacial HOAc (0.20 mL) was added to neutralize NaOH. When water was added, precipitate came out, which was collected by filtration to give the titled compound (3 mg). MS 431.0 (M+H); UV 206.1, 312.7 nm.

Example 56

1-(4-(4-(cyclobutylamino)-7H-pyrrolo[2,3-d]pyrimidin-2-ylamino)phenyl)piperidin-4

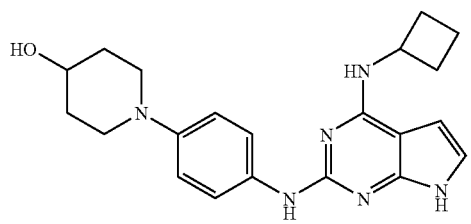

A mixture of 1-fluoro-4-nitrobenzene (0.588 mL, 5.55 mmol), 4-hydroxypiperidine (0.560 g, 5.54 mmol) and $K_2CO_3$ (1.50 g, 10.9 mmol) in DMF (10 mL) was stirred at room temperature overnight. Water was added to induce precipitation. The yellowish solid was collected by filtration (0.90 g).

A mixture of the yellowish solid (0.90 g, 4.05 mmol) and Pd—C (10%, 120 mg) in MeOH (20 mL) containing aqueous 6N HCl (0.20 mL) was hydrogenated under balloon H2 overnight. It was filtered through celite. The filtrate was concentrated in vacuo to give a solid (0.841 g) as 1-(4-aminophenyl)piperidin-4-ol.

A mixture of 2-chloro-N-cylclobutyl-7H-pyrrolo[2,3-d]pyrimidin-4-amine (80 mg, 0.36 mmol), 1-(4-aminophenyl)piperidin-4-ol (104 mg, 0.54 mmol) and trimethylsilyl chloride (0.030 mL, 0.24 mmol) in nBuOH (2 mL) was stirred at 116° C. for 3 h. The mixture was purified by reverse phase HPLC using a gradient of 5-40% $CH_3CN$ in water over 10 min. as eluents to give a powder (5 mg). MS 379.2 (M+H); UV 204.9, 229.6, 272.2, 305.5 nm.

Example 57 tert-butyl 4-(2-(1H-indazol-6-ylamino)-7H-pyrrolo[2,3-d]pyrimidin-4-ylamino)piperidine-1-carboxylate

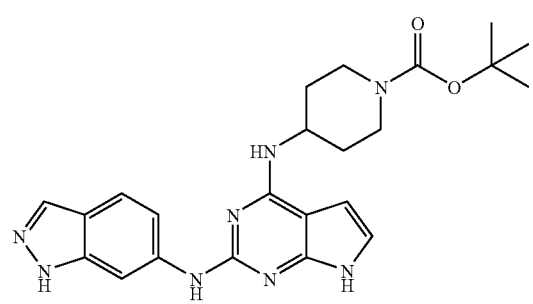

A mixture of 2,4-dichloro-7H-pyrrolo[2,3-d]pyrimidine (220 mg, 1.17 mmol), 4-amino-N—BOC-piperidine (280 mg, 1.40 mmol) and triethylamine (0.400 mL, 2.88 mmol) in nBuOH (8 mL) was stirred at 70° C. overnight. The mixture was purified by HPLC to give a powder (87 mg).

A mixture of the powder (40 mg, 0.11 mmol), 6-aminoindazole (40 mg, 0.30 mmol) and trimethylsilyl chloride (0.020 mL, 0.16 mmol) in nBuOH (2 mL) was stirred at 116° C. overnight. The mixture was purified by reverse phase HPLC using a gradient of 20-65% $CH_3CN$ in water over 10 min. as eluents to give a powder (5 mg). MS 449.0 (M+H); UV 204.9, 242.6, 307.9 nm.

Example 58

N2-(1H-indazol-6-yl)-N4-(piperidin-4-yl)-7H-pyrrolo[2,3-d]pyrimidine-2,4-diamine

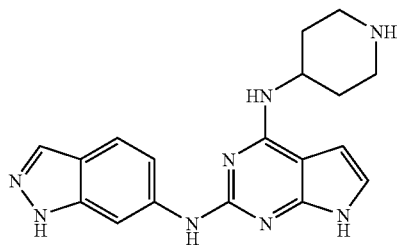

A solution of tert-butyl 4-(2-(1H-indazol-6-ylamino)-7H-pyrrolo[2,3-d]pyrimidin-4-ylamino)piperidine-1-carboxylate (4 mg, 0.009 mmol) in TFA (1 mL) was stirred at room temperature for 2 h. It was concentrated in vacuo. The residue was purified by reverse phase HPLC using a gradient of 3-30% CH₃CN in water over 10 min. as eluents to give a powder (1 mg). MS 349.0 (M+H); UV 201.4, 242.6, 306.7 nm.

Example 59

N4-cyclobutyl-N2-(1H-indazol-6-yl)-6-methyl-7H-pyrrolo[2,3-d]pyrimidine-2,4-diamine

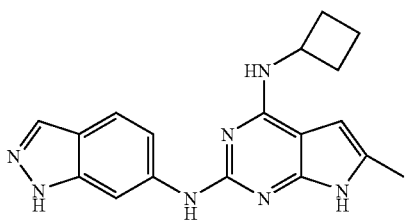

A mixture of 6-aminouracil) 1.00 g, 7.87 mmol), sodium acetate (1.00 g, 12.2 mmol) and chloroacetone (95%, 1.00 mL, 11.9 mmol) in H2O (40 mL) was heated at reflux for 72 h. The solids were collected, and dried on vacuum to give 6-methyl-7H-pyrrolo[2,3-d]pyrimidine-2,4-diol (495 mg).

A mixture of 6-methyl-7H-pyrrolo[2,3-d]pyrimidine-2,4-diol (490 mg, 2.97 mmol) in phenylphosphonic dichloride (10 mL) was heated at 180° C. for 5 h. It was poured onto ice. Et2O (100 mL) was added. The organic phase was separated, washed with 5% NaHCO₃, dried over Na₂SO₄, concentrated in vacuo to give 2,4-dichloro-6-methyl-7H-pyrrolo[2,3-d]pyrimidine as a solid (380 mg).

A solution of 2,4-dichloro-6-methyl-7H-pyrrolo[2,3-d]pyrimidine (190 mg, 0.94 mmol), cyclobutylamine (0.160 mL, 1.88 mmol) and triethylamine (0.200 mL, 1.44 mmol) in nBuOH (6 mL) was stirred at 70° C. overnight. It was then purified by HPLC to give 2-chloro-N-cyclobutyl-6-methyl-7H-pyrrolo[2,3-d]pyrimidin-4-amine (100 mg).

A mixture of 2-chloro-N-cyclobutyl-6-methyl-7H-pyrrolo[2,3-d]pyrimidin-4-amine (55 mg, 0.23 mmol), 6-aminoindazole (62 mg, 0.46 mmol) and trimethylsilyl chloride (0.040 mL, 0.31 mmol) in nBuOH (2 mL) was heated at 116° C. overnight. It was then purified by HPLC to give the titled compound (6 mg). MS 334.4 (M+H); UV 239.1, 316.2 nm Example 60

N4-(3-amino-2,2-dimethylpropyl)-N2-(1H-indazol-6-yl)-7H-pyrrolo[2,3-d]pyrimidine-2,4-diamine

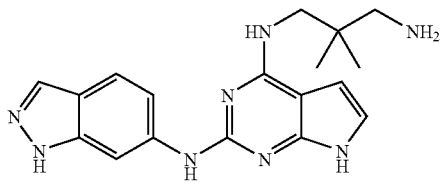

To 2,4-dichloro-7H-pyrrolo[2,3-d]pyrimidine (170 mg, 0.904 mmol) in solid form in a round-bottom flask, a solution of 2,2-dimethyl-1,3-propanediamine (0.325 mL, 2.71 mmol) and triethylamine (0.150 mL, 1.08 mmol) in nBuOH (4 mL) was added. The mixture was heated at 70° C. for 3 h. It was then purified by HPLC to give N-(3-amino-2,2-dimethylpropyl)-2-chloro-7H-pyrrolo[2,3-d]pyrimidin-4-amine as a solid (212 mg).

A mixture of N-(3-amino-2,2-dimethylpropyl)-2-chloro-7H-pyrrolo[2,3-d]pyrimidin-4-amine (70 mg, 0.28 mmol), 6-aminoindazole (93 mg, 0.70 mmol) and trimethylsilyl chloride (0.100 mL, 0.72 mmol) in nBuOH (2 mL) was heated at 116° C. overnight. It was then purified by HPLC to give the titled compound (15 mg). MS 351.4 (M+H); UV 206.1, 242.6, 304.3 nm.

Example 61

N2-(1H-indazol-6-yl)-N4-(3-morpholinopropyl)-7H-pyrrolo[2,3-d]pyrimidine-2,4-diamine

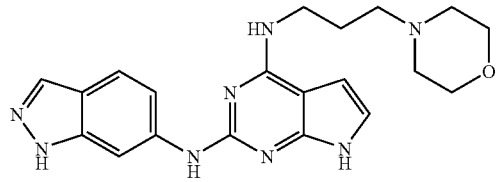

A solution of 2,4-dichloro-7H-pyrrolo[2,3-d]pyrimidine (105 mg, 0.56 mmol), 3-morpholinopropylamine (0.164 mL, 1.12 mmol) and triethylamine (0.150 mL, 1.08 mmol) in nBuOH (3 mL) was stirred at 60° C. overnight. It was then purified by HPLC to give 2-chloro-N-(3-morpholinopropyl)-7H-pyrrolo[2,3-d]pyrimidin-4-amine as a solid (204 mg).

A mixture of 2-chloro-N-(3-morpholinopropyl)-7H-pyrrolo[2,3-d]pyrimidin-4-amine (65 mg, 0.22 mmol), 6-aminoindazole (80 mg, 0.60 mmol) and trimethylsilyl chloride (0.100 mL, 0.72 mmol) in nBuOH (3 mL) was heated at 116° C. overnight. It was then purified by HPLC to give the titled compound (16 mg). MS 393.5 (M+H); UV 217.9, 239.1, 309.1 nm.

Example 62

N-(4-(4-(4-aminobutylamino)-7H-pyrrolo[2,3-d]pyrimidin-2-ylamino)phenyl)-N-methylacetamide

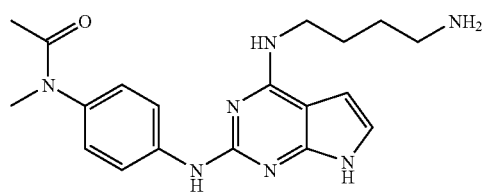

A solution of 2,4-dichloro-7H-pyrrolo[2,3-d]pyrimidine (100 mg, 0.53 mmol), 1,4-diaminobutane (0.125 mL, 1.25 mmol) and triethylamine (0.150 mL, 1.08 mmol) in nBuOH (4 mL) was stirred at 70° C. for 4 h. It was then purified by HPLC to give N-(4-aminobutyl)-2-chloro-7H-pyrrolo[2,3-d] pyrimidin-4-amine as a solid (63 mg).

A mixture of N-(4-aminobutyl)-2-chloro-7H-pyrrolo[2,3-d]pyrimidin-4-amine (63 mg, 0.26 mmol), N-(4-aminophenyl)-N-methylacetamide (81 mg, 0.49 mmol) and trimethylsilyl chloride (0.067 mL, 0.52 mmol) in nBuOH (3 mL) was heated at 116° C. for 4 h. It was then purified by HPLC to give the titled compound (5 mg). MS 368.2 (M+H); UV 203.8, 268.7, 301.9 nm.

Example 63

N-(4-(4-(2-aminocyclohexylamino)-7H-pyrrolo[2,3-d]pyrimidin-2-ylamino)phenyl)-N-methylacetamide

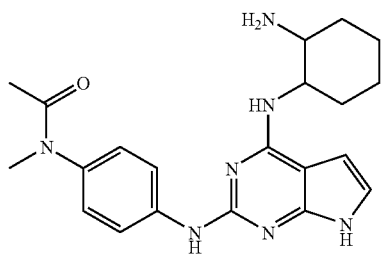

A solution of 2,4-dichloro-7H-pyrrolo[2,3-d]pyrimidine (100 mg, 0.53 mmol), cis-1,2-diaminocyclohexane (0.107 mL, 0.91 mmol) and triethylamine (0.150 mL, 1.08 mmol) in nBuOH (4 mL) was stirred at 70° C. for 4 h. It was then purified by HPLC to give N1-(2-chloro-7H-pyrrolo[2,3-d]pyrimidin-4-yl)cyclohexane-1,2-diamine as a solid (89 mg).

A mixture of N1-(2-chloro-7H-pyrrolo[2,3-d]pyrimidin-4-yl)cyclohexane-1,2-diamine (44 mg, 0.17 mmol), N-(4-aminophenyl)-N-methylacetamide (56 mg, 0.34 mmol) and trimethylsilyl chloride (0.146 mL, 1.15 mmol) in nBuOH (2 mL) was heated at 116° C. for 4 h. It was then purified by HPLC to give the titled compound (6 mg). MS 394.2 (M+H); UV 201.4, 262.7, 306.7 nm.

Example 64

N-(4-(4-(2-aminoethylamino)-7H-pyrrolo[2,3-d]pyrimidin-2-ylamino)phenyl)-N-methylacetamide

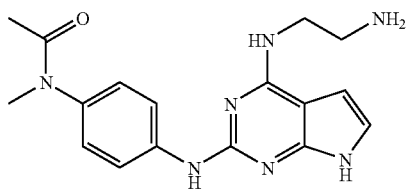

A solution of 2,4-dichloro-7H-pyrrolo[2,3-d]pyrimidine (160 mg, 0.85 mmol), ethylenediamine (0.170 mL, 2.55 mmol) and triethylamine (0.100 mL, 0.72 mmol) in nBuOH (4 mL) was stirred at 70° C. for 4 h. It was then purified by HPLC to give N-(2-aminoethyl)-2-chloro-7H-pyrrolo[2,3-d]pyrimidin-4-amine as a solid (71 mg).

A mixture of N-(2-aminoethyl)-2-chloro-7H-pyrrolo[2,3-d]pyrimidin-4-amine (71 mg, 0.34 mmol), N-(4-aminophenyl)-N-methylacetamide (110 mg, 0.67 mmol) and trimethylsilyl chloride (0.085 mL, 0.67 mmol) in nBuOH (2 mL) was heated at 116° C. for 3 h. More trimethylsilyl chloride (0.100 mL, 0.79 mmol) was added. After being stirred at 116° C. for another 2 h, the mixture was purified by HPLC to give the titled compound (28 mg). MS 340.2 (M+H); UV 201.4, 262.7, 303.1 nm.

Example 65

N-(4-(4-(5-aminopentylamino)-7H-pyrrolo[2,3-d]pyrimidin-2-ylamino)phenyl)-N-methylacetamide

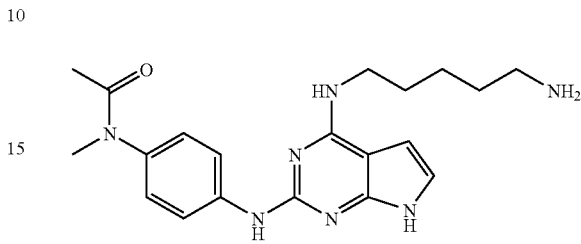

A solution of 2,4-dichloro-7H-pyrrolo[2,3-d]pyrimidine (70 mg, 0.37 mmol), 1,5-diaminopentane (0.130 mL, 1.11 mmol) and triethylamine (0.150 mL, 1.08 mmol) in nBuOH (3 mL) was stirred at 70° C. for 1 h. It was then purified by HPLC to give N-(5-aminopentyl)-2-chloro-7H-pyrrolo[2,3-d]pyrimidin-4-amine as a solid (79 mg).

A mixture of N-(5-aminopentyl)-2-chloro-7H-pyrrolo[2,3-d]pyrimidin-4-amine (79 mg, 0.31 mmol), N-(4-aminophenyl)-N-methylacetamide (100 mg, 0.61 mmol) and trimethylsilyl chloride (0.150 mL, 1.19 mmol) in nBuOH (2 mL) was heated at 116° C. for 4 h. The mixture was then purified by HPLC to give the titled compound (9 mg). MS 382.2 (M+H); UV 210.8, 267.5, 305.5 nm.

Example 66

1-(4-(4-(4-(4-aminocyclohexylamino)-7H-pyrrolo[2,3-d]pyrimidin-2-ylamino)phenyl)piperazin-1-yl)ethanone

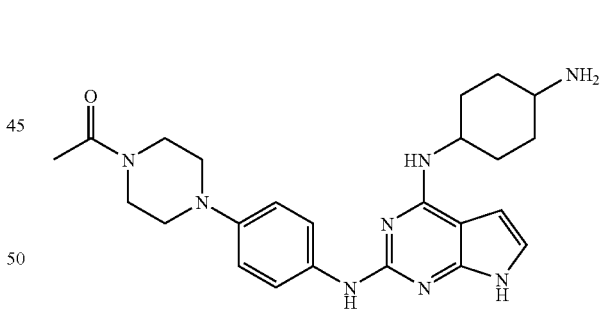

To a solution of 2,4-dichloro-7H-pyrrolo[2,3-d]pyrimidine (1.12 g, 5.96 mmol) in DMSO (8 mL), sodium thiomethoxide (0.500 g, 7.14 mmol) was added. The mixture was stirred at room temperature for 2 h. $H_2O$ was added to induce precipitation. The precipitate was collected and dried on vacuum to give 2-chloro-4-(methylthio)-7H-pyrrolo[2,3-d]pyrimidine as a solid (0.90 g).

A mixture of 2-chloro-4-(methylthio)-7H-pyrrolo[2,3-d]pyrimidine (484 mg, 2.43 mmol), 1-(4-(4-aminophenyl)piperazin-1-yl)ethanone (645 mg, 2.95 mmol) and trimethylsilyl chloride (0.500 mL, 3.95 mmol) in nBuOH (10 mL) was heated at 116° C. for 48 h. After cooling down, $H_2O$ and EtOAc were added. The organic phase was separated, washed with 5% $NaHCO_3$, dried over $Na_2SO_4$, concentrated in vacuo to give 1-(4-(4-(4-(methylthio)-7H-pyrrolo[2,3-d]pyrimidin-2-ylamino)phenyl)piperazin-1-yl)ethanone as a solid (453 mg).

To a solution of 1-(4-(4-(4-(methylthio)-7H-pyrrolo[2,3-d]pyrimidin-2-ylamino)phenyl)piperazin-1-yl)ethanone (451 mg, 1.18 mmol) in CH$_2$Cl$_2$ (12 mL), mCPBA (320 mg, 65%, 1.20 mmol) was added. The mixture was stirred at room temperature for 1 h. It was then concentrated in vacuo, the residue was purified by HPLC to give 1-(4-(4-(4-(methylsulfinyl)-7H-pyrrolo[2,3-d]pyrimidin-2-ylamino)phenyl)piperazin-1-yl)ethanone as a solid (136 mg).

To a solution of 1-(4-(4-(4-(methylsulfinyl)-7H-pyrrolo[2,3-d]pyrimidin-2-ylamino)phenyl)piperazin-1-yl)ethanone (34 mg, 0.085 mmol) in DMSO (1 mL), 1,4-diaminocyclohexane (cis and trans mixture, 35 mg, 0.31 mmol) and diisopropylethylamine (0.060 mL, 0.35 mmol) were added. The mixture was heated at 116° C. overnight. It was then purified by HPLC to give the titled compound (5 mg). MS 449.3 (M+H); UV 208.5, 265.1, 305.5 nm.

Example 67

N-(4-(4-(5-aminopentylamino)-5-bromo-7H-pyrrolo[2,3-d]pyrimidin-2-ylamino)phenyl)-N-methylacetamide and N-(4-(4-(5-aminopentylamino)-5,6-dibromo-7H-pyrrolo[2,3-d]pyrimidin-2-ylamino)phenyl)-N-methylacetamide

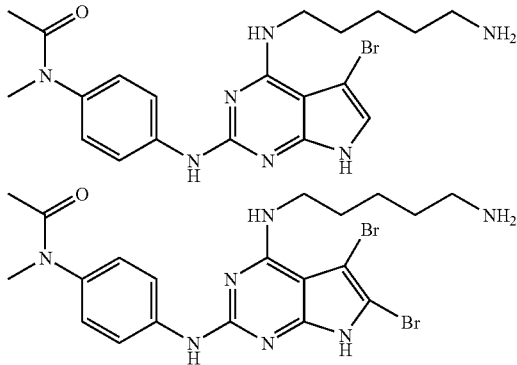

To a solution of N-(4-(4-(5-aminopentylamino)-7H-pyrrolo[2,3-d]pyrimidin-2-ylamino)phenyl)-N-methylacetamide (44 mg, 0.12 mmol) in DMF (1 mL), N-bromosuccinamide (25 mg, 0.14 mmol) was added. The mixture was stirred at room temperature for 2 h. It was then purified by HPLC to give the mono-bromo compound (3 mg) and the dibromo compound (5 mg). MS 460.1 and 462.1 (mono-bromo, M+H, Br pattern); UV 207.3, 228.5, 298.4 nm; 539.0, 540.0, 541.0 and 542.0 (di-bromo, M+H, 2 Br pattern); UV 202.6, 232.0, 300.7 nm.

Example 68

N-(4-(4-(3-aminosulfonyl-phenylamino)-7H-pyrrolo[2,3-d]pyrimidin-2-ylamino)phenyl)-N methylacetamide

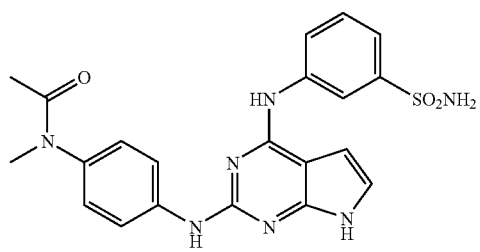

A mixture of 2,4-dichloro-7-tosyl-7H-pyrrolo[2,3-d]pyrimidine (200 mg, 0.58 mmol), 3-aminobenzenesulfonamide (111 mg, 0.65 mmol) and triethylamine (0.200 mL, 1.44 mmol) in nBuOH (6 mL) was heated at 80° C. overnight. The mixture was then heated at 110° C. for another 24 h. After cooling down, H2O and EtOAc were added. The organic phase was separated, washed with 1N HCl, then with 5% NaHCO3, and it was dried over Na2SO4, concentrated in vacuo to give 2-chloro-N-(3-aminosulfonyl-phenyl)-7-tosyl-7H-pyrrolo[2,3-d]pyrimidin-4-amine as a solid (210 mg).

A mixture of 2-chloro-N-(3-aminosulfonyl-phenyl)-7-tosyl-7H-pyrrolo[2,3-d]pyrimidin-4-amine (100 mg, 0.21 mmol), N-(4-aminophenyl)-N-methylacetamide (100 mg, 0.61 mmol) and trimethylsilyl chloride (0.050 mL, 0.40 mmol) in nBuOH (2 mL) and dioxane (2 mL) was heated at 110° C. for 4 h. More trimethylsilyl chloride (0.100 mL, 0.79 mmol) was added. The mixture was stirred at 110° C. for another 72 h. It was then purified by HPLC to give N-(4-(4-(3-aminosulfonyl-phenylamino)-7-tosyl-7H-pyrrolo[2,3-d]pyrimidin-2-ylamino)phenyl)-N-methylacetamide as a solid (20 mg).

To a solution of N-(4-(4-(3-aminosulfonyl-phenylamino)-7-tosyl-7H-pyrrolo[2,3-d]pyrimidin-2-ylamino)phenyl)-N-methylacetamide (20 mg, 0.033 mmol) in MeOH (2 mL), aq. 1N KOH (0.60 mL, 0.60 mmol) was added. The mixture was heated at 60° C. for 3 h. It was concentrated in vacuo. The residue was acidified with HOAc (1 mL) before being purified by HPLC to give the titled compound (7 mg). MS 452.0 (M+H); UV 208.5, 284.1, 317.4 nm.

Example 69

Ethyl 2-(6-(4-(cyclobutyamino)-7H-pyrrolo[2,3-d]pyrimidine-2-ylamino)-2-oxo-3,4-dihydroquinolin-1(2H)-yl)acetate

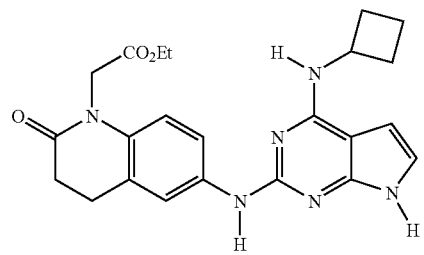

To a mixture of 6-nitro-3,4-dihydroquinolin-2(1H)-one (0.5 g, 2.6 mmol) and Cs$_2$CO$_3$ (1.70 g, 5.2 mmol) in DMF (5 mL) was added ethyl 2-bromoacetate (0.317 mL, 2.86 mmol). After stirring at 65° C. for 3 h, the mixture was diluted with H$_2$O and EtOAc, organic layer was separated, and the aqueous layer was further extracted with EtOAc, organic layers were combined, dried over Na$_2$SO$_4$, and was concentrated in vacuo to provide ethyl 2-(6-nitro-2-oxo-3,4-dihydroquinolin-1(2H)-yl)acetate, which was used directly for next step.

To a suspension of 1 ethyl 2-(6-nitro-2-oxo-3,4-dihydroquinolin-1(2H)-yl)acetate in EtOH (10 mL) and $H_2O$ (5 mL) was added ammonium formate (1.5 g, 23.8 mmol) and Fe (0.3 g, 5.4 mmol). After stirring at reflux for 2 h, the black mixture was filtered, the filtrate was diluted with EtOAc and water, EtOAc layer was separated and the aqueous layer was further extracted with EtOAc, organic layers were combined, dried over $Na_2SO_4$, and was concentrated in vacuo to provide ethyl 2-(6-amino-2-oxo-3,4-dihydroquinolin-1(2H)-yl)acetate (0.2 g, 31%).

According to the general procedure for synthesis of 1-(4-(4-(cyclobutylamino)-7H-pyrrolo[2,3-d]pyrimidin-2-ylamino)phenylsulfonyl)piperidin-4-ol, ethyl 2-(6-amino-2-oxo-3,4-dihydroquinolin-1(2H)-yl)acetate and 2-chloro-N-cylclobutyl-7H-pyrrolo[2,3-d]pyrimidin-4-amine gave Ethyl 2-(6-(4-(cyclobutylamino)-7H-pyrrolo[2,3-d]pyrimidine-2-ylamino)-2-oxo-3,4-dihydroquinolin-1(2H)-yl)acetate (MS calcd for $C_{23}H_{26}N_6O_3$ 434.2, found [MH] 435.2; UV 209.8, 304.5 nm).

Example 70

2-(6-(4-(cyclobutylamino)-7H-pyrrolo[2,3-d]pyrimidine-2-ylamino)-2-oxo-3,4-dihydroquinolin-1(2H)-yl)acetic acid

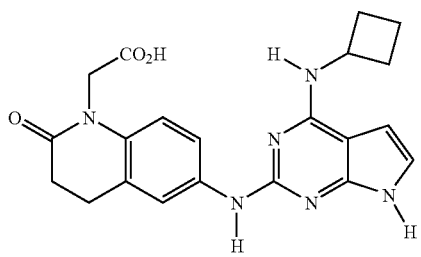

To a solution of ethyl 2-(6-(4-(cyclobutylamino)-7H-pyrrolo[2,3-d]pyrimidine-2-ylamino)-2-oxo-3,4-dihydroquinolin-1(2H)-yl)acetate (10 mg, 0.023 mmol) in THF (0.6 mL) and H2O (0.4 mL) was added NaOH (5N, 2 drops). After stirring for 3 h at room temperature, the reaction mixture was purified by preparative HPLC to yield 2-(6-(4-(cyclobutylamino)-7H-pyrrolo[2,3-d]pyrimidine-2-ylamino)-2-oxo-3,4-dihydroquinolin-1(2H)-yl)acetic acid (MS calcd for $C_{21}H_{22}N_6O_3$ 406.2, found [MH] 407.0; UV 207.5, 304.5 nm).

Example 71

2-(6-(4-(cyclobutylamino)-7H-pyrrolo[2,3-d]pyrimidine-2-ylamino)-2-oxo-3,4-dihydroquinolin-1(2H)-yl)-N-(2-(dimethylamino)ethyl)acetamide

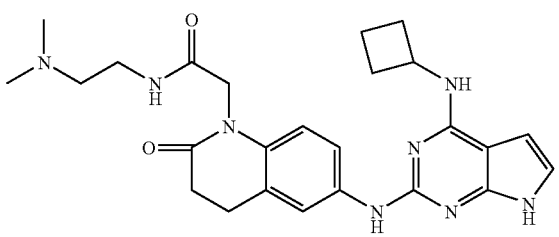

To a solution of 2-(6-(4-(cyclobutyamino)-7H-pyrrolo[2,3-d]pyrimidine-2-ylamino)-2-oxo-3,4-dihydroquinolin-1(2H)-yl)acetic acid 4 mg, 0.01 mmol) in DMF (0.3 mL) was added HATU, DIPEA and N,N-dimethylaminoethylamine. After stirring for 1 h at room temperature, it was then purified by prep HPLC to give 2-(6-(4-(cyclobutyamino)-7H-pyrrolo[2,3-d]pyrimidine-2-ylamino)-2-oxo-3,4-dihydroquinolin-1(2H)-yl)-N-(2-(dimethylamino)ethyl)acetamide (MS calcd for $C_{25}H_{32}N_8O_2$ 476.3, found [MH] 477.0; UV 205.1, 304.5 nm).

Example 72

Methyl 4-(4-(cyclobutylamino)-7H-pyrrolo[2,3-d]pyrimidin-2-ylamino)phenyl(methyl)carbamate

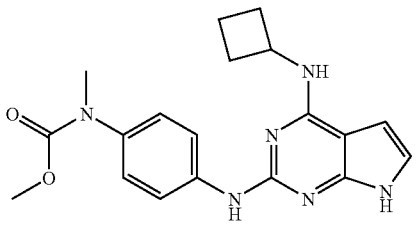

According to the general procedure for synthesis of 1-(4-(4-(cyclobutylamino)-7H-pyrrolo[2,3-d]pyrimidin-2-ylamino)phenylsulfonyl)piperidin-4-ol, methyl-4-aminophenyl(methyl)carbamate and 2-Chloro-N-cylclobutyl-7H-pyrrolo[2,3-d]pyrimidin-4-amine gave methyl 4-(4-(cyclobutylamino)-7H-pyrrolo[2,3-d]pyrimidin-2-ylamino)phenyl(methyl)carbamate (MS calcd for $C_{19}H_{22}N_6O_2$ 366.2, found [MH] 368.0; UV 209.8, 271.2, 304.5 nm).

Example 73

Methyl 4-(4-(cyclobutylamino)-7H-pyrrolo[2,3-d]pyrimidin-2-ylamino)phenyl(methyl)carbamate

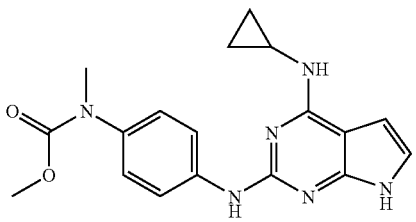

According to the general procedure for synthesis of 1-(4-(4-(cyclobutylamino)-7H-pyrrolo[2,3-d]pyrimidin-2-ylamino)phenylsulfonyl)piperidin-4-ol, Methyl-4-aminophenyl(methyl)carbamate and 2-chloro-N-cylclopropyl-7H-pyrrolo[2,3-d]pyrimidin-4-amine gave methyl 4-(4-(cyclobutylamino)-7H-pyrrolo[2,3-d]pyrimidin-2-ylamino)

Example 74

N-(4-(4-(cyclobutylamino)-7H-pyrrolo[2,3-d]pyrimidin-2-ylamino)phenyl)-2-hydroxy-N-methylacetamide

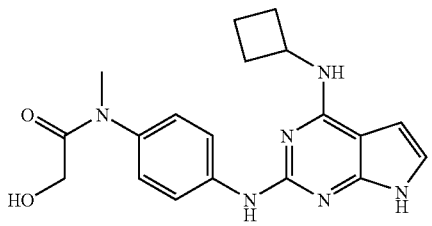

To a suspension of 4-nitro-N-methylaniline in DCM (10 mL) was added at 0° C. was added $Et_3N$ (0.63 mL, 4.5 mmol) and 2-benzoxyacetyl chloride (0.513 mL, 3.3 mmol). After stirring for 15 h at room temperature, the reaction mixture was diluted with EtOAc, washed with Sat. $NaHCO_3$, brine, dried and concentrated to give 2-benzoxy-N-methyl-N-(4-nitrophenyl)acetamide (0.63 g, 70%).

To a suspension of above 2-benzoxy-N-methyl-N-(4-nitrophenyl)acetamide in EtOH (8 mL) and $H_2O$ (4 mL) was added ammonium formate (1.3 g, 20 mmol) and Fe (0.47 g, 8.4 mmol). After heating at reflux for 2 h, the reaction was cooled to room temperature, iron was filtered off, and the filtrate was diluted with EtOAc and water, EtOAc layer was separated and the aqueous layer was further extracted with EtOAc, organic layers were combined, dried over $Na_2SO_4$, and was concentrated under vacuo to provide 2-benzoxy-N-methyl-N-(4-aminophenyl)acetamide (0.4 g, 53%).

According to the general procedure for synthesis of 1-(4-(4-(cyclobutylamino)-7H-pyrrolo[2,3-d]pyrimidin-2-ylamino)phenylsulfonyl)piperidin-4-ol, 2-benzoxy-N-methyl-N-(4-aminophenyl)acetamide and 2-Chloro-N-cylclobutyl-7H-pyrrolo[2,3-d]pyrimidin-4-amine gave 2-benzyloxy N-(4-(4-(cyclobutylamino)-7H-pyrrolo[2,3-d]pyrimidin-2-ylamino)phenyl)-N-methylacetamide (MS calcd for $C_{26}H_{28}N_6O_2$ 456.2, found [MH] 457.0).

To a solution of 2-benzyloxy N-(4-(4-(cyclobutylamino)-7H-pyrrolo[2,3-d]pyrimidin-2-ylamino)phenyl)-N-methylacetamide (0.012 g, 0.026 mmol) in EtOH (0.4 mL) was added Pd/C (10 mg), and was charged with $H_2$ (1 atm). After stirring for 15 h at room temperature, it was purified by preparative HPLC to give N-(4-(4-(cyclobutyllamino)-7H-pyrrolo[2,3-d]pyrimidin-2-ylamino)phenyl)-2-hydroxy-N-methylacetamide (MS calcd for $C_{19}H_{22}N_6O_2$ 366.2, found [MH] 367.0; UV 208.7, 272.4, 304.5 nm).

Example 75

N-(4-(4-(cyclopropylamino)-7H-pyrrolo[2,3-d]pyrimidin-2-ylamino)phenyl)-2-hydroxy-N-methylacetamide

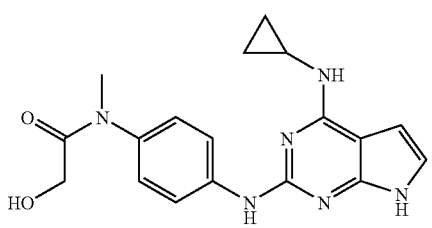

According to the general procedure for synthesis of 1-(4-(4-(cyclobutylamino)-7H-pyrrolo[2,3-d]pyrimidin-2-ylamino)phenylsulfonyl)piperidin-4-ol, 2-benzoxy-N-methyl-N-(4-aminophenyl)acetamide and 2-Chloro-N-cylclopropyl-7H-pyrrolo[2,3-d]pyrimidin-4-amine gave 2-benzyloxy N-(4-(4-(cyclopropylamino)-7H-pyrrolo[2,3-d]pyrimidin-2-ylamino)phenyl)-N-methylacetamide (MS calcd for $C_{25}H_{26}N_6O_2$ 442.2, found [MH] 443.5).

To a solution of 2-benzyloxy N-(4-(4-(cyclopropylamino)-7H-pyrrolo[2,3-d]pyrimidin-2-ylamino)phenyl)-N-methylacetamide (0.015 g, 0.034 mmol) in EtOH (0.4 mL) was added Pd/C (10 mg), and was charged with $H_2$ (1 atm). After stirring for 15 h at room temperature, it was purified by preparative HPLC to give N-(4-(4-(cyclopropylamino)-7H-pyrrolo[2,3-d]pyrimidin-2-ylamino)phenyl)-2-hydroxy-N-methylacetamide (MS calcd for $C_{18}H_{20}N_6O_2$ 352.2, found [MH] 352.8; UV 206.3, 228.7, 297.3 nm).

Example 76

$N^4$-cyclobutyl-$N^2$-(4-methylsulfonylmethyl)phenyl)-7H-pyrrolo[2,3-d]pyrimidin-2,4-diamine

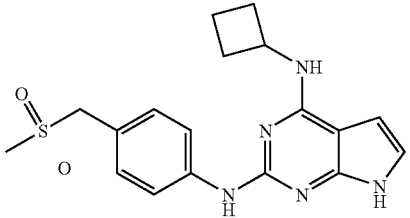

To a mixture of 4-nitrobenzyl chloride (1 g, 5.8 mmol) and TBAI (0.11 g, 0.29 mmol) in EtOH (12 mL) was added $NaOSOCH_3$ (0.77 g, 6.38 mmol). After heating at reflux for 2 h, the mixture was cooled to room temperature, and the precipitates were collected by filtration to give 1-(methylsulfonylmethyl)-4-nitrobenzene (1.5 g).

To a mixture of 1-(methylsulfonylmethyl)-4-nitrobenzene (1.5 g, 7 mmol) in EtOH (20 mL) and $H_2O$ (10 mL) was added iron (1.96 g, 35 mmol) and ammonium formate (4.41 g, 70 mmol). After heating at 90° C. for 2 h, it was diluted with EtOAc, washed with saturated $NaHCO_3$, brine, dried and concentrated to give 4-(methylsulfonylmethyl)aniline (0.5 g).

According to the general procedure for synthesis of 1-(4-(4-(cyclobutylamino)-7H-pyrrolo[2,3-d]pyrimidin-2-ylamino)phenylsulfonyl)piperidin-4-ol, 4-(methylsulfonylmethyl)aniline and 2-Chloro-N-cylclobutyl-7H-pyrrolo[2,3-d]pyrimidin-4-amine gave $N^4$-cyclobutyl-$N^2$-(4-methylsulfonylmethyl)phenyl)-7H-pyrrolo[2,3-d]pyrimidin-2,4-diamine (MS calcd for $C_{18}H_{21}N_5O_2S$ 371.5, found [MH] 372.1; UV 205.1, 273.6, 304.5 nm).

Example 77

$N^4$-cyclobutyl-$N^2$-(3-methylsulfonylmethyl)phenyl)-7H-pyrrolo[2,3-d]pyrimidin-2,4-diamine

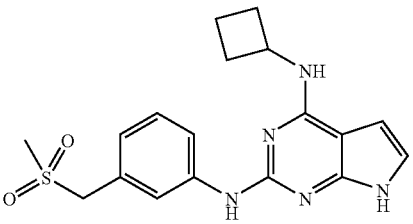

To a mixture of 3-nitrobenzyl bromide (1 g, 4.63 mmol) in EtOH (12 mL) was added NaOSOCH₃ (0.61 g, 5.09 mmol). After heating at reflux for 2 h, the mixture was cooled to room temperature, and the precipitates were collected by filtration to give 1-(methylsulfonylmethyl)-3-nitrobenzene (0.77 g).

To a mixture of 1-(methylsulfonylmethyl)-4-nitrobenzene (0.77 g, 3.56 mmol) in EtOH (10 mL) and H₂O (5 mL) was added iron (1.0 g, 17.82 mmol) and ammonium formate (2.25 g, 35.6 mmol). After heating at 90° C. for 2 h, it was diluted with EtOAc, washed with saturated NaHCO₃, brine, dried and concentrated to give 3-(methylsulfonylmethyl)aniline (0.47 g).

According to the general procedure for synthesis of 1-(4-(4-(cyclobutylamino)-7H-pyrrolo[2,3-d]pyrimidin-2-ylamino)phenylsulfonyl)piperidin-4-ol, 3-(methylsulfonylmethyl)aniline and 2-Chloro-N-cylclobutyl-7H-pyrrolo[2,3-d]pyrimidin-4-amine gave N⁴-cyclobutyl-N²-(3-methylsulfonylmethyl)phenyl)-7H-pyrrolo[2,3-d]pyrimidin-2,4-diamine (MS calcd for C₁₈H₂₁N₅O₂S 371.5, found [MH] 372.1; UV 214.5, 267.6, 304.5 nm).

Example 78

2-(3-(2-(1H-indazol-6-ylamino)-7H-pyrrolo[2,3-d]pyrimidin-4-ylamino)phenoxy-N-methylacetamide

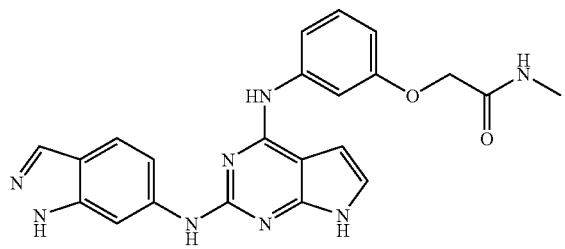

To a solution of 2,4-Dichloro-7H-pyrrolo[2,3-d]pyrimidine (0.062 g, 0.33 mmol) in DMSO (1 mL) was added DIPEA (0.117 mL, 0.66 mmol) and 2-(3-aminophenoxy)-N-methylacetamide (0.095 g, 0.49 mmol). After heating at 100° C. for 15 h, it was diluted with EtOAc, washed with saturated NaHCO₃, brine, dried and concentrated to give 2-(3-(2-chloro-7H-pyrrolo[2,3-d]pyrimidin-4-ylamino)phenoxy-N-methylacetamide (0.062 g).

To a mixture of 2-(3-(2-chloro-7H-pyrrolo[2,3-d]pyrimidin-4-ylamino)phenoxy-N-methylacetamide (0.062 g) in nBuOH (0.6 mL) was added 6-aminoindazole (0.028 g) and TMSCl (0.013 mL). After heating at 115° C. for 15 h, the mixture was purified by prep HPLC to give 2-(3-(2-(1H-indazol-6-ylamino)-7H-pyrrolo[2,3-d]pyrimidin-4-ylamino)phenoxy-N-methylacetamide (0.007 g, MS calcd for C₂₂H₂₀N₈O₂ 428.4, found [MH] 429.1; UV 238.1, 311.6 nm).

Example 79

N²-(1H-indazol-6-yl)-7H-pyrrolo[2,3-d]pyrimidin-2,4-diamine

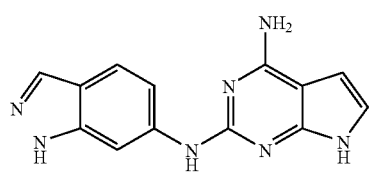

A mixture of 2,4-Dichloro-7H-pyrrolo[2,3-d]pyrimidine (0.1 g, 0.53 mmol) in Ammonia (7 N in MeOH, 1 mL) was heated at 100° C. for 24 h, then it was diluted with EtOAc, washed with Sat. NaHCO3, brine, dried and concentrated to give 2-chloro-7H-pyrrolo[2,3-d]pyrimidine-4-amine (0.06 g).

To a mixture of 2-chloro-7H-pyrrolo[2,3-d]pyrimidine-4-amine (0.06 g, 0.353 mmol) in nBuOH (0.7 mL) was added 6-aminoindazole (0.094 g, 0.70 mmol) and TMSCl (0.023 mL, 0.175 mmol). After heating at 115° C. for 8 h, it was cooled and purified by prep HPLC to give N²-(1H-indazol-6-yl)-7H-pyrrolo[2,3-d]pyrimidin-2,4-diamine (0.012 g, MS calcd for C₁₃H₁₁N₇ 265.3, found 266.1; UV 216.9, 308.0 nm).

Example 80

N-(4-(4-(cyclobutylamino)-7H-pyrrolo[2,3-d]pyrimidin-2-ylamino)phenyl)-N-methylcyclopropanecarboxamide

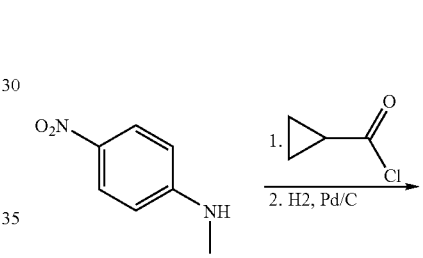

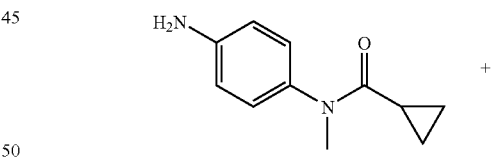

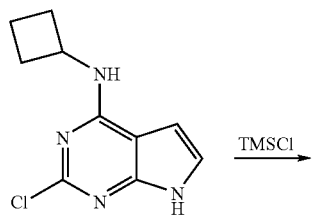

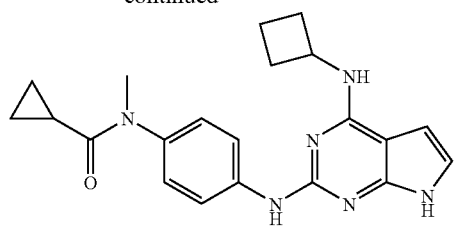

Step 1: To a mixture of N-methyl-4-nitroaniline (2 g, 13.1 mmol) in DCM (30 mL) was added Et3N (2.75 mL, 20 mmol) and cyclopropanecarbonyl chloride (1.32 mL, 14.4 mmol) at room temperature, after stirring for 1 h at room temperature, the mixture was diluted with EtOAc, the organics was washed with Sat. NaHCO$_3$, brine, dried and concentrated to give N-methyl-N-(4-nitrophenyl)cyclopropanecarboxamide as crude product (3 g).

To a suspension of the above crude product (3 g) in EtOH (20 mL) and H$_2$O (10 mL) was added iron (3.67 g, 65.5 mmol) and ammonium formate (826 g, 130 mml). The mixture was heated at 90° C. for 2 h, and was cooled to room temperature. The mixture was diluted with EtOAc, washed with Sat. NaHCO$_3$, brine, dried and concentrated to give N-(4-aminophenyl)-N-methylcyclopropanecarboxamide (1.6 g).

Step 2: To a suspension of 2-chloro-N-cyclobutyl-7H-pyrrolo[2,3-d]pyrimidin-4-amine (67 mg, 0.3 mmol) in nBuOH (0.8 mL) was added N-(4-aminophenyl)-N-methylcyclopropanecarboxamide (85 mg, 0.45 mmol) and TMSCl (0.02 mL, 0.15 mmol). After heating at 115° C. for 2 h, the mixture was cooled and purified by preparative HPLC to give N-(4-(4-(cyclobutylamino)-7H-pyrrolo[2,3-d]pyrimidin-2-ylamino)phenyl)-N-methylcyclopropanecarboxamide (7 mg). MS found for C$_{21}$H$_{24}$N$_6$O as (M+H)$^+$ 377.2. λ=208.7, 272.4, 304.5.

Example 81

N-(4-(4-(cyclopropylamino)-7H-pyrrolo[2,3-d]pyrimidin-2-ylamino)phenyl)-N-methylcyclopropanecarboxamide

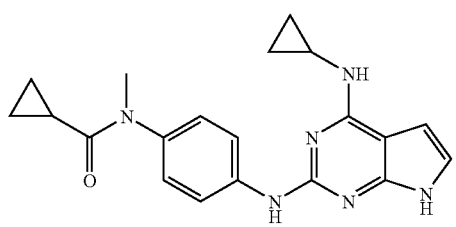

The title compound was prepared using the same synthetic scheme demonstrated in Example of N-(4-(4-(cyclobutylamino)-7H-pyrrolo[2,3-d]pyrimidin-2-ylamino)phenyl)-N-methylcyclopropanecarboxamide. MS found for C$_{20}$H$_{22}$N$_6$O as (M+H)$^+$ 363.1. λ=211.0, 228.7, 296.1.

Example 82

N-(4-(4-(methylamino)-7H-pyrrolo[2,3-d]pyrimidin-2-ylamino)phenyl)-N methylcyclopropanecarboxamide

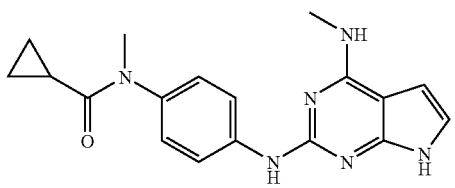

The title compound was prepared using the same synthetic scheme demonstrated in Example of N-(4-(4-(cyclobutylamino)-7H-pyrrolo[2,3-d]pyrimidin-2-ylamino)phenyl)-N-methylcyclopropanecarboxamide. MS found for C$_{18}$H$_{20}$N$_6$O as (M+H)$^+$ 337.1. λ=212.2, 303.3.

Example 83

2-(2-(1H-indazol-6-ylamino)-7H-pyrrolo[2,3-d]pyrimidin-4-ylamino)acetamide

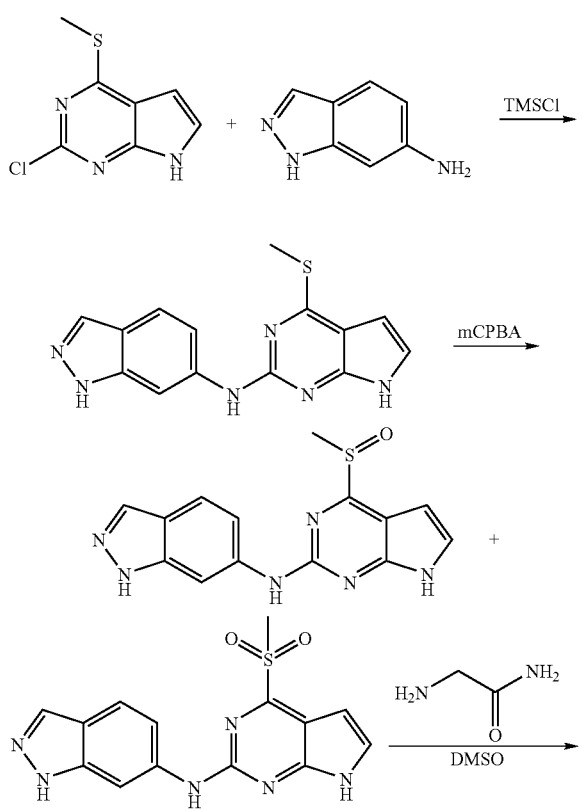

-continued

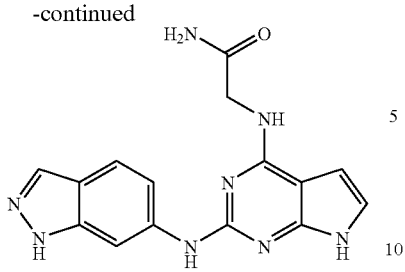

Step 1: To a suspension of 2-chloro-4-(methylthio)-7H-pyrrolo[2,3-d]pyrimidin-4-amine (177 mg, 0.88 mmol) in nBuOH (2 mL) was added TMSCl (0.111 mL, 0.88 mmol). After heating at 115° C. for 24 h, the mixture was cooled and purified by preparative HPLC to give 2-(2-(1H-indazol-6-ylamino)-4-(methylthio)-7H-pyrrolo[2,3-d]pyrimidin-4-amine (53 mg).

Step 2: To a suspension of 2-(2-(1H-indazol-6-ylamino)-4-(methylthio)-7H-pyrrolo[2,3-d]pyrimidin-4-amine (53 mg, 0.18 mmol) in DCM (1 mL) was added mCPBA (50 mg, 0.187 mmol). After stirring at room temperature for 2 h, the mixture was diluted with EtOAc, washed with Sat. NaHCO$_3$, brine, dried and concentrated to give a mixture of corresponding sulfone and sulfoxide (100 mg total).

Step 3: To a solution of the above mixture of sulfone and sulfoxide (100 mg) in DMSO (1 mL) was added glycinamide hydrogen chloride (60 mg, 0.534 mmol) and DIPEA (0.16 mL, 0.89 mmol). After heating at 65° C. for 48 h, the mixture was cooled and purified by preparative HPLC to give 2-(2-(1H-indazol-6-ylamino)-7H-pyrrolo[2,3-d]pyrimidin-4-ylamino)acetamide (6 mg). MS found for $C_{15}H_{14}N_8O$ as (M+H)$^+$ 323.2. λ=244.0, 312.8.

Example 84

N-(4-(4-(cyclobutylamino)-7H-pyrrolo[2,3-d]pyrimidin-2-ylamino)phenyl)-2-(dimethylamino)-N-methylacetamide

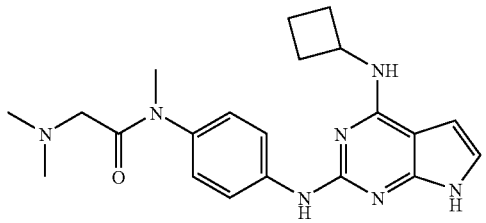

The title compound was prepared using the same synthetic scheme demonstrated in Example of N-(4-(4-(cyclobutylamino)-7H-pyrrolo[2,3-d]pyrimidin-2-ylamino)phenyl)-N-methylcyclopropanecarboxamide. MS found for $C_{21}H_{27}N_7O$ as (M+H)$^+$ 394.3. λ=206.3, 273.6. 304.5.

Example 85

N-(4-(4-(cyclobutylamino)-7H-pyrrolo[2,3-d]pyrimidin-2-ylamino)-N-(3-dimethylaminopropyl)benzamide

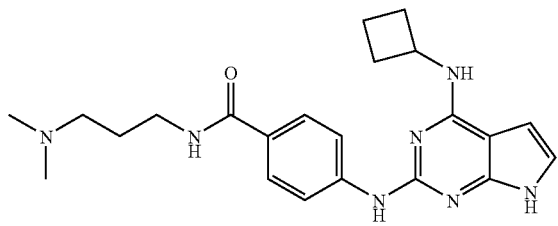

The title compound was prepared using the same synthetic scheme demonstrated in Example of N-(4-(4-(cyclobutylamino)-7H-pyrrolo[2,3-d]pyrimidin-2-ylamino)phenyl)-N-methylcyclopropanecarboxamide. MS found for $C_{22}H_{29}N_7O$ as (M+H)$^+$ 408.4. λ=208.7, 227.5, 312.8.

Example 86

N-(4-(4-(cyclobutylamino)-7H-pyrrolo[2,3-d]pyrimidin-2-ylamino)phenyl)-3-hydroxy-N-methypropanamide

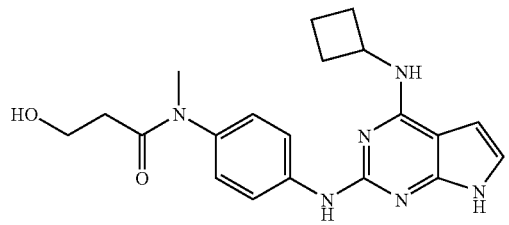

The title compound was prepared using the same synthetic scheme demonstrated in Example of N-(4-(4-(cyclobutylamino)-7H-pyrrolo[2,3-d]pyrimidin-2-ylamino)phenyl)-N-methylcyclopropanecarboxamide. MS found for $C_{20}H_{24}N_6O_2$ as (M+H)$^+$ 381.2. λ=229.8, 271.2, 304.5.

Example 87

N-(4-(4-(cyclopropylamino)-7H-pyrrolo[2,3-d]pyrimidin-2-ylamino)phenyl)-3-hydroxy-N-methypropanamide

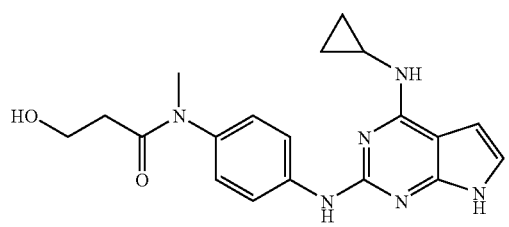

The title compound was prepared using the same synthetic scheme demonstrated in Example of N-(4-(4-(cyclobutylamino)-7H-pyrrolo[2,3-d]pyrimidin-2-ylamino)phenyl)-N-methylcyclopropanecarboxamide. MS found for $C_{19}H_{22}N_6O_2$ as (M+H)$^+$ 367.2. λ=229.8, 296.1.

Example 88

N²-(1H-indazol-6-ylamino)-N⁴-(1H-pyrazol-5-yl)-7H-pyrrolo[2,3-d]pyrimidine-2,4-diamine

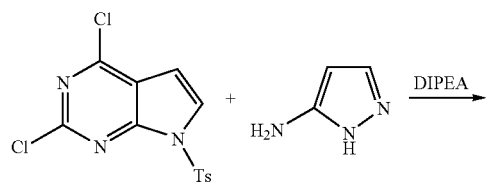

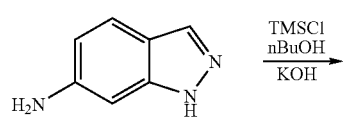

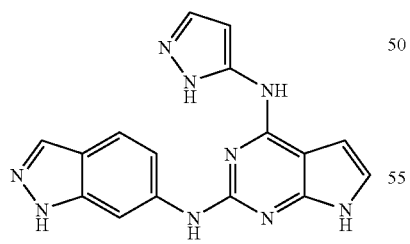

Step 1: To a suspension of 2,4-dichloro-7-tosyl-7H-pyrrolo[2,3-d]pyrimidine (100 mg, 0.29 mmol) in nBuOH (1 mL) was added 3-aminopyrazole (26 mg, 0.32 mmol) and DIPEA (0.057 mL, 0.32 mmol). After heating at 90° C. for 3 h, the mixture was diluted with EtOAc, washed with Sat. NaHCO₃, brine, dried and concentrated to give a mixture of 2-chloro-N-(1H-pyrazol-5-yl)-7-tosyl-7H-pyrrolo[2,3-d]pyrimidine-4-amine (100 mg).

Step 2: To a suspension of 2-chloro-N-(1H-pyrazol-5-yl)-7-tosyl-7H-pyrrolo[2,3-d]pyrimidine-4-amine (100 mg, 0.26 mmol) in nBuOH (1 mL) was added 6-aminoindazol (68 mg, 0.512 mmol) and TMSCl (0.016 mL, 0.128 mmol). After stirring at 115° C. for 15 h, the mixture was cooled and was added MeOH (1 mL), followed by a solution of KOH (100 mg) in H2O (0.5 mL). After heating at 65° C. for 2 h, the solution was concentrated and the residue was purified by preparative HPLC to give N2-(1H-indazol-6-ylamino)-N4-(1H-pyrazol-5-yl)-7H-pyrrolo[2,3-d]pyrimidine-2,4-diamine (7 mg). MS found for $C_{16}H_{13}N_9$ as $(M+H)^+$ 332.1. λ=209.8, 251.1, 310.4.

Example 89

N²-(1H-indazol-6-ylamino)-N⁴-(2-methoxyethyl)-7H-pyrrolo[2,3-d]pyrimidine-2,4-diamine

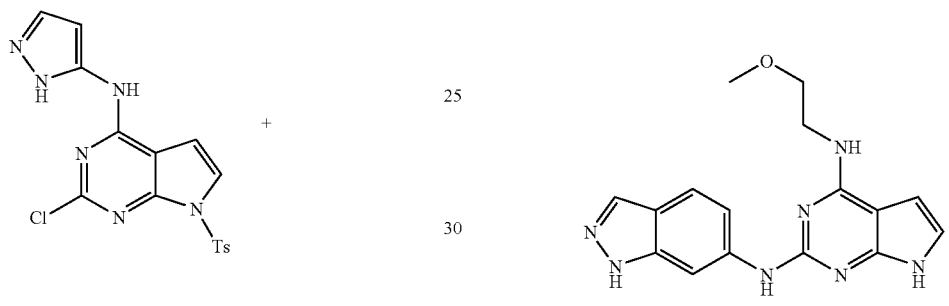

The title compound was prepared using the same synthetic scheme demonstrated in Example of N²-(1H-indazol-6-ylamino)-N⁴-(1H-pyrazol-5-yl)-7H-pyrrolo[2,3-d]pyrimidine-2,4-diamine. MS found for $C_{16}H_{17}N_7O$ as $(M+H)^+$ 324.2. λ=246.4, 315.2.

Example 90

1-(4-(4-(4-(2-methoxyethylamino)-7H-pyrrolo[2,3-d]pyrimidin-2-ylamino)phenyl)piperazin-1-yl)ethanone

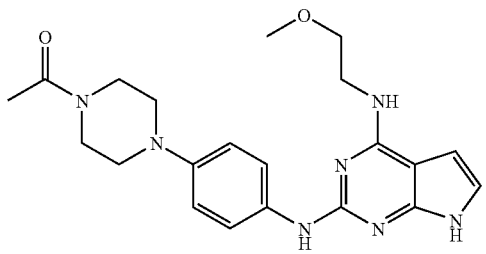

The title compound was prepared using the same synthetic scheme demonstrated in Example of N²-(1H-indazol-6- ylamino)-N$^4$-(1H-pyrazol-5-yl)-7H-pyrrolo[2,3-d]pyrimidine-2,4-diamine. MS found for $C_{22}H_{28}N_6O_2$ as (M+H)$^+$ 410.2. λ=231.0, 265.3, 302.1.

Example 91

N$^2$-(1H-indazol-6-ylamino)-N$^4$-(2-hydroxyethyl)-7H-pyrrolo[2,3-d]pyrimidine-2,4-diamine

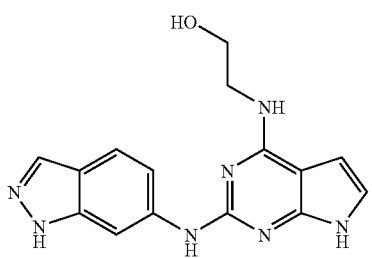

The title compound was prepared using the same synthetic scheme demonstrated in Example of N$^2$-(1H-indazol-6-ylamino)-N$^4$-(1H-pyrazol-5-yl)-7H-pyrrolo[2,3-d]pyrimidine-2,4-diamine. MS found for $C_{15}H_{15}N_7O$ as (M+H)$^+$ 310.2. λ=241.6, 309.2.

Example 92

N$^4$-(2-2-(aminoethoxy)ethyl)-N$^2$-(1H-indazol-6-ylamino)-7H-pyrrolo[2,3-d]pyrimidine-2,4-diamine

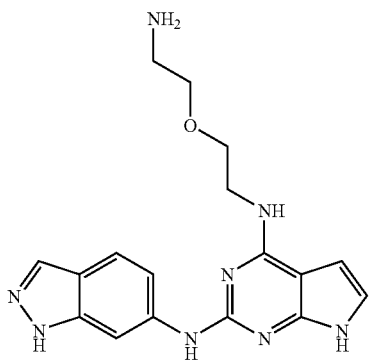

The title compound was prepared using the same synthetic scheme demonstrated in Example of N$^2$-(1H-indazol-6-ylamino)-N$^4$-(1H-pyrazol-5-yl)-7H-pyrrolo[2,3-d]pyrimidine-2,4-diamine. MS found for $C_{17}H_{20}N_8O$ as (M+H)$^+$ 353.2. λ=241.6, 308.0.

Example 93

1-(4-(4-(4-(2-(2-aminoethoxy)amino)-7H-pyrrolo[2,3-d]pyrimidin-2-ylamino)phenyl)piperazin-1-yl)ethanone

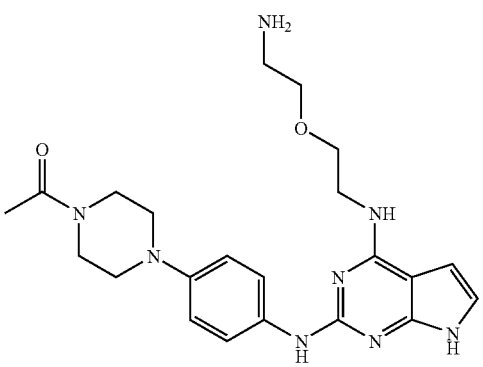

The title compound was prepared using the same synthetic scheme demonstrated in Example of N$^2$-(1H-indazol-6-ylamino)-N$^4$-(1H-pyrazol-5-yl)-7H-pyrrolo[2,3-d]pyrimidine-2,4-diamine. MS found for $C_{23}H_{31}N_7O_2$ as (M+H)$^+$ 439.1. λ=266.5, 303.3.

Example 94

(S)-1-(4-(4-(2-(2-aminoethoxy)ethylamino)-7H-pyrrolo[2,3-d]pyrimidin-2-ylamino)phenyl)pyrrolidine-2-carboxamide

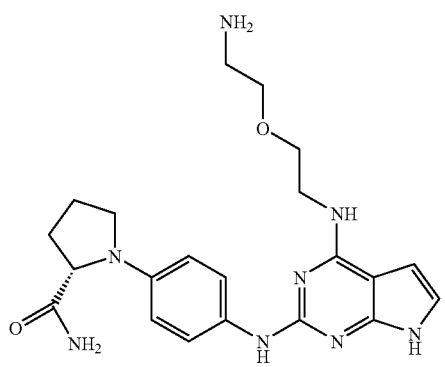

The title compound was prepared using the same synthetic scheme demonstrated in Example of N$^2$-(1H-indazol-6-ylamino)-N$^4$-(1H-pyrazol-5-yl)-7H-pyrrolo[2,3-d]pyrimidine-2,4-diamine. MS found for $C_{22}H_{29}N_7O_2$ as (M+H)$^+$ 425.1. λ=239.3, 303.3.

Example 95
3-(2-(4-(4-acetylpiperazin-1-yl)phenylamino)-7H-pyrrolo[2,3-d]pyrimidin-4-ylamino)benzamide and 3-(2-(4-(piperazin-1-yl)phenylamino)-7H-pyrrolo[2,3-d]pyrimidin-4-ylamino)benzamide
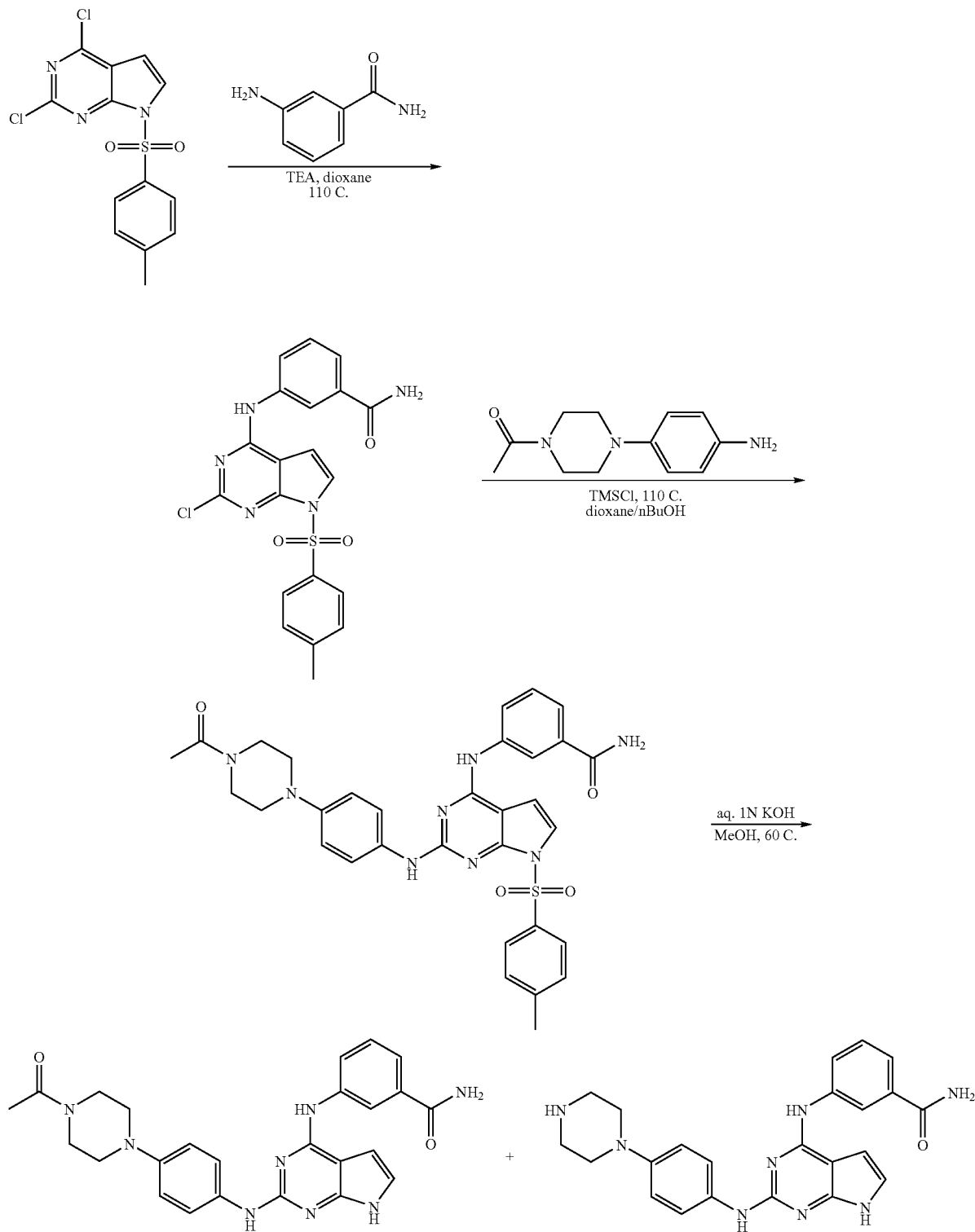

A solution of 2,4-dichloro-7-tosyl-7H-pyrrolo[2,3-d]pyrimidine (200 mg, 0.580 mmol), 3-aminobenzamide (83 mg, 0.61 mmol) and triethylamine (0.200 mL, 1.44 mmol) in dioxane (5 mL) was stirred at 110° C. for 20 h. It was concentrated in vacuo. After the residue was acidified with HOAc (1 mL), it was purified by HPLC to give 3-(2-chloro-7-tosyl-7H-pyrrolo[2,3-d]pyrimidin-4-ylamino)benzamide (85 mg).

A mixture of 3-(2-chloro-7-tosyl-7H-pyrrolo[2,3-d]pyrimidin-4-ylamino)benzamide (85 mg, 0.19 mmol), 1-(4-(4-aminophenyl)piperazin-1-yl)ethanone (105 mg, 0.480 mmol) and trimethylsilyl chloride (0.030 mL, 0.24 mmol) in dioxane (1 mL) and nBuOH (1 mL) was stirred at 110° C. for 72 h. It was concentrated in vacuo. The residue was purified by HPLC to give 3-(2-(4-(4-acetylpiperazin-1-yl)phenylamino)-7-tosyl-7H-pyrrolo[2,3-d]pyrimidin-4-ylamino) benzamide (40 mg).

To a solution of 3-(2-(4-(4-acetylpiperazin-1-yl)phenylamino)-7-tosyl-7H-pyrrolo[2,3-d]pyrimidin-4-ylamino) benzamide (40 mg, 0.064 mmol) in MeOH (3 mL), aq. 1N KOH (1.0 mL, 1.0 mmol) was added. The mixture was heated at 60° C. for 3 h. It was concentrated in vacuo. The residue was acidified with HOAc (1 mL) before being purified by HPLC to give 3-(2-(4-(4-acetylpiperazin-1-yl)phenylamino)-7H-pyrrolo[2,3-d]pyrimidin-4-ylamino)benzamide (15 mg), MS 471.1 (M+H); UV 207.3, 284.1, 311.5 nm; and 3-(2-(4-(piperazin-1-yl)phenylamino)-7H-pyrrolo[2,3-d]pyrimidin-4-ylamino)benzamide (5 mg), MS 429.1 (M+H); UV 202.6, 279.3 nm.

Example 96

3-(2-(4-(4-acetylpiperazin-1-yl)phenylamino)-7H-pyrrolo[2,3-d]pyrimidin-4-ylamino)benzenesulfonamide and 3-(2-(4-(piperazin-1-yl)phenylamino)-7H-pyrrolo[2,3-d]pyrimidin-4-ylamino)benzenesulfonamide

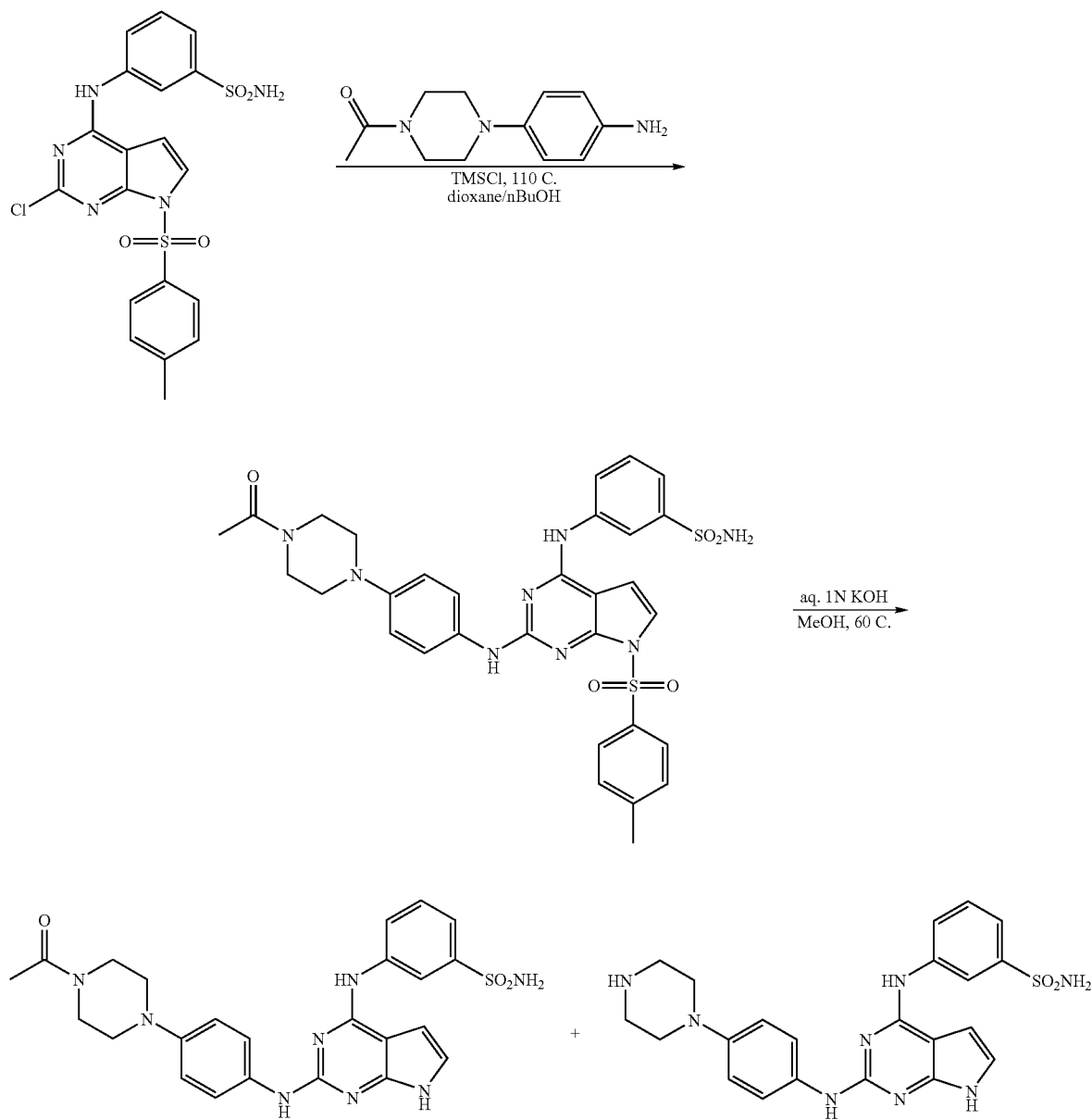

A mixture of 2-chloro-N-(3-aminosulfonyl-phenyl)-7-tosyl-7H-pyrrolo[2,3-d]pyrimidin-4-amine (100 mg, 0.210 mmol), 1-(4-(4-aminophenyl)piperazin-1-yl)ethanone (92 mg, 0.42 mmol) and trimethylsilyl chloride (0.200 mL, 1.58 mmol) in nBuOH (2 mL) and dioxane (2 mL) was heated at 110° C. for 72 h. More 1-(4-(4-aminophenyl)piperazin-1-yl) ethanone (92 mg, 0.42 mmol) was added. The mixture was stirred at 110° C. for another 72 h. It was then purified by HPLC to give 3-(2-(4-(4-acetylpiperazin-1-yl)phenylamino)-7-tosyl-7H-pyrrolo[2,3-d]pyrimidin-4-ylamino) benzenesulfonamide (40 mg)

To a solution of 3-(2-(4-(4-acetylpiperazin-1-yl)phenylamino)-7-tosyl-7H-pyrrolo[2,3-d]pyrimidin-4-ylamino) benzenesulfonamide (40 mg, 0.061 mmol) in MeOH (3 mL), aq. 1N KOH (1.0 mL, 1.0 mmol) was added. The mixture was heated at 60° C. for 3 h. It was concentrated in vacuo. The residue was acidified with HOAc (1 mL) before being purified by HPLC to give 3-(2-(4-(4-acetylpiperazin-1-yl)phenylamino)-7H-pyrrolo[2,3-d]pyrimidin-4-ylamino)benzenesulfonamide (14 mg), MS 507.1 (M+H); UV 212.0, 282.9, 313.8 nm; and 3-(2-(4-(piperazin-1-yl)phenylamino)-7H-pyrrolo[2,3-d]pyrimidin-4-ylamino)benzenesulfonamide (4 mg), MS 465.1 (M+H); UV 203.8, 281.7 nm.

Example 97

N-(4-(4-(3-(aminomethyl)phenylamino)-7H-pyrrolo[2,3-d]pyrimidin-2-ylamino)phenyl)-N-methylacetamide

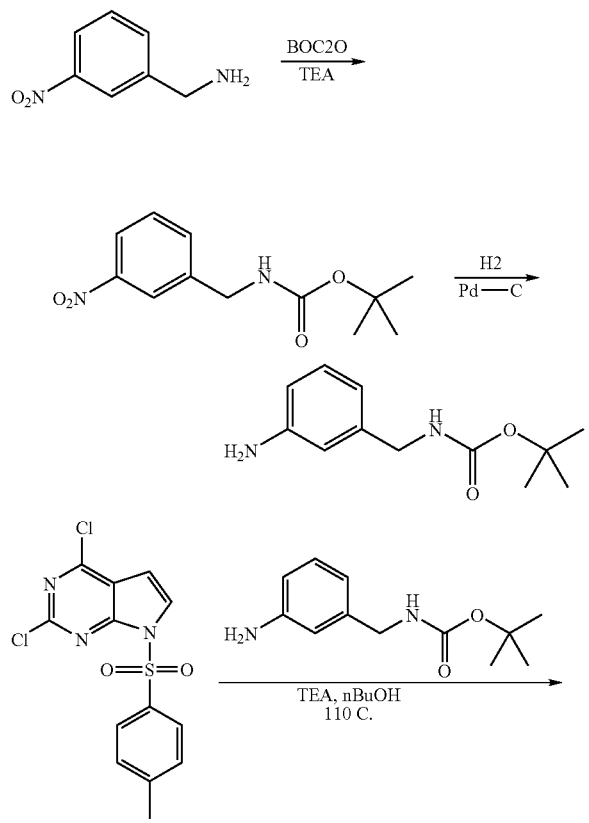

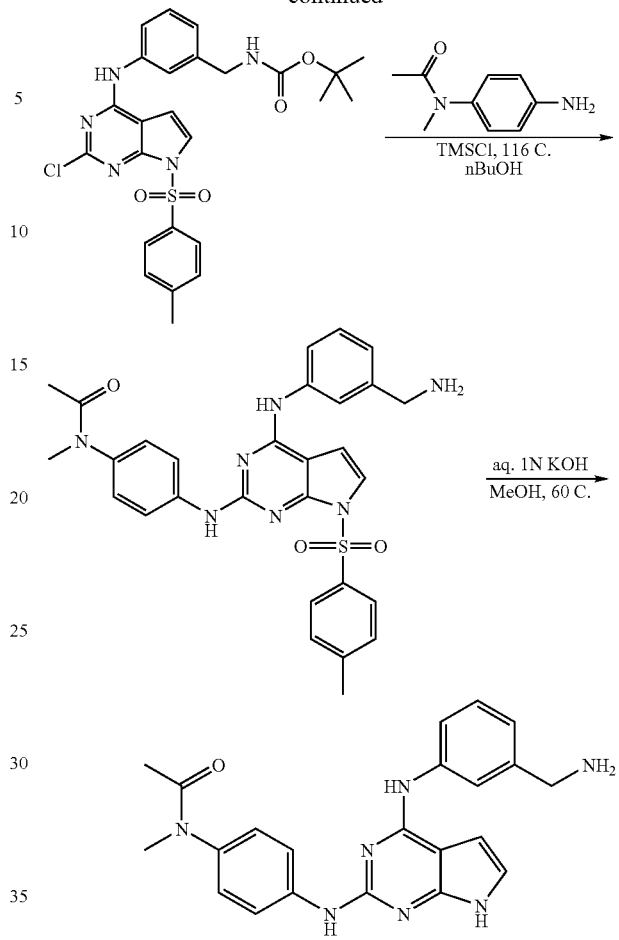

A mixture of 3-nitrobenzylamine hydrochloride (530 mg, 2.81 mmol), di-t-butyl dicarbonate (613 mg, 2.81 mmol) and TEA (0.800 mL, 5.75 mmol) in $CH_2Cl_2$ (8 mL) was stirred at room temperature for 72 h. It was concentrated in vacuo, the residue was partitioned between water and EtOAc. The organic phase was washed with 1N HCl, then with 5% NaHCO3, dried over Na2SO4, concentrated in vacuo to give tert-butyl 3-nitrobenzylcarbamate as a solid (705 mg).

A mixture of tert-butyl 3-nitrobenzylcarbamate (705 mg, 2.80 mmol) and Pd—C (10%, 125 mg) in EtOAc (25 mL) (containing 6 drops of HOAc) was hydrogenated under balloon hydrogen for 20 h. It was filtered through celite. The filtrate was concentrated in vacuo to give tert-butyl 3-nitrobenzylcarbamate (602 mg).

A mixture of 2,4-dichloro-7-tosyl-7H-pyrrolo[2,3-d]pyrimidine (200 mg, 0.585 mmol), tert-butyl 3-nitrobenzylcarbamate (137 mg, 0.617 mmol) and TEA (0.200 mL, 1.44 mmol) in nBuOH (5 mL) was stirred at 110° C. for 20 h. Water and EtOAc were added. The organic phase was washed with 1N HCl, then with 5% NaHCO3, dried over Na2SO4, concentrated in vacuo to give tert-butyl 3-(2-chloro-7-tosyl-7H-pyrrolo[2,3-d]pyrimidin-4-ylamino)benzylcarbamate (306 mg).

A solution of tert-butyl 3-(2-chloro-7-tosyl-7H-pyrrolo[2,3-d]pyrimidin-4-ylamino)benzylcarbamate (306 mg, 0.580 mmol), N-(4-aminophenyl)-N-methylacetamide (190 mg, 1.16 mmol) and trimethylsilyl chloride (0.100 mL, 0.791 mmol) in nBuOH (5 mL) was stirred at 116° C. for 20 h. The mixture was then purified by HPLC to give N-(4-(4-(3-(aminomethyl)phenylamino)-7-tosyl-7H-pyrrolo[2,3-d]pyrimidin-2-ylamino)phenyl)-N-methylacetamide (27 mg).

To a solution of N-(4-(4-(3-(aminomethyl)phenylamino)-7-tosyl-7H-pyrrolo[2,3-d]pyrimidin-2-ylamino)phenyl)-N-methylacetamide (27 mg, 0.049 mmol) in MeOH (3 mL), aq. 1N KOH (1.0 mL, 1.0 mmol) was added. The mixture was stirred at 60° C. for 3 h. It was concentrated in vacuo. The residue was acidified with HOAc (1 mL) before being purified by HPLC to give the titled compound (15 mg). MS 402.3 (M+H); UV 202.6, 282.9, 315.0 nm.

Example 98

(R)-1-(4-(4-(4-(1-hydroxypropan-2-ylamino)-7H-pyrrolo[2,3-d]pyrimidin-2-ylamino)phenyl)piperazin-1-yl)ethanone and (R)-2-(2-(4-(piperazin-1-yl)phenylamino)-7H-pyrrolo[2,3-d]pyrimidin-4-ylamino)propan-1-ol

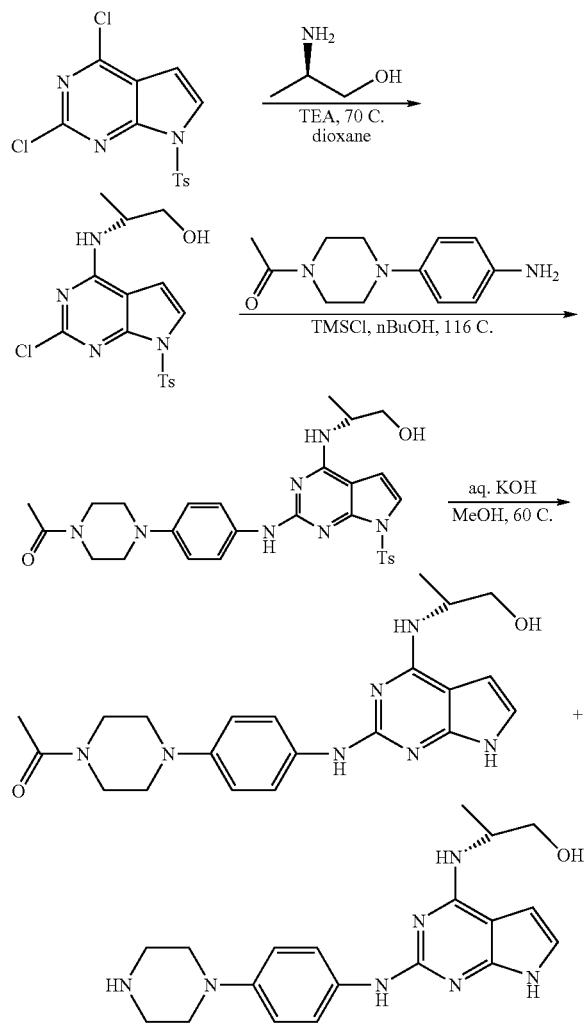

A solution of 2,4-dichloro-7-tosyl-7H-pyrrolo[2,3-d]pyrimidine (0.35 g, 1.0 mmol), D-alaminol (0.10 mL, 1.3 mmol) and TEA (0.20 mL, 1.4 mmol) in dioxane (6 mL) was stirred at 70° C. for 20 h. Water and EtOAc were added. The organic phase was washed with 1N HCl, then with 5% NaHCO3, dried over Na2SO4, concentrated in vacuo to give (R)-2-(2-chloro-7-tosyl-7H-pyrrolo[2,3-d]pyrimidin-4-ylamino)propan-1-ol (0.38 g).

A mixture of (R)-2-(2-chloro-7-tosyl-7H-pyrrolo[2,3-d]pyrimidin-4-ylamino)propan-1-ol (200 mg, 0.525 mmol), 1-(4-(4-aminophenyl)piperazin-1-yl)ethanone (140 mg, 0.639 mmol) and trimethylsilyl chloride (0.130 mL, 1.03 mmol) in nBuOH (4 mL) was stirred at 116° C. for 48 h. It was concentrated in vacuo. The residue was purified by HPLC to give (R)-1-(4-(4-(4-(1-hydroxypropan-2-ylamino)-7-tosyl-7H-pyrrolo[2,3-d]pyrimidin-2-ylamino)phenyl)piperazin-1-yl)ethanone (25 mg).

To a solution of (R)-1-(4-(4-(4-(1-hydroxypropan-2-ylamino)-7-tosyl-7H-pyrrolo[2,3-d]pyrimidin-2-ylamino)phenyl)piperazin-1-yl)ethanone (25 mg, 0.044 mmol) in MeOH (1 mL) and dioxane (1 mL), aq. 1N KOH (1.0 mL, 1.0 mmol) was added. After being stirred at 60° C. for 3 h, it was concentrated in vacuo. The residue was acidified with HOAc (1 mL), then was purified by HPLC to give (R)-1-(4-(4-(4-(1-hydroxypropan-2-ylamino)-7H-pyrrolo[2,3-d]pyrimidin-2-ylamino)phenyl)piperazin-1-yl)ethanone (7 mg), MS 410.5 (M+H); UV 202.6, 267.5, 303.1 nm; and (R)-2-(2-(4-(piperazin-1-yl)phenylamino)-7H-pyrrolo[2,3-d]pyrimidin-4-ylamino)propan-1-ol (3 mg), MS 368.5 (M+H); UV 229.6, 271.0, 301.9 nm.

Example 99

(S)-1-(4-(4-(4-(1-hydroxypropan-2-ylamino)-7H-pyrrolo[2,3-d]pyrimidin-2-ylamino)phenyl)piperazin-1-yl)ethanone and (S)-2-(2-(4-(piperazin-1-yl)phenylamino)-7H-pyrrolo[2,3-d]pyrimidin-4-ylamino)propan-1-ol

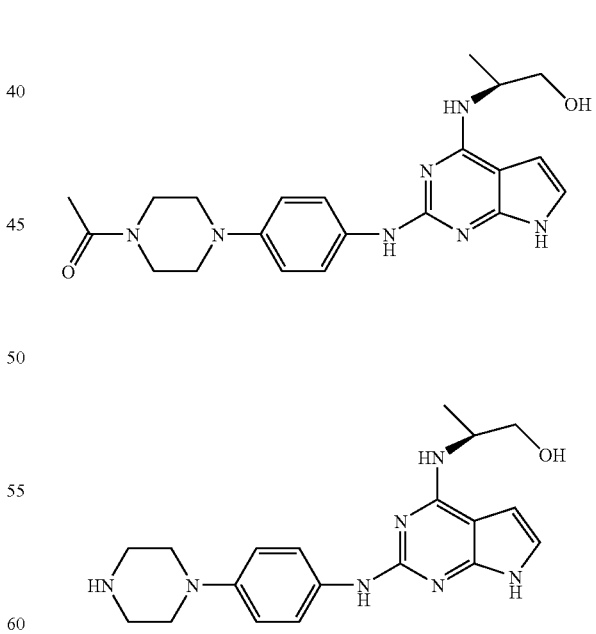

The titled compounds were synthesized analogously as (R)-1-(4-(4-(4-(1-hydroxypropan-2-ylamino)-7H-pyrrolo[2,3-d]pyrimidin-2-ylamino)phenyl)piperazin-1-yl)ethanone, MS 410.5 (M+H); UV 202.0, 266.3, 301.9; and (R)-2-(2-(4-

(piperazin-1-yl)phenylamino)-7H-pyrrolo[2,3-d]pyrimidin-4-ylamino)propan-1-ol, MS 368.5 (M+H); by using L-alaninol in place of D-alaninol.

Example 100

1-(4-(4-(4-(1,1-dioxy-tetrahydrothiophen-3-ylamino)-7H-pyrrolo[2,3-d]pyrimidin-2-ylamino)phenyl)piperazin-1-yl)ethanone and N2-(4-(piperazin-1-yl)phenyl)-N4-(1,1-dioxy-tetrahydrothiophen-3-yl)-7H-pyrrolo[2,3-d]pyrimidine-2,4-diamine

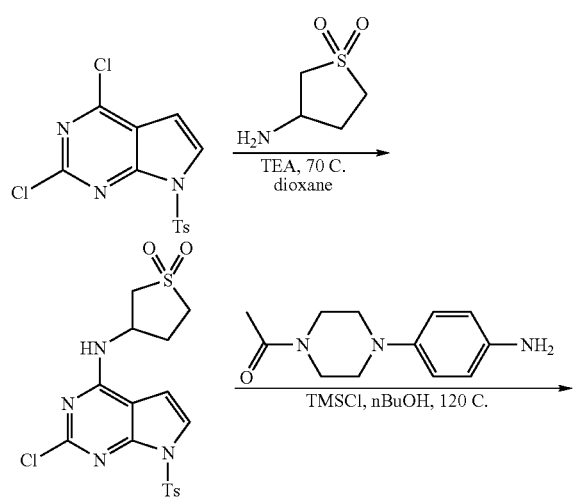

A mixture of 2,4-dichloro-7-tosyl-7H-pyrrolo[2,3-d]pyrimidine (200 mg, 0.584 mmol), 3-aminotetrahydro-1H-thiophene-1,1-dione hydrochloride (100 mg, 0.583 mmol) and TEA (0.325 mL, 2.34 mmol) in dioxane (5 mL) was stirred at 70° C. for 20 h. Water and EtOAc were added. The organic phase was separated, dried over Na2SO4, concentrated in vacuo to give 2-chloro-N-(1,2-dioxy-tetrahydrothiophen-3-yl)-7-tosyl-7H-pyrrolo[2,3-d]pyrimidin-4-amine (208 mg).

A mixture of 2-chloro-N-(1,2-dioxy-tetrahydrothiophen-3-yl)-7-tosyl-7H-pyrrolo[2,3-d]pyrimidin-4-amine (208 mg, 0.472 mmol), 1-(4-(4-aminophenyl)piperazin-1-yl)ethanone (165 mg, 0.753 mmol) and trimethylsilyl chloride (0.200 mL, 1.58 mmol) in nBuOH (5 mL) was stirred at 120° C. for 48 h. It was concentrated in vacuo. The residue was purified by HPLC to give 1-(4-(4-(4-(1,1-dioxy-tetrahydrothiophen-3-ylamino)-7-tosyl-7H-pyrrolo[2,3-d]pyrimidin-2-ylamino)phenyl)piperazin-1-yl)ethanone (65 mg).

To a solution of 1-(4-(4-(4-(1,1-dioxy-tetrahydrothiophen-3-ylamino)-7-tosyl-7H-pyrrolo[2,3-d]pyrimidin-2-ylamino)phenyl)piperazin-1-yl)ethanone (65 mg, 0.104 mmol) in MeOH (3 mL), aq. 1N KOH (1.0 mL, 1.0 mmol) was added. After being stirred at 60° C. for 4 h, it was concentrated in vacuo. The residue was acidified with HOAc (1 mL), then was purified by HPLC to give 1-(4-(4-(4-(1,1-dioxy-tetrahydrothiophen-3-ylamino)-7H-pyrrolo[2,3-d]pyrimidin-2-ylamino)phenyl)piperazin-1-yl)ethanone (15 mg), MS 470.5 (M+H); and N2-(4-(piperazin-1-yl)phenyl)-N4-(1,1-dioxy-tetrahydrothiophen-3-yl)-7H-pyrrolo[2,3-d]pyrimidine-2,4-diamine (3 mg), MS 428.5 (M+H).

Example 101

4-(4-(cyclopropylamino)-5-(pyridin-4-yl)-7H-pyrrolo[2,3-d]pyrimidin-2-ylamino)benzamide

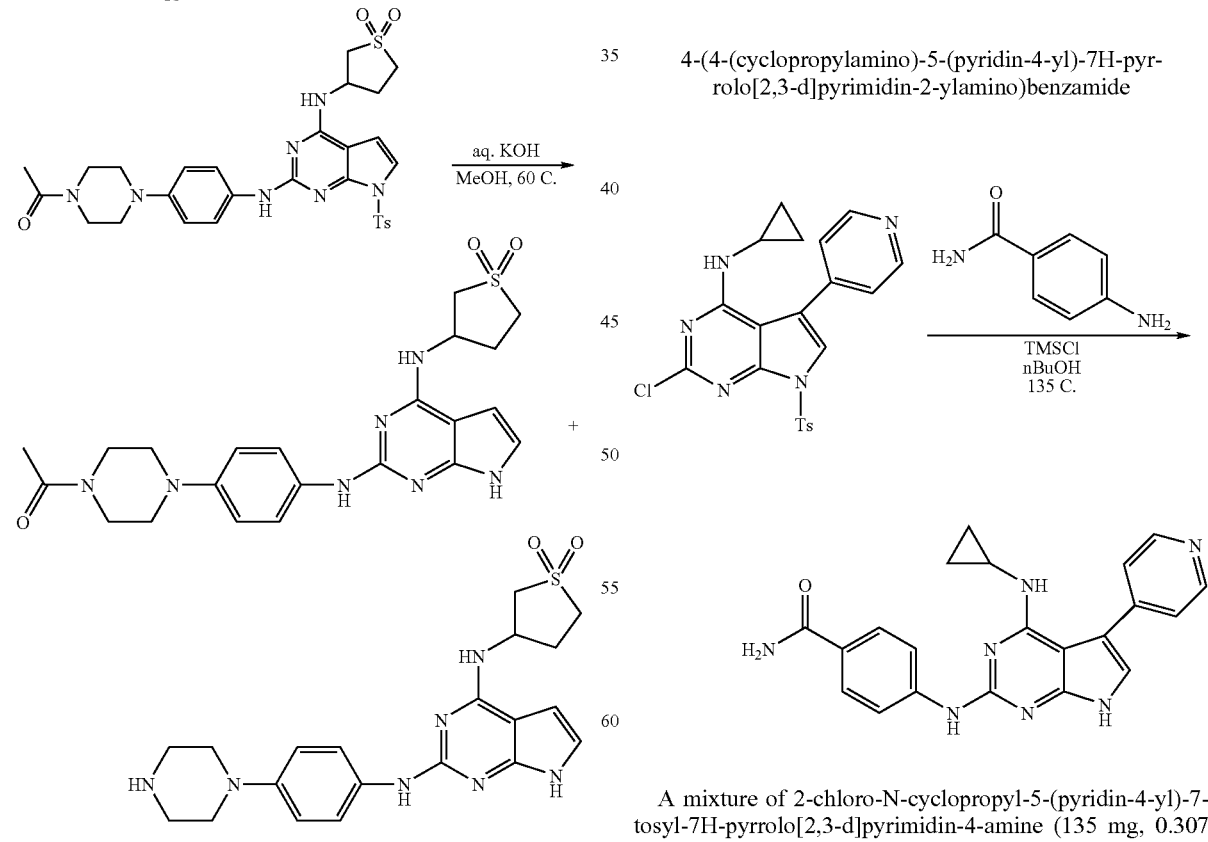

A mixture of 2-chloro-N-cyclopropyl-5-(pyridin-4-yl)-7-tosyl-7H-pyrrolo[2,3-d]pyrimidin-4-amine (135 mg, 0.307 mmol), 4-aminobenzamide (100 mg, 0.735 mmol) and trimethylsilyl chloride (0.200 mL, 1.58 mmol) in nBuOH (3 mL) was stirred at 135° C. for 48 h. It was concentrated in vacuo.

The residue was purified by HPLC to give the titled compound (9 mg). MS 386.2 (M+H); UV 201.8, 309.8 nm.

Example 102

4-(4-amino-5-(pyridin-4-yl)-7H-pyrrolo[2,3-d]pyrimidin-2-ylamino)benzoic acid

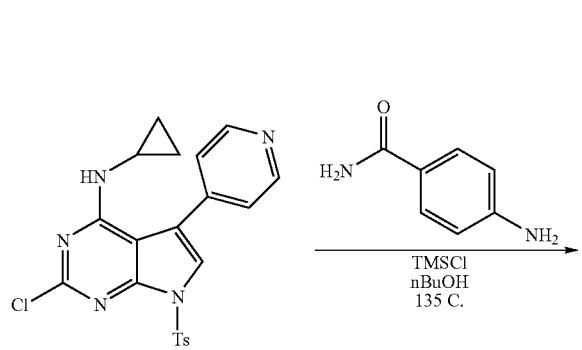

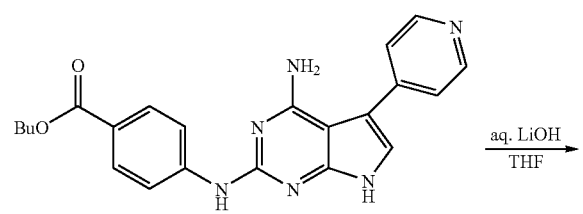

A mixture of 2-chloro-N-cyclopropyl-5-(pyridin-4-yl)-7-tosyl-7H-pyrrolo[2,3-d]pyrimidin-4-amine (245 mg, 0.557 mmol), 4-aminobenzoic acid (150 mg, 1.09 mmol) and trimethylsilyl chloride (0.300 mL, 2.37 mmol) in nBuOH (4 mL) was stirred at 135° C. for 24 h. It was concentrated in vacuo. The residue was purified by HPLC to give butyl 4-(4-amino-5-(pyridin-4-yl)-7H-pyrrolo[2,3-d]pyrimidin-2-ylamino)benzoate (137 mg).

To a solution of butyl 4-(4-amino-5-(pyridin-4-yl)-7H-pyrrolo[2,3-d]pyrimidin-2-ylamino)benzoate (137 mg, 0.340 mmol) in THF (3 mL), aq. 1N LiOH (2.0 mL, 2.0 mmol) was added. The mixture was stirred at room temperature for 20 h. It was concentrated in vacuo. The residue was acidified with HOAc (2 mL), then was purified by HPLC to give the titled compound (55 mg). MS 347.2 (M+H); UV 203.8, 306.7 nm.

Example 103

4-(cyclopropylamino)-2-(2-oxo-1,2,3,4-tetrahydroquinolin-6-ylamino)-7H-pyrrolo[2,3-d]pyrimidine-5-carbonitrile

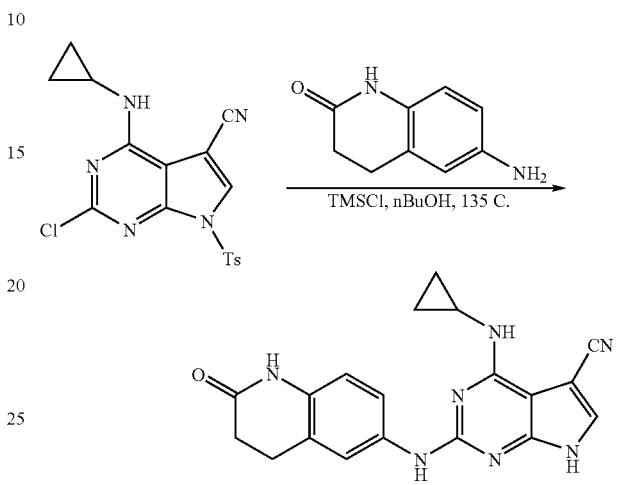

A mixture of 2-chloro-4-(cyclopropylamino)-7-tosyl-7H-pyrrolo[2,3-d]pyrimidine-5-carbonitrile (145 mg, 0.374 mmol), 6-amino-3,4-dihydroquinolin-2(1H)-one (60 mg, 0.370 mmol) and trimethylsilyl chloride (0.200 mL, 1.58 mmol) in nBuOH (4 mL) was stirred at 135° C. for 20 h. It was concentrated in vacuo. The residue was purified by HPLC to give the titled compound (50 mg). MS 360.3 (M+H); UV 202.2, 292.7 nm.

Example 104

4-(5-cyano-4-(cyclopropylamino)-7H-pyrrolo[2,3-d]pyrimidin-2-ylamino)benzamide

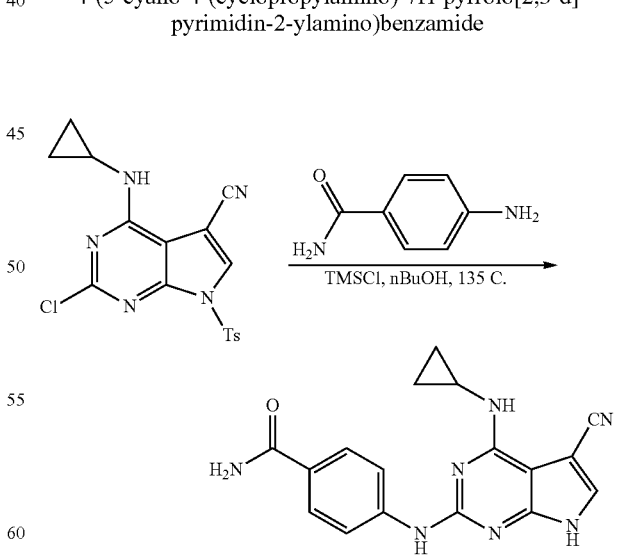

A mixture of 2-chloro-4-(cyclopropylamino)-7-tosyl-7H-pyrrolo[2,3-d]pyrimidine-5-carbonitrile (175 mg, 0.451 mmol), 4-aminobenzamide (122 mg, 0.897 mmol) and trimethylsilyl chloride (0.200 mL, 1.58 mmol) in nBuOH (4 mL) was stirred at 135° C. for 20 h. It was concentrated in vacuo.

The residue was purified by HPLC to give the titled compound (43 mg). MS 334.3 (M+H); UV 204.6, 230.2, 308.1 nm.

Example 105

N-(4-(5-cyano-4-(cyclopropylamino)-7H-pyrrolo[2,3-d]pyrimidin-2-ylamino)phenyl)-N-methylacetamide

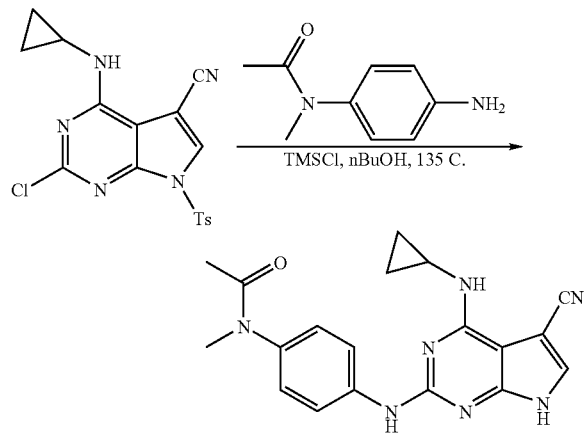

A mixture of 2-chloro-4-(cyclopropylamino)-7-tosyl-7H-pyrrolo[2,3-d]pyrimidine-5-carbonitrile (165 mg, 0.425 mmol), N-(4-aminophenyl)-N-methylacetamide (107 mg, 0.652 mmol) and trimethylsilyl chloride (0.200 mL, 1.58 mmol) in nBuOH (4 mL) was stirred at 135° C. for 20 h. It was concentrated in vacuo. The residue was purified by HPLC to give the titled compound (50 mg). MS 362.3 (M+H); UV 202.8, 254.0, 280.4 nm.

Example 106

4-(5-cyano-4-(cyclopropylamino)-7H-pyrrolo[2,3-d]pyrimidin-2-ylamino)benzenesulfonamide

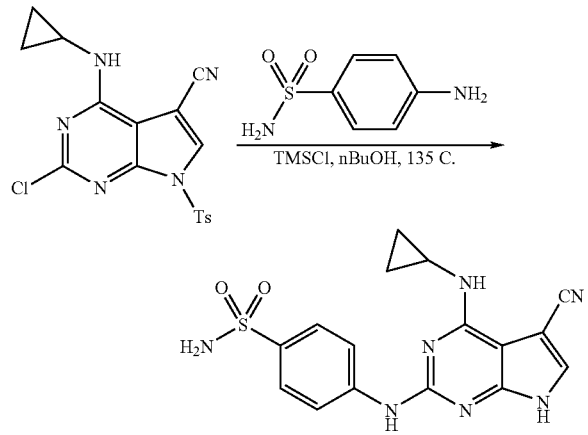

A mixture of 2-chloro-4-(cyclopropylamino)-7-tosyl-7H-pyrrolo[2,3-d]pyrimidine-5-carbonitrile (150 mg, 0.387 mmol), 4-aminobenzenesulfonamide (103 mg, 0.599 mmol) and trimethylsilyl chloride (0.200 mL, 1.58 mmol) in nBuOH (4 mL) was stirred at 135° C. for 20 h. It was concentrated in vacuo. The residue was purified by HPLC to give the titled compound (45 mg). MS 370.3 (M+H); UV 202.8, 254.6, 305.0 nm.

Example 107

2-(4-(4-acetylpiperazin-1-yl)phenylamino)-4-(cyclopropylamino)-7H-pyrrolo[2,3-d]pyrimidine-5-carbonitrile

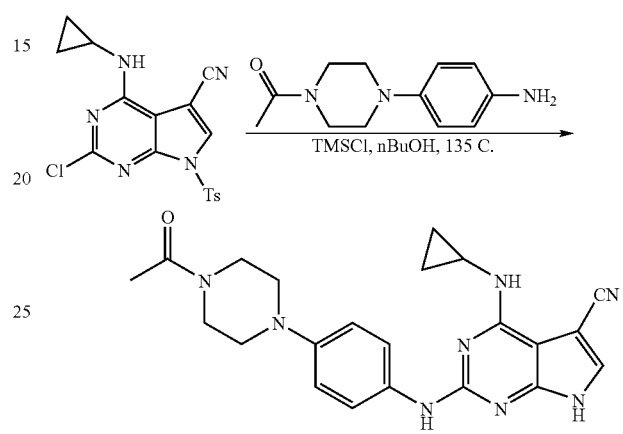

A mixture of 2-chloro-4-(cyclopropylamino)-7-tosyl-7H-pyrrolo[2,3-d]pyrimidine-5-carbonitrile (150 mg, 0.387 mmol), 1-(4-(4-aminophenyl)piperazin-1-yl)ethanone (132 mg, 0.602 mmol) and trimethylsilyl chloride (0.200 mL, 1.58 mmol) in nBuOH (4 mL) was stirred at 135° C. for 20 h. It was concentrated in vacuo. The residue was purified by HPLC to give the titled compound (25 mg). MS 417.4 (M+H); UV 203.4, 254.0, 291.5 nm.

Example 108

4-(cyclopropylamino)-2-(2-oxo-1,2,3,4-tetrahydroquinolin-6-ylamino)-7H-pyrrolo[2,3-d]pyrimidine-5-carboxamide

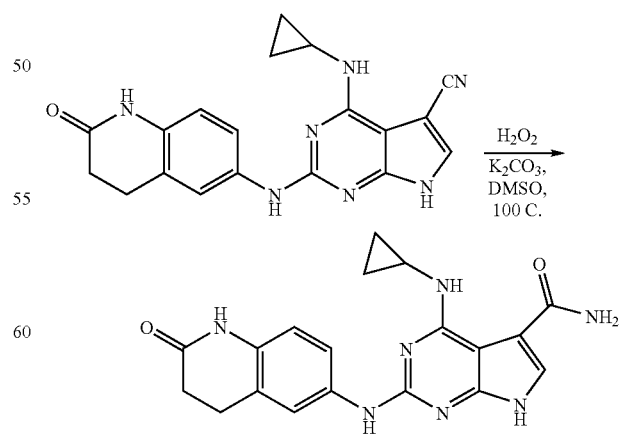

A solution of 4-(cyclopropylamino)-2-(2-oxo-1,2,3,4-tetrahydroquinolin-6-ylamino)-7H-pyrrolo[2,3-d]pyrimidine- 5-carbonitrile (30 mg, 0.083 mmol), K₂CO₃ (100 mg, 0.724 mmol) and H₂O₂ (50% aq., 0.500 mL) in DMSO (1 mL) was heated at 100° C. for 5 min. Gas evolved violently. After cooling down, the mixture was purified by HPLC to give the titled compound (7 mg). MS 378.4 (M+H); UV 200.4, 241.8, 295.8 nm.

Example 109

4-(4-(1-(2-cyanoacetyl)piperidin-4-ylamino)-7H-pyrrolo[2,3-d]pyrimidin-2-ylamino)benzamide

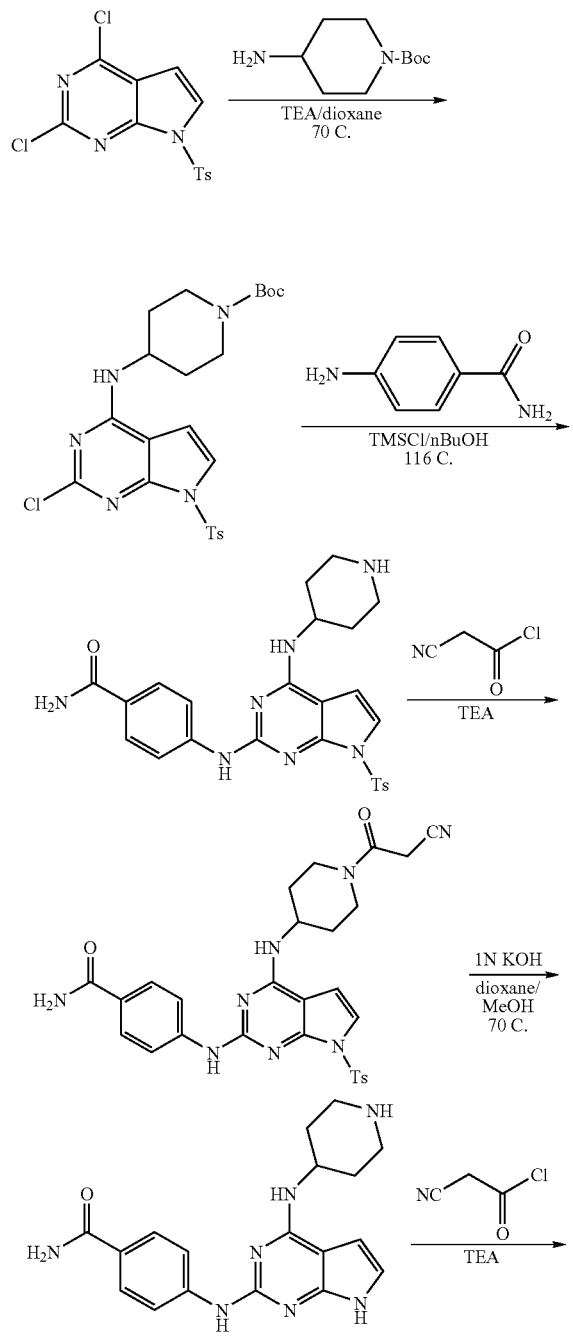

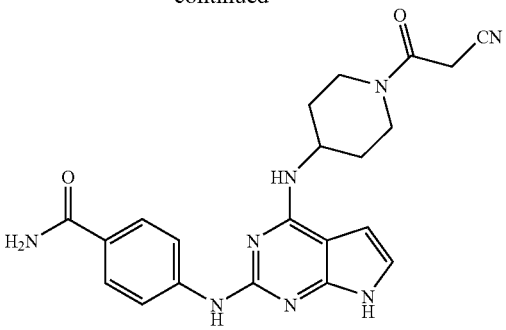

A mixture of 2,4-dichloro-7-tosyl-7H-pyrrolo[2,3-d]pyrimidine (171 mg, 0.500 mmol), 4-amino-1-N-Boc-piperidine (100 mg, 0.500 mmol) and TEA (0.150 mL, 1.08 mmol) in dioxane (4 mL) was stirred at 70° C. for 20 h. Water and EtOAc were added. The organic phase was separated, washed with 1N HCl, then with 5% NaHCO3, dried over Na2SO4, concentrated in vacuo to give tert-butyl 4-(2-chloro-7-tosyl-7H-pyrrolo[2,3-d]pyrimidin-4-ylamino)piperidine-1-carboxylate (202 mg).

A mixture of tert-butyl 4-(2-chloro-7-tosyl-7H-pyrrolo[2,3-d]pyrimidin-4-ylamino)piperidine-1-carboxylate (202 mg, 0.400 mmol), 4-aminobenzamide (82 mg, 0.60 mmol) and trimethylsilyl chloride (0.200 mL, 1.58 mmol) in nBuOH (4 mL) was stirred at 116° C. in a sealed tube for 20 h. It was concentrated in vacuo. The residue was purified by HPLC to give 4-(4-(piperidin-4-ylamino)-7-tosyl-7H-pyrrolo[2,3-d]pyrimidin-2-ylamino)benzamide (58 mg).

To a suspension of cyanoacetic acid (85 mg, 1.00 mmol) in CH₂Cl₂ (2 mL) (containing 2 drops of DMF), oxalyl chloride (0.082 mL, 0.94 mmol) was added. The mixture was stirred at room temperature for 50 min. To the above solution cooled in an ice bath, a solution of 4-(4-(piperidin-4-ylamino)-7-tosyl-7H-pyrrolo[2,3-d]pyrimidin-2-ylamino)benzamide (58 mg, 0.11 mmol) and TEA (0.450 mL, 3.22 mmol) in DMF (2 mL) was added. The mixture was stirred for 2 h. Water and EtOAc were added. The organic phase was separated, washed with 5% NaHCO3, dried over Na2SO4, concentrated in vacuo to give 4-(4-(1-(2-cyanoacetyl)piperidin-4-ylamino)-7-tosyl-7H-pyrrolo[2,3-d]pyrimidin-2-ylamino)benzamide (45 mg).

To a solution of 4-(4-(1-(2-cyanoacetyl)piperidin-4-ylamino)-7-tosyl-7H-pyrrolo[2,3-d]pyrimidin-2-ylamino)benzamide (45 mg, 0.078 mmol) in dioxane (2 mL) and MeOH (1 mL), aq. 1N KOH (1.0 mL, 1.0 mmol) was added. The mixture was stirred at 70° C. for 4 h. It was concentrated in vacuo. The residue was acidified with HOAc (1 mL) before being purified by HPLC to give 4-(4-(piperidin-4-ylamino)-7H-pyrrolo[2,3-d]pyrimidin-2-ylamino)benzamide (20 mg).

To a suspension of cyanoacetic acid (85 mg, 1.00 mmol) in CH₂Cl₂ (2 mL) (containing 2 drops of DMF), oxalyl chloride (0.082 mL, 0.94 mmol) was added. The mixture was stirred at room temperature for 50 min. To the above solution cooled in an ice bath, a solution of 4-(4-(piperidin-4-ylamino)-7H-pyrrolo[2,3-d]pyrimidin-2-ylamino)benzamide (20 mg, 0.057 mmol) and TEA (0.450 mL, 3.22 mmol) in DMF (2 mL) was added. The mixture was stirred at room temperature for 20 h.

Water was added. $CH_2Cl_2$ was removed in vacuo. The residue was purified by HPLC to give the titled compound (10 mg). MS 419.3 (M+H); UV 200.0, 311.9 nm.

Example 110

4-(4-(1-(2-cyanoacetyl)piperidin-3-ylamino)-7H-pyrrolo[2,3-d]pyrimidin-2-ylamino)benzamide

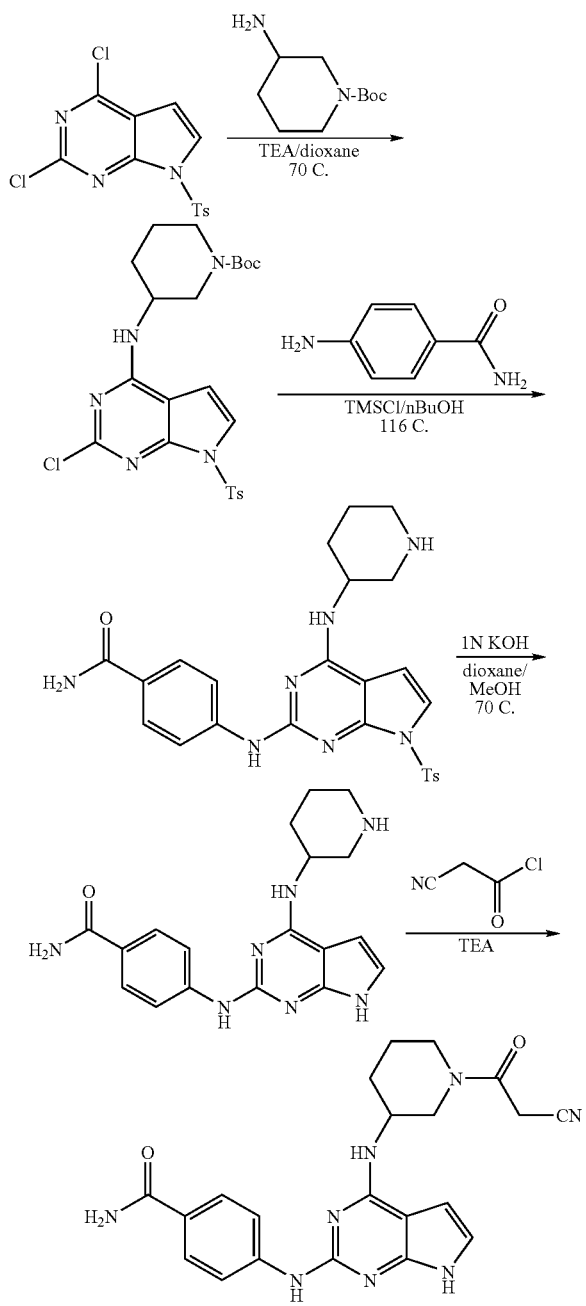

A mixture of 2,4-dichloro-7-tosyl-7H-pyrrolo[2,3-d]pyrimidine (233 mg, 0.681 mmol), 3-amino-1-N-Boc-piperidine (136 mg, 0.680 mmol) and TEA (0.200 mL, 1.44 mmol) in dioxane (5 mL) was stirred at 70° C. for 20 h. Water and EtOAc were added. The organic phase was separated, washed with 1N HCl, then with 5% NaHCO3, dried over Na2SO4, concentrated in vacuo to give tert-butyl 3-(2-chloro-7-tosyl-7H-pyrrolo[2,3-d]pyrimidin-4-ylamino)piperidine-1-carboxylate (251 mg).

A mixture of tert-butyl 3-(2-chloro-7-tosyl-7H-pyrrolo[2,3-d]pyrimidin-4-ylamino)piperidine-1-carboxylate (251 mg, 0.496 mmol), 4-aminobenzamide (102 mg, 0.750 mmol) and trimethylsilyl chloride (0.200 mL, 1.58 mmol) in nBuOH (4 mL) was stirred at 116° C. in a sealed tube for 20 h. It was concentrated in vacuo. The residue was purified by HPLC to give 4-(4-(piperidin-3-ylamino)-7-tosyl-7H-pyrrolo[2,3-d]pyrimidin-2-ylamino)benzamide (36 mg).

To a solution of 4-(4-(piperidin-3-ylamino)-7-tosyl-7H-pyrrolo[2,3-d]pyrimidin-2-ylamino)benzamide (36 mg, 0.071 mmol) in dioxane (2 mL) and MeOH (2 mL), aq. 1N KOH (1.0 mL, 1.0 mmol) was added. The mixture was stirred at 70° C. for 3 h. It was concentrated in vacuo. The residue was acidified with HOAc (1 mL) before being purified by HPLC to give the desired compound as TFA salt, which was then dissolved in MeOH (5 mL), MP-carbonate (0.10 g, 0.31 mmol) was added. After gentle agitation for 30 min, the mixture was filtered. The filtrate was concentrated in vacuo to give 4-(4-(piperidin-3-ylamino)-7H-pyrrolo[2,3-d]pyrimidin-2-ylamino)benzamide (18 mg) as free base.

To a suspension of cyanoacetic acid (46 mg, 0.54 mmol) in $CH_2Cl_2$ (1 mL) (containing 2 drops of DMF), oxalyl chloride (0.047 mL, 0.54 mmol) was added. The mixture was stirred at room temperature for 40 min. To the above solution cooled in an ice bath, a solution of 4-(4-(piperidin-3-ylamino)-7H-pyrrolo[2,3-d]pyrimidin-2-ylamino)benzamide (18 mg, 0.051 mmol) and TEA (0.250 mL, 1.80 mmol) in DMF (2 mL) was added. The mixture was stirred for 2 h. Water was added. $CH_2Cl_2$ was removed in vacuo. The residue was purified by HPLC to give the titled compound (10 mg). MS 419.3 (M+H); UV 201.6, 311.9 nm.

Example 111

4-(4-methoxyphenylamino)-2-(2-oxo-1,2,3,4-tetrahydroquinolin-6-ylamino)-7H-pyrrolo[2,3-d]pyrimidine-5-carbonitrile

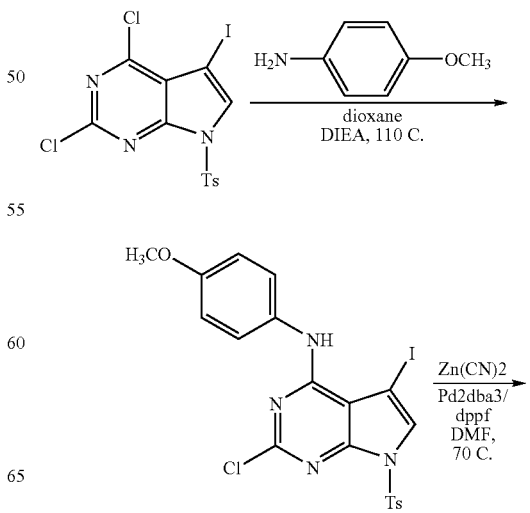

161

-continued

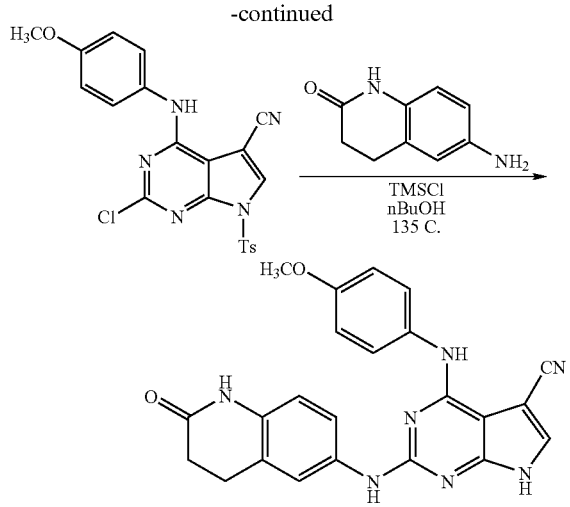

A mixture of 2,4-dichloro-5-iodo-7-tosyl-7H-pyrrolo[2,3-d]pyrimidine (260 mg, 0.556 mmol), p-anisidine (75 mg, 0.610 mmol) and DIEA (0.300 mL, 1.72 mmol) in dioxane (5 mL) was stirred at 110° C. for 20 h. Water and EtOAc were added. The organic phase was separated, washed with 1N HCl, then with 5% NaHCO3, dried over Na2SO4, concentrated in vacuo to give 2-chloro-5-iodo-N-(4-methoxyphenyl)-7-tosyl-7H-pyrrolo[2,3-d]pyrimidin-4-amine (257 mg).

A solution of 2-chloro-5-iodo-N-(4-methoxyphenyl)-7-tosyl-7H-pyrrolo[2,3-d]pyrimidin-4-amine (257 mg, 0.463 mmol), Pd2 dba3 (25 mg, 0.027 mmol) and dppf (51 mg, 0.092 mmol) in DMF (4 mL) was degassed with argon before being charged with Zn(CN)$_2$ (65 mg, 0.555 mmol). The mixture was stirred at 70° C. for 3 h. DMF was removed in vacuo. The residue was dissolved in CH$_3$CN. Water was added to induce precipitation. The precipitate was collected and dried on vacuum to give 2-chloro-4-(4-methoxyphenylamino)-7-tosyl-7H-pyrrolo[2,3-d]pyrimidine-5-carbonitrile (68 mg).

A mixture of 2-chloro-4-(4-methoxyphenylamino)-7-tosyl-7H-pyrrolo[2,3-d]pyrimidine-5-carbonitrile (68 mg, 0.15 mmol), 6-amino-3,4-dihydroquinolin-2(1H)-one (40 mg, 0.24 mmol) and trimethylsilyl chloride (0.100 mL, 0.790 mmol) in nBuOH (2 mL) was stirred at 135° C. for 20 h. More 6-amino-3,4-dihydroquinolin-2(1H)-one (24 mg, 0.15 mmol) and trimethylsilyl chloride (0.200 mL, 1.58 mmol) were added. It was stirred at 135° C. for another 20 h. nBuOH was removed in vacuo. The residue was purified by HPLC to give the titled compound (5 mg). MS 426.4 (M+H); UV 203.5, 290.3 nm.

Example 112

6-(4-(4-fluorophenylamino)-5-(pyridin-4-yl)-7H-pyrrolo[2,3-d]pyrimidin-2-ylamino)-1-methyl-3,4-dihydroquinolin-2(1H)-one

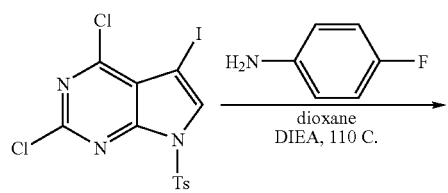

162

-continued

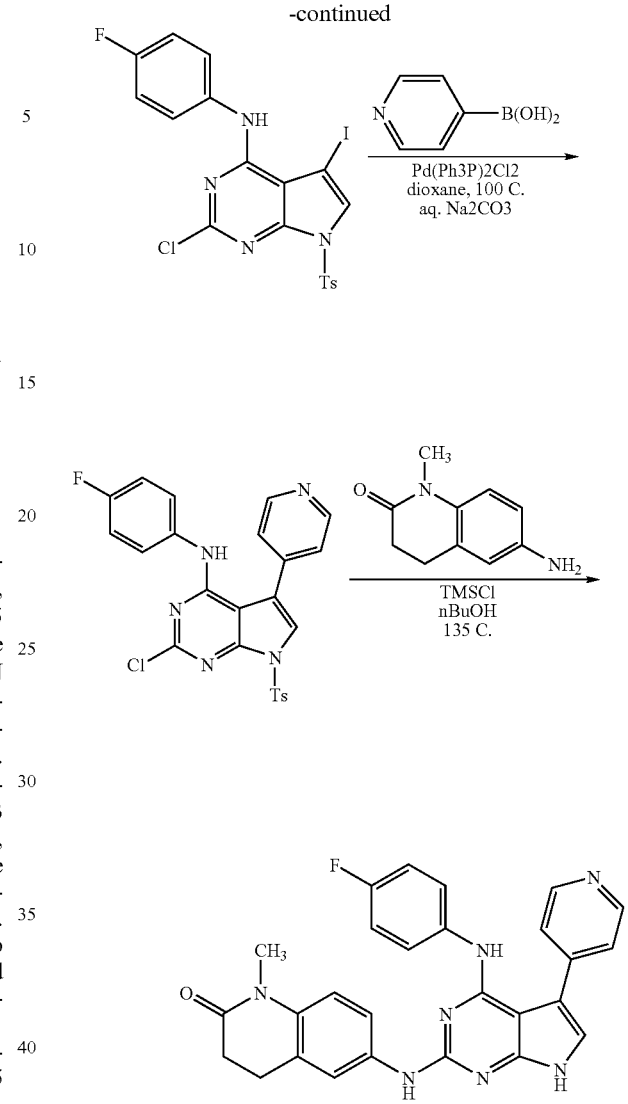

A mixture of 2,4-dichloro-5-iodo-7-tosyl-7H-pyrrolo[2,3-d]pyrimidine (260 mg, 0.556 mmol), 4-fluoroaniline (0.055 mL, 0.581 mmol) and DIEA (0.300 mL, 1.72 mmol) in dioxane (4 mL) was stirred at 110° C. for 20 h. Water and EtOAc were added. The organic phase was separated, washed with 1N HCl, then with 5% NaHCO3, dried over Na2SO4, concentrated in vacuo to give 2-chloro-N-(4-fluorophenyl)-5-iodo-7-tosyl-7H-pyrrolo[2,3-d]pyrimidin-4-amine (230 mg).

To a mixture of 2-chloro-N-(4-fluorophenyl)-5-iodo-7-tosyl-7H-pyrrolo[2,3-d]pyrimidin-4-amine (230 mg, 0.423 mmol), pyridine-4-boronic acid (57 mg, 0.463 mmol) and Pd(Ph3P)2Cl2 (30 mg, 0.042 mmol) in dioxane (4 mL), aq. Na2CO3 (135 mg, 1.27 mmol) (1.0 mL) was added. The mixture was stirred at 100° C. for 2 h. It was concentrated in vacuo. The residue was triturated. The solid was collected by filtration (86 mg). The filtrate was purified by HPLC to give 2-chloro-N-(4-fluorophenyl)-5-(pyridin-4-yl)-7-tosyl-7H-pyrrolo[2,3-d]pyrimidin-4-amine (31 mg).

A solution of 2-chloro-N-(4-fluorophenyl)-5-(pyridin-4-yl)-7-tosyl-7H-pyrrolo[2,3-d]pyrimidin-4-amine (31 mg, 0.062 mmol), 6-amino-1-methyl-3,4-dihydroquinolin-2(1H)-one (25 mg, 0.14 mmol) and trimethylsilyl chloride (0.100 mL, 0.790 mmol) in nBuOH (1 mL) was stirred at 135° C. for 20 h. It was concentrated in vacuo. The residue was purified by HPLC to give the titled compound. MS 480.5 (M+H); UV 204.7, 281.7, 314.3 nm.

Example 113

6-(4-Amino-5-(4-fluorophenyl)-7H-pyrrolo[2,3-d]pyrimidin-2-ylamino)-1-methyl-3,4-dihydroquinolin-2(1H)-one

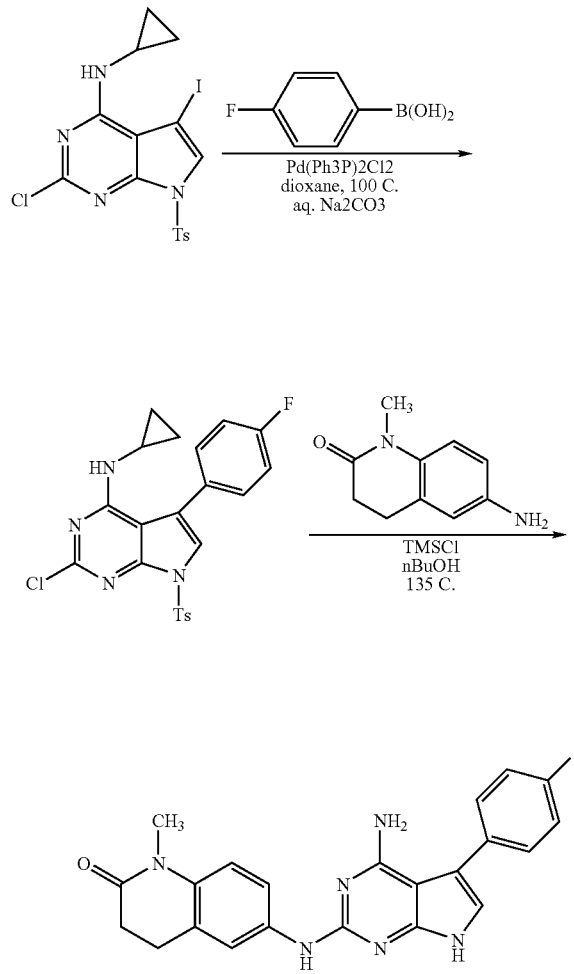

To a mixture of 2-chloro-N-cyclopropyl-5-iodo-7-tosyl-7H-pyrrolo[2,3-d]pyrimidin-4-amine (150 mg, 0.307 mmol), 4-fluorophenylboronic acid (64 mg, 0.457 mmol) and Pd(Ph3P)2Cl2 (22 mg, 0.031 mmol) in dioxane (3 mL), aq. Na2CO3 (100 mg, 0.943 mmol) (1.0 mL) was added. The mixture was stirred at 100° C. for 1 h. Water and EtOAc were added. The organic phase was separated, dried over Na2SO4, concentrated in vacuo. The residue was purified by a silica gel column, which was eluted with 5-15% EtOAc in hexane to give 2-chloro-N-cyclopropyl-5-(4-fluorophenyl)-7-tosyl-7H-pyrrolo[2,3-d]pyrimidin-4-amine (121 mg).

A solution of 2-chloro-N-cyclopropyl-5-(4-fluorophenyl)-7-tosyl-7H-pyrrolo[2,3-d]pyrimidin-4-amine (76 mg, 0.17 mmol), 6-amino-1-methyl-3,4-dihydroquinolin-2(1H)-one (60 mg, 0.34 mmol) and trimethylsilyl chloride (0.200 mL, 1.58 mmol) in nBuOH (2 mL) was stirred at 135° C. for 20 h. It was concentrated in vacuo. The residue was purified by HPLC to give the titled compound. MS 403.4 (M+H); UV 205.3, 293.4 nm.

Example 114

6-(4-(benzylamino)-5-(pyridin-4-yl)-7H-pyrrolo[2,3-d]pyrimidin-2-ylamino)-1-methyl-3,4-dihydroquinolin-2(1H)-one

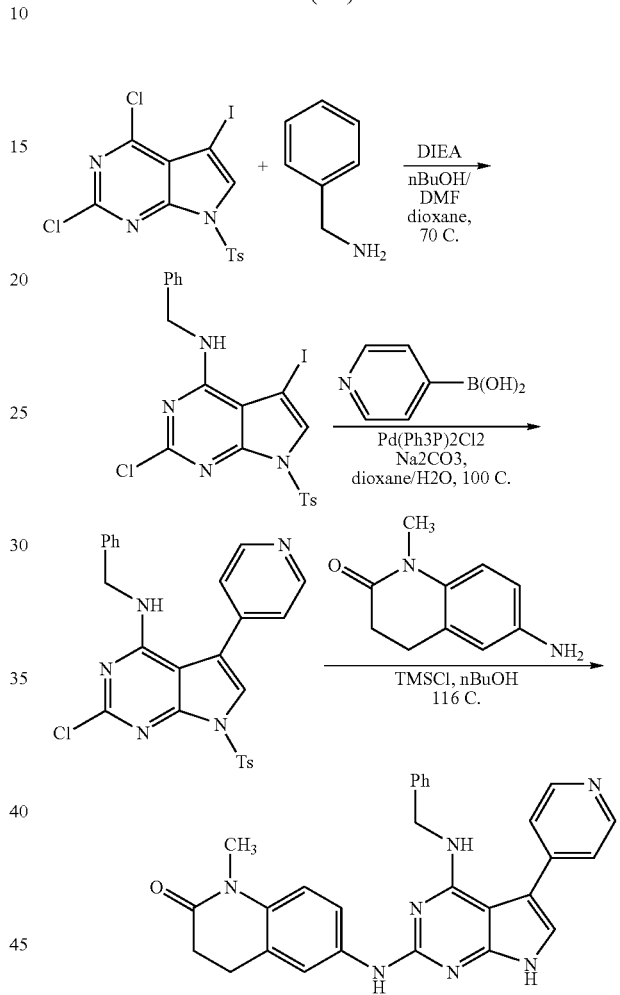

A mixture of 2,4-dichloro-5-iodo-7-tosyl-7H-pyrrolo[2,3-d]pyrimidine (1.00 g, 2.13 mmol), benzylamine (0.233 mL, 2.13 mmol) and DIEA (0.750 mL, 4.31 mmol) in dioxane (12 mL)/nBuOH (12 mL)/DMF (3 mL) was stirred at 70° C. for 2 h. It was concentrated in vacuo. The residue was partitioned between water and EtOAc. The organic phase was separated, washed with 1N HCl, then with 5% NaHCO3, dried over Na2SO4, concentrated in vacuo to give N-benzyl-2-chloro-5-iodo-7-tosyl-7H-pyrrolo[2,3-d]pyrimidin-4-amine (0.993 g).

To a mixture of N-benzyl-2-chloro-5-iodo-7-tosyl-7H-pyrrolo[2,3-d]pyrimidin-4-amine (300 mg, 0.557 mmol), pyridine-4-boronic acid (137 mg, 1.111 mmol) and Pd(Ph3P)2Cl2 (40 mg, 0.042 mmol) in dioxane (3 mL), aq. Na2CO3 (120 mg, 1.13 mmol) (1.0 mL) was added. The mixture was stirred at 100° C. for 4 h. It was concentrated in vacuo. The residue was purified by HPLC to give N-benzyl-2-chloro-5-(pyridin-4-yl)-7-tosyl-7H-pyrrolo[2,3-d]pyrimidin-4-amine (27 mg).

A solution of N-benzyl-2-chloro-5-(pyridin-4-yl)-7-tosyl-7H-pyrrolo[2,3-d]pyrimidin-4-amine (27 mg, 0.055 mmol), 6-amino-1-methyl-3,4-dihydroquinolin-2(1H)-one (20 mg, 0.11 mmol) and trimethylsilyl chloride (0.070 mL, 0.553 mmol) in nBuOH (1.5 mL) was stirred at 116° C. for 20 h. More trimethylsilyl chloride (0.100 mL, 0.790 mmol) was added. It was stirred at 116° C. for another 40 h. It was concentrated in vacuo. The residue was purified by HPLC to give the titled compound. MS 476.4 (M+H); UV 200.3, 268.7, 309.3 nm.

Example 115

4-(Benzylamino)-2-(1-methyl-2-oxo-1,2,3,4-tetrahydroquinolin-6-ylamino)-7H-pyrrolo[2,3-d]pyrimidine-5-carbonitrile

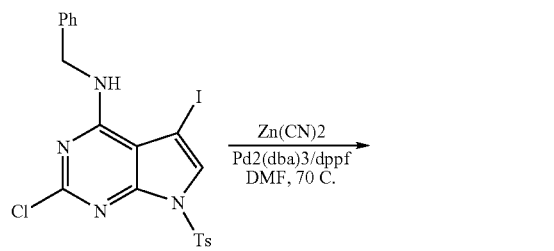

A solution of N-benzyl-2-chloro-5-iodo-7-tosyl-7H-pyrrolo[2,3-d]pyrimidin-4-amine (386 mg, 0.716 mmol), Pd2 dba3 (40 mg, 0.043 mmol) and dppf (80 mg, 0.14 mmol) in DMF (6 mL) was degassed with argon before being charged with Zn(CN)₂ (100 mg, 0.555 mmol). The mixture was stirred at 70° C. for 20 h. DMF was removed in vacuo. The residue was purified by HPLC to give 4-(benzylamino)-2-chloro-7-tosyl-7H-pyrrolo[2,3-d]pyrimidine-5-carbonitrile (54 mg).

A solution of 4-(benzylamino)-2-chloro-7-tosyl-7H-pyrrolo[2,3-d]pyrimidine-5-carbonitrile (54 mg, 0.12 mmol), 6-amino-1-methyl-3,4-dihydroquinolin-2(1H)-one (43 mg, 0.24 mmol) and trimethylsilyl chloride (0.200 mL, 1.58 mmol) in nBuOH (2.5 mL) and dioxane (1.5 mL) was stirred at 116° C. for 20 h. It was concentrated in vacuo. The residue was purified by HPLC to give the titled compound. MS 424.3 (M+H); UV 207.7, 273.1 nm.

Example 116

Butyl 1-(2-(4-(4-acetylpiperazin-1-yl)phenylamino)-9H-purin-6-yl)piperidine-3-carboxylate

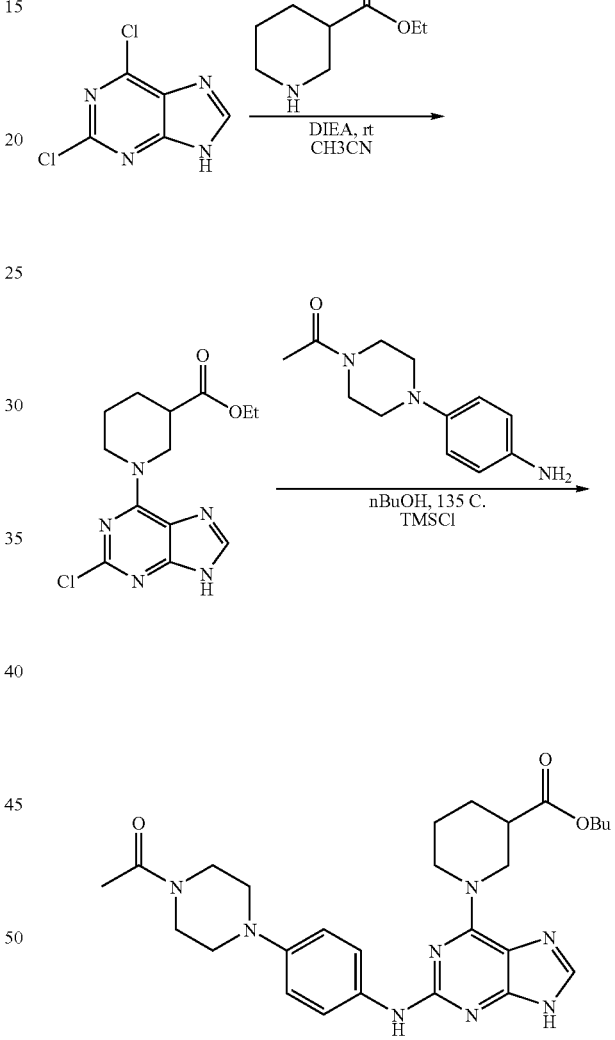

A solution of 2,6-dichloropurine (189 mg, 1.00 mmol), ethyl nipecotate (0.155 mL, 1.00 mmol) and DIEA (0.300 mL, 1.72 mmol) in CH₃CN (5 mL) was stirred at room temperature for 20 h, during which time white solids precipitated out, which was collected to give ethyl 1-(2-chloro-9H-purin-6-yl)piperidine-3-carboxylate (108 mg).

A mixture of ethyl 1-(2-chloro-9H-purin-6-yl)piperidine-3-carboxylate (108 mg, 0.349 mmol), 1-(4-(4-aminophenyl)piperazin-1-yl)ethanone (115 mg, 0.525 mmol) and trimethylsilyl chloride (0.300 mL, 2.37 mmol) in nBuOH (4 mL) was stirred at 135° C. for 20 h. It was concentrated in vacuo. The residue was purified by HPLC to give the titled compound (86 mg). MS 521.4 (M+H); UV 201.8, 272.8 nm.

Example 117

1-(2-(4-(4-acetylpiperazin-1-yl)phenylamino)-9H-purin-6-yl)piperidine-3-carboxylic acid and 1-(2-(4-(piperazin-1-yl)phenylamino)-9H-purin-6-yl)piperidine-3-carboxylic acid

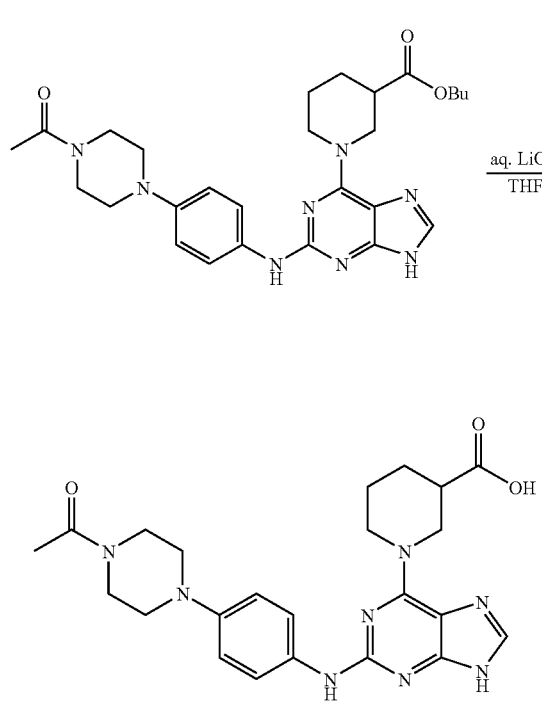

To a solution of butyl 1-(2-(4-(4-acetylpiperazin-1-yl)phenylamino)-9H-purin-6-yl)piperidine-3-carboxylate (76 mg, 0.15 mmol) in THF (2 mL), aq. 1N LiOH (1.00 mL, 1.00 mmol) was added. The mixture was stirred at room temperature for 68 h. HOAc (1 mL) was added to neutralize LiOH. The mixture was then purified by HPLC to give 1-(2-(4-(4-acetylpiperazin-1-yl)phenylamino)-9H-purin-6-yl)piperidine-3-carboxylic acid (45 mg), MS 465.3 (M+H); UV 205.8, 272.8 nm; and 1-(2-(4-(piperazin-1-yl)phenylamino)-9H-purin-6-yl)piperidine-3-carboxylic acid (8 mg), MS 423.3 (M+H).

Example 118

1-(2-(4-(4-acetylpiperazin-1-yl)phenylamino)-9H-purin-6-yl)piperidine-3-carboxamide

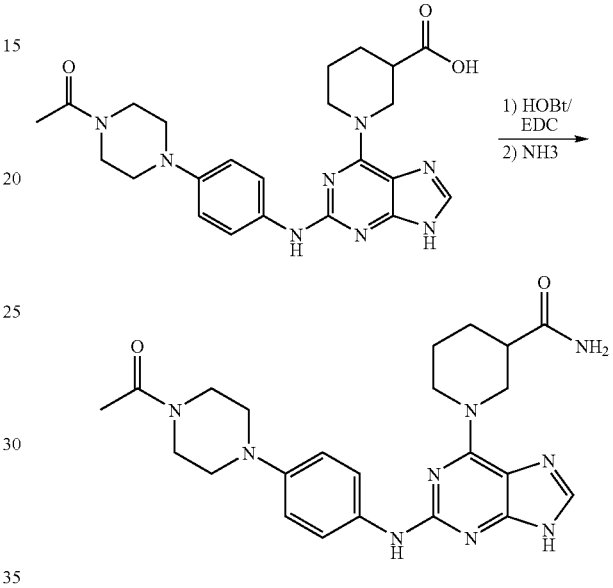

To a solution of 1-(2-(4-(4-acetylpiperazin-1-yl)phenylamino)-9H-purin-6-yl)piperidine-3-carboxylic acid (40 mg, 0.086 mmol) and HOBt (30 mg, 0.196 mmol) in DMF (2 mL), EDC (35 mg, 0.183 mmol) was added. After being stirred for 90 min, NH3 (0.5 M in dioxane, 1.00 mL, 0.500 mmol) was added. The mixture was stirred for 2 h. More EDC (52 mg, 0.271 mmol) was added. It was stirred for another 20 h. The mixture was then purified by HPLC to give the titled compound (30 mg). MS 464.3 (M+H); UV 204.8, 273.8 nm.

Example 119

Butyl 2-(1-(2-(2-oxo-1,2,3,4-tetrahydroquinolin-6-ylamino)-7H-pyrrolo[2,3-d]pyrimidin-4-yl)piperidin-4-yl)acetate

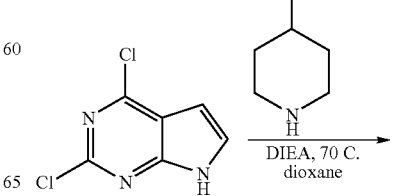

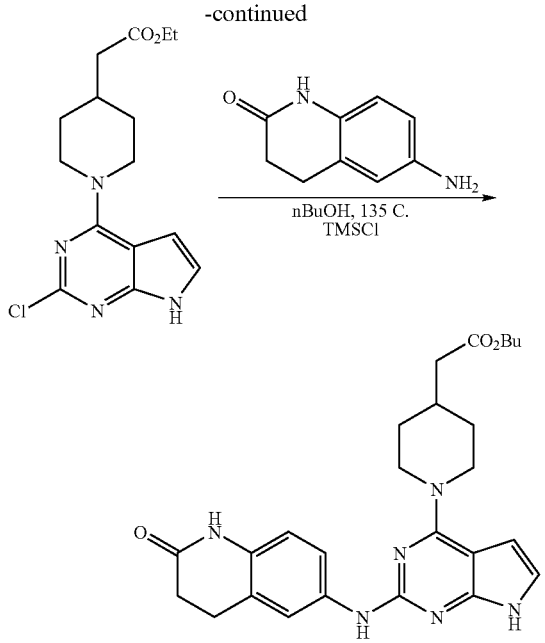

A solution of 2,4-dichloro-7H-pyrrolo[2,3-d]pyrimidine (188 mg, 1.00 mmol), 2-(4-piperidinyl)acetic acid ethyl ester (171 mg, 1.00 mmol) and DIEA (0.400 mL, 2.30 mmol) in dioxane (6 mL) was stirred at 70° C. for 20 h. Water and EtOAc were added. The organic phase was separated, washed with 1N HCl, dried over Na2SO4, concentrated in vacuo to give ethyl 2-(1-(2-chloro-7H-pyrrolo[2,3-d]pyrimidin-4-yl)piperidin-4-yl)acetate (308 mg).

A mixture of ethyl 2-(1-(2-chloro-7H-pyrrolo[2,3-d]pyrimidin-4-yl)piperidin-4-yl)acetate (135 mg, 0.419 mmol), 6-amino-3,4-dihydroquinolin-2(1H)-one (97 mg, 0.600 mmol) and trimethylsilyl chloride (0.200 mL, 1.58 mmol) in nBuOH (4 mL) was stirred at 135° C. for 20 h. More trimethylsilyl chloride (0.200 mL, 1.58 mmol) was added. It was stirred at 135° C. for another 20 h. It was concentrated in vacuo. The residue was purified by HPLC to give the titled compound (54 mg). MS 477.3 (M+H); UV 200.0, 279.8 nm.

Example 120

2-(1-(2-(2-oxo-1,2,3,4-tetrahydroquinolin-6-ylamino)-7H-pyrrolo[2,3-d]pyrimidin-4-yl)piperidin-4-yl)acetic acid

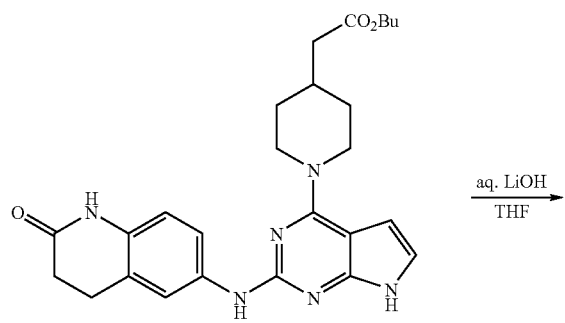

To a solution of butyl 2-(1-(2-(2-oxo-1,2,3,4-tetrahydroquinolin-6-ylamino)-7H-pyrrolo[2,3-d]pyrimidin-4-yl)piperidin-4-yl)acetate (48 mg, 0.101 mmol) in THF (2 mL), aq. 1N LiOH (1.00 mL, 1.00 mmol) was added. The mixture was stirred at room temperature for 20 h. HOAc (1 mL) was added to neutralize LiOH. It was then purified by HPLC to give the titled compound (32 mg). MS 421.3 (M+H); UV 207.8, 279.8 nm Example 121

2-(1-(2-(2-oxo-1,2,3,4-tetrahydroquinolin-6-ylamino)-7H-pyrrolo[2,3-d]pyrimidin-4-yl)piperidin-4-yl)acetamide

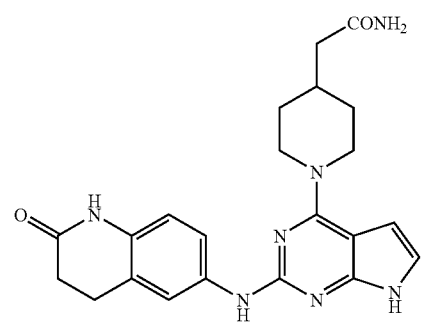

To a solution of 2-(1-(2-(2-oxo-1,2,3,4-tetrahydroquinolin-6-ylamino)-7H-pyrrolo[2,3-d]pyrimidin-4-yl)piperidin-4-yl)acetic acid (26 mg, 0.062 mmol) and HOBt (35 mg, 0.23 mmol) in DMF (2 mL), EDC (40 mg, 0.21 mmol) was added. After being stirred for 40 min, NH3 (0.5 M in dioxane, 1.00 mL, 0.500 mmol) was added. The mixture was stirred for 20 h. It was then purified by HPLC to give the titled compound (20 mg). MS 420.3 (M+H); UV 201.8, 279.8 nm.

Example 122

1-(4-(4-(4-(4-(aminomethyl)piperidin-1-yl)-5-chloropyrimidin-2-ylamino)phenyl)piperazin-1-yl)ethanone

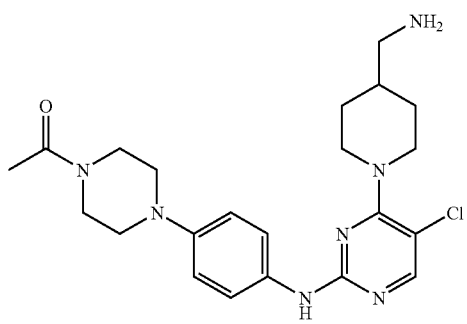

The titled compound was synthesized analogously as compound 1-(4-(4-(4-(4-(aminomethyl)piperidin-1-yl)-5-fluoropyrimidin-2-ylamino)phenyl)piperazin-1-yl)ethanone, by using 2,4,5-trichloropyrimidine. MS 444.3 and 446.3 (M+H, Cl pattern); UV 210.7, 265.7 nm.

Example 123

6-(5-fluoro-4-(3-oxopiperazin-1-yl)pyrimidin-2-ylamino)-3,4-dihydroquinolin-2(1H)-one

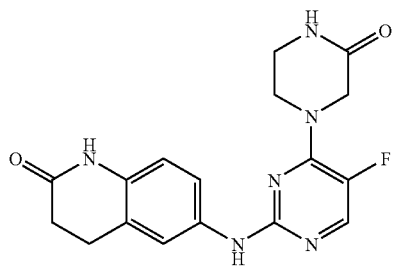

The titled compound was synthesized analogously as compound 1-(4-(4-(4-(4-(aminomethyl)piperidin-1-yl)-5-fluoropyrimidin-2-ylamino)phenyl)piperazin-1-yl)ethanone, by using piperazin-2-one. MS 414.3 (M+H); UV 214.8, 252.8 nm.

Example 124

1-(4-(4-(5-fluoro-4-(piperazin-1-yl)pyrimidin-2-ylamino)phenyl)piperazin-1-yl)ethanone

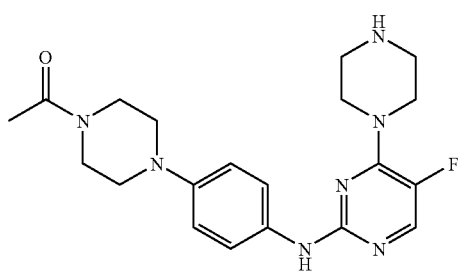

The titled compound was synthesized analogously as compound 1-(4-(4-(4-(4-(aminomethyl)piperidin-1-yl)-5-fluoropyrimidin-2-ylamino)phenyl)piperazin-1-yl)ethanone, by using 1-Boc-piperazine. MS 400.3 (M+H); UV 203.8, 268.8 nm.

Example 125

4-(2-(4-(4-acetylpiperazin-1-yl)phenylamino)-5-fluoropyrimidin-4-yl)piperazine-1-carboxamide

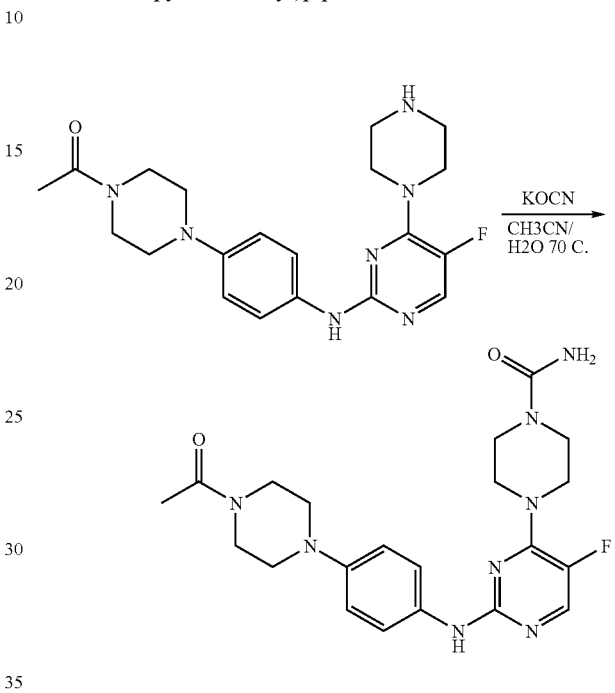

To a suspension of 1-(4-(4-(5-fluoro-4-(piperazin-1-yl)pyrimidin-2-ylamino)phenyl)piperazin-1-yl)ethanone (53 mg, 0.13 mmol) in CH$_3$CN (2 mL), a solution of KCN (60 mg, 0.74 mmol) in H$_2$O (2 mL) was added. The suspension became clear. The mixture was stirred at 70° C. for 3 h. It was then purified by HPLC to give the titled compound (15 mg). MS 443.3 (M+H); UV 201.8, 269.8 nm.

Example 126

2-(1-(2-(4-(4-acetylpiperazin-1-yl)phenylamino)-5-fluoropyrimidin-4-yl)piperidin-4-yl)acetamide

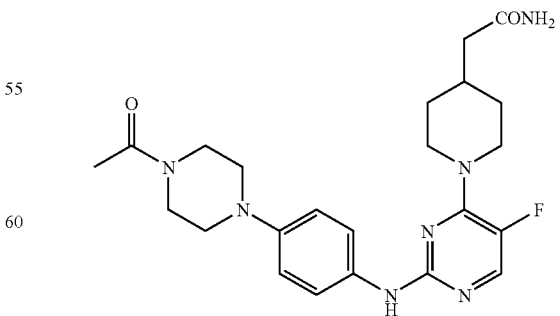

The titled compound was synthesized analogously as compound 1-(4-(4-(4-(4-(aminomethyl)piperidin-1-yl)-5-fluoropyrimidin-2-ylamino)phenyl)piperazin-1-yl)ethanone, by using 2-(piperidin-4-yl)acetamide. MS 456.3 (M+H); UV 203.8, 269.8 nm.

Example 127

Benzyl 1-(2-(4-(4-acetylpiperazin-1-yl)phenylamino)-5-fluoropyrimidin-4-yl)piperidin-4-ylcarbamate

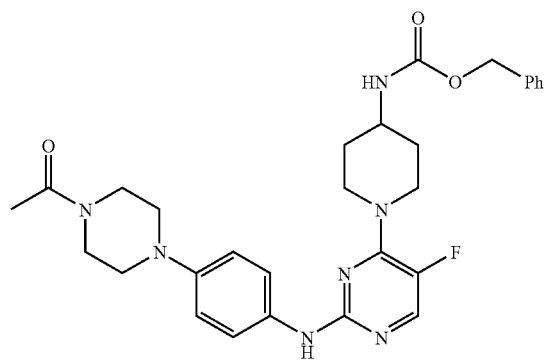

The titled compound was synthesized analogously as compound 1-(4-(4-(4-(4-(aminomethyl)piperidin-1-yl)-5-fluoropyrimidin-2-ylamino)phenyl)piperazin-1-yl)ethanone, by using benzyl piperidin-4-ylcarbamate. MS 548.4 (M+H); UV 215.8, 258.8, 279.8 nm.

Example 128

1-(4-(4-(4-(4-aminopiperidin-1-yl)-5-fluoropyrimidin-2-ylamino)phenyl)piperazin-1-yl)ethanone

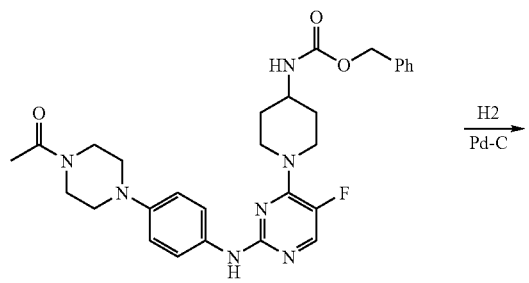

A solution of benzyl 1-(2-(4-(4-acetylpiperazin-1-yl)phenylamino)-5-fluoropyrimidin-4-yl)piperidin-4-ylcarbamate (370 mg, 0.676 mmol) and Pd—C (10%, 55 mg) in MeOH (12 mL) was hydrogenated under balloon hydrogen for 20 h. It was then filtered through celite. The filtrate was concentrated in vacuo to give the titled compound (239 mg). MS 414.3 (M+H); UV 202.8, 268.8 nm.

Example 129

1-(1-(2-(4-(4-acetylpiperazin-1-yl)phenylamino)-5-fluoropyrimidin-4-yl)piperidin-4-yl)urea

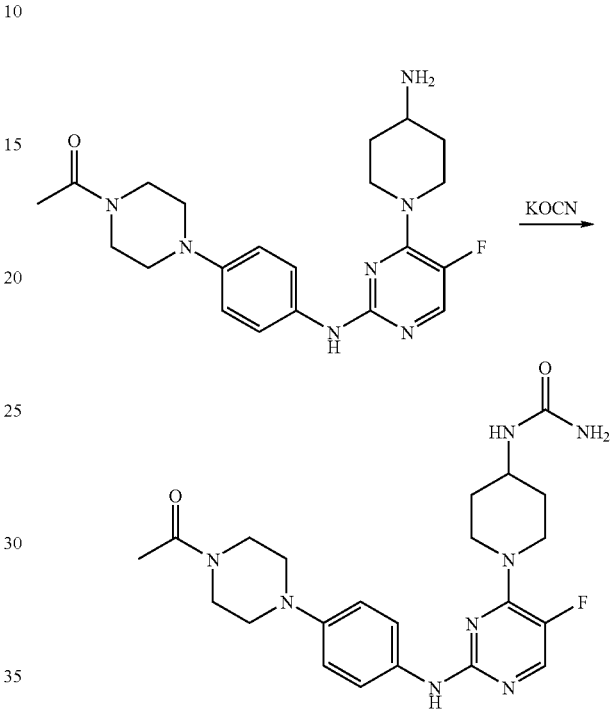

To a suspension of 1-(4-(4-(4-(4-aminopiperidin-1-yl)-5-fluoropyrimidin-2-ylamino)phenyl)piperazin-1-yl)ethanone (48 mg, 0.12 mmol) in $CH_3CN$ (2 mL), a solution of KCN (60 mg, 0.74 mmol) in $H_2O$ (2 mL) was added. The suspension became clear. The mixture was stirred at 70° C. for 2 h. It was then purified by HPLC to give the titled compound (12 mg). MS 457.3 (M+H); UV 204.8, 266.8 nm.

Example 130

2-(4-(4-acetylpiperazin-1-yl)phenylamino)-4-(4-(ureidomethyl)piperidin-1-yl)pyrimidine-5-carboxamide

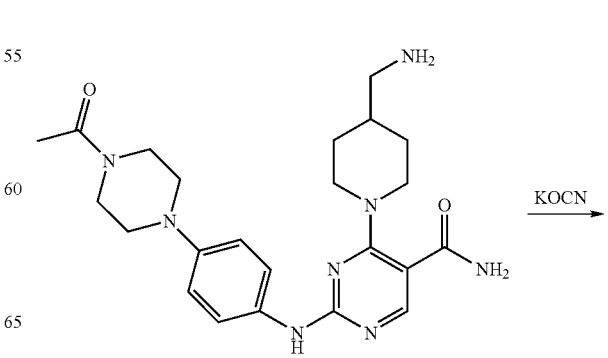

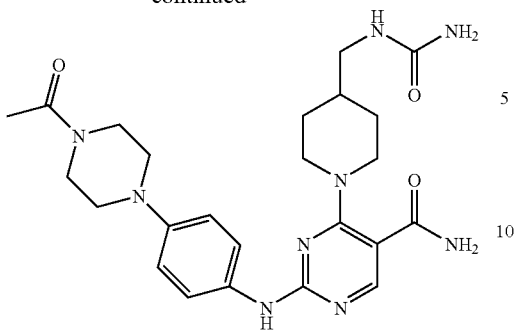

To a suspension of 2-(4-(4-acetylpiperazin-1-yl)phenylamino)-4-(4-(aminomethyl)piperidin-1-yl)pyrimidine-5-carboxamide (8 mg, 0.018 mmol) in CH$_3$CN (1 mL), a solution of KCN (18 mg, 0.22 mmol) in H$_2$O (1 mL) was added. The mixture was stirred at 70° C. for 20 h. It was then purified by HPLC to give the titled compound (6 mg). MS 496.5 (M+H); UV 200.8, 271.8 nm.

Example 131

4-(4-(4-(aminomethyl)piperidin-1-yl)-5-fluoropyrimidin-2-ylamino)benzoic acid

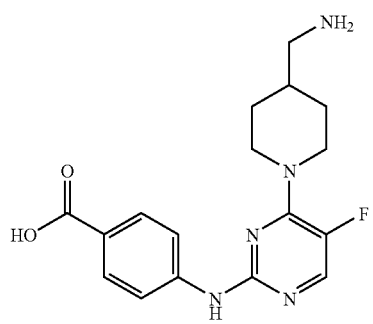

The titled compound was synthesized analogously as compound 1-(4-(4-(4-(aminomethyl)piperidin-1-yl)-5-fluoropyrimidin-2-ylamino)phenyl)piperazin-1-yl)ethanone, by using 4-aminobenzoic acid. MS 346.2 (M+H); UV 215.8, 275.8, 292.8 nm.

Example 132

6-(4-(4-(aminomethyl)piperidin-1-yl)-5-bromopyrimidin-2-ylamino)-3,4-dihydroquinolin-2(1H)-one

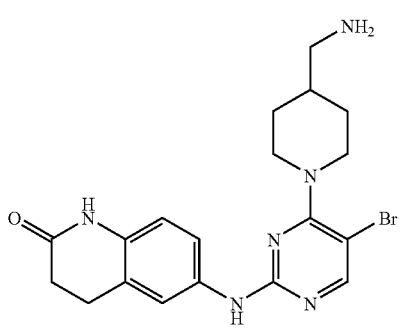

The titled compound was synthesized analogously as compound 6-(4-(4-(aminomethyl)piperidin-1-yl)-5-fluoropyrimidin-2-ylamino)-3,4-dihydroquinolin-2(1H)-one, by using 5-bromo-2,4-dichloropyrimidine. MS 431.4 and 433.3 (M+N, Br pattern); UV 222.3, 263.9 nm.

Example 133

4-(4-(4-((dimethylamino)methyl)piperidin-1-yl)-5-fluoropyrimidin-2-ylamino)benzamide

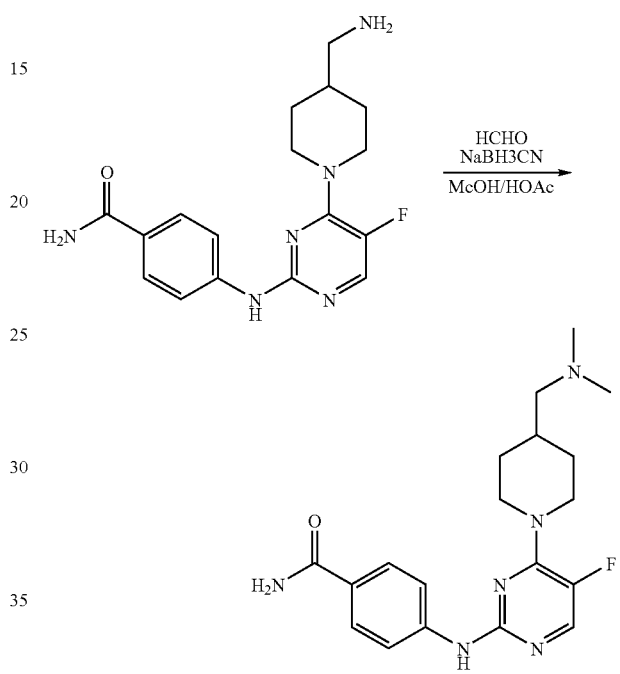

To a mixture of 4-(4-(4-(aminomethyl)piperidin-1-yl)-5-fluoropyrimidin-2-ylamino)benzamide (100 mg, 0.291 mmol) and HCHO (37% aq., 0.060 mL, 0.807 mmol) in MeOH (3 mL) and HOAc (0.3 mL), NaBH3CN (60 mg, 0.952 mmol) was added. The mixture was stirred at room temperature for 20 h. It was concentrated in vacuo. The residue was purified by HPLC to give the titled compound (20 mg). MS 373.3 (M+H); UV 213.8, 269.8, 292.8 nm.

Example 134

Ethyl 3-amino-3-(1-(5-fluoro-2-(2-oxo-1,2,3,4-tetrahydroquinolin-6-ylamino)pyrimidin-4-yl)piperidin-4-yl)propanoate

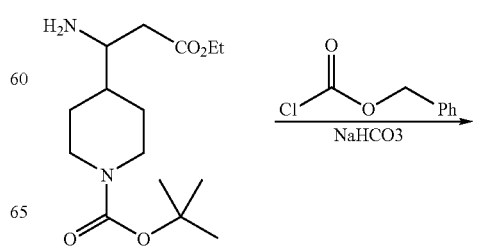

177

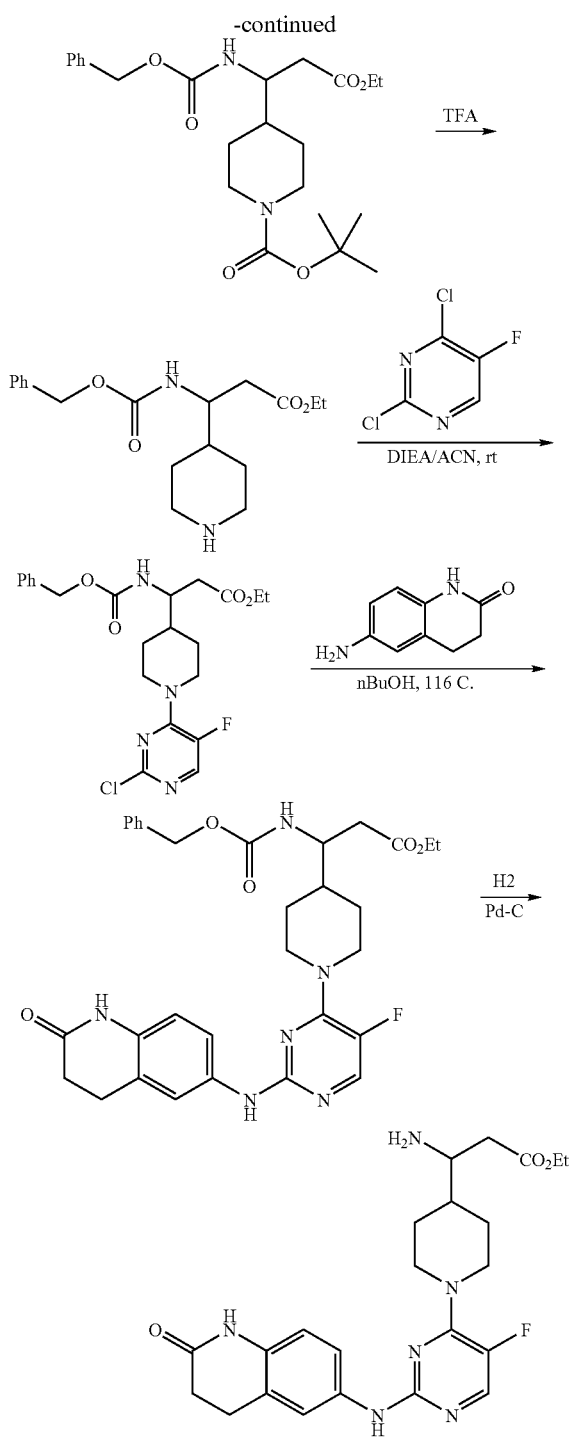

To a suspension of ethyl 3-(1-Boc-piperidine-4-yl)-beta-DL-alaninate hydrochloride (518 mg, 1.54 mmol) in CH$_2$Cl$_2$ (10 mL), a solution of NaHCO3 (1.00 g, 1.20 mmol) in H$_2$O (15 mL) was added. Benzyl chloroformate (0.246 mL, 95%, 1.66 mmol) was then added. The mixture was stirred at room temperature for 20 h. The CH$_2$Cl$_2$ layer was separated, dried over Na2SO4, concentrated in vacuo to give tert-butyl 4-(1-(benzyloxycarbonylamino)-3-ethoxy-3-oxopropyl)piperidine-1-carboxylate (660 mg).

To a solution of tert-butyl 4-(1-(benzyloxycarbonylamino)-3-ethoxy-3-oxopropyl)piperidine-1-carboxylate (660 mg, 1.52 mmol) in CH$_2$Cl$_2$ (5 mL), TFA (5 mL) was

178 added. The mixture was stirred at room temperature for 3 h. It was concentrated in vacuo. The residue was purified by HPLC to give ethyl 3-(benzyloxycarbonylamino)-3-(piperidin-4-yl)propanoate as TFA salt. The salt was dissolved in EtOAc (50 mL), which was washed with 5% NaHCO3, dried over Na2SO4, concentrated in vacuo to give ethyl 3-(benzyloxycarbonylamino)-3-(piperidin-4-yl)propanoate as free base (102 mg).

To a solution of ethyl 3-(benzyloxycarbonylamino)-3-(piperidin-4-yl)propanoate (102 mg, 0.305 mmol) and 2,4-dichloro-5-fluoropyrimidine (51 mg, 0.305 mmol) in CH$_3$CN (2 mL), DIEA (0.106 mL, 0.610 mmol) was added. The mixture was stirred at room temperature for 68 h. It was then concentrated in vacuo. The residue was dissolved in nBuOH (3 mL), 6-amino-3,4-dihydroquinolin-2(1H)-one (82 mg, 0.506 mmol) was added. The solution was stirred at 116° C. for 20 h. It was concentrated in vacuo. The residue was dissolved in MeOH (9 mL). To the solution, Pd—C (10%, 40 mg) was added. The mixture was then hydrogenated under balloon hydrogen for 20 h. It was filtered through celite. The filtrate was concentrated in vacuo. The residue was purified by HPLC to give the titled compound (66 mg). MS 457.4 (M+H); UV 211.9, 277.3 nm.

Example 135

Methyl 2-amino-2-(1-(5-fluoro-2-(2-oxo-1,2,3,4-tetrahydroquinolin-6-ylamino)pyrimidin-4-yl)piperidin-4-yl)acetate

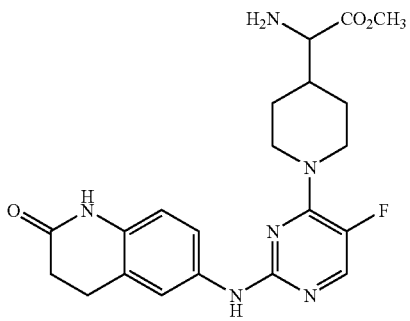

The titled compound was synthesized analogously as compound 6-(4-(4-(aminomethyl)piperidin-1-yl)-5-fluoropyrimidin-2-ylamino)-3,4-dihydroquinolin-2(1H)-one, by using methyl 2-(tert-butoxycarbonylamino)-2-(piperidin-4-yl)acetate. MS 429.3 (M+H); UV 207.0, 274.2 nm Example 136

N-(1-(2-(4-(4-acetylpiperazin-1-yl)phenylamino)-5-fluoropyrimidin-4-yl)piperidin-4-yl)-2-cyanoacetamide

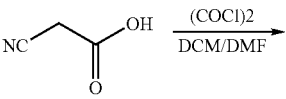

-continued

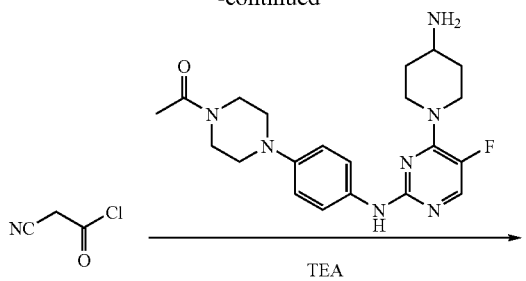
TEA

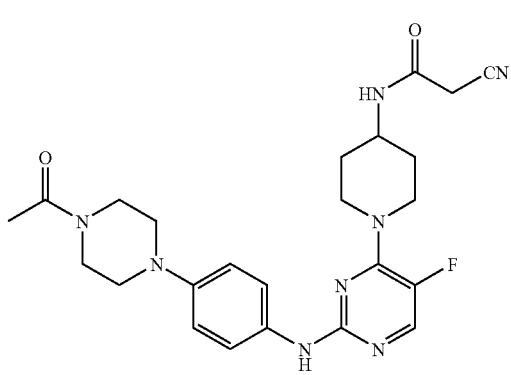

To a suspension of cyanoacetic acid (85 mg, 1.00 mmol) in CH$_2$Cl$_2$ (2 mL) (containing 2 drops of DMF) at room temperature, oxalyl chloride (0.082 mL, 0.94 mmol) was added. Gas evolved and suspension became clear. It was then stirred for 30 min. To the above solution cooled in an ice bath, a solution of 1-(4-(4-(4-(4-aminopiperidin-1-yl)-5-fluoropyrimidin-2-ylamino)phenyl)piperazin-1-yl)ethanone (70 mg, 0.17 mmol) and TEA (0.478 mL, 3.43 mmol) in DMF (2 mL) was added drop wise. The mixture was then stirred at room temperature for 3 h. It was concentrated in vacuo. The residue was purified by HPLC to give the titled compound (12 mg). MS 481.5 (M+H); UV 204.7, 266.3 nm Example 137

3-(4-(2-(4-(4-acetylpiperazin-1-yl)phenylamino)-5-fluoropyrimidin-4-yl)piperazin-1-yl)-3-oxopropanenitrile

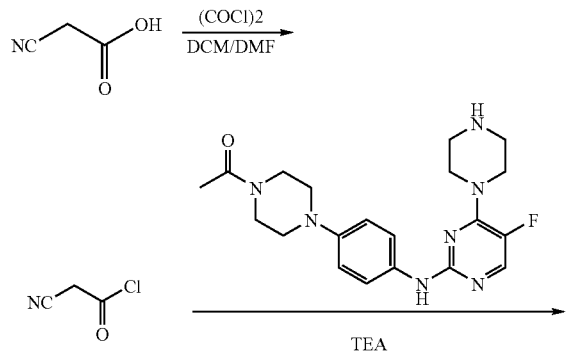
TEA

-continued

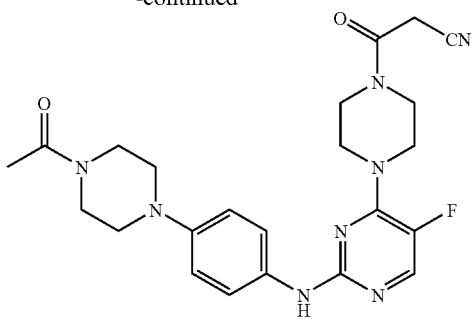

To a suspension of cyanoacetic acid (85 mg, 1.00 mmol) in CH$_2$Cl$_2$ (2 mL) (containing 2 drops of DMF) at room temperature, oxalyl chloride (0.082 mL, 0.94 mmol) was added. Gas evolved and suspension became clear. It was then stirred for 50 min. To the above solution cooled in an ice bath, a solution of 1-(4-(4-(5-fluoro-4-(piperazin-1-yl)pyrimidin-2-ylamino)phenyl)piperazin-1-yl)ethanone (23 mg, 0.057 mmol) and TEA (0.400 mL, 2.87 mmol) in DMF (1 mL) was added drop wise. The mixture was then stirred at room temperature for 90 min. It was concentrated in vacuo. The residue was purified by HPLC to give the titled compound (17 mg). MS 467.5 (M+H); UV 201.0, 269.4 nm Example 138

6-(4-(4-(aminomethyl)piperidin-1-yl)-5-(pyridin-4-yl)pyrimidin-2-ylamino)-3,4-dihydroquinolin-2(1H)-one

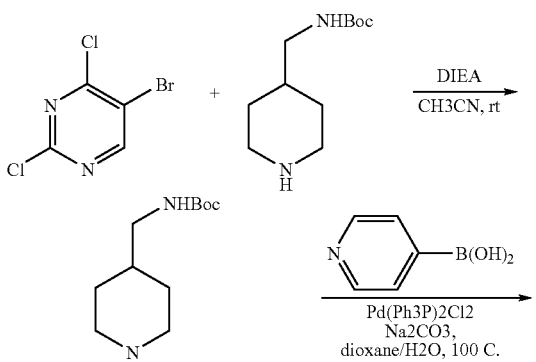

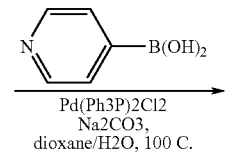

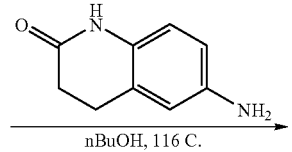
nBuOH, 116 C.

-continued

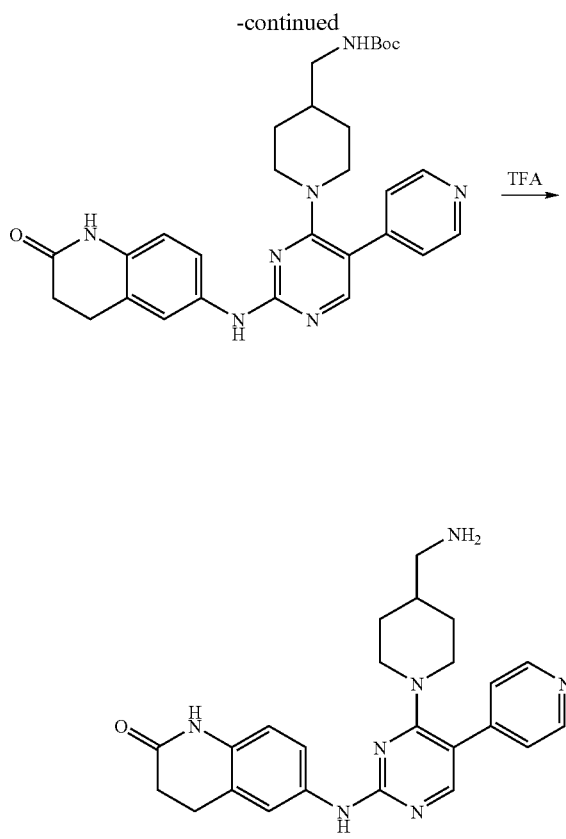

To a mixture of 5-bromo-2,4-dichloropyrimidine (0.256 mL, 2.00 mmol) and 4-N-Boc-aminomethylpiperidine (428 mg, 2.00 mmol) in CH₃CN (5 mL), DIEA (0.700 mL, 4.02 mmol) was added. The mixture was stirred at room temperature for 40 h. Water and EtOAc were added. The organic phase was separated, washed with 1N HCl, then with 5% NaHCO3, dried over Na2SO4, concentrated in vacuo to give tert-butyl (1-(5-bromo-2-chloropyrimidin-4-yl)piperidin-4-yl)methylcarbamate (610 mg).

To a mixture of tert-butyl (1-(5-bromo-2-chloropyrimidin-4-yl)piperidin-4-yl)methylcarbamate (229 mg, 0.564 mmol), pyridine-4-boronic acid (76 mg, 0.618 mmol) and Pd(Ph₃P)₂Cl₂ (40 mg, 0.056 mmol) in dioxane (3 mL), aq. Na₂CO₃ (180 mg, 1.69 mmol) (1.0 mL) was added. The mixture was stirred at 100° C. for 20 h. It was concentrated in vacuo. The residue was purified by HPLC to give tert-butyl (1-(2-chloro-5-(pyridin-4-yl)pyrimidin-4-yl)piperidin-4-yl)methylcarbamate (80 mg).

A solution of tert-butyl (1-(2-chloro-5-(pyridin-4-yl)pyrimidin-4-yl)piperidin-4-yl)methylcarbamate (80 mg, 0.20 mmol) and 6-amino-3,4-dihydroquinolin-2(1H)-one (50 mg, 0.30 mmol) in nBuOH (3 mL) was stirred at 116° C. for 20 h. It was concentrated in vacuo. The residue was dissolved in TFA (4 mL). After being stirred at room temperature for 30 min, TFA was removed in vacuo. The residue was purified by HPLC to give the titled compound. MS 430.4 (M+H); UV 207.7, 264.5 nm.

Example 139

6-(4-(4-(aminomethyl)piperidin-1-yl)-5-cyclopropylpyrimidin-2-ylamino)-3,4-dihydroquinolin-2(1H)-one

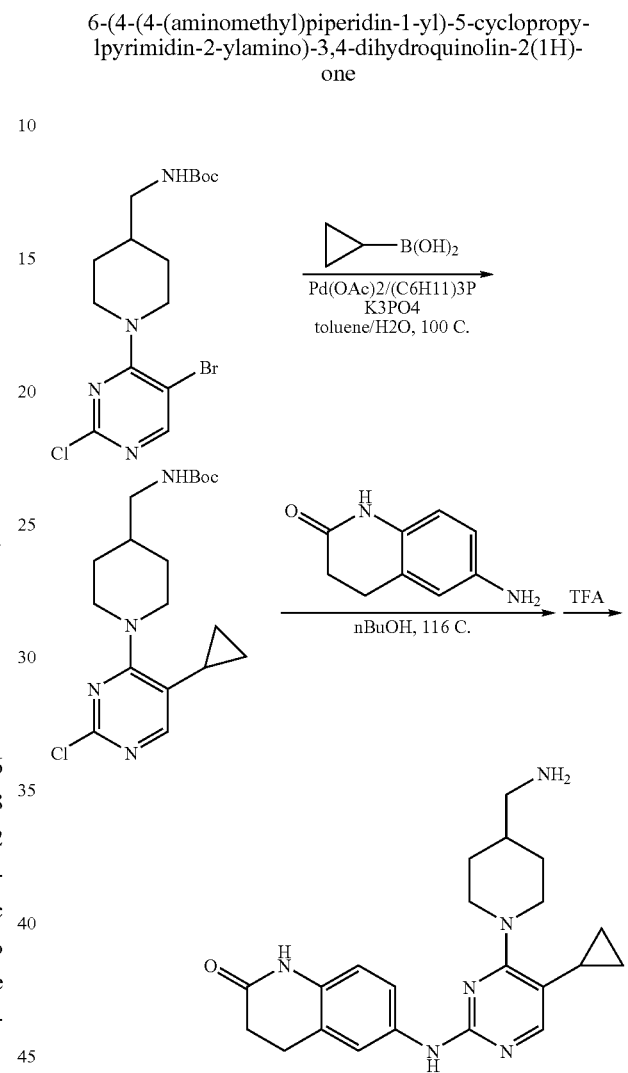

A mixture of tert-butyl (1-(5-bromo-2-chloropyrimidin-4-yl)piperidin-4-yl)methylcarbamate (112 mg, 0.276 mmol), cyclopropylboronic acid (40 mg, 0.465 mmol), K3PO4 (200 mg, 0.943 mmol) and tricyclohexyl phosphine (20 mg, 0.071 mmol) in toluene (3 mL) and H₂O (0.2 mL) was degassed with argon, then Pd(OAc)₂ (10 mg, 0.044 mmol) was added. The mixture was stirred at 100° C. for 20 h. Water and EtOAc were added. The organic phase was separated, washed with brine, dried over Na2SO4, concentrated in vacuo to give tert-butyl (1-(2-chloro-5-cyclopropylpyrimidin-4-yl)piperidin-4-yl)methycarbamate (130 mg).

A solution of tert-butyl (1-(2-chloro-5-cyclopropylpyrimidin-4-yl)piperidin-4-yl)methylcarbamate (99 mg, 0.27 mmol) and 6-amino-3,4-dihydroquinolin-2(1H)-one (50 mg, 0.30 mmol) in nBuOH (3 mL) was stirred at 116° C. for 20 h. It was then stirred at 140° C. for another 20 h. It was concentrated in vacuo. The residue was purified by HPLC to give a powder, which was then dissolved in TFA (3 mL). After being stirred at room temperature for 20 h, TFA was removed in vacuo. The residue was purified by HPLC to give the titled compound (16 mg). MS 393.5 (M+H); UV 208.9, 264.5 nm

Example 140
6-(4-((1s,4s)-4-aminocyclohexylamino)-5-fluoropyrimidin-2-ylamino)-3,4-dihydroquinolin-2(1H)-one
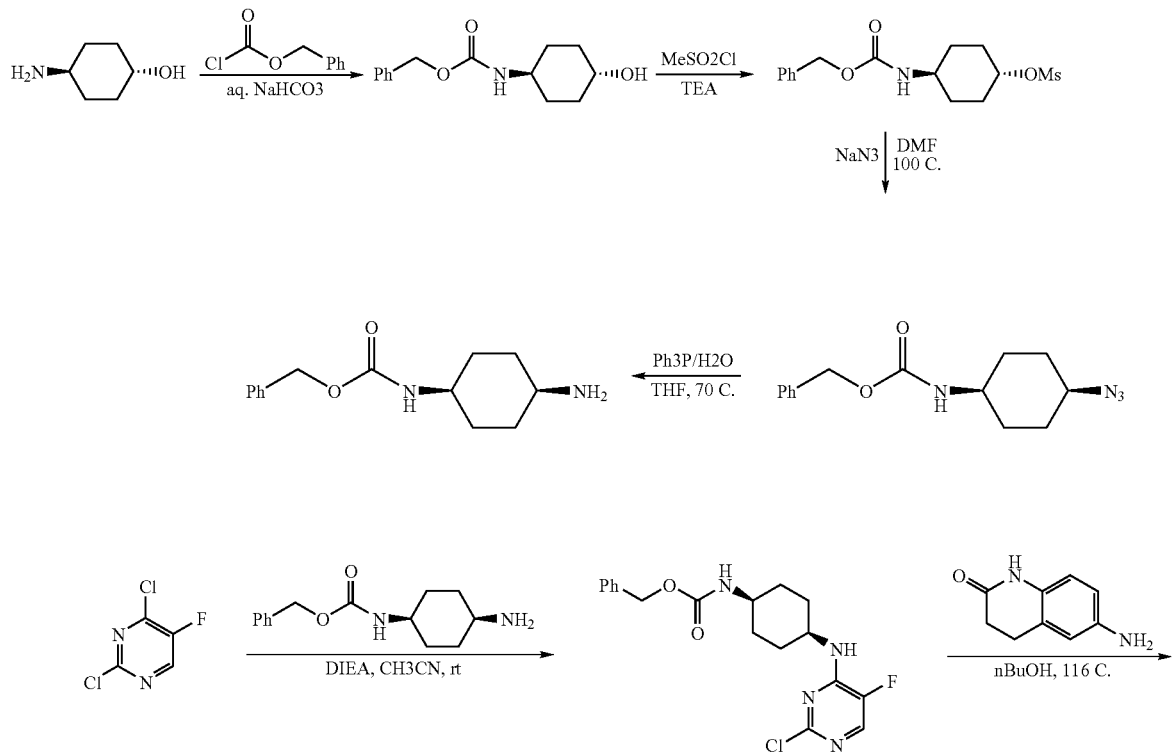
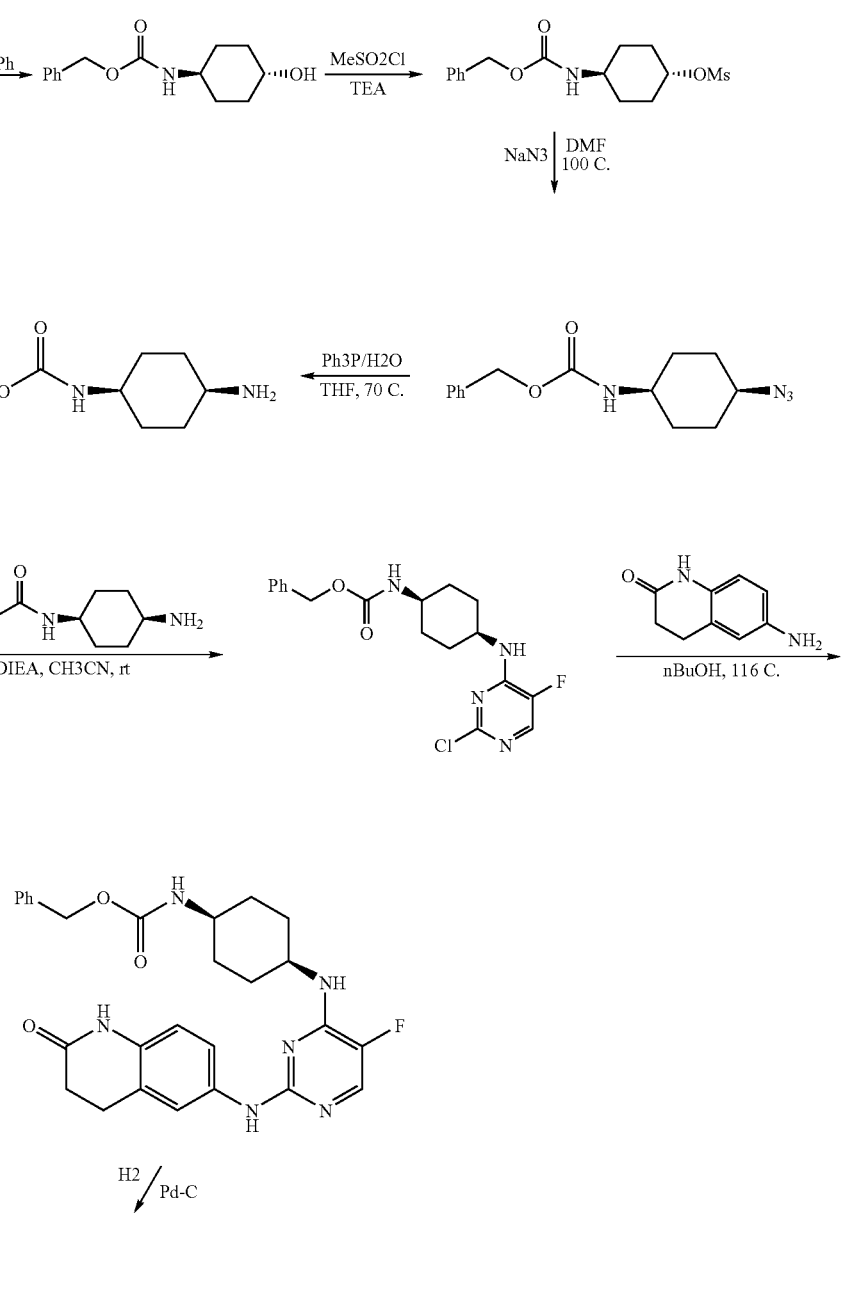
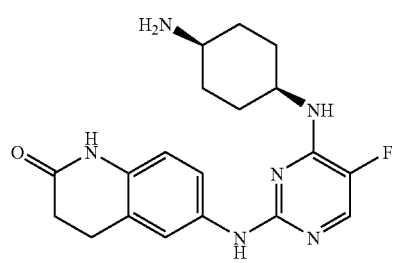

To a mixture of trans-4-aminocyclohexanol (2.07 g, 13.6 mmol) and NaHCO3 (3.50 g, 41.7 mmol) in H₂O (20 mL) at room temperature, a solution of benzyl chloroformate (1.92 mL, 13.6 mmol) in dioxane (15 mL) was added. The mixture was stirred at room temperature for 20 h. The white precipitate was collected as benzyl (1R,4R)-4-hydroxycyclohexylcarbamate (3.37 g).

To a suspension of benzyl (1R,4R)-4-hydroxycyclohexylcarbamate (1.14 g, 4.58 mmol) and triethylamine (1.30 mL, 9.34 mmol) in CH₂Cl₂ (15 mL) at room temperature, methanesulfonyl chloride (0.425 mL, 5.49 mmol) was added. The mixture was stirred at room temperature for 20 h. More methanesulfonyl chloride (0.425 mL, 5.49 mmol) and triethylamine (1.00 mL) were added. Stirring was continued for 48 h. The reaction solution was washed with 5% NaHCO₃, then with 1 N HCl. The organic phase was separated, dried over Na₂SO₄, concentrated in vacuo to give (1R,4R)-4-(benzyloxycarbonyl)cyclohexyl methanesulfonate as a solid (1.13 g).

A mixture of (1R,4R)-4-(benzyloxycarbonyl)cyclohexyl methanesulfonate (1.13 g, 3.46 mmol) and NaN₃ (0.674 g, 10.4 mmol) in DMF (10 mL) was stirred at 100° C. for 20 h. Water and EtOAc were added. The organic phase was separated, washed with water, dried over Na₂SO₄, concentrated in vacuo to give benzyl (1s,4s)-4-azidocyclohexylcarbamate (0.819 g).

To a solution of benzyl (1s,4s)-4-azidocyclohexylcarbamate (0.410 g, 1.50 mmol) in THF (8 mL) and H₂O (0.100 mL, 5.56 mmol) at room temperature, Ph₃P (0.590 g, 2.25 mmol) was added. The solution was stirred at 70° C. for 20 h. EtOAc and 1N HCl were added. The aqueous phase was separated, washed with EtOAc. It was then basified with 5N NaOH to pH 12. The free amine product was extracted with EtOAc. The EtOAc solution was dried over Na₂SO₄, and concentrated in vacuo to give benzyl (1s,4s)-4-aminocyclohexylcarbamate (0.270 g).

To a mixture of 2,4-dichloro-5-fluoropyrimidine (226 mg, 1.35 mmol) and benzyl (1s,4s)-4-aminocyclohexylcarbamate (335 mg, 1.35 mmol) in CH₃CN (6 mL), DIEA (0.600 mL, 3.45 mmol) was added. The mixture was stirred at room temperature for 20 h. Water and EtOAc were added. The organic phase was separated, washed with 1N HCl, dried over Na₂SO₄, concentrated in vacuo to give benzyl (1s,4s)-4-(2-chloro-5-fluoropyrimidin-4-ylamino)cyclohexylcarbamate (511 mg).

A solution of benzyl (1s,4s)-4-(2-chloro-5-fluoropyrimidin-4-ylamino)cyclohexylcarbamate (170 mg, 0.450 mmol) and 6-amino-3,4-dihydroquinolin-2(1H)-one (109 mg, 0.670 mmol) in nBuOH (3 mL) was stirred at 116° C. for 20 h. It was concentrated in vacuo. The residue was dissolved in MeOH (4 mL). Pd—C (10%, 30 mg) was added. The mixture was then hydrogenated under balloon hydrogen for 20 h. It was filtered through celite, and the filtrate was concentrated in vacuo. The residue was purified by HPLC to give the titled compound (30 mg). MS 371.2 (M+H); UV 215.8, 263.8 nm Example 141

4-(4-((1s,4s)-4-aminocyclohexylamino)-5-fluoropyrimidin-2-ylamino)benzamide

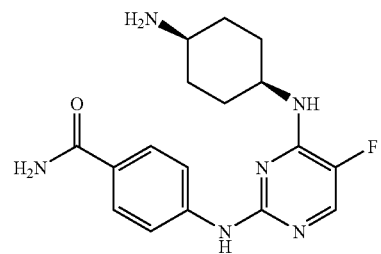

The titled compound was synthesized analogously as compound 6-(4-((1s,4s)-4-aminocyclohexylamino)-5-fluoropyrimidin-2-ylamino)-3,4-dihydroquinolin-2(1H)-one, by using 4-aminobenzamide. MS 345.3 (M+H); UV 212.8, 277.8 nm Example 142

1-(4-(4-(4-((1s,4s)-4-aminocyclohexylamino)-5-fluoropyrimidin-2-ylamino)phenyl)piperazin-1-yl)ethanone

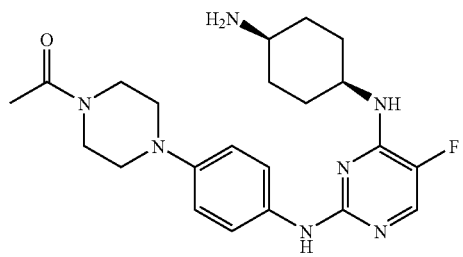

The titled compound was synthesized analogously as compound 6-(4-((1s,4s)-4-aminocyclohexylamino)-5-fluoropyrimidin-2-ylamino)-3,4-dihydroquinolin-2(1H)-one, by using 1-(4-(4-aminophenyl)piperazin-1-yl)ethanone. MS 428.3 (M+H); UV 215.8, 252.8 nm Example 143

6-(4-((1s,4s)-4-aminocyclohexylamino)-5-(pyridin-4-yl)pyrimidin-2-ylamino)-3,4-dihydroquinolin-2(1H)-one

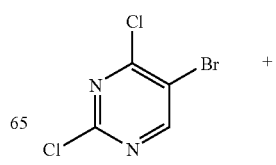 +

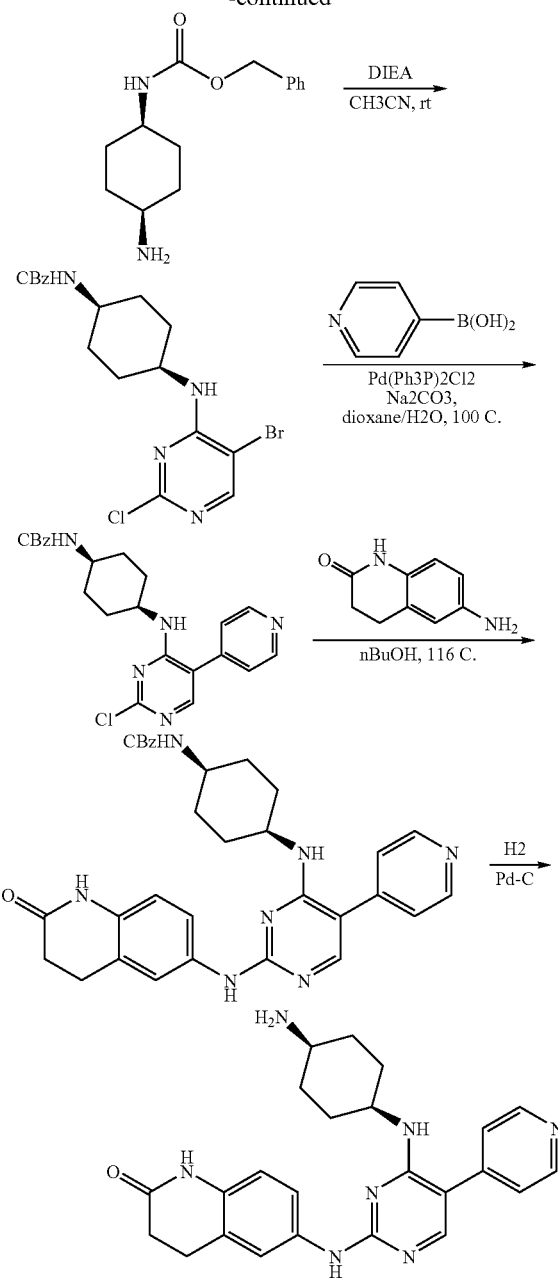

To a mixture of 2,4-dichloro-5-bromopyrimidine (244 mg, 1.07 mmol) and benzyl (1s,4s)-4-aminocyclohexylcarbamate (266 mg, 1.07 mmol) in $CH_3CN$ (5 mL), DIEA (0.373 mL, 2.14 mmol) was added. The mixture was stirred at room temperature for 20 h. Water and EtOAc were added. The organic phase was separated, washed with 1N HCl, then with 5% $NaHCO_3$, dried over $Na_2SO_4$, concentrated in vacuo to give benzyl (1s,4s)-4-(5-bromo-2-chloropyrimidin-4-ylamino)cyclohexylcarbamate (440 mg).

To a mixture of benzyl (1s,4s)-4-(5-bromo-2-chloropyrimidin-4-ylamino)cyclohexylcarbamate (220 mg, 0.500 mmol), pyridine-4-boronic acid (68 mg, 0.552 mmol) and $Pd(Ph_3P)_2Cl_2$ (35 mg, 0.050 mmol) in dioxane (3 mL), aq. $Na_2CO_3$ (160 mg, 1.50 mmol) (1.0 mL) was added. The mixture was stirred at 100° C. for 20 h. More pyridine-4-boronic acid (68 mg, 0.552 mmol) and $Pd(Ph_3P)_2Cl_2$ (35 mg, 0.050 mmol) were added. It was stirred at 100° C. for another 90 min. It was then concentrated in vacuo. The residue was purified by HPLC to give benzyl (1s,4s)-4-(2-chloro-5-(pyridin-4-yl)pyrimidin-4-ylamino)cyclohexylcarbamate (93 mg).

A solution of benzyl (1s,4s)-4-(2-chloro-5-(pyridin-4-yl)pyrimidin-4-ylamino)cyclohexylcarbamate (93 mg, 0.21 mmol) and 6-amino-3,4-dihydroquinolin-2(1H)-one (52 mg, 0.32 mmol) in nBuOH (4 mL) was stirred at 116° C. for 20 h. It was concentrated in vacuo. The residue was dissolved in MeOH (6 mL). Pd—C (10%, 44 mg) was added. The mixture was then hydrogenated under balloon hydrogen for 2 h. More Pd—C (10%, 26 mg) was added. It was stirred under balloon hydrogen for another 20 h. It was filtered through celite, and the filtrate was concentrated in vacuo. The residue was purified by HPLC to give the titled compound (70 mg). MS 430.4 (M+H); UV 210.1, 259.6, 324.8 nm Example 144

6-(4-((1s,4s)-4-aminocyclohexylamino)-5-cyclopropylpyrimidin-2-ylamino)-3,4-dihydroquinolin-2(1H)-one

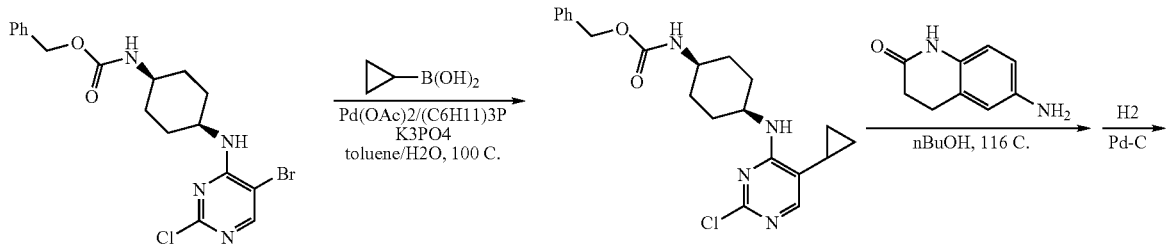

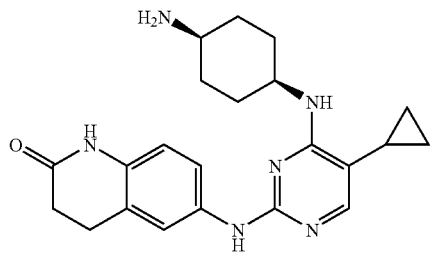

A mixture of benzyl (1s,4s)-4-(5-bromo-2-chloropyrimidin-4-ylamino)cyclohexylcarbamate (220 mg, 0.500 mmol), cyclopropylboronic acid (52 mg, 0.605 mmol), K3PO4 (310 mg, 1.46 mmol) and tricyclohexyl phosphine (25 mg, 0.089 mmol) in toluene (3 mL) and H$_2$O (0.2 mL) was degassed with argon, then Pd(OAc)$_2$ (10 mg, 0.044 mmol) was added. The mixture was stirred at 100° C. for 20 h. Water and EtOAc were added. The organic phase was separated, washed with brine, dried over Na2SO4, concentrated in vacuo to give benzyl (1s,4s)-4-(2-chloro-5-cyclopropylpyrimidin-4-ylamino)cyclohexylcarbamate (200 mg).

A solution of benzyl (1s,4s)-4-(2-chloro-5-cyclopropylpyrimidin-4-ylamino)cyclohexylcarbamate (200 mg, 0.500 mmol) and 6-amino-3,4-dihydroquinolin-2(1H)-one (105 mg, 0.648 mmol) in nBuOH (4 mL) was stirred at 116° C. for 20 h. It was concentrated in vacuo. The residue was purified by HPLC to give benzyl (1s,4s)-4-(5-cyclopropyl-2-(2-oxo-1,2,3,4-tetrahydroquinolin-6-ylamino)pyrimidin-4-ylamino)cyclohexylcarbamate (97 mg).

A mixture of benzyl (1s,4s)-4-(5-cyclopropyl-2-(2-oxo-1,2,3,4-tetrahydroquinolin-6-ylamino)pyrimidin-4-ylamino)cyclohexylcarbamate (70 mg, 0.13 mmol) and Pd—C (10%, 30 mg) in MeOH (5 mL) was hydrogenated under balloon H2 for 20 h. It was filtered through celite. The filtrate was concentrated in vacuo. The residue was purified by HPLC to give the titled compound (40 mg). MS 393.4 (M+H); UV 219.3, 260.8 nm Example 145

This example illustrates methods for evaluating the compounds of the invention, along with results obtained for such assays. The in vitro and in vivo human syk activities of the inventive compounds can be determined by various procedures known in the art, such as a test for their ability to inhibit the activity of human plasma syk. The potent affinities for human syk inhibition exhibited by the inventive compounds can be measured by an IC$_5$, value (in nM). The IC$_{50}$ value is the concentration (in nM) of the compound required to provide 50% inhibition of human syk proteolytic activity. The smaller the IC$_{50}$ value, the more active (potent) is a compound for inhibiting syk activity.

An in vitro assay for detecting and measuring inhibition activity against syk is as follows:
Inhibition of syk Tyrosine Phosphorylation Activity Potency of candidate molecules for inhibiting syk tyrosine phosphorylation activity is assessed by measuring the ability of a test compound to inhibit syk-mediated tyrosine phosphorylation of a syk-specific substrate.

SYK tyrosine phosphorylation activity is measured using the LANCE™ Technology developed by Perkin Elmer Life and Analytical Sciences (Boston, Mass.). LANCE™ refers to homogeneous time resolved fluorometry applications using techniques such as time-resolved fluorescence resonance energy transfer assay (TR-FRET) (see generally for procedures in Perkin Elmer Application Note-How to Optimize a Tyrosine Kinase Assay Using Time Resolved Fluorescence-Based LANCE Detection, wwww.perkinelmer.com/lifesciences). The assay principle involves detection of a phosphorylated substrate using energy transfer from a phosphospecific europium-labeled antibody to streptavidin-allophycocyanin as an acceptor.

To test the ability of candidate molecules to inhibit SYK tyrosine phosphorylation activity, molecules are reconstituted in 30% DMSO and serially diluted 1:3 with the final dilution containing DMSO in the absence of the candidate molecule. The final DMSO concentration in the assay is 3%. Kinase assays are performed as a two part reaction. The first reaction is a kinase reaction and which comprises of a candidate molecule, full length active recombinant SYK enzyme (Millipore, CA) and biotin-labeled SYK-specific substrate biotin-DEEDYESP-OH. The second reaction involves termination of the kinase reaction and the simultaneous addition of the detection reagents-europium-labeled anti-phosphotyrosine reagent (Eu-W1024-PY100, Perkin Elmer, Boston, Mass.) and Streptavidin-Allophycocyanin detection reagent (SA-APC, Prozyme, CA). The kinase reaction is performed in a black U-bottom 96-well microtitre plate. The final reaction volume is 50 µL and contains a final concentration of 1 nM active SYK enzyme, 550 nM SYK-substrate, and 100 µM ATP diluted in a buffer containing 50 mM Tris pH 7.5, 5 mM MgCl$_2$, and 1 mM DTT. The reaction is allowed to proceed for 1 hour at room temperature. The quench buffer contains 100 mM Tris pH 7.5, 300 mM NaCl$_2$, 20 mM EDTA, 0.02% Brij35, and 0.5% BSA. The detection reagents are added to the reaction mixture at the following dilutions-1:500 for Eu-W1024-PY100 and 1:250 for SA-APC. The kinase reaction is terminated by the addition of 50 µL quench buffer containing the detection reagents. The detection is allowed to proceed for 1 hr at room temperature. Detection of the phosphorolated substrate in the absence and presence of inhibitors is measured in the TR-FRET instrument, Analyst HT (Molecular Probes, Sunnyvale, Calif.) and the condition for measurements are set up using CriterionHost Release 2.0 (Molecular Probes, Sunnyvale, Calif.). The settings used are a follows: excitation 360 nm, emission 665-7.5 nm, beam splitter 350 nm 50/50, flash 100 pulses, delay 60 us, integration 400 us, z-height 2 mm. Inhibition of SYK-tyrosine kinase activity is calculated as the maximum response observed in the presence of inhibitor, compared to that in the absence of inhibitor. IC$_{50}$s were derived by non-linear regression analysis.

Intracellular phospho-flow cytometry was used to test compound inhibition of Syk activity in intact non-Hodgkin's lymphoma cell lines Ramos and SUDHL-6. 10×10$^6$ cells in log phase growth were aliqoted; Syk kinase is activated by incubating cells for 10 minutes with 3 µg/ml antibody specific to the B cell receptor. Directly following, cells are fixed in 1% paraformaldehyde for 5 minutes at room temperature, washed in phosphate buffered saline, and then permeabilized by incubation for 2 hours in ice cold methanol. Cells are again washed in phosphate buffered saline, then incubated for 30 minutes with antibody specific for phosphorylated Erk (Y204) and BLNK (Y84), which are indicators of Syk kinase activity, and phosphorylated Syk (Y352), a measure of Src family kinase activity. All antibodies used are purchased from BD Pharmingen (San Jose, Calif.). After incubation with antibodies, cells are again washed and subjected to flow cytometry.

The anti-proliferative effects of compounds on non-Hodgkin's lymphoma B cell lines SUDHL-4, SUDHL-6, and Toledo was also assessed. SUDHL-4 and SUDHL-6 require B cell receptor signaling for growth and survival, while the Toledo cell line (serving here as a negative control) does not. Cells were aliquoted into each well of a 96-well plate and incubated with increasing concentrations of compound for 72 hours, after which cell survival and proliferation was determined using the MTT assay (Chemicon International, Inc., Temecula, Calif.) following protocols supplied by the manufacturer.

Induction of apoptosis in non-Hodgkin's lymphoma B cell lines SUDHL-4, SUDHL-6, and Toledo was assessed by measuring the apoptotis marker Caspase 3. Cells were incubated with 1, 3, or 10 µM compound for 24, 48, and 72 hours. At the conclusion of each time point, cells were processed for flow cytometry analysis using the Monoclonal Rabbit Anti-Active Caspase-3 Antibody Kit and related protocols (BD Pharmingen). Data from two independent experiments are presented in Tables 5A and 5B, representing the percent of total cells undergoing apoptosis following incubation with compounds under the indicated conditions.

Syk activity is not only required for B cell signaling, proliferation, and survival, as shown, but is also critical for cellular activation upon cross-linking of the B cell receptor. B cell activation leads to increased cell surface expression of several proteins involved in cell signaling, antigen presentation, and adhesion. Among these, CD80, CD86, and CD69 are commonly measured to determine B cell activation status. Therefore, primary mouse B cells isolated from spleen were aliquoted and incubated with increasing concentrations of compound (0.05 to 2 µM) in the presence of goat anti-mouse IgD (eBiosciences, Inc., San Diego, Calif.) for 20 hours to cross-link the B cell receptor. Following, cells were washed and incubated for 30 minutes on ice with antibodies specific for the CD80, CD86, and CD69 B cell activation markers. B cells were identified from the pooled population by staining with the B cell marker CD45RO. All antibodies were purchased from BD Pharmingen.

In the table below, activity in the Syk and/or Jak assays is provided as follows: +++++=$IC_{50}$<0.0010 µM; ++++= 0.0010 µM<$C_{50}$<0.010+M, +++=0.010 µM<$IC_{50}$< 0.10 µM,++=0.10 µM<$C_{50}$<1 µM, +=$IC_{50}$>1 µM.

TABLE 3

| Example No. | MW | MH+ | Syk IC50 code |
| --- | --- | --- | --- |
| 1 | 356.393 | 357.1, 358.1 | +++ |
| 2 | 442.527 | 443.34, 444.47 | ++ |
| 3 | 356.393 | 357.2, 358.4 | +++ |
| 4 | 468.565 | 469.36, 470.31 | +++ |
| 5 | | | + |
| 6 | | | + |
| 7 | | | ++ |
| 28 | 472.565 | 473.4 | + |
| 37 | 413.457 | 414.3 | ++ |

TABLE 3-continued

| Example No. | MW | MH+ | Syk IC50 code |
| --- | --- | --- | --- |
| 38 | 428.512 | 429.3 | + |
| 39 | 371.416 | 372.3 | ++ |
| 40 | 330.355 | 331.1 | +++ |
| 41 | 405.506 | 406.2 | ++ |
| 42 | 347.382 | 348.1 | ++ |
| 43 | 382.431 | 383.2 | ++ |
| 44 | 525.661 | 526.47 | + |
| 45 | 473.585 | 475 | ++ |
| 46 | 473.585 | 474.5 | +++ |
| 47 | 413.485 | 414.3 | +++ |
| 48 | 411.469 | 412.3 | +++ |
| 49 | 398.273 | 398.3; 400.3; Br pattern | ++++ |
| 50 | 353.817 | 354.0, 356.0 | ++++ |
| 51 | 335.371 | 336.1 | ++ |
| 52 | 442.542 | 443.1 | +++ |
| 53 | 486.595 | 487 | ++ |
| 54 | 415.476 | 416.1 | +++ |
| 55 | 430.487 | 431 | +++ |
| 56 | 378.48 | 379.2 | +++ |
| 57 | 448.531 | 449 | + |
| 58 | 348.414 | 349 | ++ |
| 59 | 333.399 | 334.4 | + |
| 60 | 350.43 | 351.4 | + |
| 61 | 392.467 | 393.5 | + |
| 62 | 367.457 | 368.2 | +++ |
| 63 | 393.495 | 394.2 | + |
| 64 | 339.403 | 340.2 | ++ |
| 65 | 381.484 | 382.2 | ++ |
| 66 | 448.575 | 449.3 | +++ |
| 67 | 460.385 | 460.1, 462.1 | + |
| 68 | 451.509 | 452 | ++ |
| 69 | 434.5 | 435.2, 436.2 | +++ |
| 70 | 406.446 | 407.0, 408.0 | +++ |
| 71 | 476.585 | 477.0, 478.0 | ++ |
| 72 | 366.425 | 367.0, 368.0 | ++ |
| 73 | 352.398 | 352.9, 354.1 | ++ |
| 74 | 366.425 | 367.0, 368.0 | +++ |
| 75 | 352.398 | 352.8, 353.8 | +++ |
| 76 | 371.463 | 372.1, 373.1 | ++ |
| 77 | 371.463 | 372.2, 373.1 | ++ |
| 78 | 428.456 | 429.1, 430.2 | +++ |
| 79 | 265.28 | 266.1, 267.1 | ++ |
| 80 | 376.464 | 377.2, 378.2 | ++ |
| 81 | 362.437 | 363.1, 364.1 | ++ |
| 82 | 336.399 | 337.1, 338.1 | ++ |
| 83 | 322.332 | 323.2, 324.2 | ++ |
| 84 | 393.495 | 394.3, 395.3 | ++ |
| 85 | 407.522 | 408.4, 409.4 | ++ |
| 86 | 380.452 | 381.2, 382.2 | +++ |
| 87 | 366.425 | 367.2, 368.2 | +++ |
| 88 | 331.343 | 332.1, 333.1 | ++ |
| 89 | 323.36 | 324.2, 325.2 | ++ |
| 90 | 409.494 | 410.2, 411.2 | ++ |
| 91 | 309.333 | 310.2, 311.1 | +++ |
| 92 | 352.402 | 353.21 | +++ |
| 93 | 438.536 | 439.07, 440.49 | ++ |
| 94 | 424.509 | 425.07, 426.32 | ++ |
| 95B | 428.5 | 429.1 | ++ |
| 95A | 470.537 | 471.1 | ++ |
| 96B | 464.552 | 465.1 | +++ |
| 96A | 506.589 | 507.1 | ++ |
| 97 | 401.474 | 402.3 | ++ |
| 98B | 367.457 | 368.5 | ++ |
| 98A | 409.494 | 410.5 | ++ |
| 99B | 367.457 | 368.5 | ++ |
| 99A | 409.494 | 410.5 | ++ |
| 100B | 427.531 | 428.5 | + |
| 100A | 469.468 | 470.5 | + |
| 101 | 385.431 | 386.2 | +++ |
| 102 | 346.35 | 347.2 | + |
| 103 | 359.393 | 360.3 | ++++ |
| 104 | 333.355 | 334.3 | +++ |
| 105 | 361.409 | 362.3 | +++ |
| 106 | 369.407 | 370.3 | ++++ |
| 107 | 416.489 | 417.4 | +++ |
| 108 | 377.408 | 378.4 | + |
| 109 | 418.461 | 419.3 | + |

TABLE 3-continued

| Example No. | MW | MH+ | Syk IC50 code |
|---|---|---|---|
| 110 | 418.461 | 419.3 | + |
| 111 | 425.452 | 426.4 | ++ |
| 112 | 479.519 | 480.5 | ++ |
| 113 | 402.433 | 403.4 | + |
| 114 | 475.556 | 476.4 | ++ |
| 115 | 423.48 | 424.3 | ++ |
| 15 | 449.56 | 450.6 | +++ |
| 116 | 520.64 | 521.4 | + |
| 117B | 422.49 | 423.3 | + |
| 117A | 464.53 | 465.3 | + |
| 118 | 463.55 | 464.3 | ++ |
| 119 | 476.581 | 477.3 | + |
| 120 | 420.473 | 421.3 | + |
| 121 | 419.489 | 420.3 | ++ |
| 122 | 443.983 | 444.3 | +++ |
| 123 | 413.457 | 414.3 | + |
| 124 | 399.474 | 400.3 | + |
| 125 | 442.499 | 443.3 | + |
| 126 | 455.538 | 456.3 | ++ |
| 127 | 547.635 | 548.4 | + |
| 128 | 413.501 | 414.3 | + |
| 129 | 456.526 | 457.3 | + |
| 130 | 495.588 | 496.5 | + |
| 131 | 345.378 | 346.2 | +++ |
| 132 | 431.343 | 431.4, 433.3 | +++ |
| 133 | 372.448 | 373.3 | + |
| 134 | 456.522 | 457.4 | ++ |
| 135 | 428.468 | 429.3 | + |
| 136 | 480.548 | 481.5 | + |
| 137 | 466.521 | 467.5 | + |
| 138 | 429.528 | 430.4 | + |
| 139 | 392.507 | 393.5 | ++ |
| 140 | 370.432 | 371.2 | ++ |
| 141 | 344.394 | 345.3 | ++ |
| 142 | 427.528 | 428.3 | ++ |
| 143 | 429.528 | 430.4 | + |
| 144 | 392.507 | 393.4 | +++ |

Inhibition of GPVI-Mediated Platelet Function In Vitro

The ability for candidate molecules to inhibit syk-mediated platelet functions are tested by measuring the inhibition the GPVI-specific agonist Convulxin-induced human platelet calcium-mobilization or aggregation. Calcium-mobilization is assessed in human washed platelets in a 96-well microtiter format. Aggregation is assessed in a 96-well microtiter assay (see generally the procedures in Jantzen, H. M. et al. (1999) *Thromb. Hemost.* 81:111-117) or standard cuvette light transmittance aggregometry using human platelet-rich plasma (PRP).

Inhibition of Convulxin-Mediated Platelet Calcium-Mobilization In Vitro

Inhibition of Convulxin-induced calcium-mobilization was determined in human washed platelets using the FLIRP Calcium 3 Assay Kit (Molecular Devices, Sunnyvale, Calif.). For preparation of washed platelets, human venous blood is collected from healthy, drug-free volunteers into ACD (85 mM sodium citrate, 111 mM glucose, 71.4 mM citric acid) containing $PGI_2$ (1.25 ml ACD containing 0.2 µM $PGI_2$ final; $PGI_2$ was from Sigma, St. Louis, Mo.). Platelet-rich plasma (PRP) is prepared by centrifugation at 160×g for 20 minutes at room temperature. Washed platelets are prepared by centrifuging PRP for 10 minutes at 730 g and resuspending the platelet pellet in CGS (13 mM sodium citrate, 30 mM glucose, 120 mM NaCl; 2 ml CGS/10 ml original blood volume). After incubation at 37° C. for 15 minutes, the platelets are collected by centrifugation at 730 g for 10 minutes and resuspended at a concentration of $3\times10^8$ platelets/ml in Hepes-Tyrode's buffer (10 mM Hepes, 138 mM NaCl, 5.5 mM glucose, 2.9 mM KCl, 12 mM $NaHCO_3$, pH 7.4). This platelet suspension is kept >45 minutes at room temperature before use in calcium mobilization assays.

For 96-well plate Calcium-mobilization experiments, equal volumes of $3\times10^8$ washed platelets/ml were incubated with equal volumes of Calcium-3 Assay Reagent A resuspended in 1× Hank's Balanced Salt Solution, pH 7.4, 20 mM Hepes buffer. The total reaction volume of 0.2 ml/well includes $1.5\times10^8$/ml washed platelet/Calcium-3 Assay reagent A mix, 10 µM Eptifibatide (Millennium Pharmaceuticals Inc, Cambridge, Mass.), serial dilutions (1:3) of test compounds in 0.75% DMSO. DMSO alone is added to 1 well of each 8 set to allow for a maximal calcium-mobilization reading. After 20 minutes preincubation at room temperature the 96-well microplate reader is loaded into the FlexStation (Molecular Devices, Sunnyvale, Calif.). The FlexStation experimental conditions for measuring Calcium mobilization are set up using SOFTMax Pro. The settings used are detailed below. Fluorescence parameters-assay mode: flex, excitation 485 nM, 525 nM with a cut-off of 515 nM; Parameters-PMT sensitivity-6, pipette height 230 µl, read time 2 minutes and 40 seconds, read intervals 2 seconds, temperature-23-25° C. After 18 seconds of baseline reading, calcium-mobilization is initiated by the addition of Convulxin to a final concentration of 125 ng/ml. Inhibition of calcium-mobilization was calculated as the maximum response observed in the presence of inhibitor, compared to that in the absence of inhibitor. $IC_{50}$s were derived by non-linear regression analysis.

Inhibition of Convulxin-Mediated platelet Aggregation In Vitro

For preparation of human platelet-rich plasma for aggregation assays, human venous blood was collected from healthy, drug-free volunteers into 0.38% sodium citrate (0.013 M, pH 7.0 final). Platelet-rich plasma (PRP) is prepared by centrifugation of whole blood at 160×g for 20 minutes at room temperature. The PRP layer is removed, transferred to a new tube, and the platelet count is adjusted, if advantageous, to achieve a platelet concentration of ~$3\times10^8$ platelets/ml using platelet-poor plasma (PPP). PPP is prepared by centrifugation of the remaining blood sample (after removal of PRP) for 20 minutes at 800×g. This preparation of PRP can subsequently be used for aggregation assays in either a 96-well plate or standard cuvette aggregometry.

Inhibition of Convulxin-induced aggregation is determined in 96-well flat-bottom microtiter plates using a microtiter plate shaker and plate reader similar to the procedure described by Frantantoni et al., *Am. J. Clin. Pathol.* 94, 613 (1990). All steps are performed at room temperature. For 96-well plate aggregation using platelet-rich plasma (PRP), the total reaction volume of 0.2 ml/well includes 190 µl of PRP (~$3\times10^8$ platelets/ml, see above), and 5 µl of either serial dilution of test compounds in 30% DMSO or buffer (for control wells). After 20 minutes preincubation at room temperature 5 µl of 320 ng/ml Convulxin agonist solution is added to each well to give a final concentration of 8 ng/ml Convulxin. The plates are then agitated for 5 min on a microtiter plate shaker and the 5 minute reading is obtained in the microtitre plate reader (Softmax, Molecular Devices, Menlo Park, Calif.). Aggregation is calculated from the decrease of OD at 650 nm at t=5 minutes. $IC_{50}$s were derived by non-linear regression analysis.

Inhibition of Convulxin-induced aggregation was also determined for cuvette light transmittance aggregation assays, serial dilutions (1:2) of test compounds were prepared in 30% DMSO in a 96 well V-bottom plate (final DMSO concentration in the cuvette was 0.3%). The test compound (5 µl of serial dilutions in DMSO) was preincubated with PRP for 20 minutes prior to initiation of aggregation reactions, which is performed in a ChronoLog aggregometer by addition of agonist (125-250 ng/ml Convulxin) to 495 μL of PRP at 37° C. The aggregation reaction is recorded for 4 min, and maximum extent of aggregation is determined by the difference in extent of aggregation at baseline, compared to the maximum aggregation that occurs during the 4 minute period of the assay. Inhibition of aggregation was calculated as the maximum aggregation observed in the presence of inhibitor, compared to that in the absence of inhibitor. $IC_{50}$s were derived by non-linear regression analysis.

The following table 4 gives syk and PRP $IC_{50}$ values.

Calcium Flux Assay in Ramos Cells Induced by BCR Cross-Linking

Ramos cells (2G6.4C10, Burkitt's lymphoma, ATCC Item Number: CRL-1923) are sub-cultured at $5 \times 10^5$ cells/ml in fresh medium 3 or 4 days ahead of experiments. Cells are harvest and re-suspend in fresh medium at $8 \times 10^6$ cells/ml before dye-loading. An equal volume of Calcium 3 loading dye (Molecular Device) is added and mixed into cell suspension. Loading cells are dispensed in a 96 well plate and incubated 30 min. Compounds are then added in the dye-loaded cells and incubated for another 30 min. Spin cell down at 1000 rpm for 3 min before fluorescence measurement in FlexStation. BCR stimulation is carried by the addition of 5 μg/ml antibody (AffiniPure F(ab')$_2$ fragment Donkey anti-human IgM, Jackson ImmunoResearch Laboratories).

Calcium Flux Assay in Jurkat Cells Induced by TCR Cross-Linking

The protocol is very similar to B cell calcium flux as described in the previous section. The only differences are that T cells (clone E6-1, Acute T cell Leukemia, ATCC Item Number: Tib-152) and anti-human CD3 (Functional Grade Purified anti-human CD3, clone OKT3, eBioscience, No. 16-0037) replaced B cells and anti-human IgM. Cell density is kept the same but antibody is used at a concentration of 100 ng/ml.

IL-2 Secretion in Jurkat Cells Induced by TCR Cross-Linking

Jurkat cell propagation and compound incubation procedures are the same as described in Jurkat calcium flux assay in the previous section. Antibody (anti CD3, OKT3) is coated onto a fresh plate (without cells) at 100 ng/well. Cells are suspended at $8 \times 10^6$ cells/ml and incubated with compounds for 30 min in a separate plate. At the end of incubation, cells are transferred to the antibody-coated plate and incubated for 16 hours. 100 μl of cell medium after incubation is used for IL-2 measurement after incubation. IL-2 level is determined using an IL-2 ELISA kit (Human IL-2 ELISA kit II, BD Bioscience, No. 550611).

TABLE 4

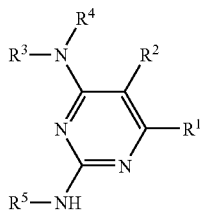

| Ex No | Structure | MW | MS | syk IC50 | PRP IC50 | Name |
|---|---|---|---|---|---|---|
| 8 | 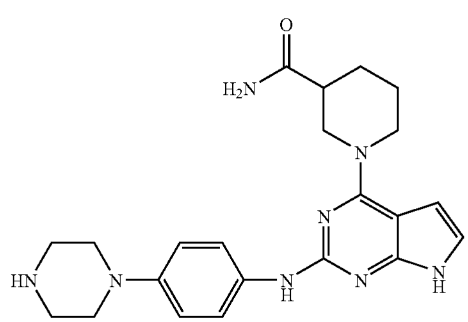 | 420.521 | 421.5 | ++ | 25.2675 | 1-(2-(4-(piperazin-1-yl)phenyl-amino)-7H-pyrrolo[2,3-d]pyrimidin-4-yl)piperidine-3-carboxamide |
| 9 | 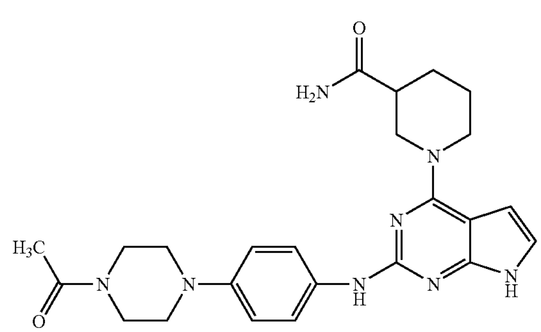 | 462.558 | 463.6 | ++ | 12.297 | 1-(2-(4-(4-acetylpiper-azin-1-yl)phenyl-amino)-7H-pyrrolo[2,3-d]pyrimidin-4-yl)piperidine-3-carboxamide |

TABLE 4-continued

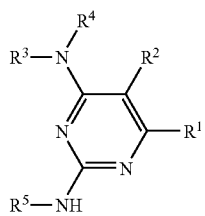

| Ex No | Structure | MW | MS | syk IC50 | PRP IC50 | Name |
|---|---|---|---|---|---|---|
| 10 | 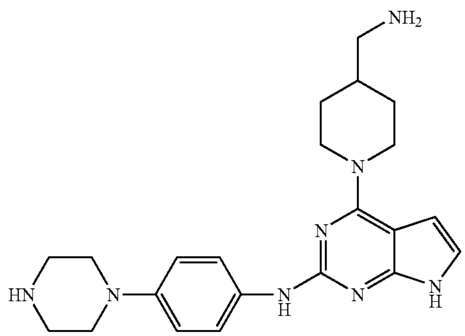 | 406.538 | 407.5 | ++++ | 33.167 | 4-(4-(aminomethyl)piperidin-1-yl)-N-(4-(piperazin-1-yl)phenyl)-7H-pyrrolo[2,3-d]pyrimidin-2-amine |
| 11 | 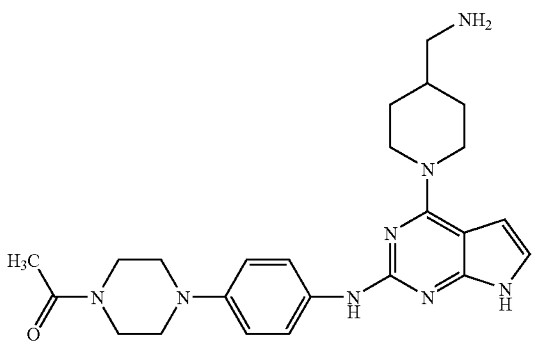 | 448.575 | 449.5 | ++++ | 5.281 | 1-(4-(4-(4-(aminomethyl)piperidin-1-yl)-7H-pyrrolo[2,3-d]pyrimidin-2-ylamino)phenyl)piperazin-1-yl)ethanone |
| | | 348.414 | 349.4, 350.4 | + | | (S)-4-(2-(aminomethyl)pyrrolidin-1-yl)-N-(1H-indazol-6-yl)-7H-pyrrolo[2,3-d]pyrimidin-2-amine |
| 12 | 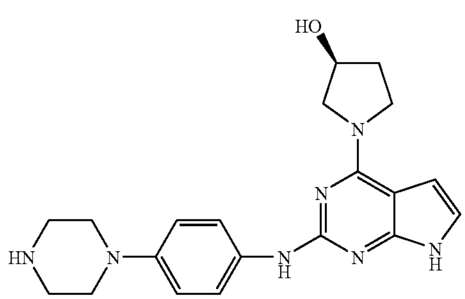 | 379.468 | 380.5 | + | | (S)-1-(2-(4-(piperazin-1-yl)phenylamino)-7H-pyrrolo[2,3-d]pyrimidin-4-yl)pyrrolidin-3-ol |

TABLE 4-continued

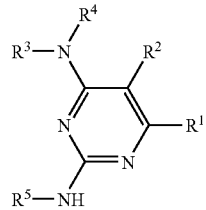

| Ex No | Structure | MW | MS | syk IC50 | PRP IC50 | Name |
|---|---|---|---|---|---|---|
| 13 | 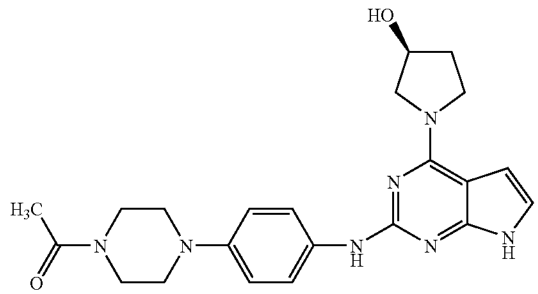 | 421.505 | 422.5 | + | | (S)-1-(4-(4-(4-(3-hydroxypyr-rolidin-1-yl)-7H-pyrrolo[2,3-d]pyrimidin-2-ylamino)phenyl)piperazin-1-yl)ethanone |
| 14 | 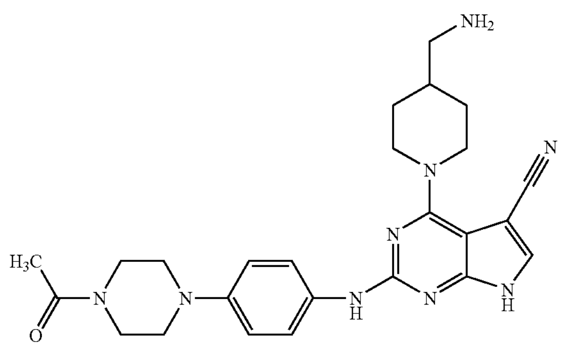 | 473.585 | 474.5 | +++ | 50 | 2-(4-(4-acetylpiper-azin-1-yl)phenyl-amino)-4-(4-(aminomethyl)piperidin-1-yl)-7H-pyrrolo[2,3-d]pyrimidine-5-carbonitrile |
| | | 453.547 | 454.6 | ++ | | 2-(4-(4-acetylpiper azin-1-yl)phenyl-amino)-4-(3-(hydroxymethyl)piperidin-1-yl)pyrimidine-5-carboxamide |
| | | 467.574 | 468.6 | + | | 2-(4-(4-acetylpiper-azin-1-yl)phenyl-amino)-4-(2-(2-hydroxyethyl)piperidin-1-yl)pyrimidine-5-carboxamide |

TABLE 4-continued
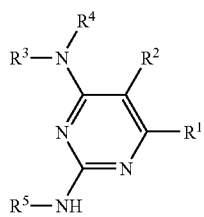
| Ex No | Structure | MW | MS | syk IC50 | PRP IC50 | Name |
|---|---|---|---|---|---|---|
| 15 | 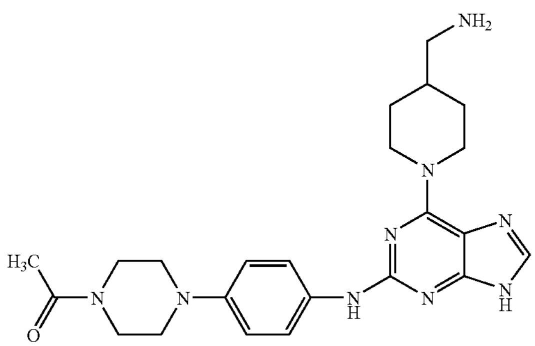 | 449.563 | 450.6 | +++ | 50 | 1-(4-(4-6-(4-(aminomethyl)piperidin-1-yl)-9H-purin-2-ylamino)phenyl)piperazin-1-yl)ethanone |
|  | | 348.414 | 349.4, 350.4 | ++ | | (S)-4-(3-aminopiperidin-1-yl)-N-(1H-indazol-6-yl)-7H-pyrrolo[2,3-d]pyrimidin-2-amine |
|  | | 434.548 | 435.41, 436.54 | ++ | 13.75 | (S)-1-(4-(4-(4-(3-aminopiperidin-1-yl)-7H-pyrrolo[2,3-d]pyrimidin-2-ylamino)phenyl)piperazin-1-yl)ethanone |
| 16 | 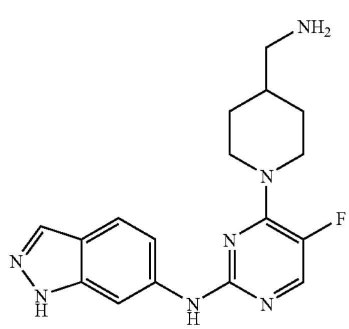 | 341.394 | 342.5 | +++ | 0.2955 | N-(4-(4-(aminomethyl)piperidin-1-yl)-5-fluoropyrimidin-2-yl)-1H-indazol-6-amine |

TABLE 4-continued

| Ex No | Structure | MW | MS | syk IC50 | PRP IC50 | Name |
|---|---|---|---|---|---|---|
| 17 | 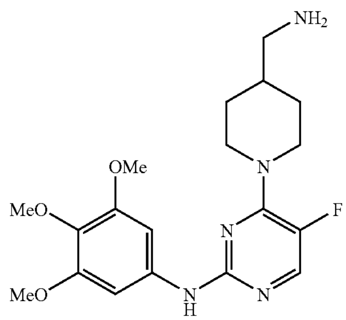 | 391.447 | 392.5 | ++ | | 4-(4-(aminomethyl)piperidin-1-yl)-5-fluoro-N-(3,4,5-trimethoxyphenyl)pyrimidin-2-amine |
| 18 | 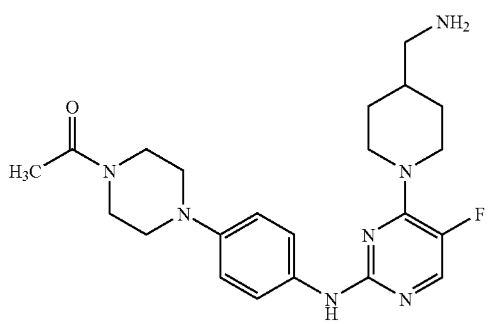 | 427.528 | 428.6 | +++ | 0.195 | 1-(4-(4-(4-(4-(aminomethyl)piperidin-1-yl)-5-fluoropyrimidin-2-ylamino)phenyl)piperazin-1-yl)ethanone |
| 19 | 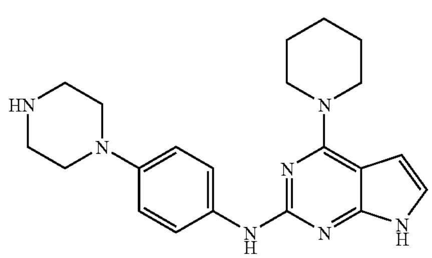 | 377.496 | 378.5 | + | | N-(4-(piperazin-1-yl)phenyl)-4-(piperidin-1-yl)-7H-pyrrolo[2,3-d]pyrimidin-2-amine |
| 20 | 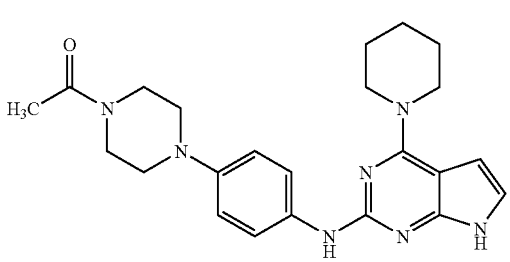 | 419.533 | 420.5 | + | | 1-(4-(4-(4-(piperidin-1-yl)-7H-pyrrolo[2,3-d]pyrimidin-2-ylamino)phenyl)piperazin-1-yl)ethanone |

TABLE 4-continued
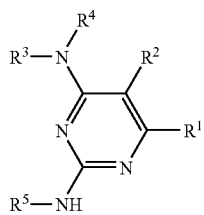
| Ex No | Structure | MW | MS | syk IC50 | PRP IC50 | Name |
|---|---|---|---|---|---|---|
| 21 | 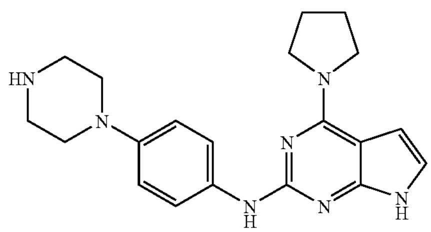 | 363.469 | 364.5 | ++ | | N-(4-(piperazin-1-yl)phenyl)-4-(pyrrolidin-1-yl)-7H-pyrrolo[2,3-d]pyrimidin-2-amine |
| 22 | 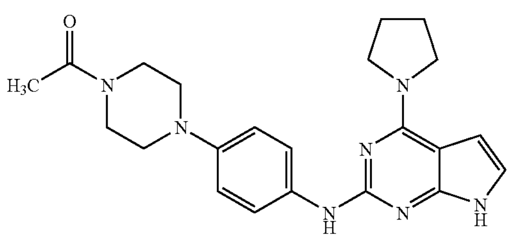 | 405.506 | 406.5 | ++ | | 1-(4-(4-(4-(pyrrolidin-1-yl)-7H-pyrrolo[2,3-d]pyrimidin-2-ylamino)phenyl)piperazin-1-yl)ethanone |
| 23 | 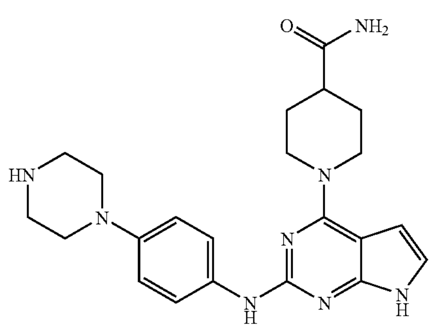 | 420.521 | 421.5 | + | | 1-(2-(4-(piperazin-1-yl)phenyl-amino)-7H-pyrrolo[2,3-d]pyrimidin-4-yl)piperidine-4-carboxamide |
| 24 | 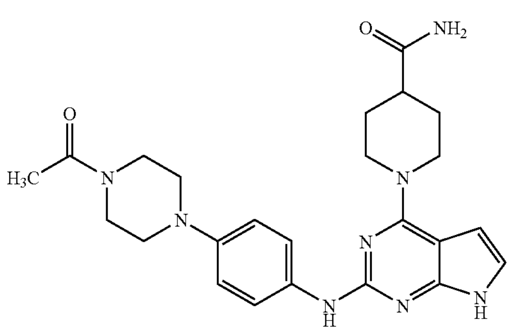 | 462.558 | 463.5 | ++ | | 1-(2-(4-(4-acetylpiperazin-1-yl)phenyl-amino)-7H-pyrrolo[2,3-d]pyrimidin-4-yl)piperidine-4-carboxamide |

TABLE 4-continued

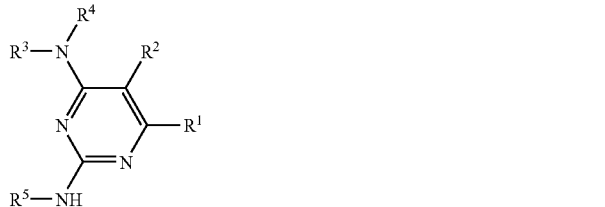

| Ex No | Structure | MW | MS | syk IC50 | PRP IC50 | Name |
|---|---|---|---|---|---|---|
| 25 | 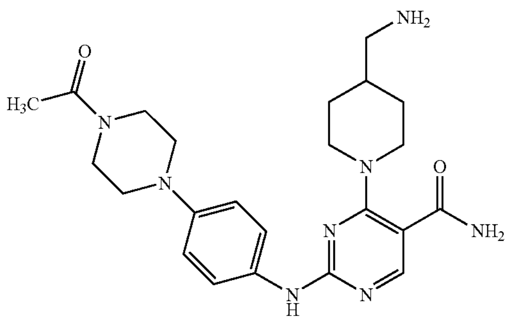 | 452.563 | 453.6 | + | | 2-(4-(4-acetylpiperazin-1-yl)phenylamino)-4-(4-(aminomethyl)piperidin-1-yl)pyrimidine-5-carboxamide |
| 26 | 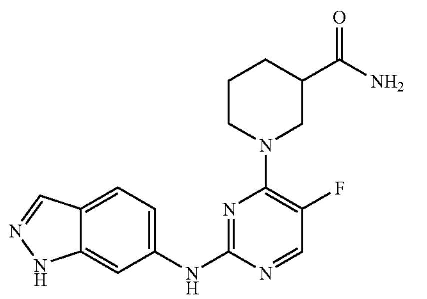 | 355.377 | 356.3 | ++ | | 1-(2-(1H-indazol-6-ylamino)-5-fluoropyrimidin-4-yl)piperidine-3-carboxamide |
| 27 | 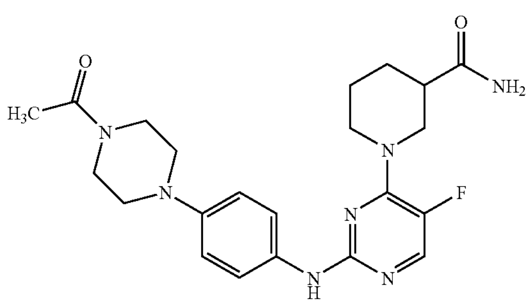 | 441.511 | 442.4 | + | | 1-(2-(4-(4-acetylpiperazin-1-yl)phenylamino)-5-fluoropyrimidin-4-yl)piperidine-3-carboxamide |
| | | 482.589 | 483.6 | ++ | | 2-(4-(4-acetylpiperazin-1-yl)phenylamino)-4-(4-(2-hydroxyethyl)-1,4-diazepan-1-yl)pyrimidine-5-carboxamide |

TABLE 4-continued

| Ex No | Structure | MW | MS | syk IC50 | PRP IC50 | Name |
|---|---|---|---|---|---|---|
|  | (structure) | 472.565 | 473.4 | + |  | tert-butyl (1-(5-fluoro-2-(4-(N-methyl-acetamido) phenylamino) pyrimidin-4-yl)piperidin-4-yl)methyl-carbamate |
| 30 | (structure) | 444.511 | 445.4 | + |  | tert-butyl (1-(2-(4-carbamoyl-phenylamino)-5-fluoro-pyrimidin-4-yl)piperidin-4-yl)methyl-carbamate |
| 31 | (structure) | 344.394 | 345.3 | +++ | 0.3455 | 4-(4-(4-(aminomethyl) piperidin-1-yl)-5-fluoropyrimidin-2-ylamino) benzamide |
| 32 | (structure) | 380.446 | 381.3 | +++ | 4.6705 | 4-(4-(4-(aminomethyl) piperidin-1-yl)-5-fluoropyrimidin-2-ylamino) benzenesulfon-amide |

TABLE 4-continued

| Ex No | Structure | MW | MS | syk IC50 | PRP IC50 | Name |
|---|---|---|---|---|---|---|
| 29 | 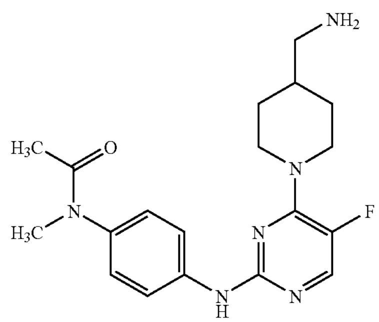 | 372.448 | 373.3 | +++ | 0.3155 | N-(4-(4-(4-(aminomethyl) piperidin-1-yl)-5-fluoropyrimidin-2-ylamino) phenyl)-N-methylacetamide |
| 33 | 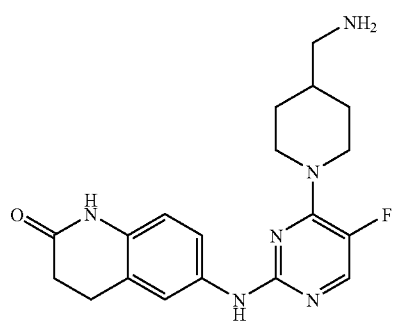 | 370.432 | 371.3 | +++ | 0.3355 | 6-(4-(4-(aminomethyl) piperidin-1-yl)-5-fluoropyrimidin-2-ylamino)-3,4-dihydroquinolin-2(1H)-one |
| 34 | 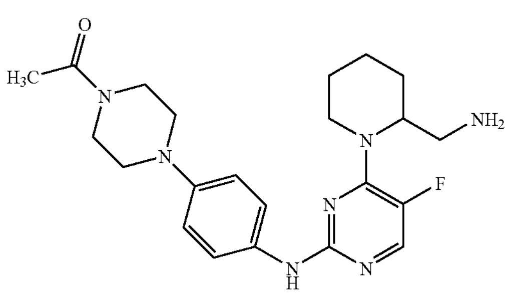 | 427.53 | 428.4 | + | | 1-(4-(4-(4-(2-(aminomethyl) piperidin-1-yl)-5-fluoropyrimidin-2-ylamino) phenyl)piperazin-1-yl)ethanone |
| 35 | 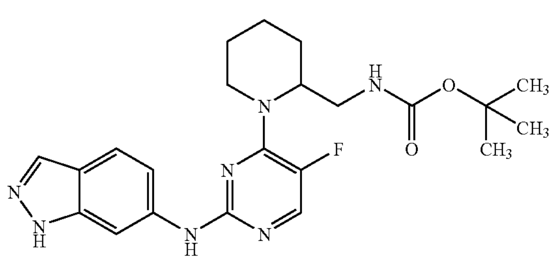 | 441.51 | 442.3 | + | | tert-butyl (1-(2-(1H-indazol-6-ylamino)-5-fluoropyrimidin-4-yl)piperidin-2-yl)methylcarbamate |

TABLE 4-continued

| Ex No | Structure | MW | MS | syk IC50 | PRP IC50 | Name |
|---|---|---|---|---|---|---|
| 36 | 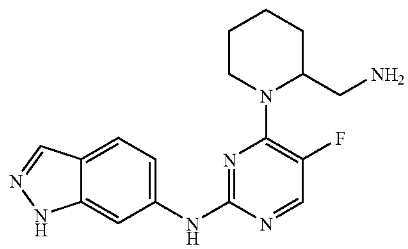 | 341.39 | 342.3 | + | | N-(4-(2-(aminomethyl)piperidin-1-yl)-5-fluoropyrimidin-2-yl)-1H-indazol-6-amine |

Example 146

Millipore Upstate KinaseProfiler™ Screening

This assay is a direct measurement of the effect of compound on the catalytic activity of JAK3. Purified human JAK3 (GenBank AF513860) sequence (residue 781—C terminus) was obtained from insect cells. The catalytic hydrolysis of ATP is measured using a radiometric filter binding method. Incubation of kinase with $^{33}$[P]ATP and substrate leads to incorporation of $^{33}$[p] into the substrate which can then be separated from the other reaction components by filtration. Assays were performed using 10 µM ATP and in the absence or presence of 1, 0.3, or 0.1 µM compound. Activity was expressed as % of inhibition of control.

In the table below, activity in the Jak assays is provided as follows: +++++=$IC_{50}$<+++++=0.0010 M<$IC_{50}$<0.010 µM, +++=0.010 µM<$IC_{50}$<0.10 µM,++=0.10M<$IC_{50}$<1 µM, +=$IC_{50}$>1 µM.

TABLE 5A

Inhibition (IC50 %) of catalytic activity of JAK1, 2 and 3 by the compound

| Compound | Concentration (µM) | | |
|---|---|---|---|
| | JAK 1 | JAK 2 | JAK 3 |
| | ++ | ++ | ++ |
| | ++ | ++ | |

TABLE 5A-continued

Inhibition (IC50 %) of catalytic activity of JAK1, 2 and 3 by the compound

| Compound | Concentration (μM) | | |
|---|---|---|---|
| | JAK 1 | JAK 2 | JAK 3 |
| (structure) | + | ++ | ++ |
| (structure) | + | + | + |
| (structure) | ++ | ++ | ++ |
| (structure) | +++ | +++ | +++ |
| (structure) | +++ | +++ | +++ |
| (structure) | + | ++ | + |

TABLE 5A-continued

Inhibition (IC50 %) of catalytic activity of JAK1, 2 and 3 by the compound

| Compound | Concentration (µM) | | |
|---|---|---|---|
| | JAK 1 | JAK 2 | JAK 3 |
| 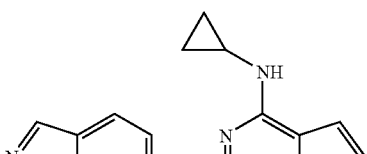 | +++ | +++ | +++ |

TABLE 5B

Inhibition (%) of catalytic activity of JAK3 by 1, 0.3 or 0.1 µM compound

| nd | Concentration (µM) | | |
|---|---|---|---|
| | 1 µM | 0.3 µM | 0.1 µM |
| 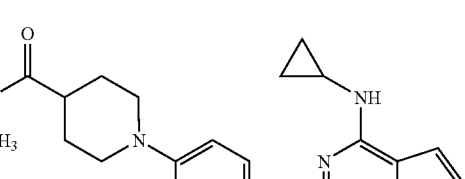 | 77 | 41 | ND |
| | ND | 82 | ND |

ND: not done

Example 147

Ambit KinomeScan Screening

This assay is an ATP-site dependent competition binding assay in which human kinases of interest are fused to a proprietary tag (T7 bacteriophage). The amount of kinase bound to an immobilized, active-site directed ligand is measured in the presence and absence of the test compound. Ambit's JAK assays use kinase domains and not full-length proteins. The domain used for JAK1 binding is the pseudo kinase domain while that for JAK3 binding is the catalytic domain (Mazen W Karaman, Sanna Herrgard, Daniel K Treiber, et. al. A Quantitative analysis of kinase inhibitor selectivity. Nature Biotechnology, 2008, Volume 26, No. 1, Page 127-132).

Example 148

JAK3/STAT6 Cellular Assay

Stimulation of Ramos B cells by interleukin 4 (IL4) leads to signaling through JAK1/JAK3 resulting in phosphorylation of STAT6 (signal transducers and activators of transcription). The effect of compounds on inhibition of JAK3 and/or JAK1 can be assessed by measuring the amount of phosphorylated STAT6. This is performed by Western blotting using a specific phospho-STAT6 antibody.

Ramos B cells were suspended in 10 mM Hepes-buffered RPMI media ($2 \times 10^7$ cells/ml). Cells (90 µl) were incubated with 10 µl 3.3 µg/ml interleukin 4 (R & D Systems Inc, cat #204-IL; final concentration: 0.33 µg/ml). Incubations were for 10 min at 37° C. in the absence or presence of 2 µl compound diluted in 30% DMSO. Reactions were terminated by the addition of an equal volume of 2× lysis buffer (100 mM TRIS-HCl pH 8.0, 2% Triton-X-100, 5 mM EDTA, 250 mM NaCl, 20% glycerol, 1.25 mM PMSF, 5 mM sodium orthovandate, 5 mM β-glycerophosphate, mini complete EDTA protease inhibitor cocktail (Sigma)).

Samples were incubated with 1 µl of the nuclease, benzonase (Novagen, cat #71205-3) for 1 hour, room temperature and then 50 µl 5× loading buffer (330 mM TRIS pH 6.8, 9.5% SDS, 34% glycerol, 0.01% bromophenol blue, 10% beta-mercaptoethanol) was added.

Cell lysates (15 µL) were subjected to SDS-PAGE (Novex 4-12% TRIS-glycine gels, Invitrogen) under reducing conditions, followed by electroblot-transfer onto nitrocellulose membranes. Membranes were then incubated in Zymed blocking buffer (Invitrogen) for 1 hr at room temperature (RT) then overnight at 4° C. with 1:500 anti phosphotyrosine-STAT6 (Cell Signaling Technology, cat #9364) primary antibody in Zymed blocking buffer. Following 5×10 min washes with Tris-buffered saline, 0.25% NP40 (TBSN), blots were incubated for 1 hr at room temperature in the presence of 1:10,000 HRP-conjugated donkey anti-rabbit secondary antibody (Amersham Biosciences, cat #NA934V) in Zymed blocking buffer. After 4×10 min TBSN washes, blots were visualized by ECL (Pierce Western Lightening, Perkin Elmer cat #NEL101). In order to determine total β3 content, blots were stripped, washed 4× with TBSN, and re-probed with 1:2000 C3A antibody in block buffer overnight at 4° C. After 4×10 min TBSN washes, blots were incubated with 1:10,000 goat anti-mouse secondary antibody in blocking buffer, washed 4 more times with TBSN and exposed to Western Lightening reagent.

Figure 4:
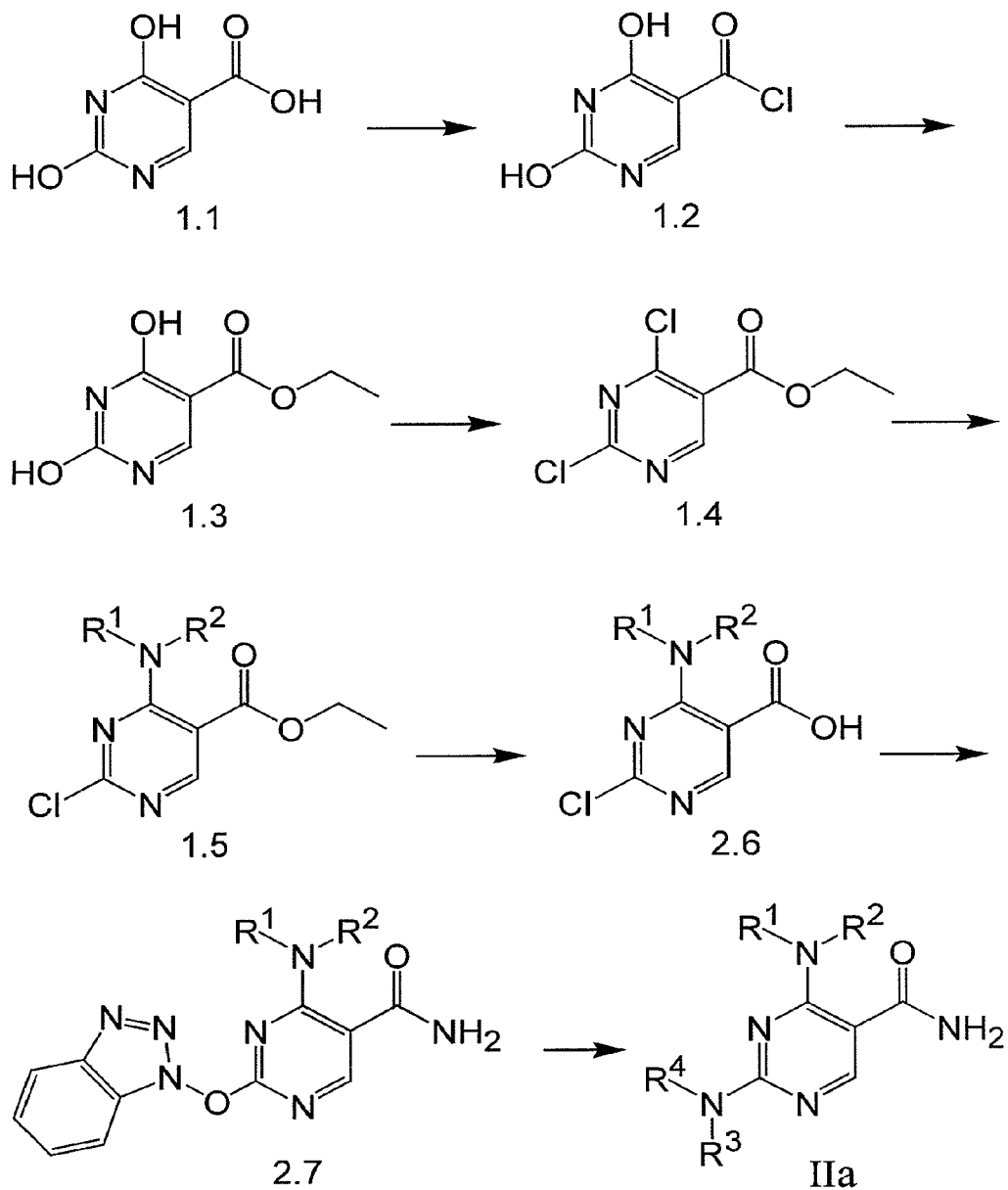
Figure 5:
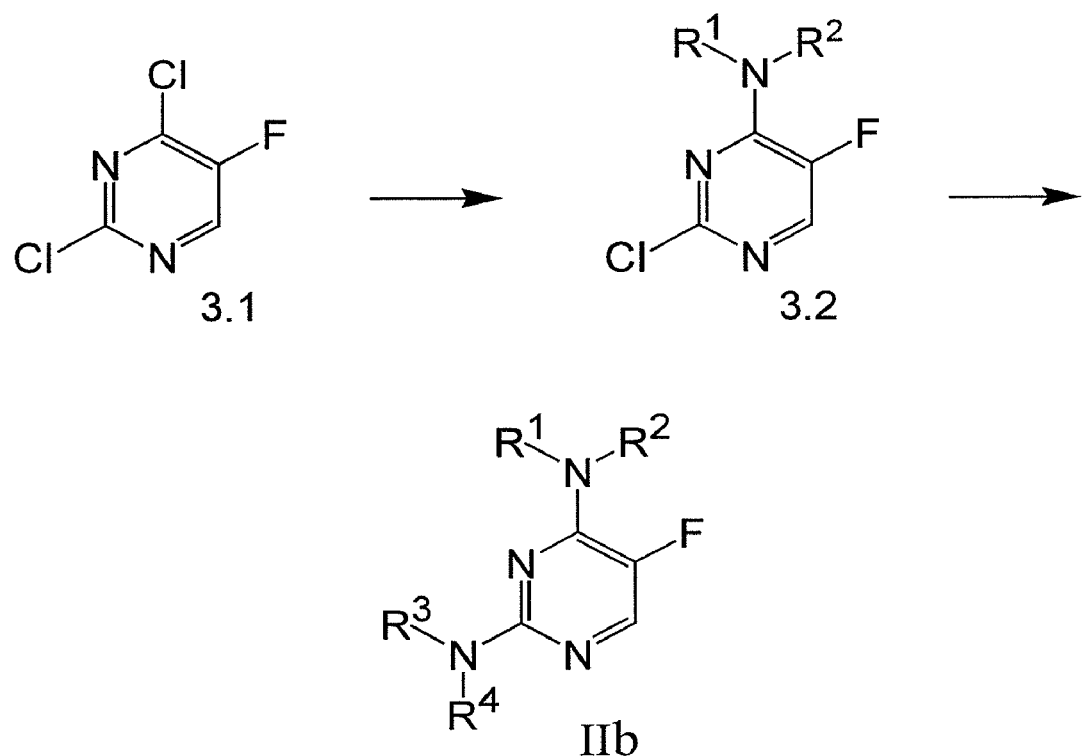
Figure 9:
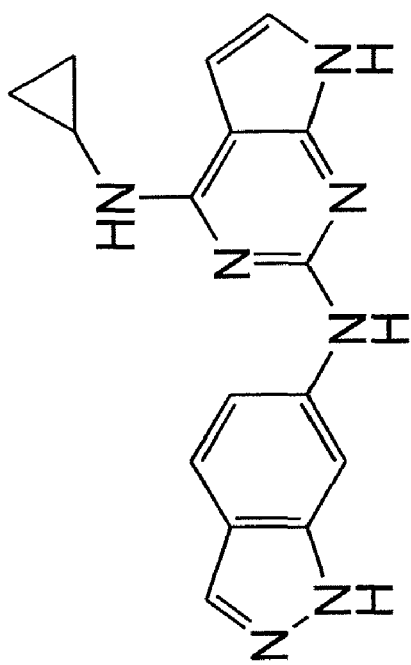
FIG. 9 shows specificity data for selected compounds.

Levels of stimulation over background and the extent of inhibition of compound were determined by densitometry. FIG. 4 shows the effect of increasing dose of a compound of the invention on pSTAT6 formation in response to IL4 stimulation of B Ramos cells.

Example 149

Inhibition of JAK Kinase Activity Assay for Ramos B-Cell Line Stimulated with IL-4

These examples illustrate methods for evaluating the in vitro and in vivo human JAK kinase activities of the inventive compounds can be determined by various procedures known in the art, such as a test for their ability to inhibit the activity of human plasma JAK kinase. The potent affinities for human JAK kinase inhibition exhibited by the inventive compounds can be measured by an $IC_5$, value (in nM). The $IC_{50}$ value is the concentration (in nM) of the compound required to provide 50% inhibition of human JAK kinase activity. The smaller the $IC_{50}$ value, the more active (potent) is a compound for inhibiting JAK kinase activity.

An in vitro assay for detecting and measuring inhibition activity against JAK kinase is as follows:

The activity of the compounds for JAK kinases is confirmed in cellular assays designed to test for JAK inhibition. Briefly, JAK inhibition is tested in human Ramos B-cells activated with cytokine Interleukin-4 (IL-4). Twenty to 24 hours post stimulation, the cells are stained for upregulation of CD23 and analyzed by FACS. Stimulation of the B-cells with IL-4 leads to the activation of the JAK/STAT pathway through phosphorylation of the JAK kinase JAK1 and JAK3, which in turn phosphorylate and activate transcription of factors STAT-5 and STAT-6. The low-affinity IgE receptor (CD23) is upregulated by activated STAT-5.

For the assay, human Ramos B-cells (ATCC, Catalog No. CRL-1596) are cultured in RPMI 1640 medium (Cellgro, Catalog No. 10-040-CM) containing 10% fetal bovine serum (JRH, Catalog No. 12106-500M) according to the propagation protocol supplied with the cells, and maintained at a density of approximately $3.5\times10^5$ cells/ml. The day before the assay, the cells are diluted to $3.5\times10^5$ cells/ml to insure they are in the logarithmic growth phase. The cells are spun down, and suspended in RPMI 1640 medium (Cellgro, MediaTech, Inc., Herndon, Va., Cat No. 10-040-CM) containing 5-10% fetal bovine serum (FBS), heat inactivated (JRH Biosciences, Inc, Lenexa, Kans., Cat No. 12106-500M) according to ATCC propagation protocol. Cells are maintained at a density of $3.5\times10^{4-5}$ cells/ml. The day before the experiment, Ramos B-cells are diluted to $3.5\times10^5$ cells/mL to ensure that they are in a logarithmic growth phase and aliquots dispensed into a 96-well tissue culture plate. Cells are incubated with test compound (dissolved in DMSO) or DMSO (control) for 1 hr at 37° C. and then stimulated with IL-4 (Pepotech, Catalog No. 200-04) for 20-24 hours (final concentration is 50 Units/ml).

Cells are spun down and suspended in RPMI with 5% serum. $5\times10^4$ cells are used per point in a 96-well tissue culture plate. Cells are pre-incubated with compound or DMSO (Sigma-Aldrich, St. Louis, Mo., Cat No. D2650) vehicle control for 1 hour in a 37° C. incubator. Cells are then stimulated with IL-4 (Peprotech Inc., Rocky Hill, N.J., Cat No. 200-04) for a final concentration of 50 units/mL for 20-24 hours. Cells are then spun down and stained with anti-CD23-PE (BD Pharmingen, San Diego, Calif., Cat No. 555711) and analyzed by FACS. Detection is performed using a BD LSR I System Flow Cytometer, purchased from Becton Dickinson Biosciences of San Jose, Calif.

Proliferation is measured using CellTiter-Glo® Luminescent Cell Viability Assay (Promega), which determines the number of viable cells in culture based on quantitation of the ATP present, as an indicator of metabolically active cells. The substrate is thawed and allowed to come to room temperature. After mixing the Cell Titer-Glo reagent and diluent together, 100 µL is added to each well. The plates are mixed on an orbital shaker for two minutes to induce lysis and incubated at room temperature for an additional ten minutes to allow the signal to equilibrate. Detection is performed using a Wallac Victor2 1420 multilabel counter purchased from Perkin Elmer, Shelton, Conn.

On day two, A549 cells are pre-incubated with a 2,4-pyrimidinediamine test compound or DMSO (control) (Sigma-Aldrich, St. Louis, Mo., Catalog No. D2650) for 1 hour. The cells are then stimulated with IFNγ (75 ng/mL) (Peprotech Inc., Rocky Hill, N.J., Cat. No. 300-02) and allowed to incubate for 24 hours. The final test compound dose range is 30 µM to 14 nM in 200 µL F12K media containing 5% FBS, 0.3% DMSO.

On day three, the cell media is removed and the cells are washed with 200 µL PBS (phosphate buffered saline). Each well is trypsinized to dissociate the cells, then neutralized by addition of 200 µL complete F12K media. Cells are pelleted and stained with an APC conjugated mouse anti-human ICAM-1 (CD54) (BD Pharmingen, San Diego, Calif., Catalog #559771) antibody for 20 minutes at 4° C. Cells are washed with ice cold FACS buffer (PBS+2% FBS) and surface ICAM-1 expression is analyzed by flow cytometry. Detection is performed using a BD LSR I System Flow Cytometer, purchased from BD Biosciences of San Jose, Calif. Events are gated for live scatter and the geometric mean is calculated (Becton-Dickinson CellQuest software version 3.3, Franklin Lakes, N.J.). Geometric means are plotted against the compound concentration to generate a dose response curve.

Example 150

Inhibition of Syk-Mediated Signal Transduction Through the B Cell Receptor in Non-Hodgkin's Lymphoma Cell Lines Cells were pre-treated for 1 hour without or with compound (0.02 to 2 uM) prior to stimulation of B cell receptor singling by incubation of cells with 3 μg/ml anti-mu antibody for 10 minutes at 37° C. $Ca^{2+}$ flux was measured using the Calcium 3 loading dye and the FlexStation (Molecular Device). B cell receptor signaling was assayed by intracellular phospho-Flow Cytometry, following protocols supplied by BD Pharmingen (San Jose, Calif.). Syk activation was measured by induction of BLNK tyrosine phosphorylation at amino acid position 84 (pBLNK Y84) and induction of ERK1/2 tyrosine phosphorylation at amino acid position 204 (pERK Y204). Activation of the Src family member Lyn was measured by induction of Syk tyrosine phosphorylation at amino acid position 352 (pSyk Y352). Data are presented as μM $IC_{50}$s. Each compound effectively inhibited B cell receptor-induced $Ca^{2+}$ fluxing and activation of Syk, but not the Src family member Lyn.

Example 151

Syk Inhibition Exerts an Anti-Proliferative Effect on Non-Hodgkin's Lymphoma Cell Lines Cells were incubated with increasing concentrations of each compound, then evaluated at 72 hours for extent of proliferation using the MTT assay (company, city, state) following the manufacturer supplied protocol. Data are presented as μM IC50 values, representing the mean plus/minus standard deviation from 5 or 6 independent experiments. Each compound inhibited proliferation of SUDHL-4 and -6 cell lines, which rely on Syk for survival and growth signals, in the low μM range. Toledo cells which do not require Syk, was noticeably less sensitive to the anti-proliferative effects of Syk inhibition.

Example 152

Syk Inhibition Induces Apoptosis in Non-Hodgkin's Lymphoma Cell Lines

Data represent two independent experiments to evaluate the effect of Syk and Syk/JAK inhibition on survival of diffuse large non-Hodgkin's lymphoma B cell lines. SUDHL-4 and SUDHL-6 cells lines rely on Syk-mediated B cell receptor signaling for survival, while Toledo cells do not. Cells are incubated with compounds at the various concentrations and times; induction of apoptosis is measured by flow cytometry using the Caspase 3 Detection Kit (Sigma-Aldrich, Saint Luis, Mo.). Data is presented as the percent of total cells positive for the apoptosis marker, caspase 3.

Example 153

Inhibition of Mouse Primary B Cell Activation by Syk Inhibitors

Mouse primary splenocytes were pre-treated for 1 hour with increasing concentrations of each compound (0.05-2 μM) prior to addition of control or goat anti-mouse IgD serum. Anti-IgD induced B cell activation was measured 16 hours later by flow cytometry, staining for the activation markers CD80/86 and CD69. Data represent $IC_{50}$ ranges for the inhibition of B cell activation.

Example 154

Mouse Model of Immune-Mediated Thrombocytopenia

Immune-mediated thrombocytopenia is caused by antibodies directed against platelet surface glycoproteins, antibodies against drug-containing complexes on the platelet surface, or by antibody-coated cells or immune complexes that interact with the platelet surface. Select compounds were evaluated for their ability to inhibit platelet clearance in a mouse model of antibody-mediated thrombocytopenia. In this model, a rapid clearance of circulating platelets (approximately 50%) results from the intravenous administration of a rat anti-mouse GPIIb (clone MWReg30) antibody (BD Biosciences, Pharmingen). To evaluate capacity for inhibition of platelet clearance, compounds were suspended into 0.5% methylcellulose in water and administered via oral gavage (100 ul/mouse) at a time prior to antibody injection when the compound would achieve maximum plasma concentration (typically 1-2 hours based on separate pharmacokinetic experiments for individual compounds). At 4 and 8 hours after injection of antibody, terminal blood samples were obtained from groups of vehicle and test article treated mice (n=5-10 mice/group) via cardiac puncture. Blood was anticoagulated using trisodium citrate or EDTA. Whole blood samples were measured for platelet counts on a hematology analyzer (Hemavet, Drew Scientific). Remaining blood was processed for plasma and compound concentrations measured by mass spectrometry.

Platelet clearance was determined by measuring the difference in platelet number between the average non-antibody treatment group and animals administered the rat anti-mouse GPIIb antibody. Inhibition of platelet clearance was determined by comparing the difference between platelet clearance of vehicle and compound treated animals.

Example 155

Mouse Model of Collagen Antibody Induced Arthritis

The inhibitory activity of select compounds was investigated in a mouse model of collagen antibody induced arthritis (CAIA). Collagen induced arthritis is mediated by autoantibodies to type II collagen and complement, thus arthritis can be induced by administration of polyclonal antibodies or a mixture of monoclonal antibodies to type II collagen. The CAIA model (Chondrex, Inc., Redmond, Wash.) uses a mixture of 4 clones which recognize individual epitopes clustered within an 83 amino acid peptide fragment of type II collagen. These epitopes share common amino acid sequences with many different species of type II collagen including chicken, mouse, rat, bovine, porcine, monkey and human. The model utilizes a monoclonal antibody cocktail followed by bacterial lipopolysaccharide (LPS) to induce a severe and consistent arthritis in mice within 7 days. This model was developed based on the hypothesis that bacterial toxins absorbed through the gastrointestinal tract play a synergistic and pathologic role with autoantibodies to type II collagen in triggering arthritis in patients with Rheumatoid Arthritis.

For these experiments, the monoclonal antibody cocktail (Lot # OC-708) was injected intravenously via tail vein at a dose of 4 mg/mouse (40 mg/ml) on day 0 followed by intraperitoneal injection of LPS diluted into normal saline at a dose of 25 ug/mouse in 8 week old, female Balb/C mice (Charles River, Inc.). Dosing of test articles was started just before or after the IV injection of antibody cocktail. Compounds were suspended into 0.5% methylcellulose in water and administered via oral gavage (100 ul/mouse) daily for the duration of the 7-10 day study. Clinical inflammation scores were obtained daily. Inhibition of clinical inflammation scores was determined based on the difference between vehicle and test article treated mice at the end of the experiment. Plasma concentrations represent peak concentration at 1 hour post last dose on the day of study termination.

Example 156

Inhibition of IL-4 Induced JAK1/3 to Stat-6 Phosphorylation in Ramos B Cells

Ramos B cells were pre-treated for 1 hour with increasing concentrations of compound, as indicated prior to addition of IL-4. Cells were incubated with IL-4 for 10 minutes, and then subjected to intracellular flow cytometry to measure the percent inhibition of IL-4 induced Stat-6.

Example 157

Analysis of B Cell Signaling

The human non-Hodgkin's lymphoma B cell lines SUDHL-4 (#ACC 495), SUDHL-6 (#ACC572), and Karpas-422 (#ACC32) were obtained from DSMZ (Braunschweig, Germany); Toledo (#CRL-2631) and Ramos (#CRL-1596) were obtained from the American Type Culture Collection (ATCC; Manassas, Va.). All cells were maintained in RPMI media (Invitrogen, Carlsbad, Calif.) supplemented with 10% fetal calf serum (ATCC) and penicillin/streptomycin (Invitrogen), and maintained in a 37° C. humidified tissue culture incubator. Antibodies used in these studies include polyclonal goat F(ab)'2 anti-human IgG (H+L) and anti-human IgM (BioSource, Camarillo, Calif.); rabbit anti-human Syk, rabbit anti-human phospho-Syk (Y525/526), rabbit anti-human phospho-Syk (Y352), anti-human BLNK, anti-human phospho-BLNK (Y84) were obtained from Cell Signaling Technologies, Inc. (Danvers, Mass.). The following antibodies were obtained from Becton Dickenson (San Jose, Calif.) for phospho-flow cytometry: Alexa fluor 488-conjugated mouse anti-human phospho-STAT6 (Y641), Phycoerythrin (PE)-conjugated mouse anti-human phospho-Zap70 (Y319)/Syk (Y352), and Fluorescein isothiocyanate (FITC)-conjugated mouse anti-human phospho-ERK1/2 (T202/Y204).

Phospho-flow cytometry was performed essentially as described elsewhere (Irish, Czerwinski et al. Blood 108(9): 3135-42 (2006). $0.5 \times 106$ cells in growth media were stimulated with 1 µg/ml anti-µ or anti-γ antibody for 10 minutes. Induced signaling was terminated immediately following the indicated time by the addition of paraformaldehyde (Electron Microscopy Sciences, Hatfield, Pa.) to a final concentration of 1%. Cells were incubated with paraformaldehyde for 5 minutes at room temperature, washed once with phosphate buffered saline (PBS), then resuspended and incubated overnight at 4° C. in pre-chilled methanol (−80° C.) (company, address). Fixed and permeabilized cells were subsequently washed once in PBS, a second time in PBS containing 1% bovine serum albumin (BSA) (Sigma-Aldrich, St. Louis, Mo.), and then stained with the indicated antibodies diluted 1:20 in PBS+1% BSA. After 30 minutes, cells were washed once in PBS and subjected to flow cytometry using the FACS Calibur (Becton Dickenson). For Western blot analyses, 106 cells were stimulated for 30 minutes with 2 µg/ml of the indicated BCR-specific antibodies. Signaling was terminated by resuspending the cells in lysis buffer and incubated on ice for 1 hour. Cell debris were removed by centrifugation, and the cleared protein lysates were resolved by 10% SDS-PAGE and probed with the indicated antibodies following recommendations made by the manufacturers. Where indicated, cells were pre-treated for 1 hour at 37° C. with Syk inhibitors or vehicle control (0.5% DMSO) at several concentrations prior to stimulation with anti-BCR antibody.

Example 158

Analysis of B Cell Signaling

The human non-Hodgkin's lymphoma B cell lines SUDHL-4 (#ACC 495), SUDHL-6 (#ACC572), and Karpas-422 (#ACC32) were obtained from DSMZ (Braunschweig, Germany); Toledo (#CRL-2631) and Ramos (#CRL-1596) were obtained from the American Type Culture Collection (ATCC; Manassas, Va.). All cells were maintained in RPMI media (Invitrogen, Carlsbad, Calif.) supplemented with 10% fetal calf serum (ATCC) and penicillin/streptomycin (Invitrogen), and maintained in a 37° C. humidified tissue culture incubator. Antibodies used in these studies include polyclonal goat F(ab)'2 anti-human IgG (H+L) and anti-human IgM (BioSource, Camarillo, Calif.); rabbit anti-human Syk, rabbit anti-human phospho-Syk (Y525/526), rabbit anti-human phospho-Syk (Y352), anti-human BLNK, anti-human phospho-BLNK (Y84) were obtained from Cell Signaling Technologies, Inc. (Danvers, Mass.). The following antibodies were obtained from Becton Dickenson (San Jose, Calif.) for phospho-flow cytometry: Alexa fluor 488-conjugated mouse anti-human phospho-STAT6 (Y641), Phycoerythrin (PE)-conjugated mouse anti-human phospho-Zap70 (Y319)/Syk (Y352), and Fluorescein isothiocyanate (FITC)-conjugated mouse anti-human phospho-ERK1/2 (T202/Y204).

Phospho-flow cytometry was performed essentially as described elsewhere (Irish, Czerwinski et al. Blood 108(9): 3135-42 (2006). $0.5 \times 106$ cells in growth media were stimulated with 1 µg/ml anti-µ or anti-γ antibody for 10 minutes. Induced signaling was terminated immediately following the indicated time by the addition of paraformaldehyde (Electron Microscopy Sciences, Hatfield, Pa.) to a final concentration of 1%. Cells were incubated with paraformaldehyde for 5 minutes at room temperature, washed once with phosphate buffered saline (PBS), then resuspended and incubated overnight at 4° C. in pre-chilled methanol (−80° C.) (company, address). Fixed and permeabilized cells were subsequently washed once in PBS, a second time in PBS containing 1% bovine serum albumin (BSA) (Sigma-Aldrich, St. Louis, Mo.), and then stained with the indicated antibodies diluted 1:20 in PBS+1% BSA. After 30 minutes, cells were washed once in PBS and subjected to flow cytometry using the FACS Calibur (Becton Dickenson). For Western blot analyses, 106 cells were stimulated for 30 minutes with 2 µg/ml of the indicated BCR-specific antibodies. Signaling was terminated by resuspending the cells in lysis buffer and incubated on ice for 1 hour. Cell debris were removed by centrifugation, and the cleared protein lysates were resolved by 10% SDS-PAGE and probed with the indicated antibodies following recommendations made by the manufacturers. Where indicated, cells were pre-treated for 1 hour at 37° C. with Syk inhibitors or vehicle control (0.5% DMSO) at several concentrations prior to stimulation with anti-BCR antibody.

Example 159

Calcium Flux Assay and Selective Inhibition of Syk in Non-Hodgkin's Lymphoma B Cell Lines Ramos cells were cultured (maintaining approximately $0.5 \times 106$ cells/ml) in growth medium 3 to 4 days ahead of experiments. Cells were harvested and re-suspended in fresh medium at $8 \times 106$ cells/ml before dye-loading. An equal volume of Calcium 3 loading dye (Molecular Device, Sunneyvale, Calif.) was added to the cell suspensions. Loaded cells were dispensed in a 96 well plate and incubated for 20 minutes. Syk inhibitors were then added to the loaded cells and incubated for another 30 minutes. B cells were stimulated with 5 μg/ml anti-μ antibody. Changes in intracellular $Ca^{2+}$ concentration was measured using the FlexSTATion (Molecular Devices, Sunnyvale, Calif.).

The selectivity and potency of Syk inhibition in B cells was initially interrogated by Western blot, measuring BCR-mediated induction of pSyk Y525/526 and pBLNK Y84, both measures of Syk kinase activity, and the induction of pSyk Y352, a measure of Src kinase activity. SUDHL-6 B cells were stimulated with anti-BCR specific antibody for 30 minutes in the presence or absence of each Syk inhibitor or vehicle control. Treatment with 0.16 or 1 μM of each compound reduced BCR-induced Syk autophorphorylation (Y525/526) by roughly 40% and 60%, respectively, as estimated by densitometry (data not shown). An expanded range of concentrations was used to further evaluate the effect of these compounds on BCR induced Syk and Src kinase activity.

Figure 10:
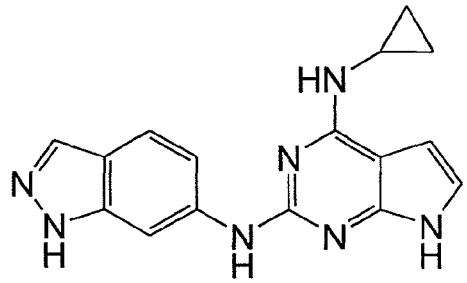
FIG. 10 shows the selective inhibition of selected bicyclic compounds.

The ability of each compound to suppress signaling events more distal to the BCR was also measured. Cells were again stimulated by anti-BCR antibody in the presence or absence of various concentrations of each Syk inhibitor. The induction of pSyk Y352 was measured as a specificity control, while that of pERK1/2/Y204 was used as a measure of more distal Syk-dependent signaling (Jiang, Craxton et al. J Exp Med 188(7): 1297-306 (1998). This experiment was repeated, in which the effect both compounds on Src and Syk activity were determined (FIG. 10). Concentrations of less than 125 nM were sufficient to suppress BCR induced Syk signaling to ERK1/2. By contrast, much higher concentrations were required to cause a modest suppression of Src activity; an effect on Src that was not observed by Western blot. None of these Syk inhibitors suppressed PMA-induced ERK1/2 tyrosine phosphorylation, demonstrating these compounds do not inhibit signaling events down-stream of PKC. This shows that selective inhibition of Syk suppressed BCR-induced Ca2+ flux in B cells with IC50 values around 100 nM. This suggests that by inhibiting Syk, these compounds suppress the signaling pathway, blocking the cellular response.

Example 160

Caspase 3 and Proliferation Assays: Syk Inhibition Disrupts Proliferation and Survival of Non-Hodgkin's Lymphoma B Cell Lines Induction of apoptosis was measured using the PE-conjugated monoclonal active caspase-3 antibody apoptosis kit (Becton Dickenson) following the supplied protocol. Cells were suspended in growth media (0.5×106 cells/ml) and treated with the indicated concentrations of each Syk inhibitor or vehicle control for 24, 48, or 72 hours prior to FACS analysis. The MTT (3-(4,5-Dimethylthiazol-2-yl)-2,5-diphenyltetrazolium bromide, a tetrazole) assay (company name) was used as a measure of cell viability and growth, following protocols supplied by the manufacturer. Cells were treated with the indicated concentrations of each Syk inhibitor or vehicle control for 72 hours.

SUDHL-4 and SUDHL-6 cells were previously classified as "BCR-type" (Monti, Savage et al. Blood 105(5): 1851-61 (2005); Polo, Juszczynski et al. Proc Natl Acad Sci USA 104(9): 3207-12 (2007) and sensitive to Syk inhibition by R406 (Chen, Monti et al. 2008). The Toledo and Karpas-422 cell lines that lack BCR and BLNK expression, respectively (Gabay, Ben-Bassat et al. Eur J Haematol 63(3): 180-91 (1999); Sprangers, Feldhahn et al. Oncogene 25(36): 5056-62 (2006), having therefore adapted to survive independent of BCR signals, were insensitive to R406 (Chen, Monti et al. 2008). The proliferation of these cell lines when cultured in the presence or absence of various concentrations of each Syk inhibitor for 72 hours was tested.

Selective inhibition of Syk was sufficient to induce apoptosis in "BCR-type" NHL cell lines. In a separate experiment, the SUDHL-6 and Toledo cells were found to be equally sensitive to induction of apoptosis by 72 h treatment with 1 μM PMA. These data demonstrate the specific requirement of Syk in the survival of certain NHL cell lines.

Example 161

Xenograft Studies and Tumor and Plasma Concentration Analysis

Syk Inhibition Protects Against Tumor Formation in a Xenograft Mouse Model. Mice were received (company) and acclimated in-house at least three days prior to use. Ramos cells (3×106) were injected subcutaneously into the hind flank area of conscious mice using a 27 gauge needle in an injection volume of less than 0.5 ml. Following injection, mice were randomized into treatment groups (n=15) and dosed twice daily by oral gavage with vehicle or 10, 15, or 20 mg/kg of the Syk inhibitor. Body weights were obtained at least once per week and caliper measurements of tumors were determined twice per week beginning when palpable tumors were formed until the end of the study. Tumor volume was assessed by caliper measurement using a formula [maximum length×width×height×π/6]. Twice daily dosing of vehicle or the Syk inhibitor continued until the vehicle or any treatment group exhibited tumors that exceeded 1.5 grams in size. At the time of termination (5 weeks post Ramos innoculation) the mice were anesthetized with a ketamine cocktail. A blood sample was obtained for CBC and plasma concentration determination via cardiac puncture and the mice were euthanized via cervical dislocation. Tumors were then be excised and weighed. One half of the tumor was snap frozen in liquid nitrogen for determination of concentration of the Syk inhibitor in the tumor tissue and the other half was placed in 10% buffered formalin for histological investigation.

The effect of Syk inhibition on Ramos tumor formation in a xenograft mouse model was assessed. Mice were dosed twice daily with 10, 15, or 20 mg/kg the Syk inhibitor or vehicle control beginning the day of tumor cell inoculation. Caliper measurements were initiated when tumors began to form, approximately three weeks post-tumor inoculation, and repeated every third day until termination of the study. The study was terminated when tumor weights began reaching approximately 1.5 mg, at which time tumors were excised and weighed. Tumor and plasma samples were subjected to pharmacokinetic analysis.

Each tumor sample was homogenized in 3 ml of saline per gram of tumor using the Kontes® Microtube Pellet Pestle® Rods and Motor (Kimble Chase, Vineland, N.J.). Plasma and tumor samples were analyzed for the Syk inhibitor concentration using a liquid chromatography tandem mass spectrometer (LC/MS/MS). In brief, plasma and tumor samples were processed in a 96-well Captiva™ filter plate (0.2 μm, Varian, Inc., Palo Alto, Calif.). Aliquots of plasma and homogenized tumor samples were precipitated with acetonitrile containing 200 ng/mL of:

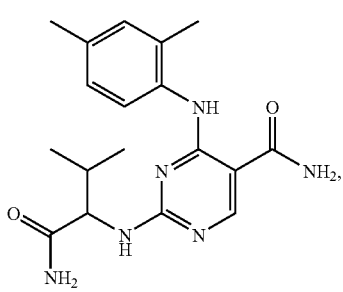

Compound A the internal standard. The mixture was vortexed and refrigerated at 4° C. for 30 minutes to allow complete protein precipitation. The mixture was filtered into a 96-well collection plate. The filtrate was injected onto a Sciex API3000 LC/MS/MS equipped with a turbo-ion spray source. The Syk inhibitor and compound A were separated on a Phenomenex Luna 5μ HILIC column (4.6×100 mm, 5 mm; Phenomenex, Torrance, Calif.). A mobile phase gradient mixture of 10% mobile phase A (0.1% formic acid in water) and 90% mobile phase B (0.1% formic acid in 90% acetonitrile, 10% water) to 65% mobile phase B was programmed over 1.1 minutes followed by a gradient of mobile phase B from 65% to 90% over 0.01 minutes. The peak areas of the m/z 394/360 product ion of the Syk inhibitor were measured against those of the m/z 357/295 product ion of the Syk inhibitor (internal standard) in positive ion mode. The analytical range was 2 to 5000 ng/ml.

Pharmacokinetic analysis revealed that at steady-state, tumor concentrations of the Syk inhibitor followed the concentration-time profiles seen with plasma in the 10, 15, and 20 mg/kg dose groups. Nonlinear increases in Cmax, AUC (0-8), and tumor Cmin were observed as the dose was increased, but a dose-proportional increase in plasma Cmin was noted. Mean Cmax and AUC (0-8) in plasma was at least 2-fold greater than that in tumor for all doses examined; however, mean nadir concentrations (Cmin) were higher in tumor than in plasma, indicating accumulation of the Syk inhibitor in the tumor compartment. Tumor/plasma ratios determined from Cmax and AUC (0-8) were similar across the various dose groups. Tumor concentrations were sustained above 60, 170, and 640 nM over the entire dosing interval at steady-state for the Syk inhibitor at 10, 15, and 20 mg/kg, respectively.

Mice dosed with all three concentrations of the Syk inhibitor were protected from Ramos tumor growth in vivo. This was first evident from caliper measurements (data not shown), which revealed a reduced rate of tumor growth in the presence of the Syk inhibitor. Upon study completion, mice were euthanized and tumors excised and weighed. Consistent with caliper measurements, a statistically significant reduction in average tumor weight was achieved in all dosing groups, relative to vehicle control. These data reveal that sub-micromolar concentrations of the Syk inhibitor can prevent tumor formation by an aggressive NHL cell line in mice.

Mice dosed with the Syk inhibitor did not present with reduced numbers in any subset of white blood cells. In fact, the only effect observed was an increase in the number of lymphocytes in mice treated with 15 mg/kg the Syk inhibitor which was not repeated in mice dosed with 10 or 20 mg/kg. The relative percent of each cell subtype analyzed was also unaffected by the Syk inhibitor (data not shown). On average, mice treated with vehicle control had a 9.45% increase in body weight. Mice treated with 10, 15, and 20 mg/kg the Syk inhibitor, on the other hand, had on average 0.27% increase, 1.67% decrease, and 2.27% decrease in body weight, respectively, over the course of the study. There was no relationship, however, between % change in body weight and tumor growth (R2=0.27). These data suggest that the inhibition of tumor growth was indeed mediated by suppression of Syk activity.

The Syk-specific inhibitor the Syk inhibitor was also tested for activity in a Ramos tumor mouse xenograft model. At all the concentrations tested, statistically significant reductions in tumor growth were observed in mice dosed BID with the Syk inhibitor. The lowest concentration tested was 10 mg/kg, achieving tumor concentrations ranging from 64 to 140 nM over the course of the day. Suppression of tumor growth at these concentrations in vivo is consistent with concentrations of <125 nM found to suppress BCR-induced Ca2+ flux and distal BCR signaling to pERK Y204. The selective pharmacological inhibition of Syk results in effects on the proliferations and survival of NHL cell lines. These data suggest that the selective targeting of Syk may similarly have clinical benefit in a variety of B-cell proliferative disorders.

As detailed herein, Syk has been implicated experimentally in B cell development, proliferation, and survival. Moreover, Syk is implicated as an oncogene. Expression of constitutively active Syk in adoptively transferred bone marrow cells induces leukemia in mice, and over-activity of Syk is associated with a variety of lymphomas in humans Given the role of Syk in B cell biology, its selective inhibition may be sufficient to provide clinical benefit in B cell proliferative disorders, while reducing toxicities that may arise due to suppression of other off-target kinases.

The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having formula Ia:

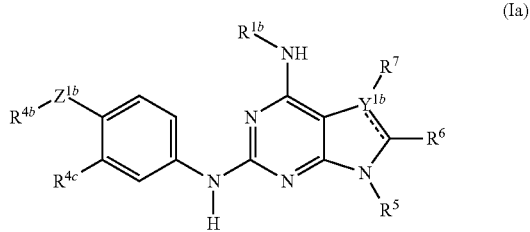

or tautomer or a pharmaceutically acceptable salt thereof, wherein:

$Y^{1b}$ is C;

$Z^{1b}$ is heterocyclyl, —NR$^4$SO$_2$—, heterocyclylsulfonyl or a bond, $R^{1b}$ is selected from the group consisting of
(a) H,
(b) $C_{1-8}$alkyl, optionally substituted with amino, amino$C_{1-8}$ alkyl, aminocarbonyl, alkoxy, $C_{1-8}$alkylaminocarbonyl, amino$C_{1-8}$alkylene, amino$C_{1-8}$ alkoxy, aryl, hydroxy or heterocyclyl,
(c) $C_{3-8}$cycloalkyl, optionally substituted with alkyl, amino, hydroxyl, $C_{1-8}$alkoxy, $C_{1-8}$alkylaminocarbonyl, amino$C_{1-8}$alkylene, amino$C_{1-8}$alkoxy;
(d) aryl, optionally substituted with alkyl, amino, aminosulfonyl, amino$C_{1-8}$alkylene, $C_{1-8}$alkylaminocarbonyl$C_{1-8}$alkoxy, hydroxyl, $C_{1-8}$alkoxy, $C_{1-8}$alkylaminocarbonyl, amino$C_{1-8}$alkylene, amino$C_{1-8}$alkoxy or halo;
(e) heterocyclyl, optionally substituted with $C_{1-8}$ alkyl, $C_{1-8}$alkoxycarbonyl, amino, hydroxyl, $C_{1-8}$alkoxy, $C_{1-8}$alkylaminocarbonyl, amino$C_{1-8}$alkylene, amino$C_{1-8}$ alkoxy, oxo, or cyano$C_{1-8}$alkylenecarbonyl;
(f) heteroaryl, optionally substituted with alkyl, amino, hydroxyl, $C_{1-8}$alkoxy, $C_{1-8}$alkylaminocarbonyl, amino$C_{1-8}$alkylene or amino$C_{1-8}$alkoxy;

$R^{4b}$ is selected from the group consisting of H, hydroxy, $C_{1-8}$alkylcarbonyl-, $C_{1-8}$alkoxycarbonyl$C_{1-8}$alkylene, $C_{1-8}$alkoxycarbonylamino, aminocarbonyl$C_{1-8}$alkylene, hydroxycarbonyl, hydroxycarbonyl$C_{1-8}$alkylene, aminocarbonyl, amino$C_{1-8}$alkylene, hydroxy, hydroxy$C_{1-8}$alkylenecarbonylamino, $C_{1-8}$alkylamino$C_{1-8}$alkylene, $C_{1-8}$alkylamino$C_{1-8}$alkyleneaminocarbonyl, aminocarbonylamino, $C_{1-8}$alkylsulfonyl$C_{1-8}$alkylene, $C_{3-8}$cycloalkylcarbonylamino and $C_{1-8}$alkylcarbonylamino; and $R^{4c}$ is H, amino, $C_{1-8}$alkylcarbonyl, aminocarbonyl$C_{1-8}$alkoxy;

$R^{4d}$ is H or $C_{1-8}$alkyl;

$R^5$ is H or $C_{1-8}$alkyl;

$R^6$ is selected from the group consisting of H, $C_{1-8}$alkyl, halo, hydroxy and oxo;

$R^7$ is selected from the group consisting of cyano, $C_{1-8}$alkoxy$C_{1-8}$alkylene, $C_{1-8}$alkylcarbonyl, hydroxy, oxo, halo, aryl and heteroaryl; and the dashed line indicates a double or single bond;

or the moiety $R^{4b}$—$Z^{1b}$ combines with $R^{4c}$ to form 5-7 membered heterocyclic ring, containing 1-3 heteroatoms, including N, O, S, optionally substituted with $C_{1-8}$alkyl, halo, cyano, oxo, =S, amino, hydroxyl, $C_{1-8}$alkylcarbonyl, $C_{1-8}$alkoxy or aryloxycarbonyl$C_{1-8}$lkylene.

2. A compound of claim 1 selected from the group consisting of N2-(1H-indazol-6-yl)-N4-methyl-5-(pyridin-4-yl)-7H-pyrrolo[2,3-d]pyrimidine-2,4-diamine; 1-(4-(4-(4-(methylamino)-5-(pyridin-4-yl)-7H-pyrrolo[2,3-d]pyrimidin-2-ylamino)phenyl)piperazin-1-yl)ethanone; N2-(1H-indazol-6-yl)-N4-methyl-5-(pyridin-3-yl)-7H-pyrrolo[2,3-d]pyrimidine-2,4-diamine; 1-(4-(4-(4-((cyclopropylamino)-5-(pyridin-4-yl)-7H-pyrrolo[2,3-d]pyrimidin-2-ylamino)phenyl)piperazin-1-yl)ethanone; 2-(1H-indazol-6-ylamino)-4-(cyclopropylamino)-7H-pyrrolo[2,3-d]pyrimidine-5-carbonitrile; 5-(1-butoxyethyl)-N4-cyclopropyl-N2-(1H-indazol-6-yl)-7H-pyrrolo[2,3-d]pyrimidine-2,4-diamine; 1-(2-(1H-indazol-6-ylamino)-4-(cyclopropylamino)-7H-pyrrolo[2,3-d]pyrimidine-5-yl)ethanone; N4-cyclopropyl-N2-(1H-indazol-6-yl)-5-(pyridin-4-yl)-7H-pyrrolo[2,3-d]pyrimidin-2,4-diamine; 1-(4-(4-(4-(piperidin-4-ylmethylamino)-5-(pyridin-4-yl)-7H-pyrrolo[2,3-d]pyrimidine-2-ylamino)phenyl)piperazin-1-yl)ethanone; 2-(4-(4-acetylpiperazin-1-yl)phenylamino)-4-(piperidin-4-ylmethylamino)-7H-pyrrolo[2,3-d]pyrimidine-5-carbonitrile; N-(4-(4-(cyclopropylamino)-5-(pyridin-4-yl)-7H-pyrrolo[2,3-d]pyrimidin-2-ylamino)-3,4-dihydroquinoline-2 (1H)-one; 5-bromo-N4-cyclobutyl-N2-(1H-indazol-6-yl)-7H-pyrrolo[2,3-d]pyrimidine-2,4-diamine; 5-chloro-N4-cyclobutyl-N2-(1H-indazol-6-yl)-7H-pyrrolo[2,3-d]pyrimidine-2,4-diamine; and 2-(1H-indazol-6-ylamino)-4-(cyclobutylamino)-6,7-dihydropyrrolo[2,3-d]pyrimidin-5-one.

3. A compound of claim 1 selected from the group consisting of N-(4-(4-(5 aminopentylamino)-5-bromo-7H-pyrrolo[2,3-d]pyrimidin-2-ylamino)phenyl)-N-methylacetamide; N-(4-(4-(5-aminopentylamino)-5,6-dibromo-7H-pyrrolo[2,3-d]pyrimidin-2-ylamino)phenyl)-N-methylacetamide; 4-(4-(cyclopropylamino)-5-(pyridin-4-yl)-7H-pyrrolo[2,3-d]pyrimidin-2-ylamino)benzamide; 4-(4-amino-5-(pyridin-4-yl)-7H-pyrrolo[2,3-d]pyrimidin-2-ylamino)benzoic acid; 4-(cyclopropylamino)-2-(2-oxo-1,2,3,4-tetrahydroquinolin-6-ylamino)-7H-pyrrolo[2,3-d]pyrimidine-5-carbonitrile; 4-(5-cyano-4-(cyclopropylamino)-7H-pyrrolo[2,3-d]pyrimidin-2-ylamino)benzamide; N-(4-(5-cyano-4-(cyclopropylamino)-7H-pyrrolo[2,3-d]pyrimidin-2-ylamino)phenyl)-N-methylacetamide; 4-(5-cyano-4-(cyclopropylamino)-7H-pyrrolo[2,3-d]pyrimidin-2-ylamino)benzenesulfonamide; 2-(4-(4-acetylpiperazin-1-yl)phenylamino)-4-(cyclopropylamino)-7H-pyrrolo[2,3-d]pyrimidine-5-carbonitrile; 4-(4-methylphenylamino)-2-(2-oxo-1,2,3,4-tetrahydroquinolin-6-ylamino)-7H-pyrrolo[2,3-d]pyrimidine-5-carbonitrile; 6-(4-(4-fluorophenylamino)-5-(pyridin-4-yl)-7H-pyrrolo[2,3-d]pyrimidin-2-ylamino)-1-methyl-3,4-dihydroquinolin-2 (1H)-one; 6-(4-Amino-5-(4-fluorophenyl)-7H-pyrrolo[2,3-d]pyrimidin-2-ylamino)-1-methyl-3,4-dihydroquinolin-2 (1H)-one; 6-(4-(benzylamino)-5-(pyridin-4-yl)-7H-pyrrolo [2,3-d]pyrimidin-2-ylamino)-1-methyl-3,4-dihydroquinolin-2(1H)-one; and 4-(Benzylamino)-2-(methyl-2-oxo-1,2,3,4-tetrahydroquinolin-6-ylamino)-7H-pyrrolo[2,3-d]pyrimidine-5-carbonitrile.

4. The compound of claim 1, wherein $R^{1a}$ is $C_{3-8}$cycloalkyl.

5. The compound of claim 1, wherein $R^{1a}$ is cyclohexyl, cyclopropyl or cyclobutyl.

6. The compound of claim 1, wherein $R^{2a}$ is H.

7. The compound of claim 1, wherein $Y^{1a}$ is C.

8. The compound of claim 1, wherein $R^{3a}$ is H.

9. The compound of claim 1, wherein $Z^1$ is a bond.

10. The compound of claim 1, wherein $R^{4b}$ is selected from the group consisting of H, $C_{1-8}$alkyl, $C_{1-8}$alkylcarbonyl, $C_{1-8}$alkylcarbonylamino, $C_{1-8}$alkylsulfonyl, $C_{1-8}$alkylsulfonylamino, $C_{1-8}$alkylsulfonyl $C_{1-8}$alkylene, $C_{1-8}$-alkylthio, $C_{1-8}$alkoxy, $C_{1-8}$alkoxycarbonylamino, $C_{1-8}$alkoxycarbonyl, $C_{1-8}$alkoxycarbonyl, $C_{1-8}$alkylene, aminocarbonyl, aminosulfonyl, $C_{1-8}$alkoxycarbonyl, $C_{1-8}$alkyleneaminosulfonyl, amino$C_8$alkyleneaminocarbonyl, amino$C_{1-8}$alkyleneaminocarbonyl, aminocarbonyl$C_{1-8}$alkoxy, aminocarbonyl, aminocarbonyl$C_{1-8}$alkyleneaminosulfonyl, carboxy, carboxy$C_{1-8}$ alkyleneaminosulfonyl, $C_{3-8}$cycloalkylcarbonylamino, halo, hydroxy, hydroxy$C_{1-8}$ alkylene, hydroxy$C_{1-8}$alkyenecarbonylamino, hydroxy$C_{1-8}$ alkyleneamino-, hydroxy$C_{1-8}$ alkyleneaminosulfonyl, hydroxy$C_{1-8}$alkyleneaminocarbonyl, oxo and heterocyclyl.

11. The compound of claim 1, having the formula selected from the group consisting of:

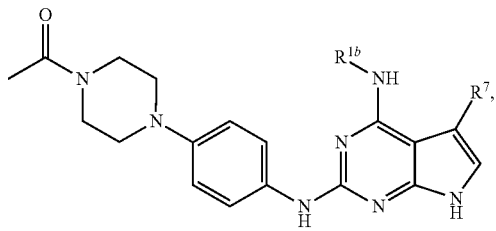

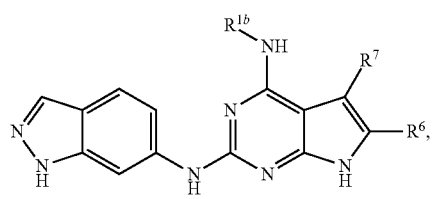

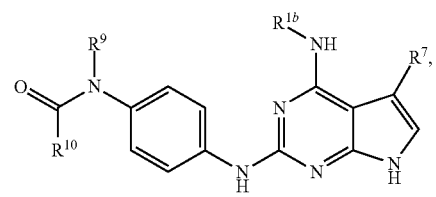

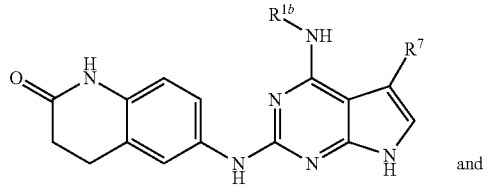

and

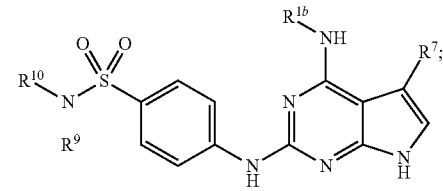

wherein $R^{1b}$ is $C_{1-8}$alkyl, optionally substituted with amino, heterocyclyl or aminoheterocyclyl, and $C_{3-8}$cycloalkyl, optionally substituted with amino; $R^7$ is halo, hydroxy, $C_{1-8}$alkoxy$C_{1-8}$alkylene, $C_{1-8}$alkylcarbonyl, cyano or phenyl, pyridinyl; and $R^6$ is H, $C_{1-8}$alkyl or halo; $R^9$ is H or $C_{1-8}$alkyl; and $R^{10}$ is H, $C_{1-8}$alkyl, $C_{1-8}$alkoxycarbonyl$C_{1-8}$alkylene, amino$C_{1-8}$alkylene, aminocarbonyl$C_{1-8}$alkylene, carboxy$C_{1-8}$alkylene, $C_{3-8}$cycloalkyl and hydroxy$C_{1-8}$alkylene; or a tautomer or a pharmaceutically acceptable salt thereof.

12. The compound of claim 1, wherein $R^{1b}$ is $C_{3-8}$cycloalkyl, optionally substituted.

13. The compound of claim 1, wherein $R^{1b}$ is cyclohexyl, cyclopropyl or cyclobutyl, each of which is optionally substituted.

14. The compound of claim 1, wherein the moiety is selected from the group consisting of

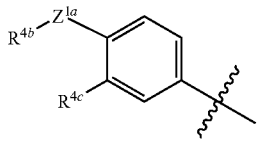

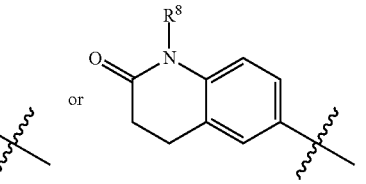

wherein $R^8$ is selected from the group consisting of H, $C_{1-8}$alkyl, hydroxycarbonyl$C_{1-8}$alkylene, alkoxycarbonyl$C_{1-8}$alkylene and $C_{1-8}$alkylamino$C_{1-8}$alkyleneaminocarbonyl$C_{1-8}$alkylene.

15. The compound of claim 1, having the formula:

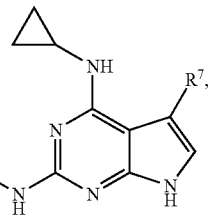

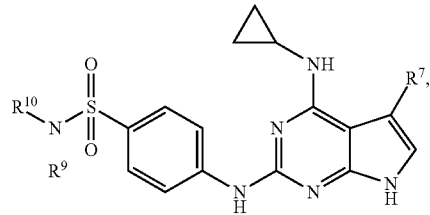

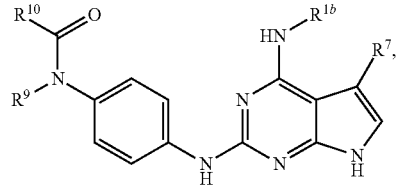

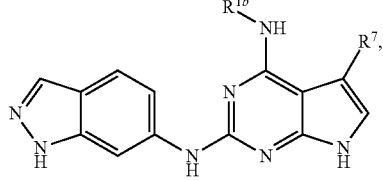

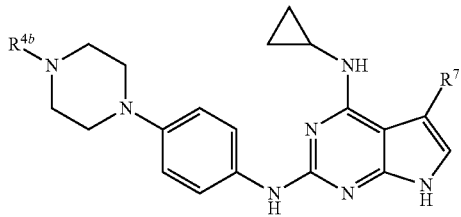

or

-continued

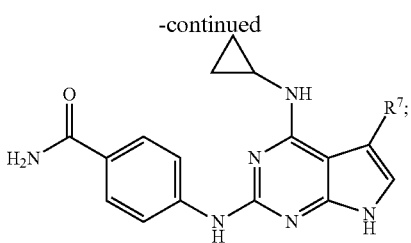

wherein $R^{1b}$ is $C_{1-8}$alkyl, $C_{3-8}$cycloalkyl, aryl or heteroaryl; each of which is optionally substituted with hydroxy, $C_{1-8}$alkoxy or amino$C_{1-8}$alkoxy; $R^{4b}$ is H or $CH_3CO-$; $R^7$ is $C_{1-8}$alkylcarbonyl, aminocarbonyl, cyano, phenyl or pyridinyl; $R^9$ is H or $C_{1-8}$alkyl; and $R^{10}$ is H, $C_{1-8}$alkyl, $C_{1-8}$alkoxy, $C_{1-8}$alkoxycarbonyl$C_{1-8}$alkylene, amino$C_{1-8}$alkylene, aminocarbonyl$C_{1-8}$alkylene, carboxy$C_{1-8}$alkylene, $C_{3-8}$cycloalkyl and hydroxy$C_{1-8}$alkylene.

16. A composition comprising a compound claim 1 in combination with a pharmaceutically acceptable carrier or diluent.

17. A kit comprising a composition of claim 16, packaging and instructions for use.

18. A method for inhibiting syk, JAK kinase or a signal transduction pathway mediated at least in part by syk or JAK kinase activity comprising the step of contacting a cell with a compound of claim 1.

19. A method for treating a condition or disorder mediated at least in part by syk or JAK kinase activity in a subject comprising the step of administering to a subject in need of such treatment a therapeutically effective amount of a composition of claim 16.

* * * * *

UNITED STATES PATENT AND TRADEMARK OFFICE
CERTIFICATE OF CORRECTION

PATENT NO. : 8,258,144 B2
APPLICATION NO. : 12/386848
DATED : September 4, 2012
INVENTOR(S) : Song et al.

It is certified that error appears in the above-identified patent and that said Letters Patent is hereby corrected as shown below:

In the Claims:

Claim 1, Column 229, Line 9: please delete "aminoC$_{1-8}$ alkyl" and insert --aminoC$_{1-8}$alkyl--.

Claim 1, Column 229, Line 10: please delete "aminoC$_{1-8}$ alkoxy" and insert --aminoC$_{1-8}$alkoxy--.

Claim 1, Column 229, Line 52: please delete "lkylene" and insert --alkylene--.

Claim 2, Column 229, Line 66: please delete "pyrrolo[2,3-d]pyrimidine-5-yl)ethanone;" and insert --pyrrolo[2,3-d]pyrimidin-5-yl)ethanone;--.

Claim 2, Column 230, Line 7: after "rolo[2,3-d]pyrimidine-2-ylamino)-" please insert --phenyl)-N-methylacetamide; 6-(4-(cyclopropylamino)-5-(pyridin-4-yl)-7H-pyrrolo[2,3-d]pyrimidin-2-ylamino--.

Claim 2, Column 230, Line 7, please delete "3,4-dihydroquinoline" and insert --3,4-dihydroquinolin--.

Claim 10, Column 230, Line 54: after "C$_{1-8}$alkylsulfonyl," please insert --C$_{1-8}$alkylsulfinyl,--.

Claim 10, Column 230, Line 55: after "C$_{1-8}$alkylsulfonyl" please insert a --,--.

Claim 10, Column 230, Line 63: please delete "carboxyC$_{1-8}$ alkyleneaminosulfonyl" and insert --carboxyC$_{1-8}$alkyleneaminosulfonyl--.

Claim 10, Column 230, Line 66: please delete "hydroxyC$_{1-8}$ alkyleneaminosulfonyl" and insert --hydroxyC$_{1-8}$alkyleneaminosulfonyl--.

Signed and Sealed this
Eighth Day of January, 2013

David J. Kappos
*Director of the United States Patent and Trademark Office*

Claim 11, Column 231, Line 57: after "$C_{1-8}$alkyl," please insert --$C_{1-8}$alkoxy,--.
Claim 14, Column 232, Line 5: please delete " 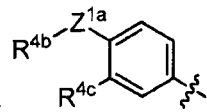 " and insert -- 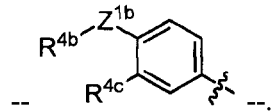 --.